US012571036B2

(12) United States Patent
Almogy et al.

(10) Patent No.: US 12,571,036 B2
(45) Date of Patent: *Mar. 10, 2026**

(54) METHODS, DEVICES, AND SYSTEMS FOR ANALYTE DETECTION AND ANALYSIS

(71) Applicant: Ultima Genomics, Inc., Newark, CA (US)

(72) Inventors: Gilad Almogy, Palo Alto, CA (US); Nathan Beckett, Oakland, CA (US); Jacob A. Wolf, Oakland, CA (US); Nathan Caswell, Sunnyvale, CA (US); Joseph Anthony, Oakland, CA (US); Jose Martin Sosa, San Jose, CA (US); Phillip Lee, South San Francisco, CA (US); Stephanie Kubecka, San Jose, CA (US)

(73) Assignee: Ultima Genomics, Inc., Fremont, CA (US)

( * ) Notice: Subject to any disclaimer, the term of this patent is extended or adjusted under 35 U.S.C. 154(b) by 1143 days.

This patent is subject to a terminal disclaimer.

(21) Appl. No.: 17/475,256

(22) Filed: Sep. 14, 2021

(65) Prior Publication Data

US 2022/0064727 A1     Mar. 3, 2022

Related U.S. Application Data

(63) Continuation of application No. 17/155,226, filed on Jan. 22, 2021, now Pat. No. 11,155,868, which is a continuation of application No. 16/445,798, filed on Jun. 19, 2019, now Pat. No. 10,900,078.

(60) Provisional application No. 62/837,684, filed on Apr. 23, 2019, provisional application No. 62/818,549, filed on Mar. 14, 2019.

(51) Int. Cl.
| | |
|---|---|
| *C12Q 1/6874* | (2018.01) |
| *B01J 19/00* | (2006.01) |
| *B01L 3/00* | (2006.01) |
| *C12Q 1/6809* | (2018.01) |
| *C12Q 1/6825* | (2018.01) |

(52) U.S. Cl.
CPC ........ *C12Q 1/6874* (2013.01); *B01J 19/0046* (2013.01); *B01L 3/502715* (2013.01); *C12Q 1/6809* (2013.01); *C12Q 1/6825* (2013.01); *B01J 2219/00536* (2013.01); *B01J 2219/00596* (2013.01); *B01J 2219/00689* (2013.01); *B01J 2219/00702* (2013.01); *B01J 2219/00722* (2013.01); *B01L 2200/0647* (2013.01); *B01L 2300/0654* (2013.01); *B01L 2400/0409* (2013.01)

(58) Field of Classification Search
None
See application file for complete search history.

(56) References Cited

U.S. PATENT DOCUMENTS

| | | | |
|---|---|---|---|
| 3,707,723 | A | 12/1972 | Levene |
| 4,611,881 | A | 9/1986 | Schmidt et al. |
| 5,216,247 | A | 6/1993 | Wang et al. |
| 5,307,146 | A | 4/1994 | Porter et al. |
| 5,409,811 | A | 4/1995 | Tabor et al. |
| 5,607,863 | A | 3/1997 | Chandler |
| 5,641,006 | A | 6/1997 | Autrey et al. |
| 5,641,658 | A | 6/1997 | Adams et al. |
| 5,674,716 | A | 10/1997 | Tabor et al. |
| 5,800,997 | A | 9/1998 | Beck |
| 6,139,831 | A | 10/2000 | Shivashankar et al. |
| 6,320,609 | B1 | 11/2001 | Buchanan et al. |
| 6,466,352 | B1 | 10/2002 | Shahar et al. |
| 6,737,238 | B2 | 5/2004 | Suzuki et al. |
| 7,623,289 | B2 | 11/2009 | Harada |
| 7,689,022 | B2 | 3/2010 | Weiner et al. |
| 7,906,285 | B2 | 3/2011 | Drmanac |
| 7,939,264 | B1 | 5/2011 | Densham |
| 8,431,903 | B2 | 4/2013 | Duhr et al. |
| 8,475,739 | B2 | 7/2013 | Holmes et al. |
| 8,574,847 | B2 | 11/2013 | Becker et al. |
| 8,597,882 | B2 | 12/2013 | Corbett et al. |

(Continued)

FOREIGN PATENT DOCUMENTS

| | | |
|---|---|---|
| CN | 1142868 A | 2/1997 |
| CN | 103547255 A | 1/2014 |

(Continued)

OTHER PUBLICATIONS

Co-pending U.S. Appl. No. 17/962,163, inventors Barbee; Kristopher et al., filed Oct. 7, 2022.

(Continued)

*Primary Examiner* — Kaijiang Zhang

(74) *Attorney, Agent, or Firm* — Wilson Sonsini Goodrich & Rosati

(57) ABSTRACT

Provided are systems and methods for analyte detection and analysis. A system can comprise an open substrate. The open substrate may be configured to rotate or otherwise move. The open substrate can comprise an array of individually addressable locations, with analytes immobilized thereto. The substrate may be spatially indexed to identify nucleic acid molecules from one or more sources, and/or sequences thereof, with the respective one or more sources. A solution comprising a plurality of probes may be directed across the array to couple at least one of the plurality of probes with at least one of the analytes to form a bound probe. A detector can be configured to detect a signal from the bound probe via scanning of the substrate while minimizing temperature fluctuations of the substrate or optical aberrations caused by bubbles.

30 Claims, 62 Drawing Sheets

(56)  References Cited

U.S. PATENT DOCUMENTS

| | | | |
|---|---|---|---|
| 8,772,473 | B2 | 7/2014 | Huang et al. |
| 9,795,961 | B1 | 10/2017 | Koh et al. |
| 9,891,177 | B2 | 2/2018 | Vazhaeparambil et al. |
| 10,267,790 | B1 | 4/2019 | Barbee et al. |
| 10,273,528 | B1 | 4/2019 | Barbee et al. |
| 10,344,328 | B2 | 7/2019 | Barbee et al. |
| 10,512,911 | B1 | 12/2019 | Beckett et al. |
| 10,830,703 | B1 | 11/2020 | Almogy et al. |
| 10,852,518 | B1 | 12/2020 | Almogy et al. |
| 10,900,078 | B2 | 1/2021 | Almogy et al. |
| 11,118,223 | B2 | 9/2021 | Almogy et al. |
| 11,155,868 | B2 | 10/2021 | Almogy et al. |
| 11,268,143 | B2 | 3/2022 | Beckett et al. |
| 11,396,015 | B2 | 7/2022 | Beckett et al. |
| 11,499,962 | B2 | 11/2022 | Barbee et al. |
| 11,512,350 | B2 | 11/2022 | Almogy et al. |
| 11,591,651 | B2 | 2/2023 | Almogy et al. |
| 11,648,554 | B2 | 5/2023 | Beckett et al. |
| 11,732,298 | B2 | 8/2023 | Almogy et al. |
| 11,747,323 | B2 | 9/2023 | Barbee et al. |
| 12,031,180 | B2 | 7/2024 | Beckett et al. |
| 12,188,924 | B2 | 1/2025 | Barbee et al. |
| 12,239,980 | B2 | 3/2025 | Beckett et al. |
| 2002/0006622 | A1 | 1/2002 | Bradley et al. |
| 2002/0009015 | A1 | 1/2002 | Laugharn et al. |
| 2002/0022261 | A1 | 2/2002 | Anderson et al. |
| 2002/0055112 | A1 | 5/2002 | Patil et al. |
| 2002/0064780 | A1 | 5/2002 | Gold et al. |
| 2002/0072243 | A1 | 6/2002 | Craighead et al. |
| 2002/0074517 | A1 | 6/2002 | Krutchinsky et al. |
| 2002/0168652 | A1 | 11/2002 | Werner et al. |
| 2002/0172980 | A1 | 11/2002 | Phan et al. |
| 2002/0177144 | A1 | 11/2002 | Remacle et al. |
| 2003/0054376 | A1 | 3/2003 | Mullis et al. |
| 2003/0193589 | A1 | 10/2003 | Lareau et al. |
| 2004/0071888 | A1 | 4/2004 | Chondroudis et al. |
| 2005/0037484 | A1 | 2/2005 | Staimer et al. |
| 2005/0186580 | A1 | 8/2005 | Dellinger et al. |
| 2005/0237480 | A1 | 10/2005 | Allbritton et al. |
| 2006/0078934 | A1 | 4/2006 | Desmet et al. |
| 2006/0078935 | A1 | 4/2006 | Werner et al. |
| 2006/0263791 | A1 | 11/2006 | Moon et al. |
| 2007/0099289 | A1 | 5/2007 | Irimia et al. |
| 2007/0275193 | A1 | 11/2007 | DeSimone et al. |
| 2007/0290702 | A1 | 12/2007 | Lee |
| 2008/0038163 | A1 | 2/2008 | Boege et al. |
| 2008/0242560 | A1 | 10/2008 | Gunderson et al. |
| 2008/0254259 | A1 | 10/2008 | Nishi et al. |
| 2009/0098541 | A1 | 4/2009 | Southern et al. |
| 2009/0135385 | A1 | 5/2009 | Gellrich et al. |
| 2009/0263002 | A1 | 10/2009 | Cremer et al. |
| 2009/0263807 | A1 | 10/2009 | Yotoriyama |
| 2009/0305431 | A1 | 12/2009 | Hodges et al. |
| 2009/0308742 | A1 | 12/2009 | Paranjape |
| 2010/0041562 | A1 | 2/2010 | Li et al. |
| 2010/0101104 | A1 | 4/2010 | Grzesiak et al. |
| 2010/0151564 | A1 | 6/2010 | Beebe et al. |
| 2010/0167308 | A1 | 7/2010 | Miller et al. |
| 2010/0210475 | A1 | 8/2010 | Lee et al. |
| 2010/0330578 | A1 | 12/2010 | Duhr et al. |
| 2011/0086361 | A1 | 4/2011 | Klunder et al. |
| 2011/0178285 | A1 | 7/2011 | Lebl et al. |
| 2011/0312622 | A1 | 12/2011 | Azimi et al. |
| 2012/0068059 | A1 | 3/2012 | Montes Usategui et al. |
| 2012/0126142 | A1 | 5/2012 | Matsui et al. |
| 2012/0282708 | A1 | 11/2012 | Corbett et al. |
| 2012/0316074 | A1 | 12/2012 | Saxonov |
| 2013/0005585 | A1 | 1/2013 | Anderson et al. |
| 2013/0038719 | A1 | 2/2013 | Canini et al. |
| 2013/0076852 | A1 | 3/2013 | Bai et al. |
| 2014/0152888 | A1 | 6/2014 | Staker et al. |
| 2014/0162275 | A1 | 6/2014 | Kotseroglou |
| 2014/0261577 | A1 | 9/2014 | Furukawa et al. |
| 2014/0287423 | A1 | 9/2014 | Nurse |
| 2015/0071898 | A1 | 3/2015 | Liu et al. |
| 2015/0125346 | A1 | 5/2015 | Schaff et al. |
| 2015/0212310 | A1 | 7/2015 | Fukuda et al. |
| 2015/0270146 | A1 | 9/2015 | Yoshihara et al. |
| 2016/0032380 | A1 | 2/2016 | Craighead et al. |
| 2016/0041135 | A1 | 2/2016 | Lannutti et al. |
| 2016/0061733 | A1 | 3/2016 | Wu et al. |
| 2016/0076025 | A1 | 3/2016 | Boutell et al. |
| 2016/0076978 | A1 | 3/2016 | Dave et al. |
| 2016/0168626 | A1 | 6/2016 | Danehy et al. |
| 2016/0184870 | A1 | 6/2016 | Miura et al. |
| 2016/0246170 | A1 | 8/2016 | Bowen et al. |
| 2016/0314575 | A1 | 10/2016 | Matsuo et al. |
| 2016/0319334 | A1 | 11/2016 | Barany et al. |
| 2017/0123198 | A1 | 5/2017 | Singer et al. |
| 2017/0136434 | A1 | 5/2017 | Barnard et al. |
| 2018/0207920 | A1 | 7/2018 | Venkatesan et al. |
| 2019/0271038 | A1 | 9/2019 | Almogy et al. |
| 2019/0271039 | A1 | 9/2019 | Almogy et al. |
| 2019/0291115 | A1 | 9/2019 | Kaplan et al. |
| 2019/0331903 | A1 | 10/2019 | Wald et al. |
| 2020/0164379 | A1 | 5/2020 | Kaplan et al. |
| 2020/0179925 | A1 | 6/2020 | Beckett et al. |
| 2020/0179926 | A1 | 6/2020 | Beckett et al. |
| 2020/0326327 | A1 | 10/2020 | Barbee et al. |
| 2021/0047688 | A1 | 2/2021 | Almogy et al. |
| 2021/0054454 | A1 | 2/2021 | Almogy et al. |
| 2021/0199647 | A1 | 7/2021 | Beckett et al. |
| 2021/0277464 | A1 | 9/2021 | Beckett et al. |
| 2021/0354126 | A1 | 11/2021 | Beckett et al. |
| 2024/0027425 | A1 | 1/2024 | Barbee et al. |
| 2024/0360505 | A1 | 10/2024 | Beckett et al. |
| 2025/0012778 | A1 | 1/2025 | Barbee et al. |
| 2025/0262618 | A1 | 8/2025 | Beckett et al. |

FOREIGN PATENT DOCUMENTS

| | | |
|---|---|---|
| CN | 105759027 A | 7/2016 |
| CN | 107735664 A | 2/2018 |
| EP | 0865606 A1 | 9/1998 |
| JP | 2000304688 A | 11/2000 |
| JP | 2003511043 A | 3/2003 |
| JP | 2005345597 A | 12/2005 |
| JP | 2008262983 A | 10/2008 |
| JP | 2010117712 A | 5/2010 |
| JP | 2010536009 A | 11/2010 |
| JP | 2012522225 A | 9/2012 |
| JP | 2015529858 A | 10/2015 |
| JP | 2018511338 A | 4/2018 |
| JP | 2018516591 A | 6/2018 |
| JP | 2018143154 A | 9/2018 |
| WO | WO-0037680 A1 | 6/2000 |
| WO | WO-0039625 A2 | 7/2000 |
| WO | WO-0039625 A3 | 10/2000 |
| WO | WO-03102535 A2 | 12/2003 |
| WO | WO-03102535 A3 | 3/2004 |
| WO | WO-2008016335 A1 | 2/2008 |
| WO | WO-2014127379 A1 | 8/2014 |
| WO | WO-2014143981 A1 | 9/2014 |
| WO | WO-2014143981 A9 | 12/2014 |
| WO | WO-2015119254 A1 | 8/2015 |
| WO | WO-2014143981 A8 | 12/2015 |
| WO | WO-2016161163 A2 | 10/2016 |
| WO | WO-2016168687 A1 | 10/2016 |
| WO | WO-2018064297 A1 | 4/2018 |
| WO | WO-2018144582 A1 | 8/2018 |
| WO | WO-2019099886 A1 | 5/2019 |
| WO | WO-2020034143 A1 | 2/2020 |
| WO | WO-2020118172 A1 | 6/2020 |
| WO | WO-2020186243 A1 | 9/2020 |
| WO | WO-2022072652 A1 | 4/2022 |

OTHER PUBLICATIONS

EP19894196.5 European Search Report dated Aug. 12, 2022.
He, R-Y., et al. Study of cell adhesion and migration by using a plasmon-enhanced total internal reflection fluorescence microscope. Imaging, Manipulation, and Analysis of Biomolecules, Cells, and Tissues IV. vol. 6088. SPIE (2006).

(56) References Cited

OTHER PUBLICATIONS

U.S. Appl. No. 16/416,856 Final Office Action dated Oct. 5, 2022.
U.S. Appl. No. 16/862,196 Notice of Allowance dated Jul. 7, 2022.
Britannica, The Editors of Encyclopedia. "fluid". Encyclopedia Britannica, May 11, 2021, https://www.britannica.com/science/fluid-physics. Accessed on Jan. 21, 2022.
PCT/US2019/064916 International Search Report and Written Opinion dated Apr. 7, 2020.
PCT/US2021/052902 International Search Report and Written Opinion dated Feb. 17, 2022.
U.S. Appl. No. 16/665,540 Non-Final Office Action dated Jan. 10, 2022.
U.S. Appl. No. 16/665,559 Non-Final Office Action dated Feb. 7, 2022.
Explanation of "Probe" in the Dictionary of Nutrition and Biochemistry. Retrieved from website on Jun. 30, 2023: https://kotobank.jp/word/%E3%83%97%E3%83%AD%E3%83%BC%E3%83%96-675975.
Spencer, Harold, and F.R.S. Jones. Variations of the Earth's Rotation. Physics and Chemistry of the Earth, vol. 4 (1961): 186-210.
U.S. Appl. No. 17/336,377 Office Action dated Sep. 28, 2023.
U.S. Appl. No. 17/543,521 Office Action dated Oct. 12, 2023.
U.S. Appl. No. 16/416,889 Office Action dated Mar. 26, 2024.
U.S. Appl. No. 17/543,521 Notice of Allowance dated Jun. 5, 2024.
U.S. Appl. No. 17/962,163 Office Action dated Mar. 3, 2023.
U.S. Appl. No. 18/224,378 Notice of Allowance dated Apr. 29, 2024.
EP20770906.4 Extended European Search Report dated Feb. 20, 2023.
Adessi et al. Solid phase DNA amplification: Charcterisation of primer attachment and amplification mechanisms, Nucl. Acids Res, 2000, 28(20):E87.
Bioptechs. Product information for the Bioptechs Objective Heater. Available at http://bioptechs.com/product/objective-heater/. Accessed on Jun. 25, 2019.
Brenner, et al. Gene expression analysis by massively parallel signature sequencing (MPSS) on microbead arrays. Nat Biotechnol. Jun. 2000;18(6):630-4.
Brenner et al. In vitro cloning of complex mixtures of DNA on microbeads: Physical separation of differentially expressed cDNAs, Proc. Natl. Acad. Sci. USA 2000, 97(4):1665-1670.
Co-pending U.S. Application No. 202117543521, inventors Beckett; Nathan et al., filed on Dec. 6, 2021.
Co-pending U.S. Application No. 202017001174, inventors Almogy; Gilad et al., filed on Aug. 24, 2020.
Co-pending U.S. Application No. 202017003400, inventors Almogy; Gilad et al., filed on Aug. 26, 2020.
Dressman, et al. Transforming single DNA molecules into fluorescent magnetic particles for detection and enumeration of genetic variations. Proc Natl Acad Sci USA. 2003; 100(15):8817-8822.
EP20180878612 European Search Report dated Jul. 14, 2021.
Lizardi, et al. Mutation detection and single-molecule counting using isothermal rolling-circle amplification. Nat Genet. Jul. 1998;19(3):225-32.
MIT Technology Review. China's BGI says it can sequence a genome for just $100. Available at https://www.technologyreview.com/2020/02/26/905658/china-bgi-100-dollar-genome. Accessed on Feb. 19, 2021.
Mitra, et al. Digital genotyping and haplotyping with polymerase colonies. Proceedings of the National Academy of Sciences of the United States of America vol. 100,10 (2003): 5926-31.

Mitra, et al. Fluorescent in situ sequencing on polymerase colonies, Anal. Biochem, 320:55-65. (2003).
PCT/US020/022816 International Search Report and Written Opinion dated Jul. 30, 2020.
PCT/US18/61598 International Search Report and Written Opinion dated Mar. 15, 2019.
Pemov, A. et al. DNA analysis with multiplex microarray-enhanced PCR. Nucleic acids research vol. 33:2 (2005).
Qin, et al. High-throughput, low-cost and rapid DNA sequencing using surface-coating techniques. bioRxiv (2020).
Reinartz, et al. Massively parallel signature sequencing (MPSS) as a tool for in-depth quantitative gene expression profiling in all organisms. Brief Funct Genomic Proteomic. Feb. 2002;1(1):95-104.
Spatial Transcriptomics. Workflow. Available at https://spatialtranscriptomics.com/workflow/. Accessed on Jun. 25, 2019.
Tabor, et al., Effect of manganese ions on the incorporation of dideoxynucleotides by bacteriophage T7 DNA polymerase and *Escherichia coli* DNA polymerase I, Proc. Natl. Acad. Sci. USA, Jun. 1989, 86:4076-80.
U.S. Appl. No. 15/974,364 Office Action dated Aug. 7, 2018.
U.S. Appl. No. 15/974,543 Notice of Allowance dated Dec. 13, 2018.
U.S. Appl. No. 15/974,543 Office Action dated Aug. 7, 2018.
U.S. Appl. No. 16/445,798 Notice of Allowance dated Dec. 18, 2020.
U.S. Appl. No. 16/445,798 Notice of Allowance dated Dec. 4, 2020.
U.S. Appl. No. 16/445,798 Notice of Allowance dated Sep. 18, 2020.
U.S. Appl. No. 16/445,798 Office Action dated May 8, 2020.
U.S. Appl. No. 16/677,067 Notice of Allowance dated Aug. 12, 2020.
U.S. Appl. No. 16/677,067 Notice of Allowance dated Jul. 1, 2020.
U.S. Appl. No. 16/677,067 Notice of Allowance dated Jun. 19, 2020.
U.S. Appl. No. 16/677,067 Notice of Allowance dated Sep. 21, 2020.
U.S. Appl. No. 16/677,115 Notice of Allowance dated Aug. 21, 2020.
U.S. Appl. No. 16/677,115 Notice of Allowance dated Jul. 14, 2020.
U.S. Appl. No. 16/953,071 Notice of Allowance dated May 26, 2021.
U.S. Appl. No. 16/953,071 Notice of Allowance dated May 5, 2021.
U.S. Appl. No. 16/953,071 Office Action dated Apr. 22, 2021.
U.S. Appl. No. 16/953,071 Office Action dated Jan. 15, 2021.
U.S. Appl. No. 17/155,226 Notice of Allowance dated Aug. 27, 2021.
U.S. Appl. No. 17/155,226 Notice of Allowance dated Jul. 6, 2021.
U.S. Appl. No. 17/155,226 Office Action dated Mar. 18, 2021.
U.S. Appl. No. 17/308,241 Notice of Allowance dated Nov. 16, 2021.
U.S. Appl. No. 17/308,241 Office Action dated Jul. 26, 2021.
U.S. Appl. No. 15/974,364 Notice of Allowance dated Feb. 28, 2019.
U.S. Appl. No. 15/974,441 Notice of Allowance dated Nov. 21, 2018.
U.S. Appl. No. 15/974,441 Office Action dated Aug. 3, 2018.
U.S. Appl. No. 16/445,798 Office Action dated Nov. 6, 2019.
U.S. Appl. No. 16/677,067 Office Action dated Feb. 28, 2020.
U.S. Appl. No. 16/677,115 Office Action dated Mar. 24, 2020.
U.S. Appl. No. 18/224,378 Notice of Allowance dated Oct. 30, 2024.
U.S. Appl. No. 18/776,046 Notice of Allowance dated Jul. 22, 2025.
U.S. Appl. No. 18/776,046 Office Action dated Jun. 18, 2025.

200

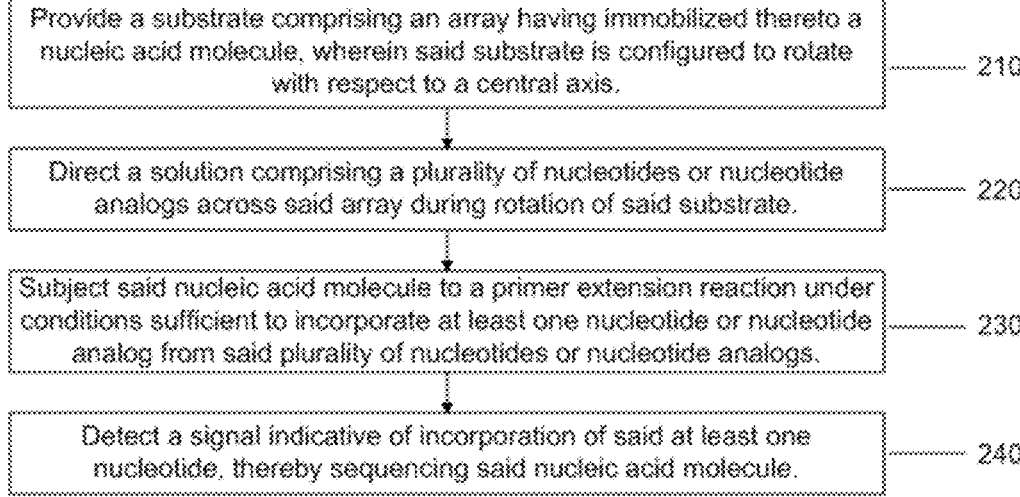

Provide a substrate comprising an array having immobilized thereto a nucleic acid molecule, wherein said substrate is configured to rotate with respect to a central axis. — 210

Direct a solution comprising a plurality of nucleotides or nucleotide analogs across said array during rotation of said substrate. — 220

Subject said nucleic acid molecule to a primer extension reaction under conditions sufficient to incorporate at least one nucleotide or nucleotide analog from said plurality of nucleotides or nucleotide analogs. — 230

Detect a signal indicative of incorporation of said at least one nucleotide, thereby sequencing said nucleic acid molecule. — 240

FIG. 2

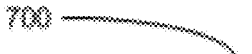
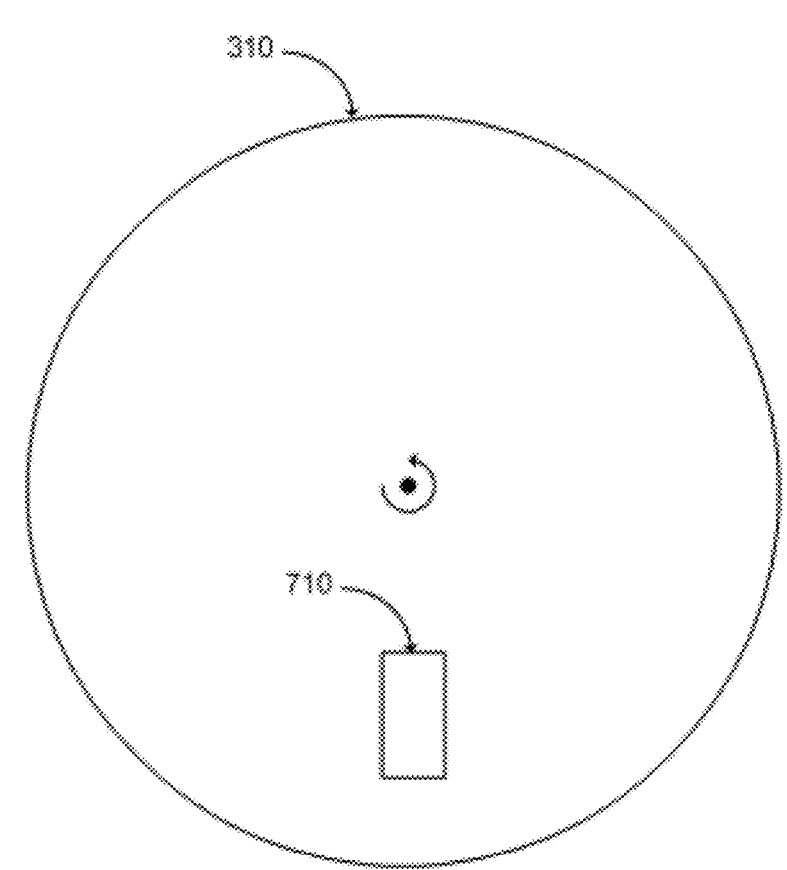
FIG. 7

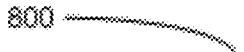
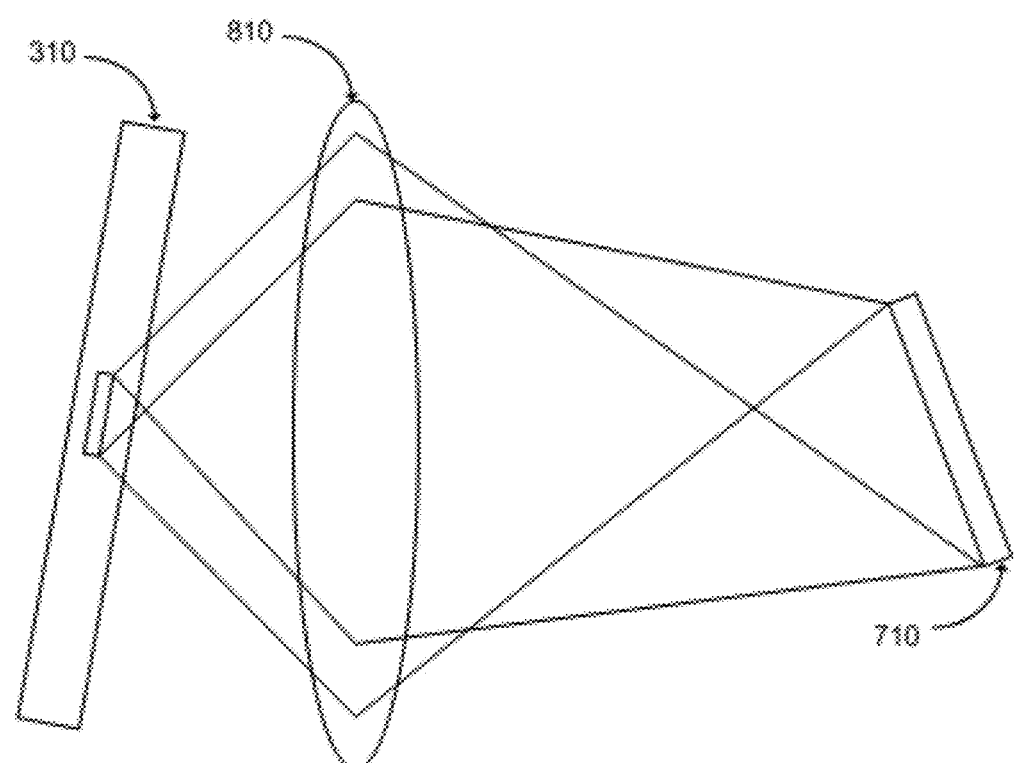
FIG. 8A

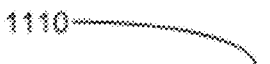
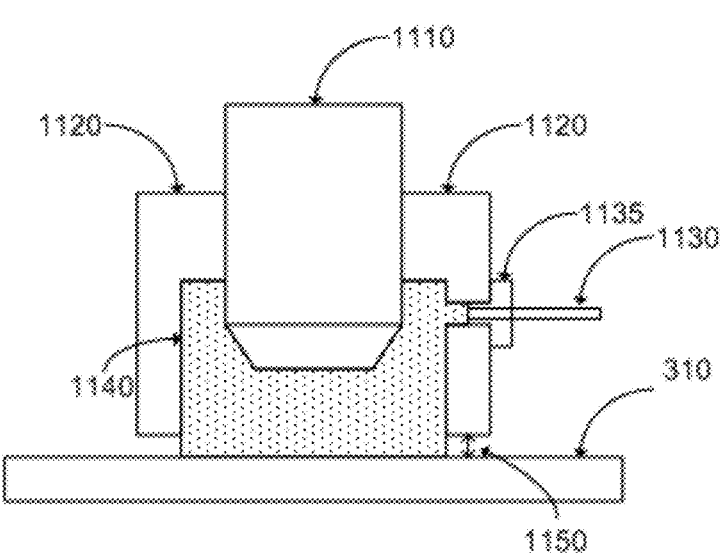
FIG. 11

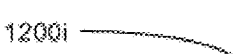
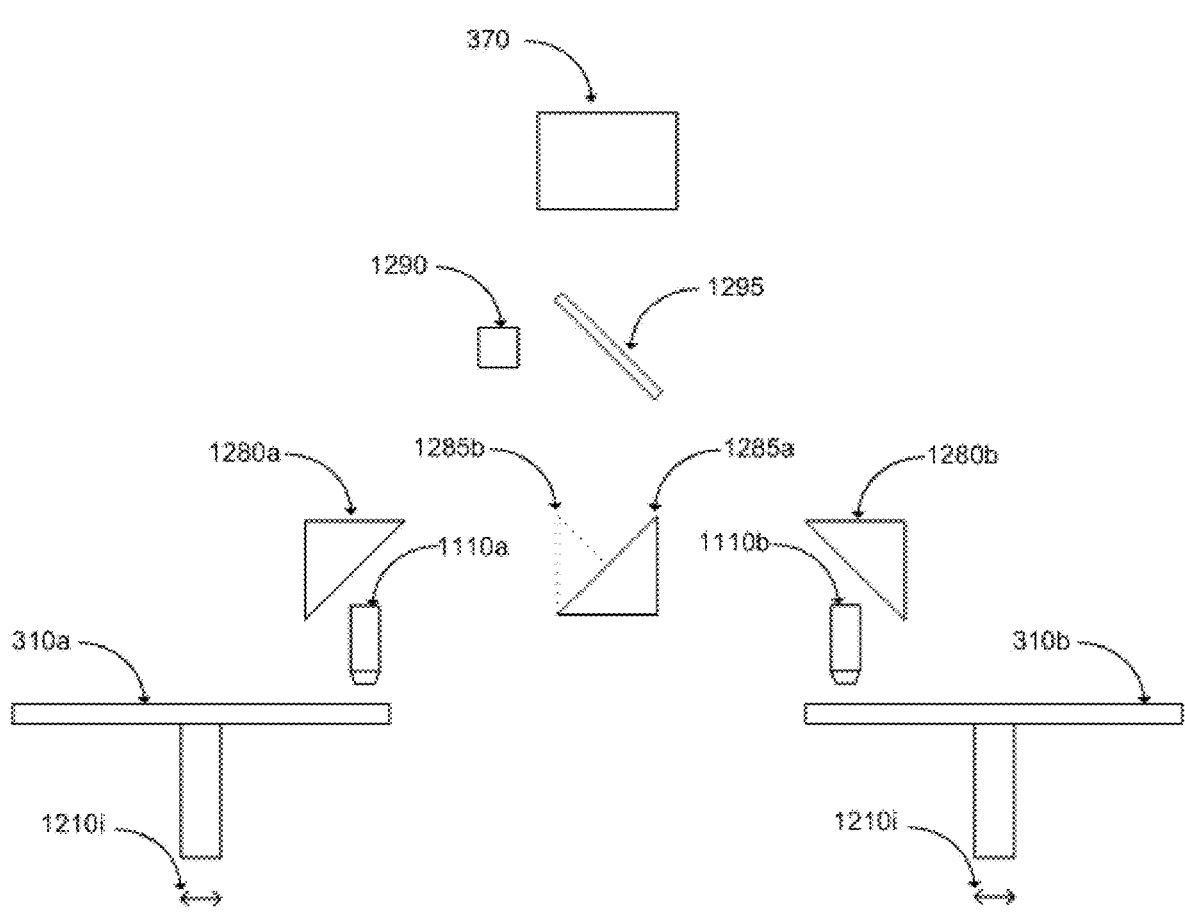
FIG. 12I

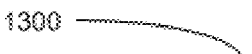
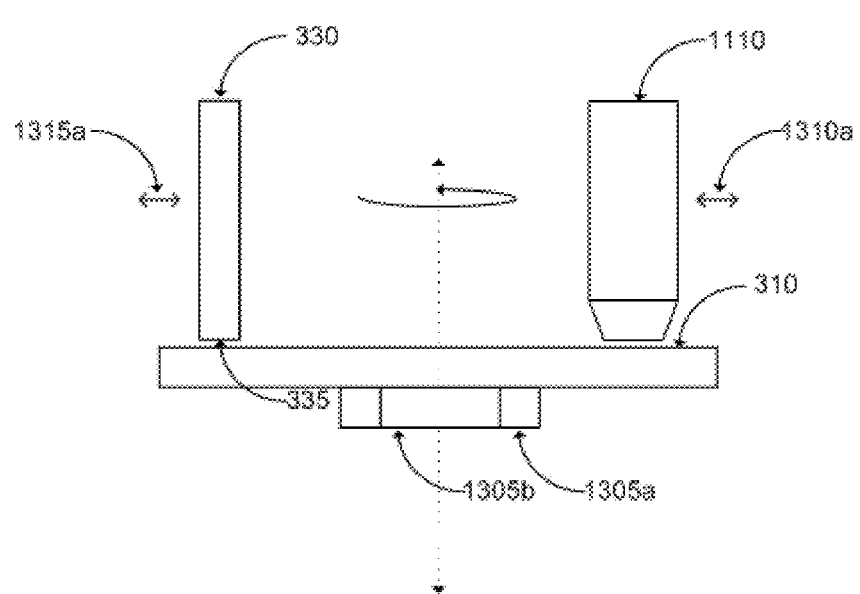
FIG. 13

1400

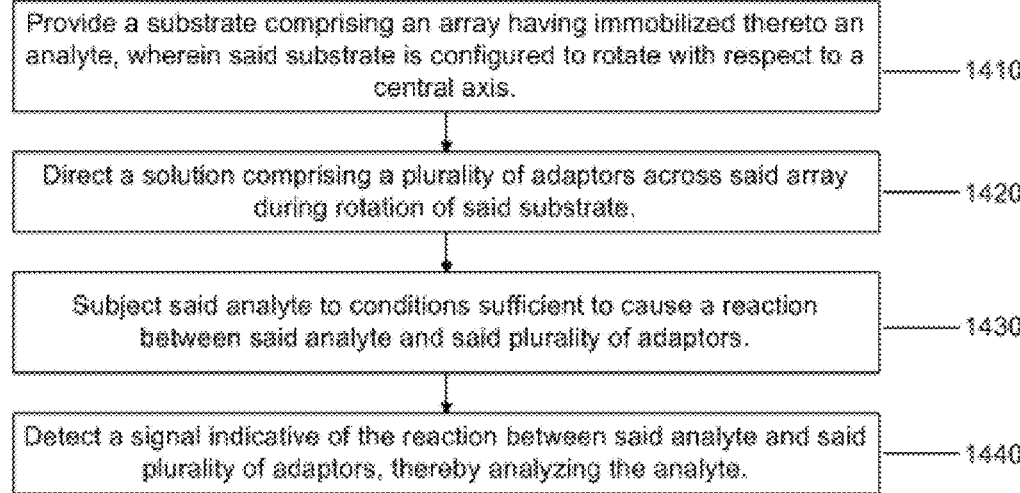

Provide a substrate comprising an array having immobilized thereto an analyte, wherein said substrate is configured to rotate with respect to a central axis. ———— 1410

Direct a solution comprising a plurality of adaptors across said array during rotation of said substrate. ———— 1420

Subject said analyte to conditions sufficient to cause a reaction between said analyte and said plurality of adaptors. ———— 1430

Detect a signal indicative of the reaction between said analyte and said plurality of adaptors, thereby analyzing the analyte. ———— 1440

FIG. 14

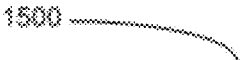
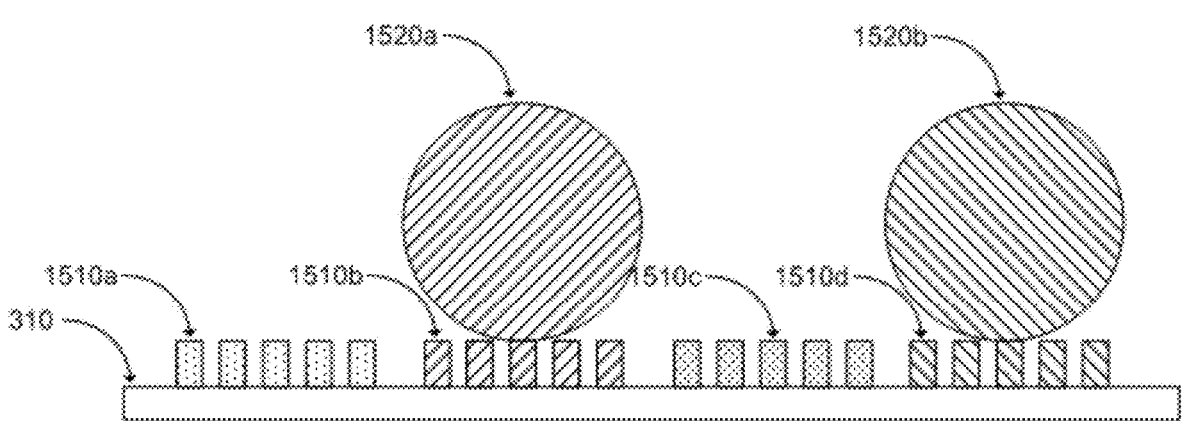
FIG. 15

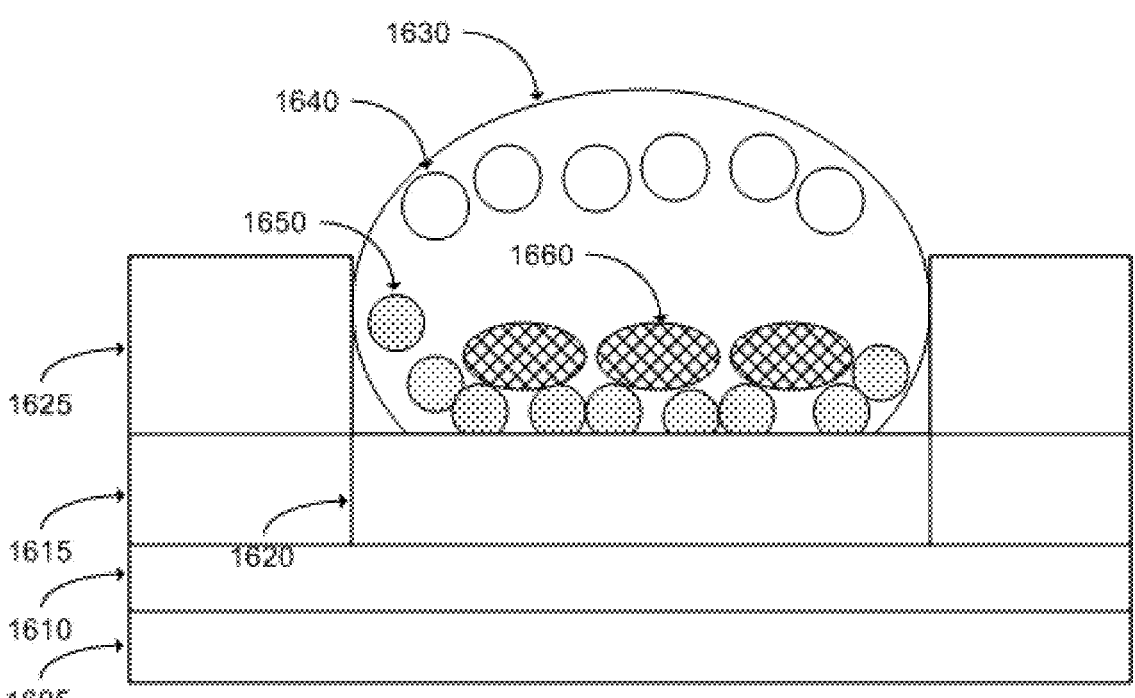
FIG. 16

2100

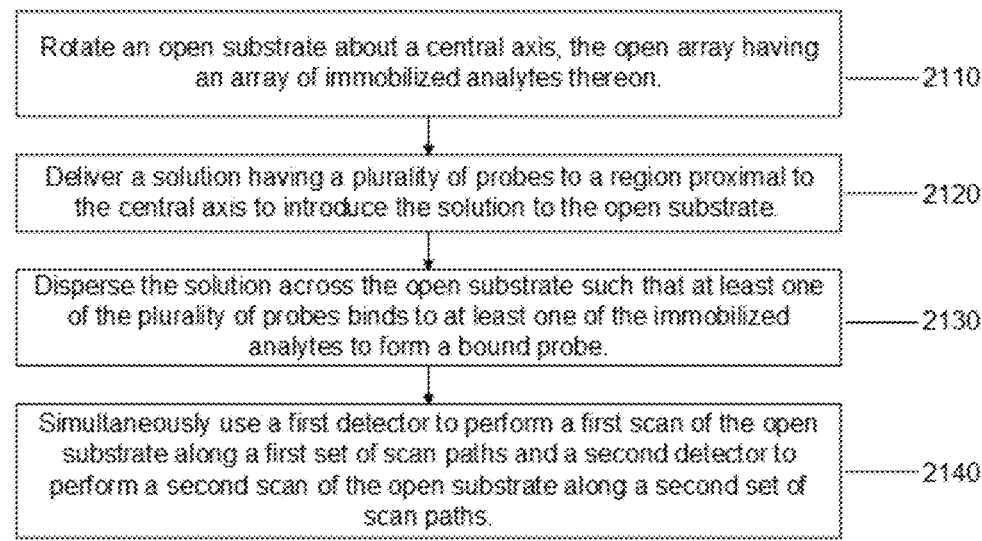

Rotate an open substrate about a central axis, the open array having an array of immobilized analytes thereon. —— 2110

Deliver a solution having a plurality of probes to a region proximal to the central axis to introduce the solution to the open substrate. —— 2120

Disperse the solution across the open substrate such that at least one of the plurality of probes binds to at least one of the immobilized analytes to form a bound probe. —— 2130

Simultaneously use a first detector to perform a first scan of the open substrate along a first set of scan paths and a second detector to perform a second scan of the open substrate along a second set of scan paths. —— 2140

FIG. 21

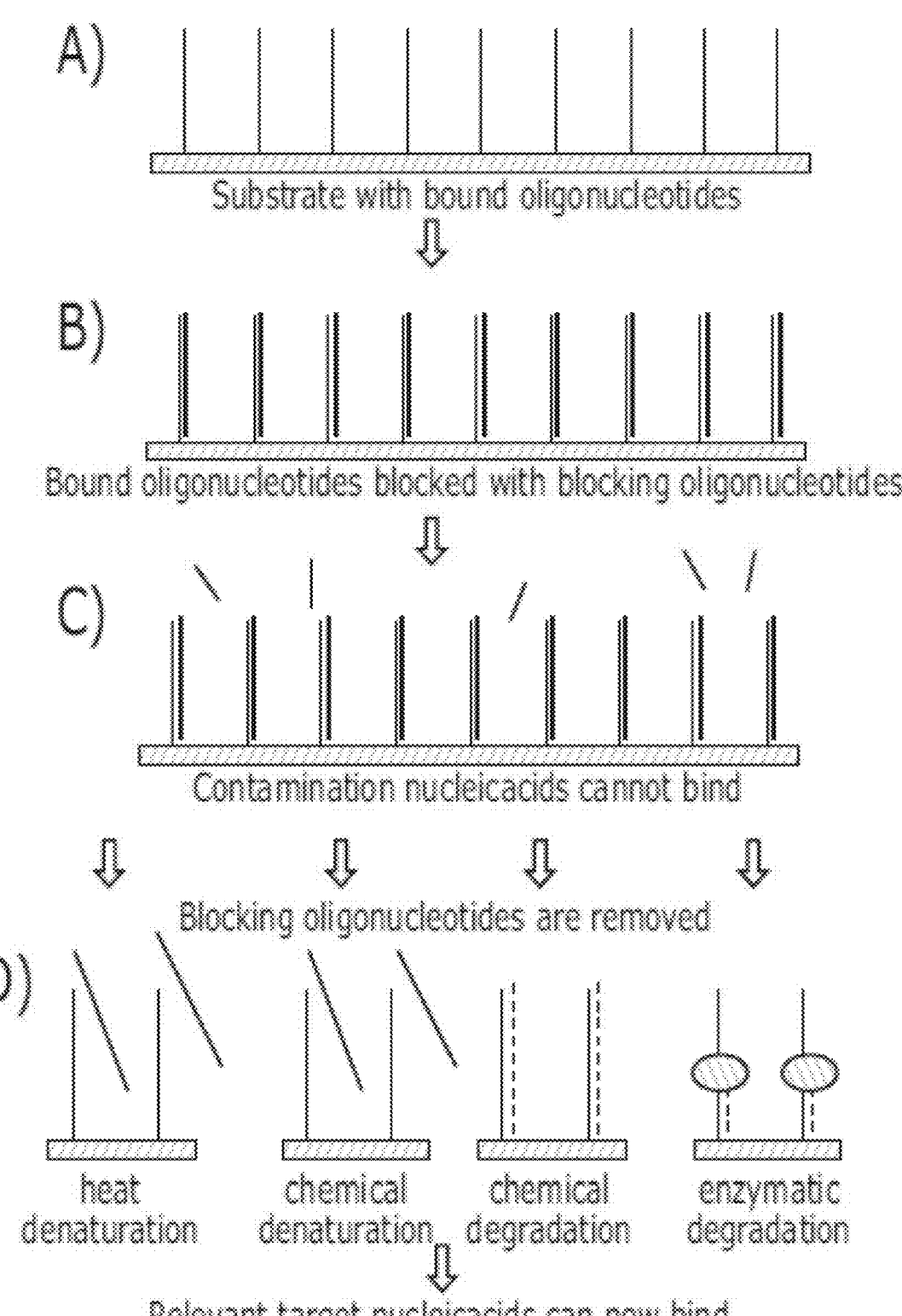

A) Substrate with bound oligonucleotides

B) Bound oligonucleotides blocked with blocking oligonucleotides

C) Contamination nucleicacids cannot bind

Blocking oligonucleotides are removed

D) heat denaturation    chemical denaturation    chemical degradation    enzymatic degradation Relevant target nucleicacids can now bind to available substrate-bound oligonucleotides

METHODS, DEVICES, AND SYSTEMS FOR ANALYTE DETECTION AND ANALYSIS

CROSS-REFERENCE

This application is a continuation of U.S. patent application Ser. No. 17/155,226, filed Jan. 22, 2021, which is a continuation of U.S. patent application Ser. No. 16/445,798, filed Jun. 19, 2019, now U.S. Pat. No. 10,900,078, which claims the benefit of U.S. Provisional Patent Application No. 62/818,549, filed Mar. 14, 2019, and U.S. Provisional Patent Application No. 62/837,684, filed Apr. 23, 2019, each of which applications is entirely incorporated herein by reference.

BACKGROUND

Biological sample processing has various applications in the fields of molecular biology and medicine (e.g., diagnosis). For example, nucleic acid sequencing may provide information that may be used to diagnose a certain condition in a subject and in some cases tailor a treatment plan. Sequencing is widely used for molecular biology applications, including vector designs, gene therapy, vaccine design, industrial strain design and verification. Biological sample processing may involve a fluidics system and/or a detection system.

SUMMARY

Despite the prevalence of biological sample processing systems and methods, such systems and methods may have low efficiency that can be time-intensive and wasteful of valuable resources, such as reagents. Recognized herein is a need for methods and systems for sample processing and/or analysis with high efficiency.

The present disclosure provides methods, devices, and systems for sample processing and/or analysis. The methods, devices, and systems described herein may comprise an open substrate, or use thereof. The open substrate may comprise one or more analytes thereon. For example, the one or more analytes may be coupled, attached, immobilized, or otherwise associated, directly or indirectly (e.g., via an intermediary object, such as a binder or linker) with the open substrate. The open substrate may comprise an array. In some instances, an environment of the open substrate, such as the local environment surrounding the open substrate, may be controlled, such as to facilitate one or more reactions, or one or more detections. The methods, devices, and systems described herein may comprise immersion optics systems, or use thereof. An immersion optics system may be configured to detect analytes, or activities thereof, on the open substrate. The methods, devices, and systems described herein may comprise spatial indexing of the open substrate, or array thereof, or use thereof.

In an aspect, the present disclosure provides a method for nucleic acid sample processing, comprising: (a) providing a first source comprising a first set of nucleic acid molecules and a second source comprising a second set of nucleic acid molecules, wherein the first source is different than the second source; (b) directing the first set of nucleic acid molecules from the first source to a substrate to yield the first set of nucleic acid molecules immobilized in a first array adjacent to the substrate; (c) imaging the substrate to identify a first set of locations on the substrate with the first array adjacent to the substrate; (d) directing the second set of nucleic acid molecules from the second source to the substrate to yield the second set of nucleic acid molecules immobilized in a second array adjacent to the substrate, wherein the second array is different than the first array; (e) imaging the substrate to identify a second set of locations on the substrate with the second array adjacent to the substrate; and (f) using (i) signals detected from the first array and the second array and (ii) locations from which the signals are detected to identify (1) the first set of nucleic acid molecules or sequences thereof with the first source and (2) the second set of nucleic acid molecules or sequences thereof with the second source, wherein the first set of locations and the second set of locations each comprise at least 1,000,000 locations.

In some embodiments, the first set of nucleic acid molecules are identified with the first array and the second set of nucleic acid molecules are identified with the second array in absence of determining a barcode sequence of the first set of nucleic acid molecules or the second set of nucleic acid molecules.

In some embodiments, the directing in (d) and the imaging in (e) are performed subsequent to (c).

In some embodiments, the directing in (b) and the directing in (d) are performed substantially simultaneously.

In some embodiments, (f) comprises sequencing nucleic acid molecules of the first array and the second array. In some embodiments, the signals are indicative of at least one nucleotide having been incorporated into a growing nucleic acid strand that is complementary to a nucleic acid molecule of the first set of nucleic acid molecules or the second set of nucleic acid molecules.

In some embodiments, nucleic acid molecules of the first set of nucleic acid molecules have sequences that are different from nucleic acid molecules of the second set of nucleic acid molecules.

In some embodiments, nucleic acid molecules of the first set of nucleic acid molecules have same sequences as nucleic acid molecules of the second set of nucleic acid molecules.

In some embodiments, in the first array, the first set of nucleic acid molecules is attached to a plurality of beads, which plurality of beads is immobilized adjacent to the substrate. In some embodiments, a bead of the plurality of beads comprises a plurality of nucleic acid molecules attached thereto, wherein the plurality of nucleic acid molecules comprises amplification products derived from a nucleic acid molecule of the first set of nucleic acid molecules. In some embodiments, the plurality of nucleic acid molecules are attached to the bead prior to (b), and wherein (b) comprises directing the plurality of beads to the substrate.

In some embodiments, the substrate comprises a plurality of individually addressable locations including set first set of locations and the second set of locations, and wherein an individually addressable location of the plurality of individually addressable locations is configured to associate with a nucleic acid molecule of the first set of nucleic acid molecules or the second set of nucleic acid molecules. In some embodiments, the individually addressable location is configured to associate with a bead, wherein the bead comprises the nucleic acid molecule attached thereto. In some embodiments, the first set of nucleic acid molecules are attached to a first plurality of beads and wherein the second set of nucleic acid molecules are attached to a second plurality of beads, wherein the first plurality of beads and the second plurality of beads are associated to the plurality of individually addressable locations. In some embodiments, the first plurality of beads and the second plurality of beads are distinguishable.

In some embodiments, each nucleic acid molecule of the first set of nucleic acid molecules and the second set of nucleic acid molecules comprises a synthetic sequence of no more than 6 bases in length, wherein a subset of nucleic acid molecules originating from the same source each comprise a common synthetic sequence, which common synthetic sequence is different from synthetic sequences of another subset of nucleic acid molecules originating from a different source. In some embodiments, a total number of the first set of nucleic acid molecules and the second set of nucleic acid molecules is greater than a total number of unique synthetic sequences.

In some embodiments, the method further comprises, prior to (f), dispersing one or more solutions across the substrate, wherein the one or more solutions comprise reagents configured to react with the first set of nucleic acid molecules and the second set of nucleic acid molecules. In some embodiments, the method further comprises rotating the substrate with respect to a reference axis of the substrate during or prior to directing the one or more solutions to the substrate, wherein the dispersing comprises movement of the reagents from a first location on the substrate to a second location on the substrate due to centrifugal forces from the rotating, wherein the first location and the second location have different radial distances from the reference axis.

In some embodiments, the first array is located on a first region of the substrate and the second array is located on a second region of the substrate. In some embodiments, the first region and the second region are of different sizes or comprise different numbers of individually addressable locations on the substrate. In some embodiments, the first region and the second region are of the same size or comprise the same number of individually addressable locations on the substrate. In some embodiments, the first region and the second region overlap one another. In some embodiments, the first region and the second region are arranged radially around the substrate with respect to a central axis of the substrate. In some embodiments, the substrate comprises a first set of one or more regions of a first type, including the first region, and a second set of one or more regions of a second type, including the second region. In some embodiments, (i) the first set of one or more regions are chemically distinct from the second set of one or more regions, or (ii) the first set of one or more regions and the second set of one or more regions are separated by barriers. In some embodiments, the first region is directly adjacent to the second region. In some embodiments, the first region and the second region are separated by a barrier on the substrate, wherein the barrier comprises a viscous solution, polyethylene glycol (PEG), a fluid that is immiscible with a loading solution comprising the first nucleic acid sample and the second nucleic acid sample, an air knife, an injection molded guide, or a hydrophobic region.

In some embodiments, (b) comprises: (i) contacting the substrate with a first loading fluid comprising the first set of nucleic acid molecules and a second loading fluid comprising the second set of nucleic acid molecules, wherein the first loading fluid and the second loading fluid are immiscible; (ii) applying a magnetic field to direct the first set of nucleic acid molecules or the second set of nucleic acid molecules to the substrate; or (iii) (1) with the first region unmasked and the second region masked, directing the first set of nucleic acid molecules to the substrate; (2) unmasking the second region; and (3) with the second region unmasked, directing the second set of nucleic acid molecules to the substrate.

In some embodiments, the imaging in (c) and (e) is performed using a detector unit.

In an aspect, provided herein is a method for sequencing a nucleic acid molecule, comprising: (a) providing an array of nucleic acid molecules on an uncovered surface; (b) dispersing a layer of a solution over the uncovered surface at a rate of at least 1 nanoliter (nL) per second when measured at a temperature of 25 degrees Celsius, wherein the solution comprises reagents including at least one nucleotide that incorporates into a growing nucleic acid strand that is complementary to a nucleic acid molecule of the array of nucleic acid molecules; and (c) detecting one or more signals that are indicative of the nucleotide incorporated into the growing nucleic acid strand.

In some embodiments, the uncovered surface is exposed to an atmosphere. In some embodiments, the layer comprises a first surface and a second surface, wherein the first surface contacts the uncovered surface and the second surface contacts a gas. In some embodiments, the uncovered surface is not a flow cell. In some embodiments, the uncovered surface does not have a surface facing the uncovered surface. In some embodiments, the uncovered surface is substantially planar. In some embodiments, the layer has a thickness of less than about 100 micrometers (μm) on the uncovered surface. In some embodiments, (b) comprises dispersing the solution to the uncovered surface across a non-solid gap. In some embodiments, the method further comprises repeating (b) with a plurality of different solutions, wherein each solution of the plurality of different solutions is dispersed over the uncovered solution using its own dedicated fluidics.

In some embodiments, the layer of solution is dispersed over the uncovered surface by rotating the uncovered surface. In some embodiments, the uncovered surface is rotated at a first angular velocity that directs the solution along a direction away from a central axis of rotation. In some embodiments, the solution comprises a fluid that is thixotropic. In some embodiments, the uncovered surface comprises a rim near an outer edge of the uncovered surface such that an amount of the solution that flows over the outer edge in (b) is reduced. In some embodiments, a viscosity of the solution is selected such that less than about 50% of the solution dispensed in (b) flows over the outer edge in (b). In some embodiments, (c) is performed by rotating the uncovered surface at a second angular velocity while the uncovered surface is in proximity to a camera.

In some embodiments, the uncovered surface is capable of folding or bending. In some embodiments, the uncovered surface is textured or patterned. In some embodiments, the layer of solution is dispersed over the uncovered surface by passing the uncovered surface through and in contact with a reservoir of the solution. In some embodiments, (c) is performed by passing the uncovered surface under a camera. In some embodiments, the uncovered surface moves through a series of solutions, including the solution, by moving against a plurality of rotating reels. In some embodiments, the series of solutions comprise a series of nucleotide solutions having reagents sufficient to incorporate one of the nucleotides (A, T/U, C or G) into the growing nucleic acid strand. In some embodiments, the uncovered surface is passed through and in contact with a washing solution after each of the nucleotide solutions. In some embodiments, the uncovered surface is imaged subsequent to passing through each of the washing solutions.

In some embodiments, the layer of solution is dispersed over the uncovered surface by spraying the solution over the surface. In some embodiments, the layer of solution is dispersed over the uncovered surface by subjecting the uncovered surface to vibration. In some embodiments, the layer of solution is dispersed over the uncovered surface by blowing a gas to displace a volume of the solution over the uncovered surface. In some embodiments, the layer of solution is dispersed over the uncovered surface by contacting the solution with a solid surface and moving the solid surface across the uncovered surface. In some embodiments, the uncovered surface is contained in a housing that encloses an atmosphere, wherein the atmosphere has a higher humidity than ambient atmosphere. In some embodiments, less than about 50% in volume of the layer of solution dispersed on the uncovered surface evaporates prior to (c). In some embodiments, the solution comprises reagents configured to reduce an evaporation rate of the solution. In some embodiments, the solution comprises glycerol. In some embodiments, the uncovered surface is maintained at a temperature near the dew point. In some embodiments, the housing contains a second surface that is separate from the uncovered surface, wherein the second surface has a temperature that (i) encourages condensation on the second surface and/or (ii) inhibits condensation on or above the uncovered surface. In some embodiments, the housing comprises walls that are shaped to direct condensation away from the uncovered surface. In some embodiments, a fluid flows in the housing to direct condensation away from the uncovered surface.

In some embodiments, (c) is performed by a camera in fluidic communication with the uncovered surface. In some embodiments, the camera includes an adapter configured to retain and/or replenish an immersion fluid between the camera and the uncovered surface. In some embodiments, the hydrophobicity or hydrophilicity of the adapter is selected to retain a volume of fluid between the camera and the uncovered surface. In some embodiments, the method further comprises removing one or more gas bubbles trapped between the camera and the uncovered surface. In some embodiments, the camera detects a single wavelength. In some embodiments, the camera has an intentional blur.

In some embodiments, the method further comprises repeating (b) and (c). In some embodiments, (b) and (c) are repeated for each of four nucleotide solutions dispersed during (b). In some embodiments, (b) is repeated at least twice within a period of time of less than about 30 seconds(s). In some embodiments, (b) is performed within a period of time of less than about 30 seconds(s).

In some embodiments, the solution comprises a plurality of nucleotides that are not reversibly terminating nucleotides. In some embodiments, the solution comprises a plurality of nucleotides that are labeled. In some embodiments, the method further comprises cleaving off a label from a nucleotide of the plurality of nucleotides that are labeled subsequent to (c). In some embodiments, the solution comprises a plurality of nucleotides that are not labeled. In some embodiments, the method further comprises washing non-incorporated nucleotides from the solution off of the uncovered surface between (b) and (c). In some embodiments, the method further comprises collecting at least a portion of the solution subsequent to (b). In some embodiments, the method further comprises recovering a reagent from the solution subsequent to (b). In some embodiments, the solution comprises a plurality of nucleotides, and wherein at least 50% of the nucleotides are natural nucleotides. In some embodiments, the one or more signals are fluorescent signals. In some embodiments, the solution comprises a polymerase, and wherein the polymerase is native. In some embodiments, the solution comprises a polymerase, and wherein the polymerase is not replenished after each repetition of (b) and (c). In some embodiments, the solution comprises a polymerase, and wherein the polymerase remains affixed to the nucleic acid molecule following (c). In some embodiments, the array of nucleic acid molecules is affixed to the uncovered surface. In some embodiments, nucleic acids of the array of nucleic acid molecules are affixed to beads which are arranged over the uncovered surface.

In another aspect, disclosed herein is a method for processing a plurality of nucleic acid samples, comprising: (a) providing said plurality of nucleic acid samples, wherein said plurality of nucleic acid samples comprises a first nucleic acid sample comprising a first set of nucleic acid molecules and a second nucleic acid sample comprising a second set of nucleic acid molecules, wherein each sample of said plurality of nucleic acid samples has an identifiable sample origin; (b) loading said first nucleic acid sample onto a first region of a substrate as a first array of said first set of nucleic acid molecules and loading said second nucleic acid sample onto a second region of said substrate as a second array of said second set of nucleic acid molecules, wherein said first region is different from said second region; (c) dispersing a solution across said substrate, wherein said solution comprises reagents sufficient to react with nucleic acid molecules of said first array or said second array; (d) detecting one or more signals that are indicative of a reaction between said reagents and said nucleic acid molecules of said first array or said second array; and (e) based at least in part on (i) said one or more signals and (ii) locations, from said first region and said second region, from which said one or more signals are detected, analyzing said first nucleic acid sample and said second nucleic acid sample, and determining (1) a first subset of said nucleic acid molecules of said first array or said second array as originating from said first nucleic acid sample and (2) a second subset of said nucleic acid molecules of said first array or said second array as originating from said second nucleic acid sample.

In some embodiments, the nucleic acid samples comprise nucleic acid molecules affixed to beads. In some embodiments, determining in (e) is performed without determining a barcode sequence of the nucleic acid molecules of the first array or the second array. In some embodiments, the first set of nucleic acid molecules and the second set of nucleic acid molecules do not have a barcode sequence indicative of an originating nucleic acid sample. In some embodiments, the first region and the second region are on a same surface of the substrate. In some embodiments, the analyzing in (e) comprises sequencing the nucleic acid molecules of the first array or the second array. In some embodiments, the solution comprises reagents sufficient to incorporate at least one nucleotide into a growing nucleic acid strand that is complementary to a nucleic acid molecule of the nucleic acid molecules of the first array or the second array. In some embodiments, the method further comprises repeating (c)-(e) with various nucleotides in the solution to provide sequence information for the nucleic acid molecules. In some embodiments, the plurality of nucleic acid samples comprises n number of nucleic acid samples, and (b) comprises loading the n number of nucleic acid samples to n number of separate regions of the substrate. In some embodiments, n is at least 3. In some embodiments, n is at least 5. In some embodiments, n is at least 10. In some embodiments, the first nucleic acid sample or the second nucleic acid sample comprises 1000 nucleic acid molecules. In some embodiments, the first nucleic acid sample or the second nucleic acid sample comprises 10,000 nucleic acid molecules. In some embodiments, the first nucleic acid sample or the second nucleic acid sample comprises 100,000 nucleic acid molecules. In some embodiments, (b) comprises depositing the first nucleic acid sample to the substrate from a dispenser through an air gap. In some embodiments, (b) comprises depositing the first nucleic acid sample to the substrate through a closed flow cell. In some embodiments, the first region and the second region have different sizes. In some embodiments, the first region and the second region have the same size. In some embodiments, the first region and the second region comprise different numbers of individually addressable locations on the substrate. In some embodiments, the first region and the second region comprise the same number of individually addressable locations on the substrate. In some embodiments, subsequent to (b), the first set of nucleic acid molecules is attached to a plurality of beads, which plurality of beads is immobilized to the substrate. In some embodiments, a bead of the plurality of beads comprises a plurality of nucleic acid molecules attached thereto, wherein the plurality of nucleic acid molecules comprises a colony of nucleic acid molecules. In some embodiments, the colony of nucleic acid molecules are amplification products derived from a nucleic acid molecule of the first set of nucleic acid molecules. In some embodiments, the plurality of nucleic acid molecules is attached to the bead prior to (b), and (b) comprises dispensing the plurality of beads to the substrate. In some embodiments, subsequent to (b), the second set of nucleic acid molecules is attached to a second plurality of beads, which second plurality of beads is immobilized to the substrate. In some embodiments, the substrate comprises a plurality of individually addressable locations. In some embodiments, an individually addressable location of the plurality of individually addressable locations is configured to associate with a nucleic acid molecule of the nucleic acid molecules of the first array or the second array. In some embodiments, the individually addressable location is configured to associate with a bead, wherein the bead comprises the nucleic acid molecule attached thereto. In some embodiments, the bead comprises a plurality of nucleic acid molecules, including the nucleic acid molecule, attached thereto. In some embodiments, the plurality of nucleic acid molecules comprises a colony of nucleic acid molecules that are amplification products derived from the nucleic acid molecule. In some embodiments, the first set of nucleic acid molecules are attached to a first plurality of beads and wherein the second set of nucleic acid molecules are attached to a second plurality of beads, wherein the first plurality of beads and the second plurality of beads are associated to the plurality of individually addressable locations. In some embodiments, the first plurality of beads and the second plurality of beads are distinguishable. In some embodiments, the first plurality of beads and the second plurality of beads emit a different wavelength of signals. In some embodiments, the first plurality of beads and the second plurality of beads emit a different intensity of signals. In some embodiments, the method further comprises, subsequent to (b), subjecting individually addressable locations unassociated with the first plurality of beads and the second plurality of beads to conditions sufficient to disallow association of subsequent sample beads to the individually addressable locations unassociated with the first plurality of beads and the second plurality of beads. In some embodiments, the method further comprises, subsequent to (b), contacting the substrate with a plurality of blank beads such that individually addressable locations unassociated with the first plurality of beads and the second plurality of beads are associated with blank beads. In some embodiments, the first nucleic acid sample and the second nucleic acid sample are distinguishable by a fluorescent dye. In some embodiments, the nucleic acid molecules each comprise a synthetic sequence of no more than 6 bases in length. In some embodiments, the synthetic sequence is no more than 4 bases in length. In some embodiments, the synthetic sequence is no more than 2 bases in length. In some embodiments, the synthetic sequence is no more than 1 base in length. In some embodiments, a total number of the nucleic acid molecules is greater than a total number of unique synthetic sequences. In some embodiments, a subset of nucleic acid molecules originating from the same nucleic acid sample of the plurality of nucleic acid samples each comprise a common synthetic sequence, which common synthetic sequence is different from synthetic sequences of another subset of nucleic acid molecules originating from a different nucleic acid sample. In some embodiments, the method further comprises rotating the substrate with respect to a reference axis of the substrate. In some embodiments, the rotating is performed subsequent to the dispersing in (c). In some embodiments, the rotating is performed during the dispersing in (c). In some embodiments, the rotating is performed prior to the dispersing in (c). In some embodiments, the dispersing in (c) comprises movement of the solution from a first location on the substrate to a second location on the substrate due to centrifugal forces from the rotating, wherein the first location and the second location have different radial distances from the reference axis. In some embodiments, the first region and the second region are disposed at least 1 millimeter (mm) distance from the reference axis on the substrate. In some embodiments, the first region and the second region are disposed at least 1 centimeter (cm) distance from the reference axis on the substrate. In some embodiments, the first region and the second region are arranged radially around the substrate with respect to a central axis of the substrate. In some embodiments, the substrate comprises a plurality of radially alternating regions, including the first region and the second region, wherein the plurality of radially alternating regions comprises a first set of regions of a first type and a second set of regions of a second type. In some embodiments, the first set of regions is chemically distinct form the second set of regions. In some embodiments, the first set of regions and the second set of regions are separated by barriers. In some embodiments, the first set of regions and the second type of regions are distinguishable only by nucleic acid samples loaded on the first set of regions and the second set of regions. In some embodiments, the first region and the second region are directly adjacent. In some embodiments, the first region and the second region are separated by another region on the substrate. In some embodiments, the first region and the second region overlap. In some embodiments, in (e) the first subset and the second subset do not include a third subset of the nucleic acid molecules of the first array or the second array that is located proximate to within 0.5 millimeter (mm) of a border of the first region and the second region. In some embodiments, (b) is performed in a first station different from a second station in which (c) or (d) is performed. In some embodiments, the substrate comprises a physical demarcation, wherein the physical demarcation is used as a reference to spatially index the substrate. In some embodiments, the demarcation comprises one or more of an indentation, notch, physical feature, dye, and ink on the substrate. In some embodiments, the demarcation comprises a control nucleic acid sample. In some embodiments, the first region and the second region are separated by a barrier on the substrate. In some embodiments, the barrier remains fixed to the substrate during (c) or (d). In some embodiments, the barrier remains fixed to the substrate during (c) and (d). In some embodiments, the barrier is removable. In some embodiments, the method further comprises removing the barrier subsequent to (b). In some embodiments, the barrier dissolves. In some embodiments, the barrier evaporates. In some embodiments, the barrier sublimes. In some embodiments, the barrier melts. In some embodiments, the barrier comprises an injection molded guide. In some embodiments, the barrier comprises polyethylene glycol (PEG). In some embodiments, the barrier comprises a viscous solution. In some embodiments, the viscosity varies in proportion to temperature. In some embodiments, the barrier comprises a fluid that is immiscible with a loading solution comprising the first nucleic acid sample and the second nucleic acid sample. In some embodiments, the barrier comprises a hydrophobic region, and wherein the first region and the second region comprise hydrophilic regions. In some embodiments, the barrier comprises an air knife. In some embodiments, prior to (b), the substrate is masked with one or more masks such that the substrate comprises a subset of one or more masked regions and a subset of one or more unmasked regions, wherein the subset of one or more unmasked regions comprises the first region and the second region. In some embodiments, the method further comprises prior to (b) masking the substrate with the one or more masks. In some embodiments, the method further comprises subsequent to (b), unmasking the substrate from the one or more masks, and loading a third nucleic acid sample onto a third region of the one or more masked regions. In some embodiments, (b) comprises (i) masking the substrate with the one or more masks such that the substrate comprises a subset of one or more masked regions and a subset of one or more unmasked regions, wherein the subset of one or more unmasked regions comprises the first region and the sample; (iii) unmasking the substrate from the one or more masks; and (iv) loading the second nucleic acid sample. In some embodiments, (b) comprises contracting the substrate with a first loading fluid comprising the first nucleic acid sample and a second loading fluid comprising the second nucleic acid sample, wherein the first loading fluid and the second loading fluid are immiscible. In some embodiments, (b) comprises loading the first nucleic acid sample and the second nucleic acid sample simultaneously. In some embodiments, (b) comprises loading the first nucleic acid sample and the second nucleic acid sample at discrete times. In some embodiments, the first nucleic acid sample is loaded prior to loading of the second nucleic acid sample. In some embodiments, the substrate is dried between loading of the first nucleic acid sample and the second nucleic acid sample. In some embodiments, (b) comprises applying a magnetic field to direct the first nucleic acid sample to the substrate. In some embodiments, the magnetic field is applied by one or more magnets. In some embodiments, the first set of nucleic acid molecules are attached to a plurality of magnetic beads. In some embodiments, a loading fluid comprising the first nucleic acid sample comprises a ferrofluid. In some embodiments, the method further comprises prior to (b), activating the first region or the second region for loading using temperature. In some embodiments, the method further comprises, prior to (b), activating the first region or the second region for loading using electromagnetic radiation. In some embodiments, the first region attracts the first nucleic acid sample. In some embodiments, the second region repels the first nucleic acid sample. In some embodiments, the substrate comprises a third region that repels the first nucleic acid sample. In some embodiments, the method further comprises, subsequent to (b), washing nucleic acid molecules unassociated with the first region or the second region from the substrate. In some embodiments, the washing comprises aspirating. In another aspect, provided herein is a method A method for processing a plurality of nucleic acid samples, comprising: (a) providing the plurality of nucleic acid samples, wherein the plurality of nucleic acid samples comprises a first nucleic acid sample comprising a first set of nucleic acid molecules and a second nucleic acid sample comprising a second set of nucleic acid molecules, wherein each sample of the plurality of nucleic acid samples has an identifiable sample origin; (b) loading the first nucleic acid sample onto a first region of a substrate as a first array of the first set of nucleic acid molecules and loading the second nucleic acid sample onto a second region of the substrate as a second array of the second set of nucleic acid molecules, wherein the first region is different from the second region; (c) dispersing a solution across the substrate, wherein the solution comprises reagents sufficient to react with nucleic acid molecules of the first array or the second array; (d) detecting one or more signals that are indicative of a reaction between the reagents and the nucleic acid molecules of the first array or the second array; and (e) based at least in part on (i) the one or more signals and (ii) locations, from the first region and the second region, from which the one or more signals are detected, analyzing the first nucleic acid sample and the second nucleic acid sample, and determining (1) a first subset of the nucleic acid molecules of the first array or the second array as originating from the first nucleic acid sample and (2) a second subset of the nucleic acid molecules of the first array or the second array as originating from the second nucleic acid sample. In some embodiments, the nucleic acid samples comprise nucleic acid molecules affixed to beads. In some embodiments, the determining in (e) is performed without determining a barcode sequence of the nucleic acid molecules of the first array or the second array. In some embodiments, the first set of nucleic acid molecules and the second set of nucleic acid molecules do not have a barcode sequence indicative of an originating nucleic acid sample. In some embodiments, the first region and the second region are on a same surface of the substrate. In some embodiments, the analyzing in (e) comprises sequencing the nucleic acid molecules of the first array or the second array. In some embodiments, the solution comprises reagents sufficient to incorporate at least one nucleotide into a growing nucleic acid strand that is complementary to a nucleic acid molecule of the nucleic acid molecules of the first array or the second array. In some embodiments, the method further comprises for the nucleic acid molecules. In some embodiments, the plurality of nucleic acid samples comprises n number of nucleic acid samples, and (b) comprises loading the n number of nucleic acid samples to n number of separate regions of the substrate. In some embodiments, n is at least 3. In some embodiments, n is at least 5. In some embodiments, n is at least 10. In some embodiments, the first nucleic acid sample or the second nucleic acid sample comprises 1000 nucleic acid molecules. In some embodiments, the first nucleic acid sample or the second nucleic acid sample comprises 10,000 nucleic acid molecules. In some embodiments, the first nucleic acid sample or the second nucleic acid sample comprises 100,000 nucleic acid molecules. In some embodiments, (b) comprises depositing the first nucleic acid sample to the substrate from a dispenser through an air gap. In some embodiments, (b) comprises depositing the first nucleic acid sample to the substrate through a closed flow cell. In some embodiments, the first region and the second region have different sizes. In some embodiments, the first region and the second region have the same size. In some embodiments, the first region and the second region comprise different numbers of individually addressable locations on the substrate. In some embodiments, the first region and the second region comprise the same number of individually addressable locations on the substrate. In some embodiments, subsequent to (b), the first set of nucleic acid molecules is attached to a plurality of beads, which plurality of beads is immobilized to the substrate. In some embodiments, a bead of the plurality of beads comprises a plurality of nucleic acid molecules attached thereto, wherein the plurality of nucleic acid molecules comprises a colony of nucleic acid molecules. In some embodiments, the colony of nucleic acid molecules are amplification products derived from a nucleic acid molecule of the first set of nucleic acid molecules. In some embodiments, the plurality of nucleic acid molecules is attached to the bead prior to (b), and (b) comprises dispensing the plurality of beads to the substrate. In some embodiments, subsequent to (b), the second set of nucleic acid molecules is attached to a second plurality of beads, which second plurality of beads is immobilized to the substrate. In some embodiments, the substrate comprises a plurality of individually addressable locations. In some embodiments, an individually addressable location of the plurality of individually addressable locations is configured to associate with a nucleic acid molecule of the nucleic acid molecules of the first array or the second array. In some embodiments, the individually addressable location is configured to associate with a bead, wherein the bead comprises the nucleic acid molecule attached thereto. In some embodiments, the bead comprises a plurality of nucleic acid molecules, including the nucleic acid molecule, attached thereto. In some embodiments, the plurality of nucleic acid molecules comprises a colony of nucleic acid molecules that are amplification products derived from the nucleic acid molecule. In some embodiments, the first set of nucleic acid molecules are attached to a first plurality of beads and wherein the second set of nucleic acid molecules are attached to a second plurality of beads, wherein the first plurality of beads and the second plurality of beads are associated to the plurality of individually addressable locations. In some embodiments, the first plurality of beads and the second plurality of beads are distinguishable. In some embodiments, the first plurality of beads and the second plurality of beads emit a different wavelength of signals. In some embodiments, the first plurality of beads and the second plurality of beads emit a different intensity of signals. In some embodiments, the method further comprises, subsequent to (b), subjecting individually addressable locations unassociated with the first plurality of beads and the second plurality of beads to conditions sufficient to disallow association of subsequent sample beads to the individually addressable locations unassociated with the first plurality of beads and the second plurality of beads. In some embodiments, the method further comprises, subsequent to (b), contacting the substrate with a plurality of blank beads such that individually addressable locations unassociated with the first plurality of beads and the second plurality of beads are associated with blank beads. In some embodiments, the plurality of blank beads has a higher affinity for the plurality of individually addressable locations than the first plurality of beads or the second plurality of beads. In some embodiments, the first nucleic acid sample and the second nucleic acid sample are distinguishable by a fluorescent dye. In some embodiments, the nucleic acid molecules each comprise a synthetic sequence of no more than 6 bases in length. In some embodiments, the synthetic sequence is no more than 4 bases in length. In some embodiments, the synthetic sequence is no more than 2 bases in length. In some embodiments, the synthetic sequence is no more than 1 base in length. In some embodiments, a total number of the nucleic acid molecules is greater than a total number of unique synthetic sequences. In some embodiments, a subset of nucleic acid molecules originating from the same nucleic acid sample of the plurality of nucleic acid samples each comprise a common synthetic sequence, which common synthetic sequence is different from synthetic sequences of another subset of nucleic acid molecules originating from a different nucleic acid sample. In some embodiments, the method further comprises rotating the substrate with respect to a reference axis of the substrate. In some embodiments, the rotating is performed subsequent to the dispersing in (c). In some embodiments, the rotating is performed during the dispersing in (c). In some embodiments, the rotating is performed prior to the dispersing in (c). In some embodiments, the dispersing in (c) comprises movement of the solution from a first location on the substrate to a second location on the substrate due to centrifugal forces from the rotating, wherein the first location and the second location have different radial distances from the reference axis. In some embodiments, the first region and the second region are disposed at least 1 millimeter (mm) distance from the reference axis on the substrate. In some embodiments, the first region and the second region are disposed at least 1 centimeter (cm) distance from the reference axis on the substrate. In some embodiments, the first region and the second region are arranged radially around the substrate with respect to a central axis of the substrate. In some embodiments, the substrate comprises a plurality of radially alternating regions, including the first region and the second region, wherein the plurality of radially alternating regions comprises a first set of regions of a first type and a second set of regions of a second type. In some embodiments, the first set of regions is chemically distinct form the second set of regions. In some embodiments, the first set of regions and the second set of regions are separated by barriers. In some embodiments, the first set of regions and the second type of regions are distinguishable only by nucleic acid samples loaded on the first set of regions and the second set of regions. In some embodiments, the first region and the second region are directly adjacent. In some embodiments, the first region and the second region are separated by another region on the substrate. In some embodiments, the first region and the second region overlap. In some embodiments, (e) the first subset and the second subset do not include a third subset of the nucleic acid molecules of the first array or the second array that is located proximate to within 0.5 millimeter (mm) of a border of the first region and the second region.

In some embodiments, (b) is performed in a first station different from a second station in which (c) or (d) is performed. In some embodiments, the substrate comprises a physical demarcation, wherein the physical demarcation is used as a reference to spatially index the substrate. In some embodiments, the demarcation comprises one or more of an indentation, notch, physical feature, dye, and ink on the substrate. In some embodiments, the demarcation comprises a control nucleic acid sample. In some embodiments, the first region and the second region are separated by a barrier on the substrate. In some embodiments, the barrier remains fixed to the substrate during (c) or (d). In some embodiments, the barrier remains fixed to the substrate during (c) and (d). In some embodiments, the barrier is removable. In some embodiments, the method further comprises removing the barrier subsequent to (b). In some embodiments, the barrier dissolves. In some embodiments, the barrier evaporates. In some embodiments, the barrier sublimes. In some embodiments, the barrier melts. In some embodiments, the barrier comprises an injection molded guide. In some embodiments, the barrier comprises polyethylene glycol (PEG). In some embodiments, the barrier comprises a viscous solution. In some embodiments, the viscosity varies in proportion to temperature. In some embodiments, the barrier comprises a fluid that is immiscible with a loading solution comprising the first nucleic acid sample and the second nucleic acid sample. In some embodiments, the barrier comprises a hydrophobic region, and wherein the first region and the second region comprise hydrophilic regions. In some embodiments, the barrier comprises an air knife. In some embodiments, prior to (b), the substrate is masked with one or more masks such that the substrate comprises a subset of one or more masked regions and a subset of one or more unmasked regions, wherein the subset of one or more unmasked regions comprises the first region and the second region. In some embodiments, the method further comprises, prior to (b) masking the substrate with the one or more masks. In some embodiments, the method further comprises, subsequent to (b), unmasking the substrate from the one or more masks, and loading a third nucleic acid sample onto a third region of the one or more masked regions. In some embodiments, wherein (b) comprises (i) masking the substrate with the one or more masks such that the substrate comprises a subset of one or more masked regions and a subset of one or more unmasked regions, wherein the subset of one or more unmasked regions comprises the first region and the subset of one or more masked regions comprises the second region; (ii) loading the first nucleic acid sample; (iii) unmasking the substrate from the one or more masks; and (iv) loading the second nucleic acid sample.

In some embodiments, (b) comprises contacting the substrate with a first loading fluid comprising the first nucleic acid sample and a second loading fluid comprising the second nucleic acid sample, wherein the first loading fluid and the second loading fluid are immiscible. In some embodiments, (b) comprises loading the first nucleic acid sample and the second nucleic acid sample simultaneously. In some embodiments, (b) comprises loading the first nucleic acid sample and the second nucleic acid sample at discrete times. In some embodiments, the first nucleic acid sample is loaded prior to loading of the second nucleic acid sample. In some embodiments, the substrate is dried between loading of the first nucleic acid sample and the second nucleic acid sample. In some embodiments, (b) comprises applying a magnetic field to direct the first nucleic acid sample to the substrate. In some embodiments, the magnetic field is applied by one or more magnets. In some embodiments, the first set of nucleic acid molecules are attached to a plurality of magnetic beads. In some embodiments, a loading fluid comprising the first nucleic acid sample comprises a ferrofluid. In some embodiments, the method further comprises prior to (b), activating the first region or the second region for loading using temperature. In some embodiments the method further comprises, prior to (b), activating the first region or the second region for loading using electromagnetic radiation. In some embodiments, the first region attracts the first nucleic acid sample. In some embodiments, the second region repels the first nucleic acid sample. In some embodiments, the substrate comprises a third region that repels the first nucleic acid sample. In some embodiments, the method further comprises, subsequent to (b), washing nucleic acid molecules unassociated with the first region or the second region from the substrate. In some embodiments, the washing comprises aspirating In another aspect, provided herein is a method for processing a plurality of nucleic acid samples, comprising: (a) providing the plurality of nucleic acid samples, wherein the plurality of nucleic acid samples comprises a first nucleic acid sample comprising a first set of nucleic acid molecules and a second nucleic acid sample comprising a second set of nucleic acid molecules; (b) loading the first nucleic acid sample onto a substrate to associate the first set of nucleic acid molecules to a first array of individually addressable locations; (c) imaging the substrate to identify the first array of individually addressable locations; (d) loading the second nucleic acid sample onto a substrate to associate the second set of nucleic acid molecules to a second array of individually addressable locations; (e) imaging the substrate to identify the second array of individually addressable locations; (f) dispersing a solution across the substrate, wherein the solution comprises reagents sufficient to react with nucleic acid molecules of the first array or the second array; (g) detecting one or more signals that are indicative of a reaction between the reagents and the nucleic acid molecules of the first array or the second array; and (h) based at least in part on (i) the one or more signals and (ii) locations, from the first array of individually addressable locations and the second array of individually addressable locations, from which the one or more signals are detected, analyzing the first nucleic acid sample and the second nucleic acid sample, and determining (1) a first subset of the nucleic acid molecules of the first array or the second array as originating from the first nucleic acid sample and (2) a second subset of the nucleic acid molecules of the first array or the second array as originating from the second nucleic acid sample. In some embodiments, the analyzing in (e) comprises sequencing the nucleic acid molecules of the first array or the second array.

In some embodiments, the solution comprises reagents sufficient to incorporate at least one nucleotide into a growing nucleic acid strand that is complementary to a nucleic acid molecule of the nucleic acid molecules of the first array or the second array. In some embodiments, the method further comprises repeating (c)-(e) with various nucleotides in the solution to provide sequence information for the nucleic acid molecules. In some embodiments, the plurality of nucleic acid samples comprises n number of nucleic acid samples, and (b) comprises loading the n number of nucleic acid samples to n number of separate regions of the substrate. In some embodiments, n is at least 3. In some embodiments, n is at least 5. In some embodiments, n is at least 10. In some embodiments, the first nucleic acid sample or the second nucleic acid sample comprises 1000 nucleic acid molecules. In some embodiments, the first nucleic acid sample or the second nucleic acid sample comprises 10,000 nucleic acid molecules. In some embodiments, the first nucleic acid sample or the second nucleic acid sample comprises 100,000 nucleic acid molecules. In some embodiments, (b) comprises depositing the first nucleic acid sample to the substrate from a dispenser through an air gap. In some embodiments, (b) comprises depositing the first nucleic acid sample to the substrate through a closed flow cell. In some embodiments, the first region and the second region have different sizes. In some embodiments, the first region and the second region have the same size. In some embodiments, the first region and the second region comprise different numbers of individually addressable locations on the substrate. In some embodiments, the first region and the second region comprise the same number of individually addressable locations on the substrate. In some embodiments, subsequent to (b), the first set of nucleic acid molecules is attached to a plurality of beads, which plurality of beads is immobilized to the substrate. In some embodiments, a bead of the plurality of beads comprises a plurality of nucleic acid molecules attached thereto, wherein the plurality of nucleic acid molecules comprises a colony of nucleic acid molecules. In some embodiments, the colony of nucleic acid molecules are amplification products derived from a nucleic acid molecule of the first set of nucleic acid molecules. In some embodiments, the plurality of nucleic acid molecules is attached to the bead prior to (b), and (b) comprises dispensing the plurality of beads to the substrate. In some embodiments, subsequent to (b), the second set of nucleic acid molecules is attached to a second plurality of beads, which second plurality of beads is immobilized to the substrate. In some embodiments, the substrate comprises a plurality of individually addressable locations. In some embodiments, an individually addressable location of the plurality of individually addressable locations is configured to associate with a nucleic acid molecule of the nucleic acid molecules of the first array or the second array. In some embodiments, the individually addressable location is configured to associate with a bead, wherein the bead comprises the nucleic acid molecule attached thereto. In some embodiments, the bead comprises a plurality of nucleic acid molecules, including the nucleic acid molecule, attached thereto. In some embodiments, the plurality of nucleic acid molecules comprises a colony of nucleic acid molecules that are amplification products derived from the nucleic acid molecule. In some embodiments, the first set of nucleic acid molecules are attached to a first plurality of beads and wherein the second set of nucleic acid molecules are attached to a second plurality of beads, wherein the first plurality of beads and the second plurality of beads are associated to the plurality of individually addressable locations. In some embodiments, the first plurality of beads and the second plurality of beads are distinguishable. In some embodiments, the first plurality of beads and the second plurality of beads emit a different wavelength of signals. In some embodiments, the first plurality of beads and the second plurality of beads emit a different intensity of signals. In some embodiments, the method further comprises, subsequent to (b), subjecting individually addressable locations unassociated with the first plurality of beads and the second plurality of beads to conditions sufficient to disallow association of subsequent sample beads to the individually addressable locations unassociated with the first plurality of beads and the second plurality of beads. In some embodiments, the method further comprises, subsequent to (b), contacting the substrate with a plurality of blank beads such that individually addressable locations unassociated with the first plurality of beads and the second plurality of beads are associated with blank beads. In some embodiments, the first nucleic acid sample and the second nucleic acid sample are distinguishable by a fluorescent dye. In some embodiments, the nucleic acid molecules each comprise a synthetic sequence of no more than 6 bases in length. In some embodiments, the synthetic sequence is no more than 4 bases in length. In some embodiments, the synthetic sequence is no more than 2 bases in length. In some embodiments, the synthetic sequence is no more than 1 base in length. In some embodiments, a total number of the nucleic acid molecules is greater than a total number of unique synthetic sequences. In some embodiments, a subset of nucleic acid molecules originating from the same nucleic acid sample of the plurality of nucleic acid samples each comprise a common synthetic sequence, which common synthetic sequence is different from synthetic sequences of another subset of nucleic acid molecules originating from a different nucleic acid sample. In some embodiments, the method further comprises rotating the substrate with respect to a reference axis of the substrate. In some embodiments, the rotating is performed subsequent to the dispersing in (c). In some embodiments, the rotating is performed during the dispersing in (c). In some embodiments, the rotating is performed prior to the dispersing in (c). In some embodiments, the dispersing in (c) comprises movement of the solution from a first location on the substrate to a second location on the substrate due to centrifugal forces from the rotating, wherein the first location and the second location have different radial distances from the reference axis. In some embodiments, the first region and the second region are disposed at least 1 millimeter (mm) distance from the reference axis on the substrate. In some embodiments, the first region and the second region are disposed at least 1 centimeter (cm) distance from the reference axis on the substrate. In some embodiments, the first region and the second region are arranged radially around the substrate with respect to a central axis of the substrate. In some embodiments, the substrate comprises a plurality of radially alternating regions, including the first region and the second region, wherein the plurality of radially alternating regions comprises a first set of regions of a first type and a second set of regions of a second type. In some embodiments, the first set of regions is chemically distinct form the second set of regions. In some embodiments, the first set of regions and the second set of regions are separated by barriers. In some embodiments, the first set of regions and the second type of regions are distinguishable only by nucleic acid samples loaded on the first set of regions and the second set of regions. In some embodiments, the first region and the second region are directly adjacent. In some embodiments, the first region and the second region are separated by another region on the substrate. In some embodiments, the first region and the second region overlap. In some embodiments, in (e) the first subset and the second subset do not include a third subset of the nucleic acid molecules of the first array or the second array that is located proximate to within 0.5 millimeter (mm) of a border of the first region and the second region. In some embodiments, (b) is performed in a first station different from a second station in which (c) or (d) is performed. In some embodiments, the substrate comprises a physical demarcation, wherein the physical demarcation is used as a reference to spatially index the substrate. In some embodiments, the demarcation comprises one or more of an indentation, notch, physical feature, dye, and ink on the substrate. In some embodiments, the demarcation comprises a control nucleic acid sample. In some embodiments, the first region and the second region are separated by a barrier on the substrate. In some embodiments, the barrier remains fixed to the substrate during (c) or (d). In some embodiments, the barrier remains fixed to the substrate during (c) and (d). In some embodiments, the barrier is removable. In some embodiments, the method further comprises removing the barrier subsequent to (b). In some embodiments, the barrier dissolves. In some embodiments, the barrier evaporates. In some embodiments, the barrier sublimes. In some embodiments, the barrier melts. In some embodiments, the barrier comprises an injection molded guide. In some embodiments, the barrier comprises polyethylene glycol (PEG). In some embodiments, the barrier comprises a viscous solution. In some embodiments, the viscosity varies in proportion to temperature. In some embodiments, the barrier comprises a fluid that is immiscible with a loading solution comprising the first nucleic acid sample and the second nucleic acid sample. In some embodiments, the barrier comprises a hydrophobic region, and wherein the first region and the second region comprise hydrophilic regions. In some embodiments, the barrier comprises an air knife. In some embodiments, prior to (b), the substrate is masked with one or more masks such that the substrate comprises a subset of one or more masked regions and a subset of one or more unmasked regions, wherein the subset of one or more unmasked regions comprises the first region and the second region. In some embodiments, the method further comprises prior to (b) masking the substrate with the one or more masks. In some embodiments, the method further comprises subsequent to (b), unmasking the substrate from the one or more masks, and loading a third nucleic acid sample onto a third region of the one or more masked regions. In some embodiments, (b) comprises (i) masking the substrate with the one or more masks such that the substrate comprises a subset of one or more masked regions and a subset of one or more unmasked regions, wherein the subset of one or more unmasked regions comprises the first region and the sample; (iii) unmasking the substrate from the one or more masks; and (iv) loading the second nucleic acid sample. In some embodiments, (b) comprises contracting the substrate with a first loading fluid comprising the first nucleic acid sample and a second loading fluid comprising the second nucleic acid sample, wherein the first loading fluid and the second loading fluid are immiscible. In some embodiments, (b) comprises loading the first nucleic acid sample and the second nucleic acid sample simultaneously. In some embodiments, (b) comprises loading the first nucleic acid sample and the second nucleic acid sample at discrete times. In some embodiments, the first nucleic acid sample is loaded prior to loading of the second nucleic acid sample. In some embodiments, the substrate is dried between loading of the first nucleic acid sample and the second nucleic acid sample. In some embodiments, (b) comprises applying a magnetic field to direct the first nucleic acid sample to the substrate. In some embodiments, the magnetic field is applied by one or more magnets. In some embodiments, the first set of nucleic acid molecules are attached to a plurality of magnetic beads. In some embodiments, a loading fluid comprising the first nucleic acid sample comprises a ferrofluid. In some embodiments, the method further comprises prior to (b), activating the first region or the second region for loading using temperature. In some embodiments, the method further comprises, prior to (b), activating the first region or the second region for loading using electromagnetic radiation. In some embodiments, the first region attracts the first nucleic acid sample. In some embodiments, the second region repels the first nucleic acid sample. In some embodiments, the substrate comprises a third region that repels the first nucleic acid sample. In some embodiments, the method further comprises, subsequent to (b), washing nucleic acid molecules unassociated with the first region or the second region from the substrate. In some embodiments, the washing comprises aspirating.

In another aspect, provided herein is a method for processing a plurality of nucleic acid samples, comprising: (a) providing the plurality of nucleic acid samples, wherein each of the plurality of nucleic acid samples comprises a fluorescent dye; (b) separating the plurality of nucleic acid samples into a first set of one or more samples and a second set of one or more samples; (c) loading the first set of one or more samples onto a first set of regions on a substrate, with one sample per region in the first set of regions; (d) imaging the substrate to identify (i) locations within the first set of regions and (ii) locations within a second set of regions on the substrate, wherein the second set of regions are different from the first set of regions, where the first set of one or more samples are associated; (e) loading the second set of one or more samples onto the second set of regions on a substrate, with one sample per region in the second set of regions; (f) imaging the substrate to identify (i) locations within the first set of regions and (ii) locations within the second set of regions where the second set of one or more samples are associated; (g) dispersing a solution across the substrate, wherein the solution comprises reagents sufficient to react with nucleic acid molecules of the first set of one or more samples or the second set of one or more samples; (h) detecting one or more signals that are indicative of a reaction between the reagents and the nucleic acid molecules; and (i) based at least in part on (i) the one or more signals and (ii) locations, from the first set of regions and the second set of regions, from which the one or more signals are detected, analyzing the each of the plurality of nucleic acid samples.

In some embodiments, the fluorescent dye is attached to a sequencing primer of a nucleic acid molecule of the each of the plurality of nucleic acid samples. In some embodiments, the method further comprises: (i) loading a primer comprising a label to the substrate, (ii) subjecting a nucleic acid molecule of the plurality of nucleic acid samples to conditions sufficient to interact with the primer, and (iii) detecting a presence of the nucleic acid molecule using the label.

In some embodiments, the solution comprises reagents sufficient to incorporate at least one nucleotide into a growing nucleic acid strand that is complementary to a nucleic acid molecule of the nucleic acid molecules of the first array or the second array. In some embodiments, the method further comprises repeating (c)-(e) with various nucleotides in the solution to provide sequence information for the nucleic acid molecules. In some embodiments, the plurality of nucleic acid samples comprises n number of nucleic acid samples, and (b) comprises loading the n number of nucleic acid samples to n number of separate regions of the substrate. In some embodiments, n is at least 3. In some embodiments, n is at least 5. In some embodiments, n is at least 10. In some embodiments, the first nucleic acid sample or the second nucleic acid sample comprises 1000 nucleic acid molecules. In some embodiments, the first nucleic acid sample or the second nucleic acid sample comprises 10,000 nucleic acid molecules. In some embodiments, the first nucleic acid sample or the second nucleic acid sample comprises 100,000 nucleic acid molecules. In some embodiments, (b) comprises depositing the first nucleic acid sample to the substrate from a dispenser through an air gap. In some embodiments, (b) comprises depositing the first nucleic acid sample to the substrate through a closed flow cell. In some embodiments, the first region and the second region have different sizes. In some embodiments, the first region and the second region have the same size. In some embodiments, the first region and the second region comprise different numbers of individually addressable locations on the substrate. In some embodiments, the first region and the second region comprise the same number of individually addressable locations on the substrate. In some embodiments, subsequent to (b), the first set of nucleic acid molecules is attached to a plurality of beads, which plurality of beads is immobilized to the substrate. In some embodiments, a bead of the plurality of beads comprises a plurality of nucleic acid molecules attached thereto, wherein the plurality of nucleic acid molecules comprises a colony of nucleic acid molecules. In some embodiments, the colony of nucleic acid molecules are amplification products derived from a nucleic acid molecule of the first set of nucleic acid molecules. In some embodiments, the plurality of nucleic acid molecules is attached to the bead prior to (b), and (b) comprises dispensing the plurality of beads to the substrate. In some embodiments, subsequent to (b), the second set of nucleic acid molecules is attached to a second plurality of beads, which second plurality of beads is immobilized to the substrate. In some embodiments, the substrate comprises a plurality of individually addressable locations. In some embodiments, an individually addressable location of the plurality of individually addressable locations is configured to associate with a nucleic acid molecule of the nucleic acid molecules of the first array or the second array. In some embodiments, the individually addressable location is configured to associate with a bead, wherein the bead comprises the nucleic acid molecule attached thereto. In some embodiments, the bead comprises a plurality of nucleic acid molecules, including the nucleic acid molecule, attached thereto. In some embodiments, the plurality of nucleic acid molecules comprises a colony of nucleic acid molecules that are amplification products derived from the nucleic acid molecule. In some embodiments, the first set of nucleic acid molecules are attached to a first plurality of beads and wherein the second set of nucleic acid molecules are attached to a second plurality of beads, wherein the first plurality of beads and the second plurality of beads are associated to the plurality of individually addressable locations. In some embodiments, the first plurality of beads and the second plurality of beads are distinguishable. In some embodiments, the first plurality of beads and the second plurality of beads emit a different wavelength of signals. In some embodiments, the first plurality of beads and the second plurality of beads emit a different intensity of signals. In some embodiments, the method further comprises, subsequent to (b), subjecting individually addressable locations unassociated with the first plurality of beads and the second plurality of beads to conditions sufficient to disallow association of subsequent sample beads to the individually addressable locations unassociated with the first plurality of beads and the second plurality of beads. In some embodiments, the method further comprises, subsequent to (b), contacting the substrate with a plurality of blank beads such that individually addressable locations unassociated with the first plurality of beads and the second plurality of beads are associated with blank beads. In some embodiments, the first nucleic acid sample and the second nucleic acid sample are distinguishable by a fluorescent dye. In some embodiments, the nucleic acid molecules each comprise a synthetic sequence of no more than 6 bases in length. In some embodiments, the synthetic sequence is no more than 4 bases in length. In some embodiments, the synthetic sequence is no more than 2 bases in length. In some embodiments, the synthetic sequence is no more than 1 base in length. In some embodiments, a total number of the nucleic acid molecules is greater than a total number of unique synthetic sequences. In some embodiments, a subset of nucleic acid molecules originating from the same nucleic acid sample of the plurality of nucleic acid samples each comprise a common synthetic sequence, which common synthetic sequence is different from synthetic sequences of another subset of nucleic acid molecules originating from a different nucleic acid sample. In some embodiments, the method further comprises rotating the substrate with respect to a reference axis of the substrate. In some embodiments, the rotating is performed subsequent to the dispersing in (c). In some embodiments, the rotating is performed during the dispersing in (c). In some embodiments, the rotating is performed prior to the dispersing in (c). In some embodiments, the dispersing in (c) comprises movement of the solution from a first location on the substrate to a second location on the substrate due to centrifugal forces from the rotating, wherein the first location and the second location have different radial distances from the reference axis. In some embodiments, the first region and the second region are disposed at least 1 millimeter (mm) distance from the reference axis on the substrate. In some embodiments, the first region and the second region are disposed at least 1 centimeter (cm) distance from the reference axis on the substrate. In some embodiments, the first region and the second region are arranged radially around the substrate with respect to a central axis of the substrate. In some embodiments, the substrate comprises a plurality of radially alternating regions, including the first region and the second region, wherein the plurality of radially alternating regions comprises a first set of regions of a first type and a second set of regions of a second type. In some embodiments, the first set of regions is chemically distinct form the second set of regions. In some embodiments, the first set of regions and the second set of regions are separated by barriers. In some embodiments, the first set of regions and the second type of regions are distinguishable only by nucleic acid samples loaded on the first set of regions and the second set of regions. In some embodiments, the first region and the second region are directly adjacent. In some embodiments, the first region and the second region are separated by another region on the substrate. In some embodiments, the first region and the second region overlap. In some embodiments, in (e) the first subset and the second subset do not include a third subset of the nucleic acid molecules of the first array or the second array that is located proximate to within 0.5 millimeter (mm) of a border of the first region and the second region. In some embodiments, (b) is performed in a first station different from a second station in which (c) or (d) is performed. In some embodiments, the substrate comprises a physical demarcation, wherein the physical demarcation is used as a reference to spatially index the substrate. In some embodiments, the demarcation comprises one or more of an indentation, notch, physical feature, dye, and ink on the substrate. In some embodiments, the demarcation comprises a control nucleic acid sample. In some embodiments, the first region and the second region are separated by a barrier on the substrate. In some embodiments, the barrier remains fixed to the substrate during (c) or (d). In some embodiments, the barrier remains fixed to the substrate during (c) and (d). In some embodiments, the barrier is removable. In some embodiments, the method further comprises removing the barrier subsequent to (b). In some embodiments, the barrier dissolves. In some embodiments, the barrier evaporates. In some embodiments, the barrier sublimes. In some embodiments, the barrier melts. In some embodiments, the barrier comprises an injection molded guide. In some embodiments, the barrier comprises polyethylene glycol (PEG). In some embodiments, the barrier comprises a viscous solution. In some embodiments, the viscosity varies in proportion to temperature. In some embodiments, the barrier comprises a fluid that is immiscible with a loading solution comprising the first nucleic acid sample and the second nucleic acid sample. In some embodiments, the barrier comprises a hydrophobic region, and wherein the first region and the second region comprise hydrophilic regions. In some embodiments, the barrier comprises an air knife. In some embodiments, prior to (b), the substrate is masked with one or more masks such that the substrate comprises a subset of one or more masked regions and a subset of one or more unmasked regions, wherein the subset of one or more unmasked regions comprises the first region and the second region. In some embodiments, the method further comprises prior to (b) masking the substrate with the one or more masks. In some embodiments, the method further comprises subsequent to (b), unmasking the substrate from the one or more masks, and loading a third nucleic acid sample onto a third region of the one or more masked regions. In some embodiments, (b) comprises (i) masking the substrate with the one or more masks such that the substrate comprises a subset of one or more masked regions and a subset of one or more unmasked regions, wherein the subset of one or more unmasked regions comprises the first region and the sample; (iii) unmasking the substrate from the one or more masks; and (iv) loading the second nucleic acid sample. In some embodiments, (b) comprises contracting the substrate with a first loading fluid comprising the first nucleic acid sample and a second loading fluid comprising the second nucleic acid sample, wherein the first loading fluid and the second loading fluid are immiscible. In some embodiments, (b) comprises loading the first nucleic acid sample and the second nucleic acid sample simultaneously. In some embodiments, (b) comprises loading the first nucleic acid sample and the second nucleic acid sample at discrete times. In some embodiments, the first nucleic acid sample is loaded prior to loading of the second nucleic acid sample. In some embodiments, the substrate is dried between loading of the first nucleic acid sample and the second nucleic acid sample. In some embodiments, (b) comprises applying a magnetic field to direct the first nucleic acid sample to the substrate. In some embodiments, the magnetic field is applied by one or more magnets. In some embodiments, the first set of nucleic acid molecules are attached to a plurality of magnetic beads. In some embodiments, a loading fluid comprising the first nucleic acid sample comprises a ferrofluid. In some embodiments, the method further comprises prior to (b), activating the first region or the second region for loading using temperature. In some embodiments, the method further comprises, prior to (b), activating the first region or the second region for loading using electromagnetic radiation. In some embodiments, the first region attracts the first nucleic acid sample. In some embodiments, the second region repels the first nucleic acid sample. In some embodiments, the substrate comprises a third region that repels the first nucleic acid sample. In some embodiments, the method further comprises, subsequent to (b), washing nucleic acid molecules unassociated with the first region or the second region from the substrate. In some embodiments, the washing comprises aspirating.

In another aspect, provided herein is a method for processing a biological analyte, comprising: (a) moving a substrate through or along a reel, wherein a surface of the substrate comprises an array having immobilized thereto the biological analyte, wherein the; (b) bringing the surface of the substrate in contact with a reservoir comprising a solution, wherein the solution comprises a plurality of probes; (c) subjecting the biological analyte to conditions sufficient to conduct a reaction between a probe of the plurality of probes and the biological analyte, to couple the probe to the biological analyte; and (d) detecting one or more signals from the probe coupled to the biological analyte, thereby analyzing the biological analyte, wherein the substrate is substrate is moved through or along the reel through in the same direction for at least two consecutive cycles of (b)-(d).

In some embodiments, the method further comprises using a recirculation tank. In some embodiments, a dimension of the substrate corresponds to a size of a field of view of an imaging system used in (d). In some embodiments, (a) is performed to bring the surface of the substrate in contact with the reservoir. In some embodiments, the method further comprises moving the substrate through or along a second reel. In some embodiments, the method further comprises bringing the surface of the substrate in contact with a second reservoir comprising a second solution. In some embodiments, the second solution comprises a wash buffer. In some embodiments, the second solution comprises a second probe, and the method further comprises subjecting the biological analyte to conditions sufficient to conduct a reaction between the second probe and the biological analyte, to couple the second probe to the biological analyte. In some embodiments, the method further comprises bringing the surface of the substrate in contact with n numbers of different reservoirs comprising n number of solutions. In some embodiments, the method further comprises repeating (b)-(d) during the moving in (a) with additional reservoirs comprising different solutions a number of times sufficient to complete an assay of the biological analyte. In some embodiments, the biological analyte is a nucleic acid molecule, and the assay comprises determining a sequence of the nucleic acid molecule. In some embodiments, the probe comprises an oligonucleotide molecule. In some embodiments, the oligonucleotide molecule comprises 1 to 10 bases in length. In some embodiments, the oligonucleotide molecule comprises 10 to 20 bases in length. In some embodiments, probe comprises a dibase probe. In some embodiments, the probe is labeled.

In some embodiments, the biological analyte comprises a nucleic acid molecule. In some embodiments, the analyzing comprises identifying a sequence of the nucleic acid molecule. In some embodiments, the plurality of probes comprises a plurality of oligonucleotide molecules. In some embodiments, (c) comprises conducting a complementarity binding reaction between the probe and the nucleic acid molecule to identify a presence of homology between the probe and the biological analyte. In some embodiments, the plurality of probes comprises a plurality of nucleotides. In some embodiments, (c) comprises subjecting the nucleic acid molecule to a primer extension reaction under conditions sufficient to incorporate at least one nucleotide from the plurality of nucleotides into a growing strand that is complementary to the nucleic acid molecule. In some embodiments, the plurality of nucleotides comprises nucleotide analogs. In some embodiments, the one or more signals are indicative of incorporation of at least one nucleotide.

In some embodiments, the detecting is conducted using a sensor that continuously scans the array. In some embodiments, the sensor scans the array linearly. In some embodiments, the method further comprises using a pulling mechanism to move the substrate through or along the reel. In some embodiments, the substrate is textured or patterned. In some embodiments, the substrate is substantially planar. In some embodiments, the array comprises a plurality of individually addressable locations, and wherein the biological analyte is disposed at an individually addressable location of the plurality of individually addressable locations. In some embodiments, the biological analyte is attached to a bead, wherein the bead is immobilized to the individually addressable location.

In another aspect, provided herein is a system for analyzing a biological analyte, comprising: (a) a substrate comprising a biological analyte, wherein the substrate is maintained at or above a first temperature that is higher than an ambient temperature of an environment exposed to the substrate; and (b) an optical imaging objective in optical communication with the substrate and exposed to the environment, wherein the optical imaging objective is subject to a temperature gradient between the first temperature of the substrate and the ambient temperature of the environment, wherein the optical imaging objective comprises a first optical element and a second optical element adjacent to the first optical element, wherein the second optical element is disposed farther from the substrate than the first optical element, wherein the first optical element is configured to be at least partially immersed in an immersion fluid in contact with the substrate, and wherein a second temperature of the first optical element is maintained such that a third temperature of the second optical element is maintained at or below a predetermined threshold.

In some embodiments, the system further comprises a movement unit operatively coupled to the substrate, wherein the movement unit is configured to subject the substrate to movement relative to the optical imaging objective. In some embodiments, the system further comprises one or more computer processors operatively coupled to the optical imaging objective and the movement unit, wherein the one or more computer processors are individually or collectively programmed to (i) direct the movement unit to subject the substrate to movement relative to the optical imaging objective during detection of the substrate by the optical imaging objective, and (ii) use the optical imaging objective to detect one or more signals from the biological analyte. In some embodiments, the first optical element is a window configured to allow optical communication between the substrate and the second optical element. In some embodiments, the window is substantially flat. In some embodiments, the window is flat. In some embodiments, the first temperature is at least 40 degrees Celsius. In some embodiments, the first temperature is at least 50 degrees Celsius. In some embodiments, the first temperature is about 50 degrees Celsius. In some embodiments, the predetermined threshold is an ambient temperature. In some embodiments, the predetermined threshold is at most 30 degrees Celsius. In some embodiments, the predetermined threshold is at most 25 degrees Celsius. In some embodiments, the predetermined threshold is about 20 degrees Celsius. In some embodiments, the second temperature of the first optical element is maintained such that at least 50% of the temperature gradient occurs within the first optical element. In some embodiments, the second temperature of the first optical element is maintained such that at least 70% of the temperature gradient occurs within the first optical element. In some embodiments, the second temperature of the first optical element is maintained such that at least 90% of the temperature gradient occurs within the first optical element.

In some embodiments, at least a portion of the first optical element is at a temperature of at least 40 degrees Celsius. In some embodiments, at least a portion of the first optical element is at a temperature of at least 50 degrees Celsius. In some embodiments, at least a portion of the first optical element is at a temperature of about 50 degrees Celsius. In some embodiments, at least a portion of the first optical element is at an ambient temperature. In some embodiments, the first optical element is at a temperature of at most 30 degrees Celsius. In some embodiments, the first optical element is at a temperature of at most 25 degrees Celsius. In some embodiments, the first optical element is at a temperature of about 20 degrees Celsius. In some embodiments, the immersion fluid is maintained at a third temperature such that the substrate is maintained at or above the first temperature and the second temperature of the second optical element is maintained at or below the predetermined threshold.

In some embodiments, the system further comprises a fluid flow unit configured to replenish the immersion fluid in contact with the substrate and the first optical element to maintain the third temperature of a volume of the immersion fluid in contact with the substrate. In some embodiments, the third temperature is at least 40 degrees Celsius. In some embodiments, the third temperature is at least 50 degrees Celsius. In some embodiments, the third temperature is about 50 degrees Celsius. In some embodiments, the third temperature is within 5 degrees Celsius of the first temperature. In some embodiments, the third temperature is an ambient temperature. In some embodiments, the third temperature is at most 30 degrees Celsius. In some embodiments, the third temperature is at most 25 degrees Celsius. In some embodiments, the third temperature is at most 20 degrees Celsius. In some embodiments, the optical imaging objective comprises an insulating spacer disposed between the first optical element and the second optical element, wherein the insulating spacer is configured to insulate heat transfer from the first optical element and the second optical element. In some embodiments, the insulating spacer has a thermal resistance higher than a thermal resistance of the first optical element.

In some embodiments, the optical imaging objective comprises a cooling element configured to decrease temperature of an outer layer of the optical imaging objective. In some embodiments, the system further comprises a fluid flow unit configured to dispense the immersion fluid to the substrate. In some embodiments, the fluid flow unit is configured to dispense the immersion fluid at a rate of less than about 1 milliliter/second. In some embodiments, the system further comprises a container configured to at least partially enclose the optical imaging objective with a cavity disposed between the optical imaging objective and a wall of the container, and a pressure unit configured to draw in a volume of the immersion fluid disposed outside the container into the container after the optical imaging objective is in contact with the immersion fluid. In some embodiments, the dispensing unit is configured to replenish the immersion fluid in contact with the first optical element at a rate of at least 1 nanoliter/second. In some embodiments, the dispensing unit is configured to dispense the immersion fluid to the substrate prior to bringing the optical imaging objective in contact with the immersion fluid. In some embodiments, the system further comprises a container configured to at least partially enclose the optical imaging objective with a cavity disposed between the optical imaging objective and a wall of the container, and a pressure unit configured to draw in a volume of the immersion fluid disposed outside the container into the container after the optical imaging objective is in contact with the immersion fluid.

In some embodiments, the system further comprises a container configured to at least partially enclose the optical imaging objective, wherein a surface of the container interfaces the immersion fluid, wherein the surface is angled with respect to a surface of the first optical element that interfaces the immersion fluid. In some embodiments, the system further comprises a casing that at least partially encloses the first optical element, wherein the casing comprises a cavity adjacent to the first optical element, wherein the cavity interfaces the immersion fluid and is configured to direct one or more bubbles in the immersion fluid away from the first optical element. In some embodiments, the cavity is annular or surrounds the first optical element. In some embodiments, the first optical element is substantially flat.

In some embodiments, the system further comprises a movement unit operatively coupled to the substrate or the optical imaging objective, wherein the movement unit is configured to subject the substrate to movement relative to the optical imaging objective. In some embodiments, the movement is in a vector that includes a vertical component that is substantially perpendicular to a plane of the substrate. In some embodiments, the movement is in a vector that includes a horizontal component that is substantially parallel to a plane of the substrate. In some embodiments, the movement is linear. In some embodiments, the movement is non-linear. In some embodiments, the movement unit is configured to subject the substrate to movement during dispensing of the immersion fluid to the substrate. In some embodiments, the system further comprises one or more computer processors operatively coupled to the optical imaging objective and the movement unit, wherein the one or more computer processors are individually or collectively programmed to (i) direct the movement unit to subject the substrate to movement relative to the optical imaging objective during detection of the substrate by the optical imaging objective, and (ii) use the optical imaging objective to detect one or more signals from the biological analyte.

In another aspect, provided herein is a method for analyzing a biological analyte, comprising: (a) providing a substrate comprising a biological analyte, wherein the substrate is at a first temperature that is higher than an ambient temperature of an environment exposed to the substrate; (b) providing an optical imaging objective in optical communication with the substrate and exposed to an environment, wherein the optical imaging objective is subject to a temperature gradient between the first temperature of the substrate and the ambient temperature of the environment, wherein the optical imaging objective comprises a first optical element and a second optical element adjacent to the first optical element, wherein the second optical element is disposed farther from the substrate than the first optical element, and wherein the first optical element is configured to be at least partially immersed in an immersion fluid in contact with the substrate; (c) controlling or maintaining a second temperature of the first optical element to regulate a magnitude or location of the temperature gradient through the optical imaging objective such that a third temperature of the second optical element is maintained below a predetermined threshold; and (d) using the optical imaging objective to detect one or more signals from the biological analyte, during movement of the substrate relative to the optical imaging objective.

In some embodiments, the method further comprises using a movement unit operatively coupled to the substrate to subject the substrate to movement relative to the optical imaging objective. In some embodiments, the method further comprises providing one or more computer processors operatively coupled to the optical imaging objective and the movement unit, using the one or more computer processors to (i) direct the movement unit to subject the substrate to movement relative to the optical imaging objective during detection of the substrate by the optical imaging objective, and (ii) use the optical imaging objective to detect one or more signals from the biological analyte. In some embodiments, the first optical element is a window configured to allow optical communication between the substrate and the second optical element. In some embodiments, the window is substantially flat. In some embodiments, the window is flat. In some embodiments, the first temperature is at least 40 degrees Celsius. In some embodiments, the first temperature is at least 50 degrees Celsius. In some embodiments, the first temperature is about 50 degrees Celsius. In some embodiments, the predetermined threshold is an ambient temperature. In some embodiments, the predetermined threshold is at most 30 degrees Celsius. In some embodiments, the predetermined threshold is at most 25 degrees Celsius. In some embodiments, the predetermined threshold is about 20 degrees Celsius. In some embodiments, the second temperature of the first optical element is maintained such that at least 50% of the temperature gradient occurs within the first optical element. In some embodiments, the second temperature of the first optical element is maintained such that at least 70% of the temperature gradient occurs within the first optical element. In some embodiments, the second temperature of the first optical element is maintained such that at least 90% of the temperature gradient occurs within the first optical element.

In some embodiments, at least a portion of the first optical element is at a temperature of at least 40 degrees Celsius. In some embodiments, at least a portion of the first optical element is at a temperature of at least 50 degrees Celsius. In some embodiments, at least a portion of the first optical element is at a temperature of about 50 degrees Celsius. In some embodiments, at least a portion of the first optical element is at an ambient temperature. In some embodiments, the first optical element is at a temperature of at most 30 degrees Celsius. In some embodiments, the first optical element is at a temperature of at most 25 degrees Celsius. In some embodiments, the first optical element is at a temperature of about 20 degrees Celsius. In some embodiments, the immersion fluid is maintained at a third temperature such that the substrate is maintained at or above the first temperature and the second temperature of the second optical element is maintained at or below the predetermined threshold.

In some embodiments, the method further comprises providing a fluid flow unit configured to replenish the immersion fluid in contact with the substrate and the first optical element to maintain the third temperature of a volume of the immersion fluid in contact with the substrate. In some embodiments, the third temperature is at least 40 degrees Celsius. In some embodiments, the third temperature is at least 50 degrees Celsius. In some embodiments, the third temperature is about 50 degrees Celsius. In some embodiments, the third temperature is within 5 degrees Celsius of the first temperature. In some embodiments, the third temperature is an ambient temperature. In some embodiments, the third temperature is at most 30 degrees Celsius. In some embodiments, the third temperature is at most 25 degrees Celsius. In some embodiments, the third temperature is at most 20 degrees Celsius. In some embodiments, the optical imaging objective comprises an insulating spacer disposed between the first optical element and the second optical element, wherein the insulating spacer is configured to insulate heat transfer from the first optical element and the second optical element. In some embodiments, the insulating spacer has a thermal resistance higher than a thermal resistance of the first optical element.

In some embodiments, the optical imaging objective comprises a cooling element configured to decrease temperature of an outer layer of the optical imaging objective. In some embodiments, the method further comprises using a fluid flow unit to dispense the immersion fluid to the substrate. In some embodiments, the fluid flow unit is configured to dispense the immersion fluid at a rate of less than about 1 millimeter/second. In some embodiments, the method further comprises enclosing the optical imaging objective with a container comprising a cavity disposed between the optical imaging objective and a wall of the container, and providing a pressure unit configured to draw in a volume of the immersion fluid disposed outside the container into the container after the optical imaging objective is in contact with the immersion fluid. In some embodiments, the dispensing unit is configured to replenish the immersion fluid in contact with the first optical element at a rate of at least 1 nanoliter/second. In some embodiments, the dispensing unit is configured to dispense the immersion fluid to the substrate prior to bringing the optical imaging objective in contact with the immersion fluid. In some embodiments, the method further comprises partially enclosing the optical imaging objective with a container comprising a cavity disposed between the optical imaging objective and a wall of the container, and a pressure unit configured to draw in a volume of the immersion fluid disposed outside the container into the container after the optical imaging objective is in contact with the immersion fluid.

In some embodiments, the method further comprises providing a container configured to at least partially enclose the optical imaging objective, wherein a surface of the container interfaces the immersion fluid, wherein the surface is angled with respect to a surface of the first optical element that interfaces the immersion fluid. In some embodiments, the method further comprises providing a casing that at least partially encloses the first optical element, wherein the casing comprises a cavity adjacent to the first optical element, wherein the cavity interfaces the immersion fluid and is configured to direct one or more bubbles in the immersion fluid away from the first optical element. In some embodiments, the cavity is annular or surrounds the first optical element. In some embodiments, the first optical element is substantially flat.

In some embodiments, the method further comprises using a movement unit operatively coupled to the substrate or the optical imaging objective and subjecting the substrate to movement relative to the optical imaging objective. In some embodiments, the movement is in a vector that includes a vertical component that is substantially perpendicular to a plane of the substrate. In some embodiments, the movement is in a vector that includes a horizontal component that is substantially parallel to a plane of the substrate. In some embodiments, the movement is linear. In some embodiments, the movement is non-linear. In some embodiments, the movement unit is configured to subject the substrate to movement during dispensing of the immersion fluid to the substrate. In some embodiments, the method further comprises providing one or more computer processors operatively coupled to the optical imaging objective and the movement unit, and (i) directing the movement unit to subject the substrate to movement relative to the optical imaging objective during detection of the substrate by the optical imaging objective, and (ii) using the optical imaging objective to detect one or more signals from the biological analyte.

In another aspect, provided is a method for analyte detection or analysis, comprising: (a) rotating an open substrate about a central axis, the open substrate having an array of immobilized analytes thereon; (b) delivering a solution having a plurality of probes to a region proximal to the central axis to introduce the solution to the open substrate; (c) dispersing the solution across the open substrate at least by centrifugal force such that at least one of the plurality of probes binds to at least one of the immobilized analytes to form a bound probe; and (d) using a detector to detect at least one signal from the bound probe via continuous rotational area scanning of the open substrate.

In some embodiments, the continuous rotational area scanning compensates for velocity differences at different radial positions of the array with respect to the central axis within a scanned area. In some embodiments, the continuous rotational area scanning comprises using an optical imaging system having an anamorphic magnification gradient substantially transverse to a scanning direction along the open substrate, and wherein the anamorphic magnification gradient at least partially compensates for tangential velocity differences that are substantially perpendicular to the scanning direction. In some embodiments, the continuous rotational area scanning comprises reading two or more regions on the open substrate at two or more scan rates, respectively, to at least partially compensate for tangential velocity differences in the two or more regions.

In some embodiments, (d) further comprises using an immersion objective lens in optical communication with the detector and the open substrate to detect the at least one signal, which immersion objective lens is in contact with a fluid that is in contact with the open substrate. In some embodiments, the fluid is in a container, and an electric field is used to regulate a hydrophobicity of one or more surfaces of the container to retain at least a portion of the fluid contacting the immersion objective lens and the open substrate.

In some embodiments, the continuous rotational area scanning is performed in a first environment having a first operating condition, and wherein the delivering of the solution is performed in a second environment having a second operating condition different from the first operating condition.

In some embodiments, the immobilized analytes comprise nucleic acid molecules, wherein the plurality of probes comprises fluorescently labeled nucleotides, and wherein at least one of the fluorescently labeled nucleotides binds to at least one of the nucleic acid molecules via nucleotide complementarity binding.

In some embodiments, the open substrate is substantially planar.

In another aspect, provided is an apparatus for analyte detection or analysis, comprising: a housing configured to receive an open substrate having an array of immobilized analytes thereon; one or more dispensers configured to deliver a solution having a plurality of probes to a region proximal to a central axis of the open substrate; a rotational unit configured to rotate the open substrate about a central axis to thereby disperse the solution across the open substrate at least by centrifugal force, such that at least one of the plurality of probes binds to at least one of the analytes to form a bound probe; and a detector configured to detect at least one signal from the bound probe via continuous rotational area scanning of the open substrate.

In some embodiments, the detector is configured to compensate for velocity differences at different radial positions of the array with respect to the central axis within a scanned area. In some embodiments, the one or more optics are configured to generate an anamorphic magnification gradient substantially transverse to a scanning direction along the open substrate, and wherein the anamorphic magnification gradient at least partially compensates for tangential velocity differences that are substantially perpendicular to the scanning direction. In some embodiments, the apparatus further comprises a processor configured to adjust the anamorphic magnification gradient to compensate for different imaged radial positions with respect to the central axis.

In some embodiments, the detector is configured to scan two or more regions on the open substrate at two or more scan rates, respectively, to at least partially compensate for tangential velocity differences in the two or more regions.

In some embodiments, the detector comprises a sensor and one or more optics in optical communication with the open substrate.

In some embodiments, the apparatus further comprises an immersion objective lens in optical communication with the detector and the open substrate, which immersion objective lens is configured to be in contact with a fluid that is in contact with the open substrate. In some embodiments, the apparatus further comprises a container configured to retain the fluid and an electric field application unit configured to regulate a hydrophobicity of one or more surfaces of the container to retain at least a portion of the fluid contacting the immersion objective lens and the open substrate. In some embodiments, the immersion objective lens is configured to separate a first environment from a second environment, wherein the first environment and second environment have different operating conditions. In some embodiments, the immersion objective lens forms a seal between the first environment and the second environment.

In some embodiments, the detector is configured to detect the at least one signal from the bound probe in a non-linear scanning path across the open substrate. In some embodiments, non-linear scanning path is a substantially spiral scanning path or a substantially ring-like scanning path.

In another aspect, provided is a computer-readable medium comprising non-transitory instructions stored thereon, which when executed cause one or more computer processors to implement a method for analyte detection or analysis, the method comprising: rotating an open substrate about a central axis, the open substrate having an array of immobilized analytes thereon; delivering a solution having a plurality of probes to a region proximal to the central axis, to introduce the solution to the open substrate; dispersing the solution across the open substrate at least by centrifugal force such that at least one of the plurality of probes binds to at least one of the immobilized analytes to form a bound probe; and using a detector to detect at least one signal from the bound probe via continuous rotational area scanning of the open substrate.

In some embodiments, the method further comprises using an immersion objective lens in optical communication with the detector and the open substrate to detect the at least one signal, which immersion objective lens is in contact with a fluid that is in contact with the open substrate. In some embodiments, the method further comprises using an electric field to regulate a hydrophobicity of one or more surfaces of a container to retain at least a portion of the fluid contacting the immersion objective lens and the open substrate.

In some embodiments, the immobilized analytes comprise nucleic acid molecules, wherein the plurality of probes comprises fluorescently labeled nucleotides, and wherein at least one of the fluorescently labeled nucleotides binds to at least one of the nucleic acid molecules via a primer extension reaction.

In some embodiments, the continuous rotational area scanning compensates for velocity differences at different radial positions of the array with respect to the central axis within a scanned area. In some embodiments, the continuous rotational area scanning comprises using an optical imaging system having an anamorphic magnification gradient substantially transverse to a scanning direction along the open substrate, and wherein the anamorphic magnification gradient at least partially compensates for tangential velocity differences that are substantially perpendicular to the scanning direction. In some embodiments, the method further comprises adjusting the anamorphic magnification gradient to compensate for different imaged radial positions with respect to the central axis. In some embodiments, the detector is configured to scan two or more regions on the open substrate at two or more scan rates, respectively, to at least partially compensate for tangential velocity differences in the two or more imaged regions.

In some embodiments, the continuous rotational area scanning comprises using an algorithmic compensation for velocity differences substantially perpendicular to a scanning direction along the open substrate.

In some embodiments, the detector is configured to detect the at least one signal from the bound probe in a non-linear scanning path across the open substrate.

In another aspect, provided is a method for processing a biological analyte, comprising: (a) providing a substrate comprising an array having immobilized thereto the biological analyte, wherein the substrate is rotatable with respect to a central axis; (b) directing a solution comprising a plurality of probes across the substrate and in contact with the biological analyte during rotation of the substrate, wherein the solution is directed centrifugally along a direction away from the central axis; (c) subjecting the biological analyte to conditions sufficient to conduct a reaction between at least one probe of the plurality of probes and the biological analyte, to couple the at least one probe to the biological analyte; and (d) detecting one or more signals from the at least one probe coupled to the biological analyte, thereby analyzing the biological analyte.

In some embodiments, the biological analyte is a nucleic acid molecule, and wherein analyzing the biological analyte comprises identifying a sequence of the nucleic acid molecule. In some embodiments, the plurality of probes is a plurality of nucleotides. In some embodiments, (c) comprises subjecting the nucleic acid molecule to a primer extension reaction under conditions sufficient to incorporate at least one nucleotide from the plurality of nucleotides into a growing strand that is complementary to the nucleic acid molecule. In some embodiments, in (d), the one or more signals are indicative of incorporation of the at least one nucleotide. In some embodiments, the plurality of nucleotides comprises nucleotide analogs. In some embodiments, the plurality of nucleotides is of a first canonical base type. In some embodiments, the method further comprises repeating (b) and (c) with an additional plurality of nucleotides that are of a second canonical base type, wherein the second canonical base type is different than the first canonical base type. In some embodiments, the plurality of probes is a plurality of oligonucleotide molecules.

In some embodiments, the biological analyte is a nucleic acid molecule, and (c) comprises conducting a complementarity binding reaction between the at least one probe and the nucleic acid molecule to identify a presence of homology between the at least one probe and the biological analyte in (d).

In some embodiments, the detecting in (d) is conducted using a sensor that continuously scans the array along a nonlinear path during rotation of the substrate.

In some embodiments, the method further comprises, prior to (b), (i) dispensing the solution on the substrate when the substrate is stationary, and (ii) subjecting the substrate to rotation to direct the solution across the array.

In some embodiments, the method further comprises (i) subjecting the substrate to rotation prior to (b), and (ii) while the substrate is rotating, dispensing the solution on the substrate.

In some embodiments, the method further comprises repeating (b)-(d) with an additional plurality of probes that is different than the plurality of probes.

In some embodiments, the fluid viscosity of the solution or a rotational velocity of the substrate is selected to yield a predetermined thickness of a layer of the solution adjacent to the array.

In some embodiments, the biological analyte is immobilized to the array via a linker.

In some embodiments, the biological analyte is coupled to a bead, which bead is immobilized to the array.

In some embodiments, the solution is directed to the array using one or more dispensing nozzles that are directed at or in proximity to the central axis of the substrate.

In some embodiments, the array comprises a plurality of individually addressable locations, and wherein the biological analyte is disposed at a given individually addressable location of the plurality of individually addressable locations.

In some embodiments, the array has immobilized thereto one or more additional biological analytes.

In some embodiments, the substrate is textured or patterned.

In some embodiments, the one or more signals include one or more optical signals.

In some embodiments, the method further comprises terminating rotation of the substrate prior to detecting the one or more signals in (d).

In some embodiments, (b) and/or (c) is performed while the substrate is rotated at a first angular velocity and (d) is performed while the substrate is rotated at a second angular velocity that is different than the first angular velocity.

In some embodiments, the substrate is movable with respect to the central axis, and wherein (b) and/or (c) is performed when the substrate is at a first location of the central axis and (d) is performed when the substrate is at a second location of the central axis, which second location is different from the first location. In some embodiments, at the first location the substrate rotates at a first angular velocity and at the second location the substrate rotates at a second angular velocity that is different than the first angular velocity.

In some embodiments, the array is a substantially planar array.

In another aspect, provided is a method for processing a biological analyte, comprising: (a) providing a substrate comprising a substantially planar array having immobilized thereto the biological analyte, wherein the substrate is rotatable with respect to a central axis; (b) directing a solution comprising a plurality of probes across the substantially planar array and in contact with the biological analyte during rotation of the substrate; (c) subjecting the biological analyte to conditions sufficient to conduct a reaction between at least one probe of the plurality of probes and the biological analyte, to couple the at least one probe to the biological analyte; and (d) detecting one or more signals from the at least one probe coupled to the biological analyte, thereby analyzing the biological analyte.

In some embodiments, the biological analyte is a nucleic acid molecule, and wherein analyzing the biological analyte comprises identifying a sequence of the nucleic acid molecule.

In some embodiments, the detecting in (d) is conducted using a sensor that continuously scans the substantially planar array along a nonlinear path during rotation of the substrate.

In some embodiments, the substantially planar array comprises a plurality of individually addressable locations, and wherein the biological analyte is disposed at a given individually addressable location of the plurality of individually addressable locations.

In another aspect, provided is a system for analyzing a biological analyte, comprising: a substrate comprising an array configured to immobilize the biological analyte, wherein the substrate is configured to rotate with respect to a central axis; a fluid flow unit comprising a fluid channel configured to dispense a solution comprising a plurality of probes to the array, wherein during rotation of the substrate, the solution is directed centrifugally along a direction away from the central axis and brought in contact with the biological analyte under conditions sufficient to couple at least one probe of the plurality of probes to the biological analyte; a detector in optical communication with the array, wherein the detector is configured to detect one or more signals from the at least one probe coupled to the biological analyte; and one or more computer processors operatively coupled to the fluid flow unit and the detector, wherein the one or more computer processors are individually or collectively programmed to (i) direct the fluid flow unit to dispense the solution through the fluid channel to the array, which solution comprising the plurality of probes is directed centrifugally along a direction away from the central axis and brought in contact with the biological analyte during rotation of the substrate, and (ii) use the detector to detect the one or more signals from the at least one probe coupled to the biological analyte.

In some embodiments, the substrate is movable along the central axis. In some embodiments, the fluid channel is configured to dispense the solution when the substrate is at a first location along the central axis, and wherein the detector is configured to detect the one or more signals when the substrate is at a second location along the central axis, which second location is different from the first location. In some embodiments, wherein at the first location, the substrate is rotatable at a first angular velocity and, at the second location, the substrate is rotatable at a second angular velocity that is different than the first angular velocity.

In some embodiments, the system further comprises an additional fluid channel comprising configured to dispense an additional solution to the array, wherein the fluid channel and the additional fluid channel are fluidically isolated upstream from one another upstream of outlet ports of the fluid channel and the additional fluid channel.

In some embodiments, the system further comprises an optical imaging objective configured to be at least partially immersed in a fluid in contact with the substrate, which optical imaging objective is in optical communication with the detector.

In some embodiments, the system further comprises a container encircling the optical imaging objective, which container is configured to retain at least a portion of the fluid. In some embodiments, the fluid channel does not contact the substrate.

In some embodiments, the array is a substantially planar array.

In some embodiments, the one or more computer processors are individually or collectively programmed to direct the fluid flow unit to dispense the solution through the fluid channel to the array prior to rotation of the substrate.

In some embodiments, the one or more computer processors are individually or collectively programmed to direct the fluid flow unit to dispense the solution through the fluid channel to the array when the substrate is undergoing rotation.

In some embodiments, the detector is configured to detect the one or more signals during rotation of the substrate. In some embodiments, the detector is configured to continuously scan the array along a nonlinear path during rotation of the substrate.

In some embodiments, the detector is configured to detect the one or more signals when the substrate is not rotating.

In some embodiments, the detector is an optical detector and wherein the one or more signals are one or more optical signals.

In some embodiments, the array comprises a plurality of individually addressable locations. In some embodiments, the individually addressable locations of the plurality of individually addressable locations are individually physically accessible.

In some embodiments, the substrate is textured or patterned.

In some embodiments, the system further comprises a container comprising the substrate. In some embodiments, the system further comprises an environmental unit that is configured to regulate a temperature or a humidity of an environment of the container. In some embodiments, the detector comprises a time delay and integration (TDI) sensor (e.g., a TDI line-scan camera) or a pseudo-TDI rapid frame rate sensor. In some embodiments, the system further comprises an additional detector in optical communication with the array, wherein the detector and the additional detector are configured to scan the array along different paths. In some embodiments, the different paths are non-linear.

In some embodiments, the system further comprises one or more optics between, and in optical communication with, the array and the detector, wherein the one or more optics are configured to provide an optical magnification gradient across the array. In some embodiments, the optical magnification gradient is anamorphic.

In another aspect, provided is a system for sequencing a nucleic acid molecule, comprising: a substrate comprising a substantially planar array configured to immobilize a biological analyte, wherein the substrate is configured to rotate with respect to a central axis; a fluid flow unit comprising a fluid channel configured to dispense a solution comprising a plurality of probes to the substantially planar array, wherein during rotation of the substrate, the solution is directed across the substantially planar array and brought in contact with the biological analyte under conditions sufficient to couple at least one probe of the plurality of probes to the biological analyte; a detector in optical communication with the substantially planar array, wherein the detector is configured to detect one or more signals from the at least one probe coupled to the biological analyte; and one or more computer processors operatively coupled to the fluid flow unit and the detector, wherein the one or more computer processors are individually or collectively programmed to (i)

direct the fluid flow unit to dispense the solution through the fluid channel to the array, which solution comprising the plurality of probes is directed across the substantially planar array and brought in contact with the biological analyte during rotation of the substrate, and (ii) use the detector to detect the one or more signals from the at least one probe coupled to the biological analyte.

In some embodiments, the system further comprises an optical imaging objective configured to be at least partially immersed in a fluid in contact with the substrate, which optical imaging objective is in optical communication with the detector. The fluid may be confined or controlled, such as by using an electrical field controlling the hydrophobicity of one or more of regions on the substrate and a fluid enclosure.

In some embodiments, the detector comprises a time delay and integration (TDI) sensor (e.g., a TDI line-scan camera) or a pseudo-TDI rapid frame rate sensor.

In some embodiments, the detector is configured to detect the one or more signals during rotation of the substrate. In some embodiments, the detector is configured to continuously scan the array along a nonlinear path during rotation of the substrate.

In another aspect, provided is a method for sequencing a nucleic acid molecule, comprising: (a) providing a substrate comprising a planar array having immobilized thereto the nucleic acid molecule, wherein the substrate is configured to rotate with respect to an axis; (b) directing a solution comprising a plurality of nucleotides across the planar array during rotation of the substrate; (c) subjecting the nucleic acid molecule to a primer extension reaction under conditions sufficient to incorporate at least one nucleotide from the plurality of nucleotides into a growing strand that is complementary to the nucleic acid molecule; and (d) detecting a signal indicative of incorporation of the at least one nucleotide, thereby sequencing the nucleic acid molecule.

The method may further comprise, prior to (b), (i) dispensing the solution on the substrate when the substrate is stationary, and (ii) subjecting the substrate to rotation to direct the solution across the planar array. The method may further comprise (i) subjecting the substrate to rotation prior to (b), and (ii) while the substrate is rotating, dispensing the solution on the substrate. The method may further comprise repeating (b)-(d) one or more times to identify one or more additional signals indicative of incorporation of one or more additional nucleotides, thereby sequencing the nucleic acid molecule.

Different solutions may be directed to the planar array during rotation of the substrate for consecutive cycles. The rotation may yield centrifugal forces that subject the solution to flow over the planar array. A layer thickness of the planar array may be engineered based on adjusting fluid viscosity. A first fluid having a first viscosity may be used for generating a layer with the nucleic acid molecule on the planar array and a second fluid having a second viscosity may be used for washing the planar array. The first viscosity may be different from the second viscosity. The first viscosity may be controlled by controlling a temperature of the first fluid. The second viscosity may be controlled by controlling a temperature of the second fluid.

The planar array may comprise a linker that is coupled to the nucleic acid sample. The nucleic acid sample may be coupled to a bead, which bead is immobilized to the planar array.

The planar array may be in fluid communication with at least one sample inlet and at least one sample outlet. The solution may be directed to the planar array using one or more dispensing nozzles. The one or more nozzles may be directed at or in proximity to a center of the substrate.

The method may further comprise recycling a subset of the solution that has contacted the substrate. Recycling may comprise collecting, filtering, and reusing the subset of the solution. The filtering may be molecular filtering.

The planar array may comprise a plurality of individually addressable locations. The planar array may be textured. The planar array may be a patterned array.

The signal may be an optical signal. The signal may be a fluorescent signal.

The method may further comprise terminating rotation of the substrate prior to detecting the signal in (d). The signal in (d) may be detected while the substrate is rotating.

The operations (b) and/or (c) may be performed at a first a location and (d) may be performed at a second location that is different from the first location. The first location may comprise a first processing bay and the second location may comprise a second processing bay that is different from the second location. The first location may comprise a first rotating spindle interior to a second rotating spindle and the second location may comprise the second rotating spindle. The first location may comprise a first rotating spindle exterior to a second rotating spindle and the second location may comprise the second rotating spindle. The first rotating spindle and second rotating spindle may be configured to rotate at different angular velocities. The operation (b) may be performed at the first location. The operation (c) may be performed at the second location. The operation (c) may be performed at the first location.

The method may further comprise transferring the substrate between the first location and the second location. The operations (b) and/or (c) may be performed while the substrate is rotated at a first angular velocity and (d) may be performed while the substrate is rotated at a second angular velocity that is different from the first angular velocity. The first angular velocity may be less than the second angular velocity. The first angular velocity may be between 0 revolutions per minute (rpm) and 100 rpm. The second angular velocity may be between 100 rpm and 5,000 rpm. The operation (b) may be performed while the substrate is rotated at the first angular velocity. The operation (c) may be performed while the substrate is rotated at the second angular velocity. The operation (c) may be performed while the substrate is rotated at the first angular velocity.

In an aspect, a method for sequencing a nucleic acid molecule may comprise: (a) providing a substrate comprising an array having immobilized thereto the nucleic acid molecule, wherein the substrate is configured to rotate with respect to an axis; (b) directing a solution comprising a plurality of natural nucleotides and/or non-natural nucleotides across the array during rotation of the substrate; (c) subjecting the nucleic acid molecule to a primer extension reaction under conditions sufficient to incorporate at least one nucleotide from the plurality of natural nucleotides and non-natural nucleotides into a growing strand that is complementary to the nucleic acid molecule; and (d) detecting a signal indicative of incorporation of the at least one nucleotide, thereby sequencing the nucleic acid molecule.

The method may further comprise, prior to (b), (i) dispensing the solution on the substrate when the substrate is stationary, and (ii) subjecting the substrate to rotation to direct the solution to the array. The method may further comprise (i) subjecting the substrate to rotation prior to (b), and (ii) while the substrate is rotating, dispensing the solution on the substrate. The method may further comprise, subsequent to (c), modifying the at least one nucleotide. The modifying may comprise labeling the at least one nucleotide. The at least one nucleotide may be cleavably labeled. The method may further comprise, subsequent to (d), cleaving or modifying a label of the at least one nucleotide. The method may further comprise repeating (b)-(d) one or more times to identify one or more additional signals indicative of incorporation of one or more additional nucleotides, thereby sequencing the nucleic acid molecule.

Different solutions may be directed to the array during rotation of the substrate for consecutive cycles. Subsequent to (d), and prior to a next iteration of (b), the at least one nucleotide may be modified. The rotation may yield centrifugal forces that subject the solution to flow over the array. A layer thickness of the array may be engineered based on fluid viscosity. A first fluid having a first viscosity may be used for generating a layer with the nucleic acid molecule on the array and a second fluid having a second viscosity may be used for washing the array. The first viscosity may be different from the second viscosity. The first viscosity may be controlled by controlling a temperature of the first fluid. The second viscosity may be controlled by controlling a temperature of the second fluid.

The array may comprise a linker that is coupled to the nucleic acid sample. The nucleic acid sample may be coupled to a bead, which bead is immobilized to the array.

The array may be in fluid communication with at least one sample inlet and at least one sample outlet. The solution may be directed to the array using one or more dispensing nozzles. The one or more nozzles may be directed at or in proximity to a center of the substrate.

The method may further comprise recycling a subset of the solution that has contacted the substrate. Recycling may comprise collecting, filtering, and reusing the subset of the solution. The filtering may be molecular filtering.

The array may comprise a plurality of individually addressable locations. The array may be planar. The array may be textured. The array may be a patterned array.

The signal may be an optical signal. The signal may be a fluorescent signal.

The method may further comprise, prior to (b), subjecting the substrate to rotation with respect to the axis. The method may further comprise terminating rotation of the substrate prior to detecting the signal in (d). The signal in (d) may be detected while the substrate is rotating.

The operations (b) and/or (c) may be performed at a first a location and (d) may be performed at a second location that is different from the first location. The first location may comprise a first processing bay and the second location may comprise a second processing bay that is different from the first processing bay. The first location may comprise a first rotating spindle interior to a second rotating spindle and the second location may comprise the second rotating spindle. The first location may comprise a first rotating spindle exterior to a second rotating spindle and the second location may comprise the second rotating spindle. The first rotating spindle and second rotating spindle may be configured to rotate at different angular velocities. The operation (b) may be performed at the first location. The operation (c) may be performed at the second location. The operation (c) may be performed at the first location.

The method may further comprise transferring the substrate between the first location and the second location. The operations (b) and/or (c) may be performed while the substrate is rotated at a first angular velocity and (d) may be performed while the substrate is rotated at a second angular velocity that is different from the first angular velocity. The first angular velocity may be less than the second angular velocity. The first angular velocity may be between 0 rpm and 100 rpm. The second angular velocity may be between 100 rpm and 5,000 rpm. The operation (b) may be performed while the substrate is rotated at the first angular velocity. The operation (c) may be performed while the substrate is rotated at the second angular velocity. The operation (c) may be performed while the substrate is rotated at the first angular velocity.

In an aspect, a system for sequencing a nucleic acid molecule may comprise: a substrate comprising an array configured to immobilize the nucleic acid molecule, wherein the substrate is configured to (i) rotate with respect to an axis and (ii) undergo a change in relative position with respect to a longitudinal axis; a first fluid channel comprising a first fluid outlet port that is configured to dispense a first fluid to the array; a second fluid channel comprising a second fluid outlet port that is configured to dispense a second fluid to the array, wherein the first fluid channel and the second fluid channel are fluidically isolated upstream of the first fluid outlet port; and a detector configured to detect a signal from the array.

The first fluid outlet port and the second fluid outlet port may be external to the substrate. The first fluid outlet port and the second fluid outlet port may not contact the substrate. The first fluid outlet port and the second fluid outlet port may be nozzles.

The axis may be substantially parallel with the longitudinal axis. The longitudinal axis may be coincident with the axis. The longitudinal axis may be substantially perpendicular to a surface of the substrate. The relative position of the substrate may be configured to alternate between at least a first position and a second position with respect to the longitudinal axis.

The system may further comprise (i) a third fluid channel comprising a first fluid inlet port located at a first level of the longitudinal axis, wherein the first fluid inlet port is downstream of and in fluid communication with the substrate when the substrate is in the first relative position, and (ii) a fourth fluid channel comprising a second fluid inlet port located at a second level of the longitudinal axis, wherein the second fluid inlet port is downstream of and in fluid communication with the substrate when the substrate is in the relative second position. The third fluid channel may be in fluid communication with the first fluid channel and the fourth fluid channel may be in fluid communication with the second fluid channel. The substrate may be configured to have (i) the first relative position prior to, during, or subsequent to receiving the first fluid from the first fluid outlet port and (ii) the second relative position prior to, during, or subsequent to receiving the second fluid from the second fluid outlet port. The third fluid channel and the first fluid channel may define at least part of a first cyclic fluid flow path and the fourth fluid channel and the second fluid channel may define at least part of a second cyclic fluid flow path. At least one of the first cyclic fluid flow path and the second cyclic fluid flow path may comprise a filter. The filter may be a molecular filter.

The system may further comprise a shield that prevents fluid communication between the substrate and (i) the second fluid inlet port when the substrate is in the first position and (ii) the first fluid inlet port when the substrate is in the second position. The substrate may be translatable along the longitudinal axis. The substrate may be stationary along the longitudinal axis. At least one of a first axis of the first fluid outlet port and a second axis of the second fluid outlet port may be substantially coincident with the axis. At least one of a first axis of the first fluid outlet port and a second axis of the second fluid outlet port may be substantially parallel to the axis.

The first fluid and the second fluid may comprise different types of reagents. The first fluid may comprise a first type of nucleotide or nucleotide mixture and the second fluid may comprise a second type of nucleotide or nucleotide mixture. The first fluid or the second fluid may comprise a washing reagent.

The detector may be configured to detect the signal from the substrate during rotation of the substrate. The detector may be configured to detect the signal from the substrate when the substrate is not rotating.

The signal may be an optical signal. The signal may be a fluorescent signal.

The first fluid outlet port may be configured to dispense the first fluid to the array during rotation of the substrate. The second fluid outlet port may be configured to dispense the second fluid to the array during rotation of the substrate. The first fluid outlet port and the second fluid outlet port may be configured to dispense at non-overlapping times. The substrate may be configured to rotate with at least one of (i) different speeds and (ii) different number of rotations when the first fluid outlet port dispenses and when the second fluid outlet port dispenses. During the rotation, the array may be configured to direct the first fluid in a substantially radial direction away from the axis. The first fluid outlet port may be configured to dispense the first fluid to the array during more than one full rotation of the substrate.

The array may comprise a plurality of individually addressable locations. The array may comprise a plurality of individually addressable locations. The array may comprise a linker that is coupled to the nucleic acid sample. The nucleic acid sample may be coupled to a bead, which bead is immobilized to the array. The array may be textured. The array may be a patterned array. The array may be planar.

In an aspect, a system for sequencing a nucleic acid molecule may comprise: a substrate comprising a planar array configured to immobilize the nucleic acid molecule, wherein the substrate is configured to rotate with respect to an axis; a fluid flow unit configured to direct a solution comprising a plurality of nucleotides to the planar array during rotation of the substrate; a detector in sensing communication with the planar array; and one or more computer processors operatively coupled to the fluid flow unit and the detector, wherein the one or more computer processors are individually or collectively programmed to (i) direct the fluid flow unit to direct the solution comprising the plurality of nucleotides across the planar array during rotation of the substrate; (ii) subject the nucleic acid molecule to a primer extension reaction under conditions sufficient to incorporate one or more nucleotides from the plurality of nucleotides into a growing strand that is complementary to the nucleic acid molecule; and (iii) use the detector to detect one or more signals indicative of incorporation of the at one or more nucleotides, thereby sequencing the nucleic acid molecule.

In an aspect, a system for sequencing a nucleic acid molecule may comprise: a substrate comprising an array configured to immobilize the nucleic acid molecule, wherein the substrate is configured to rotate with respect to an axis; a fluid flow unit configured to direct a solution comprising a plurality of nucleotides to the array during rotation of the substrate, wherein the plurality of nucleotides comprises natural nucleotides and/or non-natural nucleotides; a detector in sensing communication with the planar array; and one or more computer processors operatively coupled to the fluid flow unit and the detector, wherein the one or more computer processors are individually or collectively programmed to (i) direct the fluid flow unit to direct the solution comprising the plurality of nucleotides across the array during rotation of the array; (ii) subject the nucleic acid molecule to a primer extension reaction under conditions sufficient to incorporate one or more nucleotides of the plurality of nucleotides into a growing strand that is complementary to the nucleic acid molecule; and (iii) use the detector to detect one or more signals indicative of incorporation of the one or more nucleotides, thereby sequencing the nucleic acid molecule.

In an aspect, an optical system for continuous area scanning of a substrate during rotational motion of the substrate, wherein the rotational motion is with respect to an axis of the substrate, may comprise: a focal plane segmented into a plurality of regions; one or more sensors in optical communication with the plurality of regions; and a controller operatively coupled to the one or more sensors, wherein the controller is programmed to process optical signals from each region of the plurality of regions with independent clocking during the rotational motion, wherein the independent clocking is based at least in part on a distance of each region from a projection of the axis and an angular velocity of the rotational motion.

The focal plane may be segmented into the plurality of regions along an axis substantially normal to a projected direction of the rotational motion. The focal plane may be segmented into the plurality of regions along an axis parallel to a projected direction of the rotational motion. The focal plane may be optically segmented.

A given sensor of the one or more sensors may be configured to process each region of the plurality of regions with independent clocking during the rotational motion. The one or more sensors may be a plurality of sensors, wherein each of the plurality of sensors is in optical communication with a different region of the plurality of regions, and wherein the controller is configured to process optical signals from each of the plurality of regions with independent clocking during the rotational motion. The one or more sensors may comprise one or more time delay and integration (TDI), pseudo-TDI rapid frame rate, charge coupled device (CCD), or complementary metal oxide semiconductor (CMOS) detectors. The independent clocking may comprise TDI line rate or pseudo-TDI frame rate. A sensor may comprise a TDI line-scan camera.

One or more of the sensors may be configured to be in optical communication with at least 2 of the plurality of regions in the focal plane. One or more of the sensors may comprise a plurality of segments. Each segment of the plurality of segments may be in optical communication with a region of the plurality of regions. Each segment of the plurality of segments may be independently clocked. The independent clocking of a segment may correspond to a velocity of an image in an associated region of the focal plane.

The optical system may further comprise an optical imaging objective configured to be immersed in a fluid. The optical system may further comprise an enclosure encircling the optical imaging objective. The optical system may further comprise a fluidic line coupled to the enclosure, the fluidic line configured to provide a fluid to the enclosure. The fluid may be in contact with the substrate. The fluid may be confined or controlled, such as by using an electrical field controlling the hydrophobicity of one or more of regions on the substrate and/or a fluid enclosure.

In an aspect, an optical system for imaging a substrate during rotational motion of the substrate, wherein the rotational motion is with respect to an axis of the support, may comprise: a sensor; and an optical element in optical communication with the sensor, wherein the optical element is configured to direct optical signals from the substrate to the sensor, and wherein at least one of the sensor and the optical element is configured to generate an optical magnification gradient across the detector along a direction substantially perpendicular to a projected direction of the rotational motion. The system may further comprise a controller operatively coupled to the detector and the optical element, wherein the controller is programmed to direct adjustment of at least one of the sensor and the optical element to generate the optical magnification gradient across the sensor along the direction substantially perpendicular to a projected direction of the rotational motion.

The optical element may be a lens. The controller may be programmed to direct adjustment of at least one of the sensor and the optical element to produce an anamorphic optical magnification gradient. A ratio of (i) a first optical magnification at a first radial position of a field dimension having a least distance in the field dimension from a projection of the axis to (ii) a second optical magnification at a second radial position of the field dimension having a greatest distance in the field dimension from the projection of the axis may be substantially equal to a ratio of the greatest distance to the least distance. The optical magnification gradient may be generated by rotation of the optical element and a focal plane substantially perpendicular to the projected direction of the rotational motion. The controller may be programmed to direct rotation of the optical element. The controller may be programmed to direct adjustment the gradient of magnification based at least in part on a radial range of a field dimension relative to a projection of the axis. The controller may be programmed to subject the rotational motion to the substrate.

The optical system may further comprise an optical imaging objective configured to be immersed in a fluid. The optical system may further comprise an enclosure encircling the optical imaging objective. The optical system may further comprise a fluidic line coupled to the enclosure, the fluidic line configured to provide a fluid to the enclosure. The fluid may be in contact with the substrate.

In an aspect, an optical system for imaging a substrate during rotational motion of the substrate, wherein the rotational motion is with respect to an axis of the support, may comprise: a plurality of sensors, each sensor of the plurality of sensors in optical communication with the substrate; and a controller operatively coupled to each sensor of the plurality of sensors, wherein the controller is programmed to direct each sensor of the plurality of sensors along an imaging path, wherein an imaging path for one or more sensors of the plurality of sensors is distinct from an imaging path of another sensor of the plurality of sensors. The controller may be programmed to direct each sensor of the plurality of sensors along an imaging path having a spiral shape or a ring shape. Each sensor of the plurality of sensors may be configured to receive light having a wavelength in a predetermined wavelength range.

The optical system may further comprise an optical imaging objective configured to be immersed in a fluid. The optical system may further comprise an enclosure encircling the optical imaging objective. The optical system may further comprise a fluidic line coupled to the enclosure, the fluidic line configured to provide a fluid to the enclosure.

In an aspect, a method for processing an analyte may comprise: (a) providing a substrate comprising a planar array having immobilized thereto said analyte, wherein said substrate is configured to rotate with respect to an axis; (b) directing a solution comprising a plurality of adaptors across said planar array during rotation of said substrate; (c) subjecting said analyte to conditions sufficient to cause a reaction between said analyte and said plurality of adaptors; and (d) detecting a signal indicative of said reaction between said analyte and said plurality of adaptors, thereby analyzing said analyte.

The planar array may comprise two or more types of analytes. The two or more types of analytes may be arranged randomly. The two or more types of analytes may be arranged in a regular pattern. The analyte may be a single cell analyte. The analyte may be a nucleic acid molecule. The analyte may be a protein molecule. The analyte may be a single cell. The analyte may be a particle. The analyte may be an organism. The analyte may be part of a colony. The analyte may be immobilized in an individually addressable location on the planar array.

The plurality of adaptors may comprise a plurality of probes. A given probe of the plurality of probes may be oligonucleotides 1 to 10 bases in length. A given probe may be a dibase probe. A given probe may be 10 to 20 bases in length. The plurality of probes may be labeled.

The substrate may comprise a linker that is coupled to the analyte. The linker may comprise a carbohydrate molecule. The linker may comprise an affinity binding protein. The linker may be hydrophilic. The linker may be hydrophobic. The linker may be electrostatic. The linker may be labeled. The linker may be integral to the substrate. The linker may be an independent layer on the substrate.

The method may further comprise, prior to (a), directing the analyte across the substrate comprising the linker. The analytic may be coupled to a bead, which bead is immobilized to the planar array. The planar array may be in fluid communication with at least one sample inlet and at least one sample outlet. The solution may be directed to the planar array using one or more dispensing nozzles. The one or more nozzles may be directed at or in proximity of the center of the substrate.

The method may further comprise recycling a subset of the solution that has contacted the substrate. The recycling may comprise collecting, filtering, and reusing the subset of the solution. The filtering may be molecular filtering.

The planar array may comprise a plurality of individually addressable locations. The planar array may be textured. The planar array may be a patterned array.

The signal may be an optical signal. The signal may be a fluorescence signal. The signal may be a light absorption signal. The signal may be a light scattering signal. The signal may be a luminescent signal. The signal may be a phosphorescence signal. The signal may be an electrical signal. The signal may be an acoustic signal. The signal may be a magnetic signal.

The method may further comprise, prior to (b), subjecting the substrate to rotation with respect to the axis. The method may further comprise terminating rotation of the substrate prior to detecting the signal in (d). The signal may be detected in (d) while the substrate is rotating.

The signal may be generated by binding of a label to the analyte. The label may be bound to a molecule, particle, cell, or organism. The label may be bound to the molecule, particle, cell, or organism prior to (a). The label may be bound to the molecule, particle, cell, or organism subsequent to (a). The signal may be generated by formation of a detectable product by a chemical reaction. The reaction may comprise an enzymatic reaction. The signal may be generated by formation of a detectable product by physical association. The signal may be generated by formation of a detectable product by proximity association. The proximity association may comprise Förster resonance energy transfer (FRET). The proximity association may comprise association with a complementation enzyme. The signal may be generated by a single reaction. The signal may be generated by a plurality of reactions. The plurality of reactions may occur in series. The plurality of reactions may occur in parallel. The plurality of reactions may comprise one or more repetitions of a reaction. The reaction may comprise a hybridization reaction or ligation reaction. The reaction may comprise a hybridization reaction and a ligation reaction.

The plurality of adaptors may comprise a plurality of carbohydrate molecules. The plurality of adaptors may comprise a plurality of lipid molecules. The plurality of adaptors may comprise a plurality of affinity binding proteins. The plurality of adaptors may comprise a plurality of aptamers. The plurality of adaptors may comprise a plurality of antibodies. The plurality of adaptors may be hydrophilic. The plurality of adaptors may be hydrophobic. The plurality of adaptors may be electrostatic. The plurality of adaptors may be labeled. The plurality of adaptors may comprise a plurality of oligonucleotide molecules. The plurality of adaptors may comprise a random sequence. The plurality of adaptors may comprise a targeted sequence. The plurality of adaptors may comprise a repeating sequence. The repeating sequence may be a homopolymer sequence.

The method may further comprise repeating (b)-(d) one or more times. Different solutions may be directed to the planar array during rotation of the substrate for consecutive cycles.

In an aspect, a method for analyte detection or analysis may comprise: (a) rotating an open substrate about a central axis, the open substrate having an array of immobilized analytes thereon; (b) delivering a solution having a plurality of probes to a region proximal to the central axis to introduce the solution to the open substrate; (c) dispersing the solution across the open substrate at least by centrifugal force such that at least one of the plurality of probes binds to at least one of the immobilized analytes to form a bound probe; and (d) during rotation of the open substrate, simultaneously using a first detector to perform a first scan of the open substrate along a first set of one or more scan paths and a second detector to perform a second scan of the open substrate along a second set of one or more scan paths, wherein the first set of one or more scan paths and the second set of one or more scan paths are different, wherein the first detector or the second detector detects at least one signal from the bound probe, wherein the first detector is disposed at a first radial position relative to the central axis, wherein the second detector is disposed at a second radial position relative to the central axis, and wherein the first detector and the second detector undergo relative motion with respect to the central axis along a same linear vector, to generate the first set of one or more scan paths and the second set of one or more scan paths, respectively. The relative motion along the same linear vector may common relative motion with respect to the central axis.

In some embodiments, the first detector and the second detector operate at different scan rates. In some embodiments, the different scan rates of the first detector and the second detector are a function of the first radial position and the second radial position, respectively.

In some embodiments, the first set of one or more scan paths comprises a plurality of circular scan paths having different radii. In some embodiments, the first set of one or more scan paths comprises a spiral scan path.

In some embodiments, the same linear vector is in a radial direction through the central axis. In some embodiments, the same linear vector is not in a radial direction. In some embodiments, the method further comprises compensating for velocity direction differences of different areas at different radial positions with respect to the central axis, wherein a given scan path of the first set of one or more scan paths comprises the different areas. In some embodiments, the compensating comprises using one or more prisms, using one or more mirrors, and/or rotating one or more sensors.

In some embodiments, the first detector and the second detector are substantially stationary during the relative motion. In some embodiments, the open substrate undergoes both rotational and translational motion during the relative motion. In some embodiments, the first detector and the second detector undergo common motion during the relative motion. In some embodiments, (i) the open substrate undergoes rotational motion relative to the first detector and the second detector and (ii) the first detector and the second detector undergo linear motion relative to the central axis. The linear motion can be perpendicular to the central axis. In some embodiments, the first detector undergoes the relative motion during scanning (e.g., rotational scanning) of the open substrate. In some embodiments, the first detector undergoes the relative motion when not scanning (e.g., rotational scanning).

In some embodiments, a given scan path of the first set of one or more scan paths includes an area scanned during the relative motion along the same linear vector. In some embodiments, the first set of one more scan paths does not include an area scanned during the relative motion along the same linear vector.

In some embodiments, the first detector and the second detector have the same angular position relative to the central axis. In some embodiments, the first detector and the second detector have different angular positions relative to the central axis. In some embodiments, the first detector and the second detector have opposite angular positions relative to the central axis.

In some embodiments, a given scan path of the first set of one or more scan paths includes a first area and a second area, wherein the first area and the second area are at different radial positions of the open substrate with respect to the central axis, and wherein the first area and the second area are spatially resolved by the first detector.

In an aspect, the present disclosure provides a method for storing a substrate comprising a nucleic acid molecule-coated surface, comprising: (a) providing the substrate having a surface comprising a first set of nucleic acid molecules immobilized thereto, wherein nucleic acid molecules of the first set of nucleic acid molecules are configured to capture sample nucleic acid molecules derived from one or more nucleic acid samples; (b) bringing the substrate comprising the surface comprising the first set of nucleic acid molecules into contact with a second set of nucleic acid molecules under conditions sufficient to yield a treated surface in which at least 90% of nucleic acid molecules of the first set of nucleic acid molecules are hybridized to nucleic acid molecules of the second set of nucleic acid molecules, wherein the second set of nucleic acid molecules are not the sample nucleic acid molecules; and (c) storing the substrate having the treated surface for a time period of at least 1 hour.

In some embodiments, the method further comprises, subsequent to (c), removing the nucleic acid molecules of the second set of nucleic acid molecules from the treated surface. In some embodiments, the method further comprises, subsequent to the removing, using the first set of nucleic acid molecules immobilized to the surface for hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof. In some embodiments, the nucleic acid molecules of the second set of nucleic acid molecules are removed from the treated surface via enzymatic degradation. In some embodiments, the nucleic acid molecules of the second set of nucleic acid molecules are removed from the treated surface via denaturing via chemical or thermal stimulation. In some embodiments, a chemical stimulus is used to remove the nucleic acid molecules of the second set of nucleic acid molecules from the treated surface. In some embodiments, the chemical stimulus comprises sodium hydroxide.

In some embodiments, during storage of the treated surface, each nucleic acid molecule of the first set of nucleic acid molecules that is hybridized to a nucleic acid molecule of the second set of nucleic acid molecules does not hybridize to another nucleic acid molecule.

In some embodiments, at least 95% of nucleic acid molecules of the first set of nucleic acid molecules are hybridized to nucleic acid molecules of the second set of nucleic acid molecules. In some embodiments, the treated surface is stored at temperatures between about 18° C. to about 30° C.

In some embodiments, the treated surface is stored for at least 6 hours. In some embodiments, the treated surface is stored for at least 24 hours. In some embodiments, the treated surface is stored for at least 2 days.

In some embodiments, the second set of nucleic acid molecules is provided to the surface of the substrate in a solution. In some embodiments, each nucleic acid molecule of the second set of nucleic acid molecules comprises a sequence that is substantially complementary to a sequence of the first set of nucleic acid molecules. In some embodiments, the sequence of the first set of nucleic acid molecules comprises at least 6 bases.

In some embodiments, the nucleic acid molecules of the first set of nucleic acid molecules are immobilized to the surface at independently addressable locations. In some embodiments, the independently addressable locations are substantially planar. In some embodiments, the independently addressable locations comprise one or more wells. In some embodiments, the nucleic acid molecules of the first set of nucleic acid molecules are immobilized to the surface of the substrate according to a predetermined pattern. In some embodiments, a density of the first set of nucleic acid molecules on the surface is at least 1,000,000 molecules per mm$^2$.

In some embodiments, each nucleic acid molecule of the first set of nucleic acid molecules comprises the same nucleic acid sequence. In some embodiments, the first set of nucleic acid molecules comprises one or more different nucleic acid sequences. In some embodiments, the first set of nucleic acid molecules comprises a first subset of nucleic acid molecules comprising a first nucleic acid sequence and a second subset of nucleic acid molecules comprising a second nucleic acid sequence, which first and second nucleic acid sequences are different. In some embodiments, the first subset of nucleic acid molecules and the second subset of nucleic acid molecules both comprise a third nucleic acid sequence. In some embodiments, the third nucleic acid sequence comprises a poly(T) sequence.

In some embodiments, the second set of nucleic acid molecules comprises DNA nucleotides. In some embodiments, the second set of nucleic acid molecules comprises RNA nucleotides. In some embodiments, the second set of nucleic acid molecules comprises a mixture of RNA and DNA nucleotides. In some embodiments, each nucleic acid molecule of the second set of nucleic acid molecules comprises at least 6 bases.

In some embodiments, the surface of the substrate is substantially planar. In some embodiments, the substrate comprises one or more particles immobilized thereto.

In another aspect, the present disclosure provides a method for nucleic acid processing, comprising: (a) providing a substrate having a treated surface comprising a first set of nucleic acid molecules immobilized thereto, wherein at least 90% of nucleic acid molecules of the first set of nucleic acid molecules are hybridized to nucleic acid molecules of a second set of nucleic acid molecules, wherein nucleic acid molecules of the first set of nucleic acid molecules are configured to capture sample nucleic acid molecules derived from one or more nucleic acid samples, wherein the second set of nucleic acid molecules are not the sample nucleic acid molecules, and wherein the substrate having the treated substrate has been stored for a time period of at least 1 hour; and (b) removing the nucleic acid molecules of the second set of nucleic acid molecules from the treated surface.

In some embodiments, the method further comprises, subsequent to (b), using the first set of nucleic acid molecules immobilized to the surface for hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof. In some embodiments, the nucleic acid molecules of the second set of nucleic acid molecules are removed from the treated surface via enzymatic degradation. In some embodiments, the nucleic acid molecules of the second set of nucleic acid molecules are removed from the treated surface via denaturing via chemical or thermal stimulation. In some embodiments, a chemical stimulus is used to remove the nucleic acid molecules of the second set of nucleic acid molecules from the treated surface. In some embodiments, the chemical stimulus comprises sodium hydroxide.

In some embodiments, during storage of the treated surface, each nucleic acid molecule of the first set of nucleic acid molecules that is hybridized to a nucleic acid molecule of the second set of nucleic acid molecules does not hybridize to another nucleic acid molecule.

In some embodiments, at least 95% of nucleic acid molecules of the first set of nucleic acid molecules are hybridized to nucleic acid molecules of the second set of nucleic acid molecules.

In some embodiments, the treated surface has been stored at temperatures between about 18° C. to about 30° C. In some embodiments, the treated surface has been stored for a time period of at least 6 hours. In some embodiments, the treated surface has been stored for a time period of at least 24 hours. In some embodiments, the treated surface has been stored for a time period of at least 2 days.

In some embodiments, each nucleic acid molecule of the second set of nucleic acid molecules comprises a sequence that is substantially complementary to a sequence of the first set of nucleic acid molecules. In some embodiments, the sequence of the first set of nucleic acid molecules comprises at least 6 bases.

In some embodiments, the nucleic acid molecules of the first set of nucleic acid molecules are immobilized to the surface at independently addressable locations. In some embodiments, the independently addressable locations are substantially planar. In some embodiments, the independently addressable locations comprise one or more wells. In some embodiments, the nucleic acid molecules of the first set of nucleic acid molecules are immobilized to the surface of the substrate according to a predetermined pattern. In some embodiments, a density of the first set of nucleic acid molecules on the surface is at least 1,000,000 molecules per $mm^2$.

In some embodiments, each nucleic acid molecule of the first set of nucleic acid molecules comprises the same nucleic acid sequence. In some embodiments, the first set of nucleic acid molecules comprises one or more different nucleic acid sequences. In some embodiments, the first set of nucleic acid molecules comprise a first subset of nucleic acid molecules comprising a first nucleic acid sequence and a second subset of nucleic acid molecules comprising a second nucleic acid sequence, which first and second nucleic acid sequences are different. In some embodiments, the first subset of nucleic acid molecules and the second subset of nucleic acid molecules both comprise a third nucleic acid sequence. In some embodiments, the third nucleic acid sequence comprises a poly(T) sequence.

In some embodiments, the second set of nucleic acid molecules comprises DNA nucleotides. In some embodiments, the second set of nucleic acid molecules comprises RNA nucleotides. In some embodiments, the second set of nucleic acid molecules comprises a mixture of RNA and DNA nucleotides. In some embodiments, each nucleic acid molecule of the second set of nucleic acid molecules comprises at least 6 bases.

In some embodiments, the surface of the substrate is substantially planar. In some embodiments, the substrate comprises one or more particles immobilized thereto.

In a further aspect, the present disclosure provides a kit comprising: a substrate comprising a treated surface, wherein the treated surface comprises a plurality of pairs of bound nucleic acid molecules, wherein each pair of the plurality of pairs comprises a first nucleic acid molecule of a first set of nucleic acid molecules at least partially hybridized to a second nucleic acid molecule of a second set of nucleic acid molecules, wherein the first set of nucleic acid molecules is immobilized to the surface, wherein at least 90% of nucleic acid molecules of the first set of nucleic acid molecules are paired with a nucleic acid molecule of the second set of nucleic acid molecules, wherein nucleic acid molecules of the first set of nucleic acid molecules are configured to capture sample nucleic acid molecules derived from one or more nucleic acid samples when the nucleic acid molecules of the first set of nucleic acid molecules are not paired with nucleic acid molecules of the second set of nucleic acid molecules.

In some embodiments, the treated surface is stored for at least 24 hours. In some embodiments, the treated surface is stored for at least 2 days. In some embodiments, during storage of the treated surface, each nucleic acid molecule of the first set of nucleic acid molecules in the each pair of the plurality of pairs does not hybridize to another nucleic acid molecule.

In some embodiments, the kit further comprises a chemical stimulus configured to remove second nucleic acid molecules from the treated surface. In some embodiments, the chemical stimulus comprises sodium hydroxide.

In some embodiments, at least 95% of nucleic acid molecules of the first set of nucleic acid molecules are at least partially hybridized to nucleic acid molecules of the second set of nucleic acid molecules. In some embodiments, the treated surface is stored at temperatures between about 18° C. to about 30° C.

In some embodiments, the second nucleic acid molecule comprises a sequence that is substantially complementary to a sequence of the first nucleic acid molecule. In some embodiments, the sequence of the first nucleic acid molecule comprises at least 6 bases. In some embodiments, the sequence of the second nucleic acid molecule comprises at least 6 bases. In some embodiments, the first nucleic acid molecule and the second nucleic acid molecule comprise the same number of nucleotides. In some embodiments, the first nucleic acid molecule and the second nucleic acid molecule comprise different numbers of nucleotides.

In some embodiments, nucleic acid molecules of the first set of nucleic acid molecules are immobilized to the surface at independently addressable locations. In some embodiments, the independently addressable locations are substantially planar. In some embodiments, the independently addressable locations comprise one or more wells. In some embodiments, a density the first set of nucleic acid molecules on the surface is at least 1,000,000 molecules per mm$^2$.

In some embodiments, each nucleic acid molecule of the first set of nucleic acid molecules comprises the same nucleic acid sequence. In some embodiments, the first set of nucleic acid molecules comprises one or more different nucleic acid sequences. In some embodiments, the first set of nucleic acid molecules comprises a first subset of nucleic acid molecules comprising a first nucleic acid sequence and a second subset of nucleic acid molecules comprising a second nucleic acid sequence, which first and second nucleic acid sequences are different. In some embodiments, the first subset of nucleic acid molecules and the second subset of nucleic acid molecules both comprise a third nucleic acid sequence. In some embodiments, the third nucleic acid sequence comprises a poly(T) sequence.

In some embodiments, the second set of nucleic acid molecules comprises DNA nucleotides. In some embodiments, the second set of nucleic acid molecules comprises RNA nucleotides. In some embodiments, the second set of nucleic acid molecules comprises a mixture of RNA and DNA nucleotides. In some embodiments, each nucleic acid molecule of the second set of nucleic acid molecules comprises at least 6 bases.

In some embodiments, the surface of the substrate is substantially planar. In some embodiments, the surface of the substrate comprises a plurality of wells. In some embodiments, the substrate comprises one or more particles immobilized thereto.

In another aspect, the present disclosure provides a kit comprising: a substrate comprising a surface comprising a first set of nucleic acid molecules immobilized thereto, wherein the first set of nucleic acid molecules comprises one or more first nucleic acid molecules, which one or more first nucleic acid molecules are configured to capture sample nucleic acid molecules derived from one or more nucleic acid samples; and a solution comprising a second set of nucleic acid molecules, wherein the second set of nucleic acid molecules comprises one or more second nucleic acid molecules, which one or more second nucleic acid molecules are not the sample nucleic acid molecules; wherein the second set of nucleic acid molecules is selected such that, upon bringing the solution in contact with the surface, at least 70% of the one or more first nucleic acid molecules bind to a second nucleic acid molecule of the second set of nucleic acid molecules to generate one or more pairs of bound nucleic acid molecules, wherein each pair of the one or more pairs comprises (i) a first nucleic acid molecule of the first set of nucleic acid molecules and a second nucleic acid molecule of the second set of nucleic acid molecules, and (ii) a section of substantially complementary sequences.

In some embodiments, the kit further comprises a chemical stimulus configured to remove second nucleic acid molecules from the surface. In some embodiments, the chemical stimulus comprises sodium hydroxide.

In some embodiments, upon bringing the solution in contact with the surface, at least 90% of the one or more first nucleic acid molecules of the first set of nucleic acid molecules bind to a second nucleic acid molecule of the second set of nucleic acid molecules.

In some embodiments, each nucleic acid molecule of the first set of nucleic acid molecules in each pair of the one or more pairs does not hybridize to another nucleic acid molecule.

In some embodiments, the section of substantially complementary sequences of each pair of the one or more pairs comprises a first sequence of a first nucleic acid molecule of the one or more first nucleic acid molecules and a second sequence of a second nucleic acid molecule of the one or more second nucleic acid molecules, which first sequence is substantially complementary to the second sequence. In some embodiments, the first sequence and the second sequence each comprise between about 6-20 bases. In some embodiments, a first nucleic acid molecule of the one or more first nucleic acid molecules and a second nucleic acid molecule of the one or more second nucleic acid molecules have the same number of nucleotides. In some embodiments, a first nucleic acid molecule of the one or more first nucleic acid molecules and a second nucleic acid molecule of the one or more second nucleic acid molecules have different numbers of nucleotides.

In some embodiments, the first set of nucleic acid molecules is immobilized to the surface at independently addressable locations. In some embodiments, the independently addressable locations are substantially planar. In some embodiments, the independently addressable locations comprise one or more wells. In some embodiments, the first set of nucleic acid molecules is immobilized to the surface according to a predetermined pattern. In some embodiments, a density the first set of nucleic acid molecules on the surface is at least 1,000,000 molecules per mm$^2$.

In some embodiments, the first set of nucleic acid molecules comprises one or more different nucleic acid sequences. In some embodiments, the first set of nucleic acid molecules comprises a first subset of nucleic acid molecules comprising a first nucleic acid sequence and a second subset of nucleic acid molecules comprising a second nucleic acid sequence, which first and second nucleic acid sequences are different. In some embodiments, the first subset of nucleic acid molecules and the second subset of nucleic acid molecules both comprise a third nucleic acid sequence. In some embodiments, the third nucleic acid sequence comprises a poly(T) sequence.

In some embodiments, the second set of nucleic acid molecules comprises DNA nucleotides. In some embodiments, the second set of nucleic acid molecules comprises RNA nucleotides. In some embodiments, the second set of nucleic acid molecules comprises a mixture of RNA and DNA nucleotides. In some embodiments, each nucleic acid molecule of the second set of nucleic acid molecules comprises at least 6 bases.

In some embodiments, the surface of the substrate is substantially planar. In some embodiments, the surface of the substrate comprises a plurality of wells. In some embodiments, the substrate comprises one or more particles immobilized thereto.

In another aspect, the present disclosure provides a method for storing a substrate comprising a nucleic acid molecule-coated surface, comprising: (a) providing a substrate having a surface comprising a first set of nucleic acid molecules immobilized thereto, wherein nucleic acid molecules of the first set of nucleic acid molecules are configured to capture sample nucleic acid molecules derived from one or more nucleic acid samples, and wherein each nucleic acid molecule of the first set of nucleic acid molecules comprises a first nucleic acid sequence and a second nucleic acid sequence, which second nucleic acid sequence is substantially complementary to the first nucleic acid sequence; (b) generating a treated surface by subjecting the surface to conditions sufficient to bind the first nucleic acid sequence of a nucleic acid molecule of the first set of nucleic acid molecules to the second nucleic acid sequence of the nucleic acid molecule to provide an immobilized hairpin molecule; and (c) storing the substrate having the treated surface for a time period of at least 1 hour.

In some embodiments, the method further comprises subsequent to (c), separating the second sequence from the first sequence of the immobilized hairpin molecule. In some embodiments, the separating comprises an enzymatic degradation or denaturation using a chemical or thermal stimulus. In some embodiments, the chemical stimulus comprises sodium hydroxide.

In some embodiments, the method further comprises subsequent to the separating, using the first set of nucleic acid molecules immobilized to the surface for hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof.

In some embodiments, each nucleic acid molecule of the first set of nucleic acid molecules comprises a cleavable base, which cleavable base is disposed between the first sequence and the second sequence of the nucleic acid molecule. In some embodiments, the method further comprises, subsequent to separating the second sequence from the first sequence of the immobilized hairpin molecule, cleaving the nucleic acid molecule at the cleavable base, thereby removing the second sequence of the nucleic acid molecule from the surface. In some embodiments, during storage of the treated surface, each nucleic acid molecule of the first set of nucleic acid molecules does not hybridize to another nucleic acid molecule. In some embodiments, during storage of the treated surface, at least 70% of nucleic acid molecules of the first set of nucleic acid molecules are present as immobilized hairpin molecules.

In some embodiments, the treated surface is stored at temperatures between about 18° C. to about 30° C. In some embodiments, the treated surface is stored for at least 6 hours. In some embodiments, the treated surface is stored for at least 24 hours.

In some embodiments, the first sequence and the second sequence each comprise at least 6 bases.

In some embodiments, the nucleic acid molecules of the first set of nucleic acid molecules are immobilized to the surface at independently addressable locations. In some embodiments, the independently addressable locations are substantially planar. In some embodiments, the independently addressable locations comprise one or more wells. In some embodiments, a density the first set of nucleic acid molecules on the surface is at least 1,000,000 molecules per $mm^2$.

In some embodiments, the first set of nucleic acid molecules comprises one or more different nucleic acid sequences. In some embodiments, the first set of nucleic acid molecules comprises a first subset of nucleic acid molecules comprising the first nucleic acid sequence and the second nucleic acid sequence and a second subset of nucleic acid molecules comprising a third nucleic acid sequence and a fourth nucleic acid sequence, which third nucleic acid sequence is substantially complementary to the fourth nucleic acid sequences, and which first nucleic acid sequence is different from the third and fourth nucleic acid sequences. In some embodiments, the first subset of nucleic acid molecules and the second subset of nucleic acid molecules both comprise a fifth nucleic acid sequence. In some embodiments, the fifth nucleic acid sequence comprises a poly(T) sequence.

In some embodiments, the surface of the substrate is substantially planar. In some embodiments, the surface of the substrate comprises a plurality of wells. In some embodiments, the substrate comprises one or more particles immobilized thereto.

In a further aspect, the present disclosure provides a method for storing a substrate comprising an nucleic acid molecule-coated surface, comprising: (a) providing a substrate having a surface comprising a first set of nucleic acid molecules immobilized thereto, wherein nucleic acid molecules of the first set of nucleic acid molecules are configured to capture sample nucleic acid molecules derived from one or more nucleic acid samples, and wherein each nucleic acid molecule of the nucleic acid molecules of the first set of nucleic acid molecules comprises a first nucleic acid sequence; (b) providing a second set of nucleic acid molecules, wherein each nucleic acid molecule of the second set of nucleic acid molecules comprises a second nucleic acid sequence that is substantially complementary to the first nucleic acid sequence, and wherein the second set of nucleic acid molecules are not the sample nucleic acid molecules; (c) bringing the surface comprising the first set of nucleic acid molecules into contact with the second set of nucleic acid molecules to generate a treated surface in which at least 70% of nucleic acid molecules of the first set of nucleic acid molecules are hybridized to nucleic acid molecules of the second set of nucleic acid molecules; and (d) storing the treated surface for at least one hour, wherein, for each nucleic acid molecule of the first set of nucleic acid molecules hybridized to a nucleic acid molecule of the second set of nucleic acid molecules, the first nucleic acid sequence is hybridized to the second nucleic acid sequence, and wherein the first nucleic acid sequence hybridized to the second nucleic acid sequence at least partially denatures between about 40° C. and 60° C.

In some embodiments, the first nucleic acid sequence hybridized to the second nucleic acid sequence at least partially denatures between about 50° C. and 60° C.

In some embodiments, the method further comprises, subsequent to (d), removing the nucleic acid molecules of the second set of nucleic acid molecules from the treated surface. In some embodiments, the method further comprises, subsequent to the removing, using the first set of nucleic acid molecules immobilized to the surface for hybridization capture, single nucleotide polymorphism (SNP) genotyping, sequencing library capture, synthesis of nucleic acid molecules, on-surface amplification, downstream processing or analysis of nucleic acid molecules or derivative thereof, or combinations thereof. In some embodiments, the nucleic acid molecules of the second set of nucleic acid molecules are removed from the treated surface via enzymatic degradation. In some embodiments, the nucleic acid molecules of the second set of nucleic acid molecules are removed from the treated surface via dena- turing via chemical or thermal stimulation. In some embodi- ments, the nucleic acid molecules of the second set of nucleic acid molecules are removed from the treated surface by denaturing the first nucleic acid sequence hybridized to the second nucleic acid sequence. In some embodiments, the nucleic acid molecules of the second set of nucleic acid molecules are removed from the treated surface by heating the treated surface to between about 40° C. and 60° C. In some embodiments, the nucleic acid molecules of the sec- ond set of nucleic acid molecules are removed from the treated surface by heating a solution in contact with the treated surface to between about 40° C. and 60° C. In some embodiments, a chemical stimulus is used to remove the nucleic acid molecules of the second set of nucleic acid molecules from the treated surface. In some embodiments, the chemical stimulus comprises sodium hydroxide.

In some embodiments, during storage of the treated surface, each nucleic acid molecule of the first set of nucleic acid molecules that is hybridized to a nucleic acid molecule of the second set of nucleic acid molecules does not hybrid- ize to another nucleic acid molecule. In some embodiments, at least 90% of nucleic acid molecules of the first set of nucleic acid molecules are hybridized to nucleic acid mol- ecules of the second set of nucleic acid molecules.

In some embodiments, the treated surface is stored at temperatures between about 18° C. to about 30° C. In some embodiments, the treated surface is stored for at least 6 hours. In some embodiments, the treated surface is stored for at least 24 hours. In some embodiments, the treated surface is stored for at least 2 days.

In some embodiments, the second set of nucleic acid molecules is provided to the surface in a solution.

In some embodiments, the first nucleic acid sequence and the second nucleic acid sequence each comprise at least 6 bases. In some embodiments, a given nucleic acid molecule of the first set of nucleic acid molecules and a given nucleic acid molecule of the second set of nucleic acid molecules comprise the same number of nucleotides. In some embodi- ments, a given nucleic acid molecule of the first set of nucleic acid molecules and a given nucleic acid molecule of the second set of nucleic acid molecules comprise different numbers of nucleotides.

In some embodiments, the first set of nucleic acid mol- ecules is immobilized to the surface at independently addressable locations. In some embodiments, the indepen- dently addressable locations are substantially planar. In some embodiments, the independently addressable locations comprise one or more wells. In some embodiments, the first set of nucleic acid molecules is immobilized to the surface according to a predetermined pattern. In some embodiments, a density the first set of nucleic acid molecules on the surface is at least 1,000,000 molecules per mm².

In some embodiments, the first set of nucleic acid mol- ecules comprises one or more different nucleic acid sequences. In some embodiments, the first set of nucleic acid molecules comprises a first subset of nucleic acid molecules comprising the first nucleic acid sequence and a second subset of nucleic acid molecules comprising a third nucleic acid sequence, which first and third nucleic acid sequences are different. In some embodiments, the first subset of nucleic acid molecules and the second subset of nucleic acid molecules both comprise a fourth nucleic acid sequence. In some embodiments, the fourth nucleic acid sequence com- prises a poly(T) sequence.

In some embodiments, the second set of nucleic acid molecules comprises DNA nucleotides. In some embodi- ments, the second set of nucleic acid molecules comprises RNA nucleotides. In some embodiments, the second set of nucleic acid molecules comprises a mixture of RNA and DNA nucleotides. In some embodiments, each nucleic acid molecule of the second set of nucleic acid molecules com- prises at least 6 bases.

In some embodiments, the surface of the substrate is substantially planar. In some embodiments, the surface of the substrate comprises a plurality of wells. In some embodi- ments, the substrate comprises one or more particles immo- bilized thereto.

In another aspect, the present disclosure provides a method for detecting or analyzing an analyte, comprising: (a) providing an open substrate comprising a central axis, the open substrate comprising an array of analytes immobilized adjacent to the open substrate, wherein at least one analyte of the array of analytes is bound to a probe; and (b) using a detector system to perform a non-linear scan of the open substrate to detect at least one signal or signal change from the bound probe, wherein the detector system comprises a line-scan camera and an illumination source, wherein the illumination source is configured to generate an illuminated region on the open substrate, wherein the open substrate comprises a first area and a second area, wherein the first area and the second area: (i) comprise different subsets of the array of analytes, (ii) are at different radial positions of the open substrate with respect to the central axis, and (iii) are spatially resolved by the detector system; and wherein the bound probe is disposed in the first area of the open substrate, and wherein the non-linear scan is performed during relative non-linear motion between the open substrate and one or both of (i) the line-scan camera and (ii) the illuminated region.

In some embodiments, the illuminated region has a maxi- mum dimension of at most about 2 millimeters. In some embodiments, the illuminated region has a maximum width of at most about 0.5 millimeters.

In some embodiments, the line-scan camera is a time delay and integration line-scan camera. In some embodi- ments, the illumination source comprises a laser. In some embodiments, the laser is a continuous wave laser. In some embodiments, the detector system comprises an optical element configured to change a shape of a beam of light emitted by the laser. In some embodiments, the optical element comprises a cylindrical lens. In some embodiments, the illumination source comprises a light emitting diode.

In some embodiments, during (b), the open substrate is rotating. In some embodiments, during (b), the line-scan camera of the detector system is stationary. In some embodi- ments, during (b), the line-scan camera of the detector system is rotating. In some embodiments, during (b), the illuminated region is rotating. In some embodiments, during (b), the illuminated region is rotating at a same rate as the line-scan camera. In some embodiments, during (b), the line-scan camera of the detector system translates radially across the open substrate. In some embodiments, during (b), the illuminated region translates radially across the open substrate.

In some embodiments, during (b), the open substrate is stationary. In some embodiments, during (b), the line-scan camera of the detector system is rotating. In some embodi- ments, during (b), the illuminated region is rotating. In some embodiments, during (b), the illumination region is rotating at a same rate as the line-scan camera. In some embodiments, during (b), the line-scan camera is stationary. In some embodiments, during (b), the illuminated region of the detector system is rotating. In some embodiments, the detector system further comprises a prism, which prism is rotating during (b).

In some embodiments, the detector system is configured to detect a signal from the illuminated region using the line-scan camera.

In some embodiments, the array of analytes comprises a second analyte bound to an additional probe, which additional probe is disposed in the second area of the open substrate, and wherein during (b), at least one signal or signal change is detected from the additional probe at the same time as the at least one signal or signal change detected from the bound probe.

In some embodiments, the detector system compensates for velocity differences at different radial positions of the array with respect to the central axis within a scanned area. In some embodiments, the detector system comprises an optical imaging system having an anamorphic magnification gradient substantially transverse to a scanning direction along the open substrate, and wherein the anamorphic magnification gradient at least partially compensates for tangential velocity differences that are substantially perpendicular to the scanning direction. In some embodiments, (b) comprises reading two or more regions on the open substrate at two or more different scan rates, respectively, to at least partially compensate for tangential velocity differences in the two or more regions.

In some embodiments, (b) further comprises using an immersion objective lens in optical communication with the detector system and the open substrate to detect the at least one signal or signal change, which immersion objective lens is in contact with a fluid that is in contact with the open substrate. In some embodiments, the fluid is in a container, and wherein an electric field is used to regulate a hydrophobicity of one or more surfaces of the container to retain at least a portion of the fluid contacting the immersion objective lens and the open substrate.

In some embodiments, the array of analytes comprise nucleic acid molecules, wherein the plurality of probes comprises fluorescently labeled nucleotides, and wherein at least one fluorescently labeled nucleotide of the fluorescently labeled nucleotides binds to at least one nucleic acid molecule of the nucleic acid molecules via nucleotide complementarity binding. In some embodiments, the open substrate is substantially planar. In some embodiments, an analyte of the array of analytes is immobilized adjacent to the open substrate through one or more binders. In some embodiments, the open substrate comprises at least 100,000 binders, wherein a binder of the at least 100,000 binders immobilizes an analyte of the array of analytes immobilized adjacent to the open substrate. In some embodiments, an analyte of the array of analytes is coupled to a bead, which bead is immobilized to the open substrate. In some embodiments, an analyte of the array of analytes comprises a nucleic acid molecule. In some embodiments, the plurality of probes comprises a plurality of oligonucleotide molecules. In some embodiments, the plurality of probes comprises a plurality of nucleotides or analogs thereof.

In an additional aspect, the present disclosure provides an apparatus for analyte detection or analysis, comprising: a housing configured to receive an open substrate having an array of analytes immobilized adjacent thereto, wherein at least one analyte of the array of analytes is bound to a probe;

and a detector system, wherein the detector system comprises a line-scan camera and an illumination source, wherein the illumination source is configured to generate an illuminated region on the open substrate, wherein the open substrate comprises a first area and a second area, wherein the first area and the second area: (i) comprise subsets of the array of immobilized analytes, (ii) are at different radial positions of the open substrate with respect to the central axis, and (iii) are spatially resolved by the detector system; wherein the bound probe is disposed in the first area of the open substrate, and wherein the detector system is programmed to perform a non-linear scan of the open substrate and detect at least one signal or signal change from the bound probe at the first area of the open substrate, wherein the non-linear scan is performed during relative non-linear motion between the open substrate and one or both of (i) the line-scan camera and (ii) the illuminated region.

In some embodiments, the illuminated region has a maximum dimension of at most about 2 millimeters. In some embodiments, the illuminated region has a maximum width of at most about 0.5 millimeters.

In some embodiments, the apparatus further comprises a processor programmed to direct the detector system to compensate for velocity differences at different radial positions of the array with respect to the central axis within a scanned area. In some embodiments, the processor is programmed to direct the detector system to scan two or more regions on the open substrate at two or more different scan rates, respectively, to at least partially compensate for tangential velocity differences in the two or more regions.

In some embodiments, the apparatus further comprises one or more optics that are configured to generate an anamorphic magnification gradient substantially transverse to a scanning direction along the open substrate, and wherein the anamorphic magnification gradient at least partially compensates for tangential velocity differences that are substantially perpendicular to the scanning direction. In some embodiments, the apparatus further comprises a processor programmed to adjust the anamorphic magnification gradient to compensate for different imaged radial positions with respect to the central axis.

In some embodiments, the line-scan camera is a time delay and integration line-scan camera. In some embodiments, the illumination source comprises a laser. In some embodiments, the laser is a continuous wave laser. In some embodiments, the detector system comprises an optical element configured to change a shape of a beam of light emitted by the laser. In some embodiments, the optical element comprises a cylindrical lens. In some embodiments, the illumination source comprises a light emitting diode.

In some embodiments, the detector system and the rotational unit are disposed in different areas of the apparatus.

In some embodiments, the apparatus further comprises a rotational unit configured to rotate the detector system or an element thereof, and wherein the detector system is programmed to detect the at least one signal from the bound probe while the line-scan camera of the detector system is rotating. In some embodiments, the detector system is programmed to detect the at least one signal from the bound probe while the illuminated region of the detector system is rotating. In some embodiments, the detector system is programmed to detect the at least one signal from the bound probe while the line-scan camera and the illuminated region are rotating at a same rate.

In some embodiments, the detector system is programmed to detect the at least one signal from the bound probe while the open substrate is stationary. In some embodiments, the detector system is programmed to detect the at least one signal from the bound probe while the open substrate is rotating. In some embodiments, the detector system is programmed to detect the at least one signal from the bound probe while the line-scan camera translates radially across the open substrate. In some embodiments, the detector system is programmed to detect the at least one signal from the bound probe while the illuminated region translates radially across the open substrate. In some embodiments, the detector system further comprises a prism, and wherein the detector system is programmed to detect the at least one signal from the bound probe while the prism is rotating.

In some embodiments, the apparatus further comprises an immersion objective lens in optical communication with the detector system and the open substrate, which immersion objective lens is configured to be in contact with a fluid that is in contact with the open substrate. In some embodiments, the apparatus further comprises a container configured to retain the fluid and an electric field application unit configured to regulate a hydrophobicity of one or more surfaces of the container to retain at least a portion of the fluid contacting the immersion objective lens and the open substrate. In some embodiments, the immersion objective lens separates a first environment from a second environment, wherein the first environment and the second environment have different operating conditions. In some embodiments, the immersion objective lens forms a seal between the first environment and the second environment.

In some embodiments, the open substrate is substantially planar. In some embodiments, an analyte of the array of analytes is immobilized adjacent to the open substrate through one or more binders. In some embodiments, the open substrate comprises at least 100,000 binders, wherein a binder of the at least 100,000 binders immobilizes an analyte of the array of analytes immobilized adjacent to the open substrate. In some embodiments, an analyte of the array of analytes is coupled to a bead, which bead is immobilized to the open substrate. In some embodiments, an analyte of the array of analytes comprises a nucleic acid molecule. In some embodiments, the plurality of probes comprises a plurality of oligonucleotide molecules. In some embodiments, the plurality of probes comprises a plurality of nucleotides or analogs thereof.

In another aspect, the present disclosure provides a computer-readable medium comprising non-transitory instructions stored thereon, which when executed cause one or more computer processors to implement a method for detecting or analyzing an analyte, the method comprising: providing an open substrate about a central axis, the open substrate comprising an array of analytes immobilized adjacent to the open substrate, wherein at least one analyte of the array of analytes is bound to a probe; and using a detector system to perform a non-linear scan of the open substrate to detect at least one signal or signal change from the bound probe, wherein the detector system comprises a line-scan camera and an illumination source, wherein the illumination source is configured to generate an illuminated region on the open substrate, wherein the open substrate comprises a first area and a second area, wherein the first area and the second area (i) comprise different subsets of the array of analytes, (ii) are at different radial positions of the open substrate with respect to the central axis, and (iii) are spatially resolved by the detector system; wherein the bound probe is disposed in the first area of the open substrate; and wherein the non-linear scan is performed during relative non-linear motion between the open substrate and one or both of (i) the line-scan camera and (ii) the illuminated region.

In some embodiments, the line-scan camera is a time delay and integration line-scan camera. In some embodiments, the illumination source comprises a laser. In some embodiments, the laser is a continuous wave laser. In some embodiments, the detector system comprises an optical element configured to change a shape of a beam of light emitted by the laser. In some embodiments, the optical element comprises a cylindrical lens. In some embodiments, the illumination source comprises a light emitting diode.

In some embodiments, during the detecting, the open substrate is stationary. In some embodiments, during the detecting, the line-scan camera of the detector system is rotating. In some embodiments, during the detecting, the illuminated region is rotating. In some embodiments, during the detecting, the illuminated region is rotating at a same rate as the line-scan camera. In some embodiments, during the detecting, the line-scan camera translates radially across the open substrate. In some embodiments, during the detecting, the illuminated region translates radially across the open substrate.

In some embodiments, during the detecting, the open substrate is rotating. In some embodiments, during the detecting, the line-scan camera of the detector system is stationary. In some embodiments, during the detecting, the illuminated region of the detector system is rotating. In some embodiments, during the detecting, the line-scan camera of the detector system is rotating. In some embodiments, during the detecting, the illuminated region is rotating. In some embodiments, during the detecting, the illuminated region is rotating at a same rate as the line-scan camera. In some embodiments, during the detecting, the line-scan camera translates radially across the open substrate. In some embodiments, during the detecting, the illuminated region translates radially across the open substrate. In some embodiments, the detector system further comprises a prism, which prism is rotates during the detecting.

In some embodiments, the detector system is configured to detect a signal from the illuminated region using the line-scan camera. In some embodiments, the detector system compensates for velocity differences at different radial positions of the array with respect to the central axis within a scanned area. In some embodiments, the detector system comprises an optical imaging system having an anamorphic magnification gradient substantially transverse to a scanning direction along the open substrate, and wherein the anamorphic magnification gradient at least partially compensates for tangential velocity differences that are substantially perpendicular to the scanning direction. In some embodiments, the detecting comprises reading two or more regions on the open substrate at two or more different scan rates, respectively, to at least partially compensate for tangential velocity differences in the two or more regions.

In some embodiments, the detecting further comprises using an immersion objective lens in optical communication with the detector system and the open substrate to detect the at least one signal or signal change, which immersion objective lens is in contact with a fluid that is in contact with the open substrate. In some embodiments, the fluid is in a container, and wherein an electric field is used to regulate a hydrophobicity of one or more surfaces of the container to retain at least a portion of the fluid contacting the immersion objective lens and the open substrate.

In some embodiments, the array of analytes comprise nucleic acid molecules, wherein the plurality of probes comprises fluorescently labeled nucleotides, and wherein at least one fluorescently labeled nucleotide of the fluorescently labeled nucleotides binds to at least one nucleic acid molecule of the nucleic acid molecules via nucleotide complementarity binding. In some embodiments, the open substrate is substantially planar. In some embodiments, an analyte of the array of analytes is immobilized adjacent to the open substrate through one or more binders. In some embodiments, the open substrate comprises at least 100,000 binders, wherein a binder of the at least 100,000 binders immobilizes an analyte of the array of analytes immobilized adjacent to the open substrate. In some embodiments, an analyte of the array of analytes is coupled to a bead, which bead is immobilized to the open substrate. In some embodiments, an analyte of the array of analytes comprises a nucleic acid molecule. In some embodiments, the plurality of probes comprises a plurality of oligonucleotide molecules. In some embodiments, the plurality of probes comprises a plurality of nucleotides or analogs thereof.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2 shows a flowchart for an example of a method for sequencing a nucleic acid molecule;

FIG. 7 shows an optical system for continuous area scanning of a substrate during rotational motion of the substrate;

FIG. 8A shows an optical system for imaging a substrate during rotational motion of the substrate using tailored optical distortions;

FIG. 11 shows a cross-sectional view of an immersion optical system;

FIG. 12I shows an architecture for a system comprising multiple spindles scanning with a shared optical detection system;

FIG. 13 shows an architecture for a system comprising a plurality of rotating spindles;

FIG. 14 shows a flowchart for an example of a method for processing an analyte;

FIG. 15 shows a first example of a system for isolating an analyte; and

FIG. 16 shows a second example of a system for isolating an analyte.

FIG. 21 shows a flowchart for an example of a method for analyte detection or analysis.

FIGS. 29A-29E illustrate exemplary methods of temperature regulation in the system.

FIGS. 34A-34B illustrate schematically exemplary adapters for optical imaging objectives.

FIG. 38 illustrates a method of making an oligonucleotide-coated surface resistant to nucleic acid contaminants.

FIG. 39A illustrates a scheme in which an open substrate rotates and a detector system remains stationary during detection. FIG. 39B illustrates a scheme in which an open substrate remains stationary and a detector system rotates during detection. FIG. 39C illustrates a scheme in which an open substrate rotates during delivery and dispersal of a solution to the open substrate (left panel) and remains stationary during detection with a rotating detector system (right panel).

FIGS. 40A-40D illustrate schemes for line-scan cameras. FIG. 40A illustrates rows of pixels for a time delay and integration (TDI) line-scan camera. FIG. 40B illustrates a trilinear pixel scheme for a color line-scan camera including red (R), green (G), and blue (B) pixels. FIGS. 40C and 40D illustrate bilinear pixel schemes for a color line-scan camera including red, green, and blue pixels.

DETAILED DESCRIPTION

Figure 1:
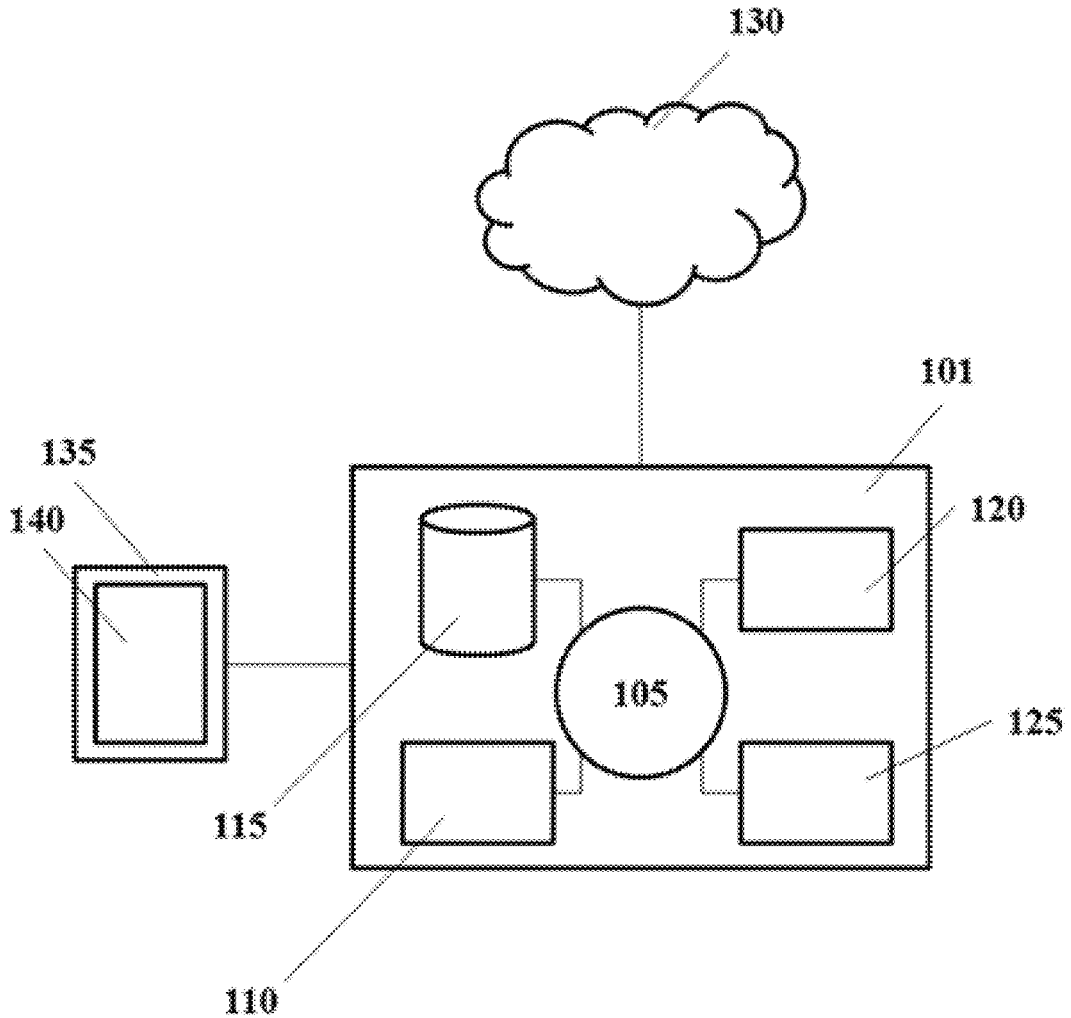
FIG. 1 shows a computer control system that is programmed or otherwise configured to implement methods provided herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "processing an analyte," as used herein, generally refers to one or more stages of interaction with one more sample substances. Processing an analyte may comprise conducting a chemical reaction, biochemical reaction, enzymatic reaction, hybridization reaction, polymerization reaction, physical reaction, any other reaction, or a combination thereof with, in the presence of, or on, the analyte. Processing an analyte may comprise physical and/or chemical manipulation of the analyte. For example, processing an analyte may comprise detection of a chemical change or physical change, addition of or subtraction of material, atoms, or molecules, molecular confirmation, detection of the presence of a fluorescent label, detection of a Forster resonance energy transfer (FRET) interaction, or inference of absence of fluorescence. The term "analyte" may refer to molecules, cells, biological particles, or organisms. In some instances, a molecule may be a nucleic acid molecule, antibody, antigen, peptide, protein, or other biological molecule obtained from or derived from a biological sample. An analyte may originate from, and/or be derived from, a biological sample, such as from a cell or organism. An analyte may be synthetic.

The term "sequencing," as used herein, generally refers to a process for generating or identifying a sequence of a biological molecule, such as a nucleic molecule. Such sequence may be a nucleic acid sequence, which may include a sequence of nucleic acid bases. Sequencing may be single molecule sequencing or sequencing by synthesis, for example. Sequencing may be performed using template nucleic acid molecules immobilized on a support, such as a flow cell or one or more beads.

The term "biological sample," as used herein, generally refers to any sample from a subject or specimen. The biological sample can be a fluid or tissue from the subject or specimen. The fluid can be blood (e.g., whole blood), saliva, urine, or sweat. The tissue can be from an organ (e.g., liver, lung, or thyroid), or a mass of cellular material, such as, for example, a tumor. The biological sample can be a feces sample, collection of cells (e.g., cheek swab), or hair sample. The biological sample can be a cell-free or cellular sample. Examples of biological samples include nucleic acid molecules, amino acids, polypeptides, proteins, carbohydrates, fats, or viruses. In an example, a biological sample is a nucleic acid sample including one or more nucleic acid molecules, such as deoxyribonucleic acid (DNA) and/or ribonucleic acid (RNA). The nucleic acid molecules may be cell-free or cell-free nucleic acid molecules, such as cell free DNA or cell free RNA. The nucleic acid molecules may be derived from a variety of sources including human, mammal, non-human mammal, ape, monkey, chimpanzee, reptilian, amphibian, avian, or plant sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject), or may be derived from tissue of the subject itself.

The term "subject," as used herein, generally refers to an individual from whom a biological sample is obtained. The subject may be a mammal or non-mammal. The subject may be an animal, such as a monkey, dog, cat, bird, or rodent. The subject may be a human. The subject may be a patient. The subject may be displaying a symptom of a disease. The subject may be asymptomatic. The subject may be undergoing treatment. The subject may not be undergoing treatment. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. The subject can have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease.

The terms "nucleic acid," "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or deoxyribonucleic acids (DNA) or ribonucleotides or ribonucleic acids (RNA), or analogs thereof. Non-limiting examples of nucleic acids include DNA, RNA, genomic DNA or synthetic DNA/RNA or coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, and isolated RNA of any sequence. A nucleic acid molecule can have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 20 kb, 30 kb, 40 kb, 50 kb, 100 kb, 200 kb, 300 kb, 400 kb, 500 kb, 1 megabase (Mb), or more. A nucleic acid molecule (e.g., polynucleotide) can comprise a sequence of four natural nucleotide bases: adenine (A); cytosine (C); guanine (G); and thymine (T) (uracil (U) for thymine (T) when the polynucleotide is RNA). A nucleic acid molecule may include one or more nonstandard nucleotide(s), nucleotide analog(s) and/or modified nucleotide(s).

Nonstandard nucleotides, nucleotide analogs, and/or modified analogs may include, but are not limited to, diaminopurine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids and the like. In some cases, nucleotides may include modifications in their phosphate moieties, including modifications to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Nucleotide analogs may be capable of reacting or bonding with detectable moieties for nucleotide detection.

The term "nucleotide," as used herein, generally refers to any nucleotide or nucleotide analog. The nucleotide may be naturally occurring or non-naturally occurring. The nucleotide analog may be a modified, synthesized or engineered nucleotide. The nucleotide analog may not be naturally occurring or may include a non-canonical base. The naturally occurring nucleotide may include a canonical base. The nucleotide analog may include a modified polyphosphate chain (e.g., triphosphate coupled to a fluorophore). The nucleotide analog may comprise a label. The nucleotide analog may be terminated (e.g., reversibly terminated). The nucleotide analog may comprise an alternative base.

The terms "amplifying," "amplification," and "nucleic acid amplification" are used interchangeably and generally refer to generating one or more copies of a nucleic acid or a template. For example, "amplification" of DNA generally refers to generating one or more copies of a DNA molecule. Moreover, amplification of a nucleic acid may be linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, recombinase polymerase reaction (RPA), and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR and touchdown PCR. Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C.C. PNAS, 1989, 86, 4076-4080 and U.S. Pat. Nos. 5,409, 811 and 5,674,716, each of which is herein incorporated by reference in its entirety.

The terms "dispense" and "disperse" may be used interchangeably herein. In some cases, dispensing may comprise dispersing and/or dispersing may comprise dispensing. Dispensing generally refers to distributing, depositing, providing, or supplying a reagent, solution, or other object, etc. Dispensing may comprise dispersing, which may generally refer to spreading.

Useful methods for clonal amplification from single molecules include rolling circle amplification (RCA) (Lizardi et al., Nat. Genet. 19:225-232 (1998), which is incorporated herein by reference), bridge PCR (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., Nucl. Acids Res. 28:E87 (2000); Pemov et al., Nucl. Acids Res. 33:e11 (2005); or U.S. Pat. No. 5,641,658, each of which is incorporated herein by reference), polony generation (Mitra et al., Proc. Natl. Acad. Sci. USA 100:5926-5931 (2003); Mitra et al., Anal. Biochem. 320:55-65 (2003), each of which is incorporated herein by reference), and clonal amplification on beads using emulsions (Dressman et al., Proc. Natl. Acad. Sci. USA 100:8817-8822 (2003), which is incorporated herein by reference) or ligation to bead-based adapter libraries (Brenner et al., Nat. Biotechnol. 18:630-634 (2000); Brenner et al., Proc. Natl. Acad. Sci. USA 97:1665-1670 (2000)); Reinartz, et al., Brief Funct. Genomic Proteomic 1:95-104 (2002), each of which is incorporated herein by reference).

The term "detector," as used herein, generally refers to a device that is capable of detecting a signal, including a signal indicative of the presence or absence of one or more incorporated nucleotides or fluorescent labels. The detector may detect multiple signals. The signal or multiple signals may be detected in real-time during, substantially during a biological reaction, such as a sequencing reaction (e.g., sequencing during a primer extension reaction), or subsequent to a biological reaction. In some cases, a detector can include optical and/or electronic components that can detect signals. The term "detector" may be used in detection methods. Non-limiting examples of detection methods include optical detection, spectroscopic detection, electrostatic detection, electrochemical detection, acoustic detection, magnetic detection, and the like. Optical detection methods include, but are not limited to, light absorption, ultraviolet-visible (UV-vis) light absorption, infrared light absorption, light scattering, Rayleigh scattering, Raman scattering, surface-enhanced Raman scattering, Mie scattering, fluorescence, luminescence, and phosphorescence. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The term "continuous area scanning," as used herein, generally refers to area scanning in rings, spirals, or arcs on a rotating substrate using an optical imaging system and a detector. Continuous area scanning may scan a substrate or array along a nonlinear path. Alternatively or in addition, continuous area scanning may scan a substrate or array along a linear or substantially linear path. The detector may be a continuous area scanning detector. The scanning direction may be substantially $\theta$ in an $(R, \theta)$ coordinate system in which the object rotation motion is in a $\theta$ direction. Across any field of view on the object (substrate) imaged by a scanning system, the apparent velocity may vary with the radial position (R) of the field point on the object as $$R\frac{d\theta}{dt}.$$

Continuous area scanning detectors may scan at the same rate for all image positions and therefore may not be able to operate at the correct scan rate for all imaged points in a curved (or arcuate or non-linear) scan. Therefore the scan may be corrupted by velocity blur for imaged field points moving at a velocity different than the scan velocity. Continuous rotational area scanning may comprise an optical detection system or method that makes algorithmic, optical, and/or electronic corrections to substantially compensate for this tangential velocity blur, thereby reducing this scanning aberration. For example, the compensation is accomplished algorithmically by using an image processing algorithm that deconvolves differential velocity blur at various image positions corresponding to different radii on the rotating substrate to compensate for differential velocity blur. In some cases, the camera or scanner may apply or use a blur to compensate for differential velocity blur.

In another example, the compensation is accomplished by using an anamorphic magnification gradient. This may serve to magnify the substrate in one axis (anamorphic magnification) by different amounts at two or more substrate positions transverse to the scan direction. The anamorphic magnification gradient may modify the imaged velocities of the two or more positions to be substantially equal thereby compensating for tangential velocity differences of the two positions on the substrate. This compensation may be adjustable to account for different velocity gradients across the field of view at different radii on the substrate.

The imaging field of view may be segmented into two or more regions, each of which can be electronically controlled to scan at a different rate. These rates may be adjusted to the mean projected object velocity within each region. The regions may be optically defined using one or more beam splitters or one or more mirrors. The two or more regions may be directed to two or more detectors. The regions may be defined as segments of a single detector.

The term "continuous area scanning detector," as used herein, generally refers to an imaging array sensor capable of continuous integration over a scanning area wherein the scanning is electronically synchronized to the image of an object in relative motion. A continuous area scanning detector may comprise a time delay and integration (TDI) charge coupled device (CCD), Hybrid TDI, or complementary metal oxide semiconductor (CMOS) pseudo TDI device. For example, a continuous area scanning detector may comprise a TDI line-scan camera.

The term "open substrate", as used herein, generally refers to a substantially planar substrate in which a single active surface is physically accessible at any point from a direction normal to the substrate. Substantially planar may refer to planarity at a micrometer level or nanometer level. Alternatively, substantially planar may refer to planarity at less than a nanometer level or greater than a micrometer level (e.g., millimeter level).

The term "anamorphic magnification", as used herein, generally refers to differential magnification between two axes of an image. An anamorphic magnification gradient may comprise differential anamorphic magnification in a first axis across a displacement in the second axis. The magnification in the second axis may be unity or any other value that is substantially constant over the field.

The term "field of view", as used herein, generally refers to the area on the sample or substrate that is optically mapped to the active area of the detector.

Processing an Analyte Using an Open Substrate

Prior microfluidic systems have utilized substrates containing numerous long, narrow channels. The typical flow cell geometry for such substrates introduces a need to compromise between two competing requirements: 1) minimizing volume to minimize reagent usage; and 2) maximizing effective hydraulic diameter to minimize flow time. This trade-off may be especially important for washing operations, which may require large wash volumes and thus long amounts of time to complete. The tradeoff is illustrated by the Poiseuille equation that dictates flow in the laminar regime and is thus inherent to microfluidic systems that utilize such flow cell geometries. Such flow cell geometries may also be susceptible to contamination. Because such flow cell geometries allow for a finite, limited number of channels in the microfluidic systems, such finite number of channels may be shared between a plurality of different mixtures comprising different analytes, reagents, agents, and/or buffers. Contents of fluids flowing through the same channels may be contaminated.

Described herein are devices, systems, and methods for processing analytes using open substrates or flow cell geometries that can address at least the abovementioned problems. The devices, systems and methods may be used to facilitate any application or process involving a reaction or interaction between an analyte and a fluid (e.g., a fluid comprising reagents, agents, buffers, other analytes, etc.). Such reaction or interaction may be chemical (e.g., polymerase reaction) or physical (e.g., displacement). The systems and methods described herein may benefit from higher efficiency, such as from faster reagent delivery and lower volumes of reagents required per surface area. The systems and methods described herein may avoid contamination problems common to microfluidic channel flow cells that are fed from multiport valves which can be a source of carryover from one reagent to the next. The devices, systems, and methods may benefit from shorter completion time, use of fewer resources (e.g., various reagents), and/or reduced system costs. The open substrates or flow cell geometries may be used to process any analyte, such as but not limited to, nucleic acid molecules, protein molecules, antibodies, antigens, cells, and/or organisms, as described herein. The open substrates or flow cell geometries may be used for any application or process, such as, but not limited to, sequencing by synthesis, sequencing by ligation, amplification, proteomics, single cell processing, barcoding, and sample preparation, as described herein.

The systems and methods may utilize a substrate comprising an array (such as a planar array) of individually addressable locations. Each location, or a subset of such locations, may have immobilized thereto an analyte (e.g., a nucleic acid molecule, a protein molecule, a carbohydrate molecule, etc.). For example, an analyte may be immobilized to an individually addressable location via a support, such as a bead. A plurality of analytes immobilized to the substrate may be copies of a template analyte. For example, the plurality of analytes may have sequence homology. In other instances, the plurality of analytes immobilized to the substrate may be different. The plurality of analytes may be of the same type of analyte (e.g., a nucleic acid molecule) or may be a combination of different types of analytes (e.g., nucleic acid molecules, protein molecules, etc.). One or more surfaces of the substrate may be exposed to a surrounding open environment, and accessible from such surrounding open environment. For example, the array may be exposed and accessible from such surrounding open environment. In some cases, as described elsewhere herein, the surrounding open environment may be controlled and/or confined in a larger controlled environment.

Reagents may be dispensed to the substrate to multiple locations, and/or multiple reagents may be dispensed to the substrate to a single location, via different mechanisms. In some cases, dispensing (to multiple locations and/or of multiple reagents to a single location) may be achieved via relative motion of the substrate and the dispenser (e.g., nozzle). For example, a reagent may be dispensed to the substrate at a first location, and thereafter travel to a second location different from the first location due to forces (e.g., centrifugal forces, centripetal forces, inertial forces, etc.) caused by motion of the substrate. In another example, a reagent may be dispensed to a reference location, and the substrate may be moved relative to the reference location such that the reagent is dispensed to multiple locations of the substrate. In some cases, dispensing (to multiple locations and/or of multiple reagents to a single location) may be achieved without relative motion between the substrate and the dispenser. For example, multiple dispensers may be used to dispense reagents to different locations, and/or multiple reagents to a single location, or a combination thereof (e.g., multiple reagents to multiple locations). In another example, an external force (e.g., involving a pressure differential), such as wind, may be applied to one or more surfaces of the substrate to direct reagents to different locations across the substrate. In another example, the method for dispensing reagents (e.g., to multiple locations and/or of multiple reagents to a single location) may comprise vibration. In such an example, reagents may be distributed or dispensed onto a single region or multiple regions of the substrate (or a surface of the substrate). The substrate (or a surface thereof) may then be subjected to vibration, which may spread the reagent to different locations across the substrate (or the surface). Alternatively or in conjunction, the method may comprise using mechanical, electric, physical, or other means to dispense reagents to the substrate. For example, the solution may be dispensed onto a substrate and a physical scraper (e.g., a squeegee) may be used to spread the dispensed material or spread the reagents to different locations and/or to obtain a desired thickness or uniformity across the substrate. Beneficially, such flexible dispensing may be achieved without contamination of the reagents. In some instances, where a volume of reagent is dispensed to the substrate at a first location, and thereafter travels to a second location different from the first location, the volume of reagent may travel in a path or paths, such that the travel path or paths are coated with the reagent. In some cases, such travel path or paths may encompass a desired surface area (e.g., entire surface area, partial surface area(s), etc.) of the substrate.

Reagents may be dispensed over the uncovered surface or substrate at a desired flow rate. The flow rate of fluid dispensing may be about (e.g., at ambient temperature, or about 25 degrees Celsius) 1 picoliter/min, 10 picoliters/min, 100 picoliters/min, 1 nanoliter/min, 10 nanoliters/min, 100 nanoliters/min, 1 microliter/min, 10 microliters/min, 100 microliters/min, 1 milliliter/min, 10 milliliters/min, 100 milliliters/min, up to 1 liter/min. The flow rate of fluid dispensing may be between any of these flow rates. The flow rate of fluid dispensing may be at least any of these flow rates. Alternatively, the flow rate of fluid dispensing may be at most any of these flow rates. The flow rate may be tuned according to desired properties of the reagent or solution layer (e.g., thickness).

Solutions may comprise reagents, samples, or any useful substance. The solution may comprise a fluid that has desirable flow properties. For example, the fluid may have a temperature-variable viscosity. The solution may comprise a non-Newtonian fluid. The solution may comprise a power law fluid, such as a shear-thinning (thixotropic) or shear-thickening fluid. The solution may comprise a Newtonian fluid.

In some cases, the substrate may be rotatable about an axis. The analytes may be immobilized to the substrate during rotation. Reagents (e.g., nucleotides, antibodies, washing reagents, enzymes, etc.) may be dispensed onto the substrate prior to or during rotation (for instance, spun at a high rotational velocity) of the substrate to coat the array with the reagents and allow the analytes to interact with the reagents. For example, when the analytes are nucleic acid molecules and when the reagents comprise nucleotides, the nucleic acid molecules may incorporate or otherwise react with (e.g., transiently bind) one or more nucleotides. In another example, when the analytes are protein molecules and when the reagents comprise antibodies, the protein molecules may bind to or otherwise react with one or more antibodies. In another example, when the reagents comprise washing reagents, the substrate (and/or analytes on the substrate) may be washed of any unreacted (and/or unbound) reagents, agents, buffers, and/or other particles.

In some cases, the substrate may be movable in any vector or direction, as described elsewhere herein. For example, such motion may be non-linear (e.g., in rotation about an axis). In another example, such motion may be linear. In other examples, the motion may be a hybrid of linear and non-linear motion. The analytes may be immobilized to the substrate during any such motion. Reagents (e.g., nucleotides, antibodies, washing reagents, enzymes, etc.) may be dispensed onto the substrate prior to or during motion of the substrate to facilitate coating of the array with the reagents and allow the analytes to interact with the reagents.

In some cases, where the substrate is rotatable, high speed coating across the substrate may be achieved via tangential inertia directing unconstrained spinning reagents in a partially radial direction (that is, away from the axis of rotation) during rotation, a phenomenon commonly referred to as centrifugal force. High speed rotation may involve a rotational speed of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, at least 10,000 rpm, or greater. This mode of directing reagents across a substrate may be herein referred to as centrifugal or inertial pumping. Inertial forces may direct unconstrained reagents across the substrate in any direction during any type of motion (e.g., rotational motion, non-rotational motion, linear motion, non-linear motion, accelerated motion, etc.) of the substrate.

One or more signals (such as optical signals) may be detected from a detection area on the substrate prior to, during, or subsequent to, the dispensing of reagents to generate an output. For example, the output may be an intermediate or final result obtained from processing of the analyte. Signals may be detected in multiple instances. The dispensing, rotating (or other motion), and/or detecting operations, in any order (independently or simultaneously), may be repeated any number of times to process an analyte. In some instances, the substrate may be washed (e.g., via dispensing washing reagents) between consecutive dispensing of the reagents. One or more detection operations can be performed within a desired time frame. For example, the detection operation can be performed within about 1 minute, 50 seconds, 40 seconds, 30 seconds, 20 seconds, 10 seconds or less than 10 seconds. In some instances, at least two detection operations can be performed within 1 minute, 50 seconds, 40 seconds, 30 seconds, 20 seconds, 10 seconds or less than 10 seconds etc. In some instances, at least three detection operations can be performed within 1 minute, 50 seconds, 40 seconds, 30 seconds, 20 seconds, 10 seconds or less than 10 seconds.

Provided herein is a method for processing a biological analyte, comprising providing a substrate comprising an array having immobilized thereto the biological analyte, wherein the substrate is rotatable with respect to a central axis. In some instances, the array can be a planar array. In some instances, the array can be an array of wells. In some instances, the substrate can be textured and/or patterned. The method can comprise directing a solution across the substrate and bringing the solution in contact with the biological analyte during rotation of the substrate. The solution may be directed in a radial direction (e.g., outwards) with respect to the substrate to coat the substrate and contact the biological analytes immobilized to the array. In some instances, the solution may comprise a plurality of probes. In some instances, the solution may be a washing solution. The method can comprise subjecting the biological analyte to conditions sufficient to conduct a reaction between at least one probe of the plurality of probes and the biological analyte. The reaction may generate one or more signals from the at least one probe coupled to the biological analyte. The method can comprise detecting one or more signals, thereby analyzing the biological analyte.

In other cases, provided herein is a method for processing a biological analyte, comprising providing a substrate comprising an array having immobilized thereto the biological analyte, wherein the substrate is movable with respect to a reference axis. The method can comprise directing a solution across the substrate and bringing the solution in contact with the biological analyte during motion of the substrate. In some instances, the motion can be linear. In some instances, the motion can be non-linear. In some instances, the motion can be a hybrid between linear and non-linear motion.

In other cases, provided herein is a method for processing a biological analyte, comprising providing a substrate comprising an array having immobilized thereto the biological analyte. In some instances, the method can comprise dispensing a solution to two different locations on the substrate and/or array. In some instances, the method can comprise dispensing multiple solutions to a single location on the substrate and/or array, such as using multiple dispensers. In some instances, the method can comprise dispensing multiple solutions to multiple locations on the substrate and/or array. In some instances, the method can comprise dispensing a single solution to a single location. The substrate may be in relative motion with respect to one or more dispensers. The substrate may be stationary with respect to one or more dispensers. One or more dispensing operations can be performed within a desired time frame. For example, the dispensing operation can be performed within 1 minute, 50 seconds, 40 seconds, 30 seconds, 20 seconds, 10 seconds or less than 10 seconds. In some instances, at least two dispensing operations can be performed within 1 minute, 50 seconds, 40 seconds, 30 seconds, 20 seconds, 10 seconds or less than 10 seconds etc. In some instances, at least three dispensing operations can be performed within 1 minute, 50 seconds, 40 seconds, 30 seconds, 20 seconds, 10 seconds or less than 10 seconds.

Any operation or process of one or more methods disclosed herein may be performed within a desired time frame. In some instances, a combination of two or more operations or processes disclosed herein may be performed within a desired time frame. For example, the dispensing operation and the detection method may both be performed within 1 minute, 50 seconds, 40 seconds, 30 seconds, 20 seconds, 10 seconds or less than 10 seconds. In some instances, at least two dispensing and detection operations can be performed within 1 minute, 50 seconds, 40 seconds, 30 seconds, 20 seconds, 10 seconds or less than 10 seconds etc. In some instances, at least three dispensing and detection operations can be performed within 1 minute, 50 seconds, 40 seconds, 30 seconds, 20 seconds, 10 seconds or less than 10 seconds.

One or more methods disclosed herein may obviate the need for barcoding of analytes (e.g., nucleic acid molecules), which may be time-consuming and expensive. For example, alternative or in addition to barcoding, the substrate and/or array may be spatially indexed to identify the analytes, as described elsewhere herein. One or more methods disclosed herein may obviate the need for unique barcoding of individual analytes (e.g., individual nucleic acid molecules).

The biological analyte may be any analyte that comes from a sample. For instance, the biological analyte may be a macromolecule, e.g., a nucleic acid molecule, a carbohydrate, a protein, a lipid, etc. The biological analyte may comprise multiple macromolecular groups, e.g., glycoproteins, proteoglycans, ribozymes, liposomes, etc. The biological analyte may be an antibody, antibody fragment, or engineered variant thereof, an antigen, a cell, a peptide, a polypeptide, etc. In some cases, the biological analyte comprises a nucleic acid molecule. The nucleic acid molecule may comprise at least about 10, 100, 1000, 10,000, 100,000, 1,000,000, 10,000,000, 100,000,000, 1,000,000,000 or more nucleotides. Alternatively or in addition, the nucleic acid molecule may comprise at most about 1,000,000,000, 100,000,000, 10,000,000, 1,000,000, 100,000, 10,000, 1000, 100, 10 or fewer nucleotides. The nucleic acid molecule may have a number of nucleotides that is within a range defined by any two of the preceding values. In some cases, the nucleic acid molecule may also comprise a common sequence, to which an N-mer may bind. An N-mer may comprise 1, 2, 3, 4, 5, or 6 nucleotides and may bind the common sequence. In some cases, the nucleic acid molecules may be amplified to produce a colony of nucleic acid molecules attached to the substrate or attached to beads that may associate with or be immobilized to the substrate. In some instances, the nucleic acid molecules may be attached to beads and subjected to a nucleic acid reaction, e.g., amplification, to produce a clonal population of nucleic acid molecules attached to the beads.

Nucleic acid molecules in any given nucleic acid sample may each comprise a key sequence. The key sequence may be a synthetic sequence. In some instances, the key sequence may be at most about 6 bases in length, 5 bases in length, 4 bases in length, 3 bases in length, 2 bases in length, or 1 base in length. Alternatively, the key sequence may be greater than 6 bases in length. The key sequence may be indicative of the originating sample. For example, the key sequence may be unique to a sample such that each sample of a plurality of samples has a unique key sequence. Individual analytes in a single sample may share the same key sequence. Alternatively, each sample may have a unique key sequence between its immediate neighboring samples when loaded onto the substrate. Beneficially, where two samples comprising different key sequences are loaded into adjacent or otherwise proximate regions on the substrate, nucleic acid molecules originating from different samples may be readily differentiated based on the different key sequences even where there is cross-contamination between regions (e.g., outlying nucleic acid molecules that are inadvertently loaded onto a neighboring region due to spillover, etc.) with relatively short reads (e.g., which are much shorter than reads of unique barcode sequences that are configured to differentiate individual molecules).

The substrate may be a solid substrate. The substrate may entirely or partially comprise one or more of rubber, glass, silicon, a metal such as aluminum, copper, titanium, chromium, or steel, a ceramic such as titanium oxide or silicon nitride, a plastic such as polyethylene (PE), low-density polyethylene (LDPE), high-density polyethylene (HDPE), polypropylene (PP), polystyrene (PS), high impact polystyrene (HIPS), polyvinyl chloride (PVC), polyvinylidene chloride (PVDC), acrylonitrile butadiene styrene (ABS), polyacetylene, polyamides, polycarbonates, polyesters, polyurethanes, polyepoxide, polymethyl methacrylate (PMMA), polytetrafluoroethylene (PTFE), phenol formaldehyde (PF), melamine formaldehyde (MF), urea-formaldehyde (UF), polyetheretherketone (PEEK), polyetherimide (PEI), polyimides, polylactic acid (PLA), furans, silicones, polysulfones, any mixture of any of the preceding materials, or any other appropriate material. The substrate may be entirely or partially coated with one or more layers of a metal such as aluminum, copper, silver, or gold, an oxide such as a silicon oxide ($SiO_xO_y$, where x, y may take on any possible values), a photoresist such as SU8, a surface coating such as an aminosilane or hydrogel, polyacrylic acid, polyacrylamide dextran, polyethylene glycol (PEG), or any combination of any of the preceding materials, or any other appropriate coating. The one or more layers may have a thickness of at least 1 nanometer (nm), at least 2 nm, at least 5 nm, at least 10 nm, at least 20 nm, at least 50 nm, at least 100 nm, at least 200 nm, at least 500 nm, at least 1 micrometer (μm), at least 2 μm, at least 5 μm, at least 10 μm, at least 20 μm, at least 50 μm, at least 100 μm, at least 200 μm, at least 500 μm, or at least 1 millimeter (mm). The one or more layers may have a thickness that is within a range defined by any two of the preceding values. A surface of the substrate may be modified to comprise any of the binders or linkers described herein. A surface of the substrate may be modified to comprise active chemical groups, such as amines, esters, hydroxyls, epoxides, and the like, or a combination thereof. In some instances, such binders, linkers, active chemical groups, and the like may be added as an additional layer or coating to the substrate.

The substrate may have the general form of a cylinder, a cylindrical shell or disk, a rectangular prism, or any other geometric form. The substrate may have a thickness (e.g., a minimum dimension) of at least 100 μm, at least 200 μm, at least 500 μm, at least 1 mm, at least 2 mm, at least 5 mm, or at least 10 mm. The substrate may have a thickness that is within a range defined by any two of the preceding values. The substrate may have a first lateral dimension (such as a width for a substrate having the general form of a rectangular prism or a radius for a substrate having the general form of a cylinder) of at least 1 mm, at least 2 mm, at least 5 mm, at least 10 mm, at least 20 mm, at least 50 mm, at least 100 mm, at least 200 mm, at least 500 mm, or at least 1,000 mm. The substrate may have a first lateral dimension that is within a range defined by any two of the preceding values. The substrate may have a second lateral dimension (such as a length for a substrate having the general form of a rectangular prism) or at least 1 mm, at least 2 mm, at least 5 mm, at least 10 mm, at least 20 mm, at least 50 mm, at least 100 mm, at least 200 mm, at least 500 mm, or at least 1,000 mm. The substrate may have a second lateral dimension that is within a range defined by any two of the preceding values.

A surface of the substrate may be planar. A surface of the substrate may be uncovered and may be exposed to an atmosphere. Alternatively or in addition, a surface of the substrate may be textured or patterned. For example, the substrate may comprise grooves, troughs, hills, and/or pillars. The substrate may define one or more cavities (e.g., micro-scale cavities or nano-scale cavities). The substrate may define one or more channels. The substrate may have a regular textures and/or patterns across the surface of the substrate. For example, the substrate may have regular geometric structures (e.g., wedges, cuboids, cylinders, spheroids, hemispheres, etc.) above or below a reference level of the surface. Alternatively, the substrate may have irregular textures and/or patterns across the surface of the substrate. For example, the substrate may have any arbitrary structure above or below a reference level of the substrate. In some instances, a texture of the substrate may comprise structures having a maximum dimension of at most about 100%, 90%, 80%, 70%, 60%, 50%, 40%, 30%, 20%, 10%, 9%, 8%, 7%, 6%, 5%, 4%, 3%, 2%, 1%, 0.1%, 0.01%, 0.001%, 0.0001%, 0.00001% of the total thickness of the substrate or a layer of the substrate. In some instances, the textures and/or patterns of the substrate may define at least part of an individually addressable location on the substrate. A textured and/or patterned substrate may be substantially planar.

Figure 36:
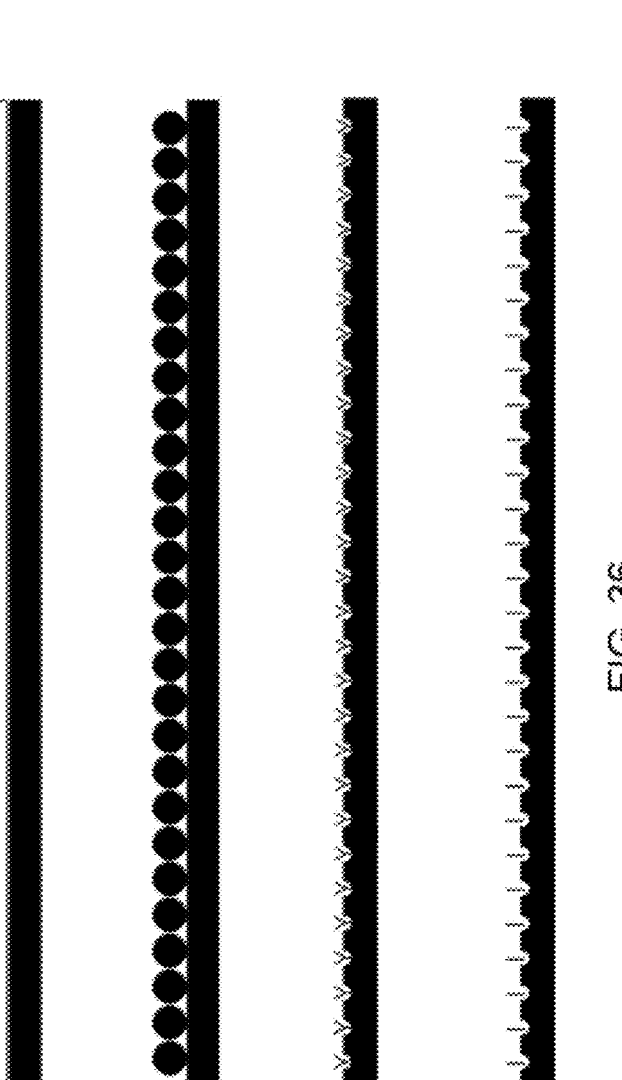
FIG. 36 illustrates different examples of cross-sectional surface profiles of a substrate.

For example, FIG. 36 illustrates different examples of cross-sectional surface profiles of a substrate. Panel A illustrates a cross-sectional surface profile of a substrate having a completely planar surface. Panel B illustrates a cross-sectional surface profile of a substrate having semi-spherical troughs or grooves. Panel C illustrates a cross-sectional surface profile of a substrate having pillars, or alternatively or in conjunction, wells. Panel D illustrates a cross-sectional surface profile of a substrate having a coating. Panel E illustrates a cross-sectional surface profile of a substrate having spherical particles. Panel F illustrates a cross-sectional surface profile of Panel B, with a first type of binders seeded or associated with the respective grooves. Panel G illustrates a cross-sectional surface profile of Panel B, with a second type of binders seeded or associated with the respective grooves.

The substrate may comprise an array. For instance, the array may be located on a lateral surface of the substrate. The array may be a planar array. The array may have the general shape of a circle, annulus, rectangle, or any other shape. The array may comprise linear and/or non-linear rows. The array may be evenly spaced or distributed. The array may be arbitrarily spaced or distributed. The array may have regular spacing. The array may have irregular spacing. The array may be a textured array. The array may be a patterned array. The array may comprise a plurality of individually addressable locations. The individually addressable locations may be arranged in any convenient pattern. For example, the individually addressable locations may be randomly oriented on the array. The plurality of individually addressable locations may form separate radial regions around a disk-shaped substrate. The plurality of individually addressable locations may form a square, rectangle, disc, circular, annulus, pentagonal, hexagonal, heptagonal, octagonal, array, or any other pattern. One or more types of individually addressable locations may be generated. The one or more types of individually addressable locations may form alternating regions of the different types of individually addressable locations. The one or more types of individually addressable locations may form blocked regions of the different types of individually addressable locations. For example, in cases when two types (A and B) of individually addressable locations are desired, the individually addressable locations may be arrayed as alternating ABABAB, blocked AAABBB, or random, e.g. ABBAAB, AABBBA, BABBAA, etc. The types of individually addressable locations may be arrayed in any useful pattern, such as a square, rectangle, disc, annulus, pentagon, hexagon, radial pattern, etc. In some cases, the two types of individually addressable locations may have different chemical, physical, and/or biological properties (e.g., hydrophobicity, charge, color, topography, size, dimensions, geometry, etc.). For example, a first type of individually addressable location may bind a first type of biological analyte but not a second type of biological analyte, and a second type of individually addressable location may bind the second type of biological analyte but not the first type of biological analyte.

The analyte to be processed may be immobilized to the array. The array may comprise one or more binders described herein, such as one or more physical or chemical linkers or adaptors, that are coupled to a biological analyte. For instance, the array may comprise a linker or adaptor that is coupled to a nucleic acid molecule. Alternatively or in addition, the biological analyte may be coupled to a bead, which bead may be immobilized to the array. In some cases, a subset of the array may not be coupled to a sample or analyte. For example, in substrates that are configured to rotate about a central axis, the samples may not be coupled to a plurality of individually addressable locations of the array located near the central axis. In some cases, the array may be coupled to a sample or an analyte, but not all of the array may be processed. For example, the substrate may be coupled to a sample or analyte (e.g., comprising nucleic acid molecules), but the region of the array that is in proximity to the border of the array may not be subjected to further processing (e.g., detection).

The individually addressable locations may comprise locations of analytes or groups of analytes that are accessible for manipulation. The manipulation may comprise placement, extraction, reagent dispensing, seeding, heating, cooling, or agitation. The extraction may comprise extracting individual analytes or groups of analytes. For instance, the extraction may comprise extracting at least 2, at least 5, at least 10, at least 20, at least 50, at least 100, at least 200, at least 500, or at least 1,000 analytes or groups of analytes. Alternatively or in addition, the extraction may comprise extracting at most 1,000, at most 500, at most 200, at most 100, at most 50, at most 20, at most 10, at most 5, or at most 2 analytes or groups of analytes. The manipulation may be accomplished through, for example, localized microfluidic, pipet, optical, laser, acoustic, magnetic, and/or electromagnetic interactions with the analyte or its surroundings.

In some cases, the individually addressable locations may be indexed, e.g., spatially, such that the analyte immobilized or coupled to each individually addressable location may be identified. In some embodiments, the individually addressable locations are indexed by demarcating part of the substrate. In some embodiments, the surface of the substrate is demarcated using etching. In some embodiments, the surface of the substrate is demarcated using a notch in the surface. In some embodiments, the surface of the substrate is demarcated using a dye or ink. In some embodiments, the surface of the substrate is demarcated by depositing a topographical mark on the surface. In some embodiments, a sample, such as a control nucleic acid sample, may be used to demarcate the surface of the substrate. As will be appreciated, a combination of positive demarcations and negative demarcations (lack thereof) may be used to index the individually addressable locations. In some instances, a single reference point or axis (e.g., single demarcation) may be used to index all individually addressable locations. In some embodiments, each of the individually addressable locations is indexed. In some embodiments, a subset of the individually addressable locations is indexed. In some embodiments, the individually addressable locations are not indexed, and a different region of the substrate is indexed.

Individually addressable locations, or individual regions comprising the individually addressable locations, may be indexed, or otherwise distinguished. In some instances, the individually addressable locations, or individual regions may be distinguished solely by sample loading (e.g., without physical demarcations). In some instances, a single region may be distinguished from other regions. In some instances, a single type of region may be distinguished from other types of regions. For example, different types of regions may comprise different types of analytes or different sets of samples. For example, a first type of region ("A") may comprise a first set of samples (or first type of sample), and a second type of region ("B") may comprise a second set of samples (or second type of sample). The substrate may comprise a set of multiple region A's and a set of multiple region B's, wherein the multiple region A's are distinguishable from the multiple region B's. Different samples may be loaded onto the different types of regions in a predetermined spatial configuration to allow such distinction.

In some cases, a key or barcode sequence on the sample may be used to distinguish and/or index the spatial locations, originating sample, or a combination thereof. For example, nucleic acid molecules in any given nucleic acid sample may each comprise a key sequence. The key sequence may be a synthetic sequence. The key sequence may be at most about 6 bases in length, 5 bases in length, 4 bases in length, 3 bases in length, 2 bases in length, or 1 base in length. Alternatively, the key sequence may be greater than 6 bases in length. The key sequence may be indicative of the originating sample. For example, the key sequence may be unique to a sample such that each sample of a plurality of samples has a unique key sequence. Individual analytes of a single sample may share a common key sequence. Alternatively, each sample may have a unique key sequence between its immediate neighboring samples when loaded onto the substrate. Beneficially, where two samples comprising different key sequences are loaded into adjacent or otherwise proximate regions on the substrate, nucleic acid molecules originating from different samples may be readily differentiated based on the different key sequences even where there is cross-contamination between regions (e.g., outlying nucleic acid molecules that are inadvertently loaded onto a neighboring region due to spillover, etc.) with relatively short reads (e.g., which are much shorter than reads of barcode sequences that are configured to differentiate individual molecules).

Figure 42:
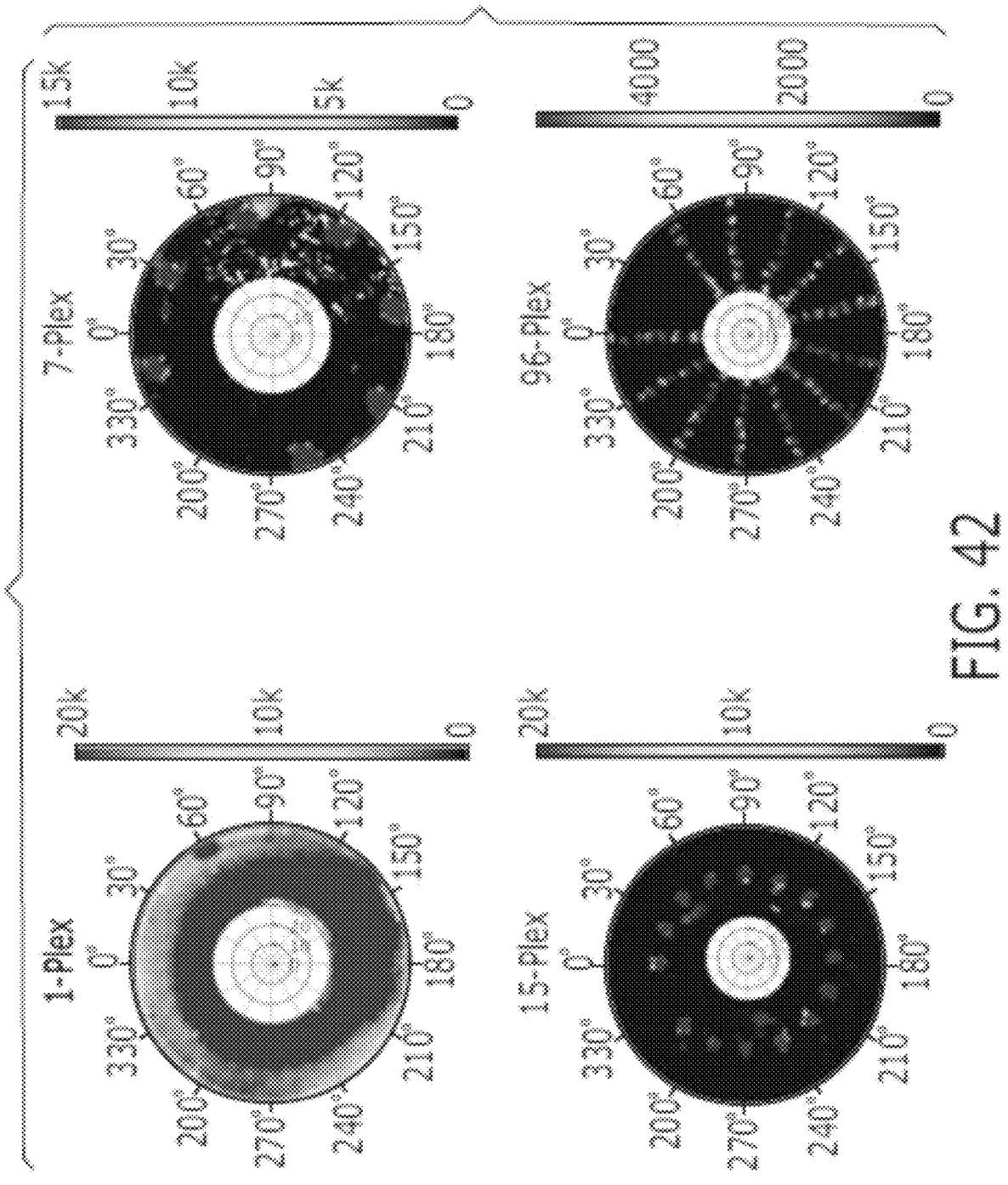
FIG. 42 illustrates multiplex sample processing schemes.

In some cases, spatial separation of analytes may be used to augment or replace the use of key or barcode sequences. For example, FIG. 42 illustrates schemes for analysis of analytes in a single region or in multiple regions, including 7, 15, and 96 regions.

In some cases, different types of regions may be used for sample processing. A first type of region ("A") may comprise a first set of samples (or first type of sample), and a second type of region ("B") may comprise a second set of samples (or second type of sample). The first type of region and the second type of region may be disposed apart from one another in an ordered fashion, as described elsewhere herein. In some cases, the first type of region and the second type of region may be disposed at a distance from a reference axis of the substrate. For example, the first type of region may be disposed at least 1 micrometer, 10 micrometers, 100 micrometers, 1 millimeter, 10 millimeters, 100 millimeters, 1 centimeter, 10 centimeters, 100 centimeters or more from the reference axis of the substrate. Similarly, the second type of region may be disposed at a distance from a reference axis of the substrate. For example, the first type of region may be disposed at least 1 micrometer, 10 micrometers, 100 micrometers, 1 millimeter, 10 millimeters, 100 millimeters, 1 centimeter, 10 centimeters, 100 centimeters or more from the reference axis of the substrate. Both types of regions may be disposed at least 1 micrometer, 10 micrometers, 100 micrometers, 1 millimeter, 10 millimeters, 100 millimeters, 1 centimeter, 10 centimeters, 100 centimeters or more from the reference axis of the substrate.

Figures 37A, 37B:
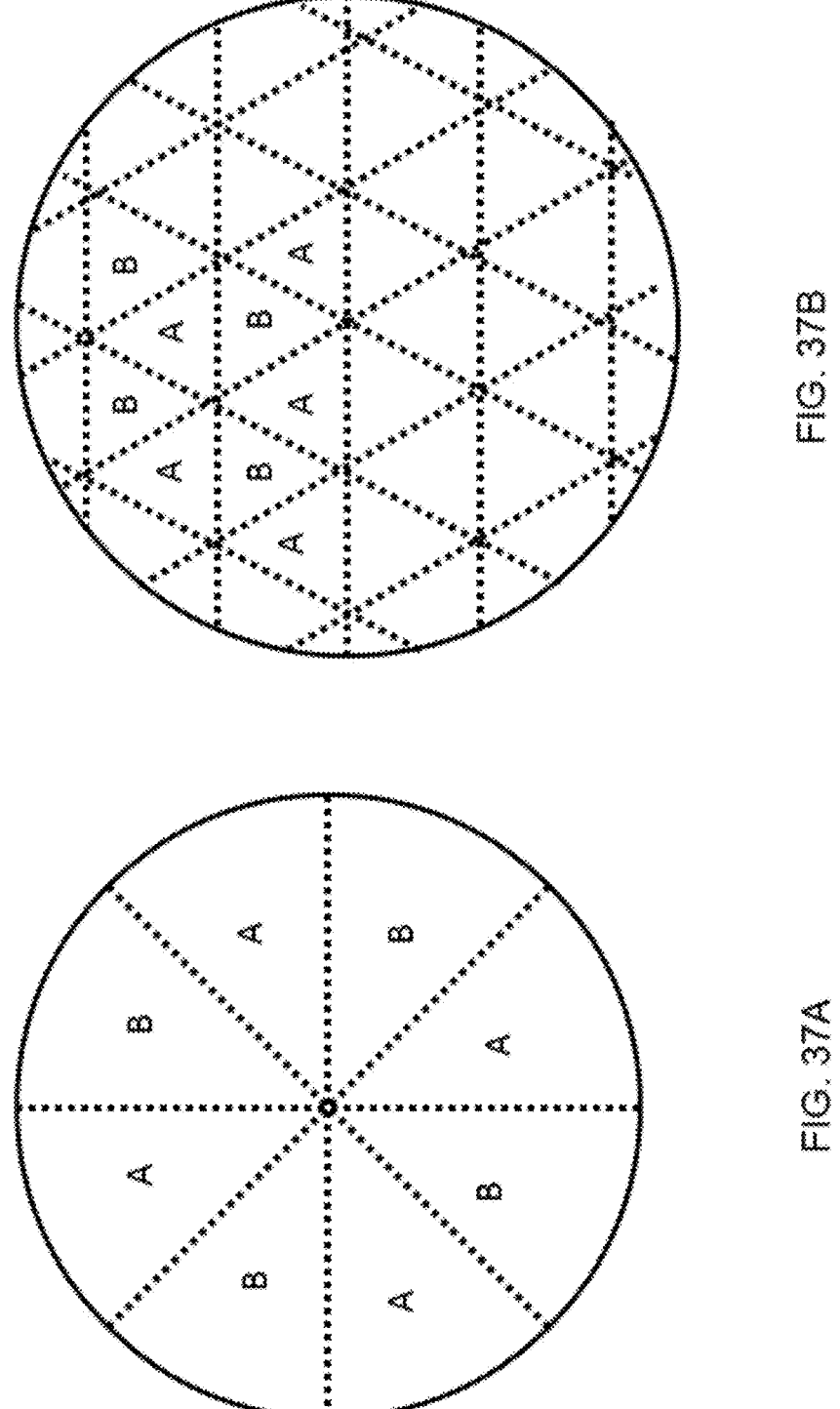
FIGS. 37A-37B illustrate two examples of spatial loading schemes.

For example, FIGS. 37A-37B illustrate two examples of spatial loading schemes. In FIG. 37A, a substrate comprises two types of regions "A"s and "B"s which are disposed in radially alternating fashion with respect to a central axis of the substrate. In FIG. 37B, a substrate comprises two types of regions "A"s and "B"s which are disposed in triangularly alternating fashion across the substrate. Sample locations may be determined by loading a first set of samples to the A regions, wherein the first set of samples comprises a plurality of beads coupled to analytes of the first set of samples, and detecting the plurality of beads and/or analytes and their locations on the substrate, and then loading the second set of samples to the B regions, wherein the second set of samples comprises a plurality of beads coupled to analytes of the second set of samples, and detecting the plurality of beads and/or analytes and their locations on the substrate. Each sample in the first set of samples and the second set of samples may be associated with a label (e.g., fluorescent dye). Even though the first set of samples is primarily loaded onto the A regions, there may be some crossovers in which stray beads from the first set of samples are immobilized to the B regions. Even though the second set of samples is primarily loaded onto the B regions, there may be some crossovers in which stray beads from the second set of samples are immobilized to the A regions. The locations of the analytes of the first set of samples, including the cross-over beads, can be determined from the first image. The locations of the analytes of the second set of samples, including the cross-over beads, can be determined from the second image. Beneficially, where the same type of fluorescent dye identifies analytes of two different samples ("P" and "Q"), and "P" is deposited to an A region, and "Q" is deposited to a B region, based on the type of region where the fluorescent signal is detected, one may identify if the analyte is of the "P" sample or the "Q" sample. The different regions may be alternating. The plurality of regions may form any pattern, such as a triangular, square, rectangle, disc, circular, annulus, pentagonal, hexagonal, heptagonal, octagonal, array, or any other pattern. The plurality of regions may form irregular patterns. The plurality of regions may be discrete regions that are not patterned. The plurality of regions may be interleaved, interspersed, non-contiguous, and/or different in size.

While examples herein describe two types of regions, there may be any number of regions (e.g., alternating regions) to achieve the alternating spatial distinction described herein. For example, there may be at 1 at least 1, at least 2, at least 3, at least 4, at least 5, at least 6, at least 7, at least 8, at least 9, or at least 10 regions.

While examples herein generally describe the loading of two samples or two sets of samples, any number of samples, or sets of samples, may be immobilized to the substrate. For example, the substrate may have immobilized thereto at least 1, at least 2, at least 3, at least 4, at least 5, at least 6, at least 7, at least 8, at least 9, at least 10 samples, or sets of samples. In some cases, at least about 10, 100, 1000, 10,000, 100,000, 1,000,000, 10,000,000, 100,000,000, 1,000,000,000 or more samples, or sets of samples, may be immobilized. Alternatively or in addition, the substrate may comprise at most about 1,000,000,000, 100,000,000, 10,000,000, 1,000,000, 100,000, 10,000, 1000, 100, 10 or fewer samples, or sets of samples. When the sample is a nucleic acid sample, at least 1, at least 2, at least 3, at least 4, at least 5, at least 6, at least 7, at least 8, at least 9, at least 10 nucleic acid samples may be immobilized to the substrate. In some cases, at least about 10, 100, 1000, 10,000, 100,000, 1,000,000, 10,000,000, 100,000,000, 1,000,000,000 or more nucleic acid samples may be immobilized. Alternatively or in addition, the substrate may comprise at most about 1,000,000,000, 100,000,000, 10,000,000, 1,000,000, 100,000, 10,000, 1000, 100, 10 or fewer nucleic acid samples. Beneficially, multiple samples may be simultaneously processed on the same substrate, without needing to otherwise barcode the multiple samples (e.g., with a common barcode sequence per sample) to distinguish them.

Indexing may be performed using a detection method and may be performed at any convenient or useful step. A substrate that is indexed, e.g., demarcated, may be subjected to detection, such as optical imaging, to locate the indexed locations, individually addressable locations, and/or the biological analyte. Imaging may be performed using a detection unit. Imaging may be performed using one or more sensors. Imaging may not be performed using the naked eye. The substrate that is indexed may be imaged prior to loading of the biological analyte. Following loading of the biological analyte onto the individually addressable locations, the substrate may be imaged again, e.g. to determine occupancy or to determine the positioning of the biological analyte relative to the substrate. In some cases, the substrate may be imaged after iterative cycles of nucleotide addition (or other probe or other reagent), as described elsewhere herein. The indexing of the substrate and known initial position (individually addressable location) of the biological analyte may allow for analysis and identification of the sequence information for each individually addressable location and/or position. Additionally, spatial indexing may allow for identification of errors that may occur, e.g., sample contamination, sample loss, etc.

In some cases, indexing may be performed to identify, process, and/or analyze more than one type of biological analyte, as described above. For example, a first type of biological analyte, which may be labeled, may be loaded onto a first set of locations within a substrate. The substrate may be imaged for a first indexing step of the first type of biological analyte. A second type of biological analyte may be loaded onto a second set of locations within the substrate, and imaged for a second indexing step of the second type of biological analyte. In some cases, the second type of biological analyte may be labeled in a way such that the second type of biological analyte is distinguishable from the first type of biological analyte. Alternatively, the first type of biological analyte and the second type of biological analyte may be labeled in substantially the same detectable manner (e.g., same dye), and the first and second images may be processed to generate a differential image, wherein overlapping signals are attributed to the locations of the first type of biological analyte and different signals are attributed to the locations of the second type of biological analyte. Alternatively, the first type of biological analyte and the second type of biological analyte may be labeled by cleavable (or otherwise removable) labels or tags (e.g., fluorescent tags), and the label cleaved after each imaging operation, such that only the relevant analyte locations are imaged at each imaging operation. Henceforth, the substrate may be analyzed and all of the locations comprising the first biological analyte may be attributed to the first biological analyte, and all of the locations comprising the second biological analyte may be attributed to the second analyte. In some cases, labeling of the first and second analyte may not be necessary, and the attribution of the location to either the first or second analyte may be performed based on spatial location alone. This process may be repeated for any number or types of biological analytes.

The array may be coated with binders. For instance, the array may be randomly coated with binders. Alternatively, the array may be coated with binders arranged in a regular pattern (e.g., in linear arrays, radial arrays, hexagonal arrays etc.). The array may be coated with binders on at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% of the number of individually addressable locations, or of the surface area of the substrate. The array may be coated with binders on a fraction of individually addressable locations, or of the surface areas of the substrate, that is within a range defined by any two of the preceding values. The binders may be integral to the array. The binders may be added to the array. For instance, the binders may be added to the array as one or more coating layers on the array.

The binders may immobilize biological analytes through non-specific interactions, such as one or more of hydrophilic interactions, hydrophobic interactions, electrostatic interactions, physical interactions (for instance, adhesion to pillars or settling within wells), and the like. The binders may immobilize biological analytes through specific interactions. For instance, where the biological analyte is a nucleic acid molecule, the binders may comprise oligonucleotide adaptors configured to bind to the nucleic acid molecule. Alternatively or in addition, such as to bind other types of analytes, the binders may comprise one or more of antibodies, oligonucleotides, nucleic acid molecules, aptamers, affinity binding proteins, lipids, carbohydrates, and the like. The binders may immobilize biological analytes through any possible combination of interactions. For instance, the binders may immobilize nucleic acid molecules through a combination of physical and chemical interactions, through a combination of protein and nucleic acid interactions, etc. The array may comprise at least about 10, 100, 1000, 10,000, 100,000, 1,000,000, 10,000,000, 100,000,000 or more binders. Alternatively or in addition, the array may comprise at most about 100,000,000, 10,000,000, 1,000,000, 100,000, 10,000, 1000, 100, 10 or fewer binders. The array may have a number of binders that is within a range defined by any two of the preceding values. In some instances, a single binder may bind a single biological analyte (e.g., nucleic acid molecule). In some instances, a single binder may bind a plurality of biological analytes (e.g., plurality of nucleic acid molecules). In some instances, a plurality of binders may bind a single biological analyte. Though examples herein describe interactions of binders with nucleic acid molecules, the binders may immobilize other molecules (such as proteins), other particles, cells, viruses, other organisms, or the like.

In some instances, each location, or a subset of such locations, may have immobilized thereto an analyte (e.g., a nucleic acid molecule, a protein molecule, a carbohydrate molecule, etc.). In other instances, a fraction of the plurality of individually addressable location may have immobilized thereto an analyte. A plurality of analytes immobilized to the substrate may be copies of a template analyte. For example, the plurality of analytes (e.g., nucleic acid molecules) may have sequence homology. In other instances, the plurality of analytes immobilized to the substrate may not be copies. The plurality of analytes may be of the same type of analyte (e.g., a nucleic acid molecule) or may be a combination of different types of analytes (e.g., nucleic acid molecules, protein molecules, etc.).

In some instances, the array may comprise a plurality of types of binders. For example, the array may comprise different types of binders to bind different types of analytes. For example, the array may comprise a first type of binders (e.g., oligonucleotides) configured to bind a first type of analyte (e.g., nucleic acid molecules), and a second type of binders (e.g., antibodies) configured to bind a second type of analyte (e.g., proteins), and the like. In another example, the array may comprise a first type of binders (e.g., first type of oligonucleotide molecules) to bind a first type of nucleic acid molecules and a second type of binders (e.g., second type of oligonucleotide molecules) to bind a second type of nucleic acid molecules, and the like. For example, the substrate may be configured to bind different types of analytes in certain fractions or specific locations on the substrate by having the different types of binders in the certain fractions or specific locations on the substrate.

A biological analyte may be immobilized to the array at a given individually addressable location of the plurality of individually addressable locations. An array may have any number of individually addressable locations. For instance, the array may have at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, at least 1,000,000,000, at least 2,000,000,000, at least 5,000,000,000, at least 10,000,000,000, at least 20,000,000,000, at least 50,000,000,000, or at least 100,000,000,000 individually addressable locations. The array may have a number of individually addressable locations that is within a range defined by any two of the preceding values. Each individually addressable location may be digitally and/or physically accessible individually (from the plurality of individually addressable locations). For example, each individually addressable location may be located, identified, and/or accessed electronically or digitally for mapping, sensing, associating with a device (e.g., detector, processor, dispenser, etc.), or otherwise processing. As described elsewhere herein, each individually addressable location may be indexed. Alternatively, the substrate may be indexed such that each individually addressable location may be identified during at least one step of the process. Alternatively or in addition, each individually addressable location may be located, identified, and/or accessed physically, such as for physical manipulation or extraction of an analyte, reagent, particle, or other component located at an individually addressable location.

Multiple biological analytes may be immobilized to the array at spatially discrete locations. Spatial separation of biological analytes may be obtained using masks or barriers, as described elsewhere herein. Alternatively or in conjunction, biological analytes may be separated using different fluid compositions. In some cases, the fluid compositions may be immiscible. For example, a first solution (e.g., an oil, organic solution, or other hydrophobic or oleophilic solution) may comprise a first biological analyte, and a second solution (e.g., a hydrophilic, aqueous, polar or ionic solution) may comprise a second biological analyte. The first and second solutions may be immiscible. The substrate may be exposed to the first solution in defined regions, e.g., using a mask (e.g., covering or shielding the other regions of the substrate). In some cases, the first biological analyte associates with defined regions (e.g., individually addressable locations), and the first solution may be removed from the substrate. The substrate may then be exposed to the second solution. The second biological analyte may then associate with the unoccupied sites of the substrate. Alternatively, the substrate may be pre-treated such that biological analytes may be loaded in discrete locations. In one non-limiting example, the substrate may be patterned with discrete hydrophobic and hydrophilic regions (e.g., using photolithography, soft lithography, etching, etc.) that can attract or repel a subset of the biological analytes. In another non-limiting example, an inert polymer such as polyethylene glycol (PEG) may be patterned in discrete regions to prevent attachment or the biological analyte to the substrate in the discrete regions.

Each individually addressable location may have the general shape or form of a circle, pit, bump, rectangle, or any other shape or form. Each individually addressable location may have a first lateral dimension (such as a radius for individually addressable locations having the general shape of a circle or a width for individually addressable locations having the general shape of a rectangle). The first lateral dimension may be at least 1 nanometer (nm), at least 2 nm, at least 5 nm, at least 10 nm, at least 20 nm, at least 50 nm, at least 100 nm, at least 200 nm, at least 500 nm, at least 1,000 nm, at least 2,000 nm, at least 5,000 nm, or at least 10,000 nm. The first lateral dimension may be within a range defined by any two of the preceding values. Each individually addressable location may have a second lateral dimension (such as a length for individually addressable locations having the general shape of a rectangle). The second lateral dimension may be at least 1 nanometer (nm), at least 2 nm, at least 5 nm, at least 10 nm, at least 20 nm, at least 50 nm, at least 100 nm, at least 200 nm, at least 500 nm, at least 1,000 nm, at least 2,000 nm, at least 5,000 nm, or at least 10,000 nm. The second lateral dimension may be within a range defined by any two of the preceding values. In some instances, each individually addressable locations may have or be coupled to a binder, as described herein, to immobilize an analyte thereto. In some instances, only a fraction of the individually addressable locations may have or be coupled to a binder. In some instances, an individually addressable location may have or be coupled to a plurality of binders to immobilize an analyte thereto.

The individually addressable locations may be generated using a variety of methods. In one embodiment, the method may comprise generation of individually addressable locations using one or more barriers. In some embodiments, the barrier may be removed during any convenient operation. For example, the barrier may be removed prior to or after coupling the analyte to the individually addressable locations. The barrier may be removed prior to or after loading of the solution comprising a plurality of probes. The barrier may be removed prior to or after subjecting the analyte to conditions sufficient to conduct a reaction between the probe and the analyte. The barrier may be removed prior to or after detection of one or more signals from the coupled probe and analyte. The barrier may be removed prior to or after detection of the coupled probe and analyte. The barrier may be removed prior to or after repeating any of the abovementioned processes. In some cases, the barriers may not be removed.

The barrier may comprise a physical, chemical, biological, or any other type of obstruction. In some embodiments, the barrier comprises a physical obstruction. In one such example, a mold may be used, wherein a portion of the mold may obstruct the movement of fluid to a specified region. The mold may be generated using a variety of means, such as injection molding, machining, heat treatment, fiber spinning, joining and bonding, casting, rolling, forging, 3D printing, etc. In some embodiments, the barrier may be configured to dissolve at any convenient step. The barrier may be configured to dissolve, evaporate, or sublime. In some cases, the barrier may be melted and removed. In some cases, removal of the barrier or part of the barrier may be achieved using an air knife. In some cases, the barrier comprises a chemical obstruction. In some cases, the barrier comprises a polymer. The barrier may comprise polyethylene glycol (PEG). In some cases, the barrier may comprise a solution. The solution may be viscous. The solution may have a temperature-variable viscosity. The solution may be a non-Newtonian fluid. The solution may be a power law fluid, such as a shear-thinning (e.g., thixotropic) or shear-thickening fluid. The solution may be a Newtonian fluid. In some embodiments, the barrier comprises a fluid that is immiscible with a loading solution. In some cases, the barrier is a hydrophobic region on the substrate.

A mask may be additionally or alternatively used to prevent coupling of the sample and/or biological analyte with a region of the substrate. Alternatively or in conjunction, a subset of the individually addressable locations comprising the biological analyte may be masked, e.g., to prevent coupling of the probe to the biological analyte. A mask may comprise a barrier, such as a physical, chemical or biological barrier. A mask may comprise a film with removed sections. In some cases, the mask may be interfaced with the substrate prior to introduction of the biological analyte. In such cases, introduction of the biological analyte may allow for coupling of the biological analyte to exposed regions of the mask-substrate interface, whereas the non-exposed regions may remain free of the biological analyte. At any convenient process, the substrate may be un-masked. Any combinations of masks may be used. For example, a first mask may be used to load a first biological analyte to a desired region. Subsequently, the first mask may be removed, and a second mask may be used to load a second biological analyte to a desired region. The first and second region may have overlapping regions, or may remain spatially distinct. A barrier and mask may be used in conjunction or separately.

The analytes bound to the individually addressable locations may include, but are not limited to, molecules, cells, organisms, nucleic acid molecules, nucleic acid colonies, beads, clusters, polonies, DNA nanoballs, or any combination thereof (e.g., bead having attached thereto one or more nucleic acid molecules). The bound analytes may be immobilized to the array in a regular, patterned, periodic, random, or pseudo-random configuration, or any other spatial arrangement. In some embodiments, the analytes are bound to bead(s) which may then associate with or be immobilized to the substrate or regions of the substrate (e.g., individually addressable locations). In some embodiments, the analytes comprise a bead or a plurality of beads. In some cases, the bead or plurality of beads may comprise another analyte (e.g., nucleic acid molecule) or a clonal population of other analytes (e.g., a nucleic acid molecule that has been amplified on the bead). Such other analytes may be attached or otherwise coupled to the bead. For example, an analyte may comprise a plurality of beads, each bead having a clonal population of nucleic acid molecules attached thereto. In some cases, the bead is magnetic, and application of a magnetic field or using a magnet may be used to direct the analytes or beads comprising the analytes to the individually addressable locations. In some cases, a fluid may be used to direct the analyte to the individually addressable locations. The fluid may be a ferrofluid, and a magnet may be used to direct the fluid to the individually addressable locations. The individually addressable locations may alternatively or in conjunction comprise a material that is sensitive to a stimulus, e.g., thermal, chemical, or electrical or magnetic stimulus. For example, the individually addressable location may comprise a photo-sensitive polymer or reagent that is activated when exposed to electromagnetic radiation. In some cases, a caged molecule may be used to reveal binding (e.g., biotin) moieties on the substrate. Subsequent exposure to a particular wavelength of light may result in un-caging of the binding moieties. A bead, e.g. with streptavidin, comprising the analyte may then associate with the uncaged binding moieties. In some cases, a subset of the individually address-able locations may not contain beads. In such cases, blank beads may be added to the substrate. The blank beads may then occupy the regions that are unoccupied by an analyte. In some cases, the blank beads have a higher binding affinity or avidity for the individually addressable locations than the beads comprising the analyte. In some cases, unoccupied locations may be destroyed. In some cases, unoccupied locations may be subjected to a process to remove any unbound analyte, e.g., aspiration, washing, air blasting etc. In some cases, the sample comprising the biological analyte may be loaded onto the substrate using a device, e.g., a microfluidic device, closed flow cell, etc. The loaded bio-logical analyte may then associate with or be immobilized to the substrate or the individually addressable locations of the substrate. In such cases, the device may be removed fol-lowing loading of the sample.

A biological analyte may be bound to any number of beads. Different biological analytes may be bound to any number of beads. The beads may be unique (i.e., distinct from each other). Any number of unique beads may be used. For instance, at least about 10, 100, 1000, 10,000, 100,000, 1,000,000, 10,000,000, 100,000,000 or more different beads may be used. Alternatively or in addition, at most about 100,000,000, 10,000,000, 1,000,000, 100,000, 10,000, 1000, 100, 10 or fewer different beads may be used. A number of different beads can be within a range defined by any two of the preceding values. The beads may be distinguishable from one another using a property of the beads, such as color, reflectance, anisotropy, brightness, fluorescence, etc.

A sample may be diluted such that the approximate occupancy of the individually addressable locations is con-trolled. A sample may be diluted at least to a dilution of 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900, 1:1000, 1:10000, 1:100000, 1:1000000, 1:10000000, 1:100000000. Alterna-tively, a sample may be diluted at most to a dilution of A sample may be diluted at least to a dilution of 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900, 1:1000, 1:10000, 1:100000, 1:1000000, 1:10000000, 1:100000000. A dilution between any of these dilution values may also be used.

The substrate may be configured to rotate with respect to an axis. In some instances, the systems, devices, and appa-ratus described herein may further comprise a rotational unit configured to rotate the substrate. The rotational unit may comprise a motor and/or a rotor to rotate the substrate. Such motor and/or rotor may be mechanically connected to the substrate directly or indirectly via intermediary components (e.g., gears, stages, actuators, discs, pulleys, etc.). The rotational unit may be automated. Alternatively or in addi-tion, the rotational unit may receive manual input. The axis of rotation may be an axis through the center of the substrate. The axis may be an off-center axis. For instance, the substrate may be affixed to a chuck (such as a vacuum chuck) of a spin coating apparatus. The substrate may be configured to rotate with a rotational velocity of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, or at least 10,000 rpm. The substrate may be configured to rotate with a rotational velocity that is within a range defined by any two of the preceding values. The substrate may be configured to rotate with different rotational velocities during different opera-tions described herein. The substrate may be configured to rotate with a rotational velocity that varies according to a time-dependent function, such as a ramp, sinusoid, pulse, or other function or combination of functions. The time-vary-ing function may be periodic or aperiodic.

The substrate may be configured to move in any vector with respect to a reference point. In some instances, the systems, devices, and apparatus described herein may fur-ther comprise a motion unit configured to move the sub-strate. The motion unit may comprise any mechanical com-ponent, such as a motor, rotor, actuator, linear stage, drum, roller, pulleys, etc., to move the substrate. Such components may be mechanically connected to the substrate directly or indirectly via intermediary components (e.g., gears, stages, actuators, discs, pulleys, etc.). The motion unit may be automated. Alternatively or in addition, the motion unit may receive manual input. The substrate may be configured to move with any velocity. In some instances, the substrate may be configured to move with different velocities during different operations described herein. The substrate may be configured to move with a velocity that varies according to a time-dependent function, such as a ramp, sinusoid, pulse, or other function or combination of functions. The time-varying function may be periodic or aperiodic.

A solution may be provided to the substrate prior to or during rotation (or other motion) of the substrate to cen-trifugally (or otherwise inertially) direct the solution across the array. In some instances, the solution may be provided to the planar array during rotation of the substrate in pulses, thereby creating an annular wave of the solution moving radially outward. In some instances, the solution may be provided to the planar array during other motion of the substrate in pulses, thereby creating a wave of the solution moving in a certain direction. The pulses may have periodic or non-periodic (e.g., arbitrary) intervals. A series of pulses may comprise a series of waves producing a surface-reagent exchange. The surface-reagent exchange may comprise washing in which each subsequent pulse comprises a reduced concentration of the surface reagent. The solution may have a temperature different than that of the substrate, thereby providing a source or sink of thermal energy to the substrate or to an analyte located on the substrate. The thermal energy may provide a temperature change to the substrate or to the analyte. The temperature change may be transient. The temperature change may enable, disable, enhance, or inhibit a chemical reaction, such as a chemical reaction to be carried out upon the analyte. For example, the chemical reaction may comprise denaturation, hybridiza-tion, or annealing of nucleic acid molecules. The chemical reaction may comprise a step in a polymerase chain reaction (PCR), bridge amplification, or other nucleic acid amplifi-cation reaction. The temperature change may modulate, increase, or decrease a signal detected from the analyte.

The array may be in fluid communication with at least one sample inlet (of a fluid channel). The array may be in fluid communication with the sample inlet via a non-solid gap, e.g., an air gap. In some cases, the array may additionally be in fluid communication with at least one sample outlet. The array may be in fluid communication with the sample outlet via an airgap. The sample inlet may be configured to direct a solution to the array. The sample outlet may be configured to receive a solution from the array. The solution may be directed to the array using one or more dispensing nozzles. For example, the solution may be directed to the array using at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 dispensing nozzles. The solution may be directed to the array using a number of nozzles that is within a range defined by any two of the preceding values. In some cases, different reagents (e.g., nucleotide solutions of different types, different probes, washing solutions, etc.) may be dispensed via different nozzles, such as to prevent contamination. Each nozzle may be connected to a dedicated fluidic line or fluidic valve, which may further prevent contamination. A type of reagent may be dispensed via one or more nozzles. The one or more nozzles may be directed at or in proximity to a center of the substrate. Alternatively, the one or more nozzles may be directed at or in proximity to a location on the substrate other than the center of the substrate. Alternatively or in combination, one or more nozzles may be directed closer to the center of the substrate than one or more of the other nozzles. For instance, one or more nozzles used for dispensing washing reagents may be directed closer to the center of the substrate than one or more nozzles used for dispensing active reagents. The one or more nozzles may be arranged at different radii from the center of the substrate. Two or more nozzles may be operated in combination to deliver fluids to the substrate more efficiently. One or more nozzles may be configured to deliver fluids to the substrate as a jet, spray (or other dispersed fluid), and/or droplets. One or more nozzles may be operated to nebulize fluids prior to delivery to the substrate. For example, the fluids may be delivered as aerosol particles.

The solution may be dispensed on the substrate while the substrate is stationary; the substrate may then be subjected to rotation (or other motion) following the dispensing of the solution. Alternatively, the substrate may be subjected to rotation (or other motion) prior to the dispensing of the solution; the solution may then be dispensed on the substrate while the substrate is rotating (or otherwise moving).

Rotation of the substrate may yield a centrifugal force (or inertial force directed away from the axis) on the solution, causing the solution to flow radially outward over the array. In this manner, rotation of the substrate may direct the solution across the array. Continued rotation of the substrate over a period of time may dispense a fluid film of a nearly constant thickness across the array. The rotational velocity of the substrate may be selected to attain a desired thickness of a film of the solution on the substrate. The film thickness may be related to the rotational velocity by equation (1):

$$h(t) = \frac{\sqrt{3\mu/2}}{\sqrt{2t\rho\omega^2 - 3\mu C}} \tag{1}$$

Here, h(t) is the thickness of the fluid film at time t, μ is the viscosity of the fluid, ω is the rotational velocity, and C is a constant.

Alternatively or in combination, the viscosity of the solution may be chosen to attain a desired thickness of a film of the solution on the substrate. For instance, the rotational velocity of the substrate or the viscosity of the solution may be chosen to attain a film thickness of at least 10 nanometers (nm), at least 20 nm, at least 50 nm, at least 100 nm, at least 200 nm, at least 500 nm, at least 1 micrometer (μm), at least 2 μm, at least 5 μm, at least 10 μm, at least 20 μm, at least 50 μm, at least 100 μm. at least 200 μm, at least 500 μm, or at least 1 mm. The rotational velocity of the substrate and/or the viscosity of the solution may be chosen to attain a film thickness that is within a range defined by any two of the preceding values. The viscosity of the solution may be controlled by controlling a temperature of the solution. The thickness of the film may be measured or monitored. Measurements or monitoring of the thickness of the film may be incorporated into a feedback system to better control the film thickness. The thickness of the film may be measured or monitored by a variety of techniques. For instances, the thickness of the film may be measured or monitored by thin film spectroscopy with a thin film spectrometer, such as a fiber spectrometer.

In some instances, one or more factors such as the rotational velocity of the substrate, the acceleration of the substrate (e.g., the rate of change of velocity), viscosity of the solution, angle of dispensing (e.g., contact angle of a stream of reagents) of the solution, radial coordinates of dispensing of the solution (e.g., on center, off center, etc.), temperature of the substrate, temperature of the solution, and other factors may be adjusted and/or otherwise optimized to attain a desired wetting on the substrate and/or a film thickness on the substrate, such as to facilitate uniform coating of the substrate. Such optimization may prevent the solution from exiting the substrate along a relatively focused stream or travel path such that the fluid only contacts the substrate at partial surface areas (as opposed to the entire surface area)—in such cases, a significantly larger volume of reagents may have to be dispensed to achieve uniform and full coating of the substrate. Such optimization may also prevent the solution from scattering or otherwise reflecting or bouncing off the substrate upon contact, and disturbing the surface fluid. Alternatively or in conjunction, the thickness of the solution may be adjusted using mechanical, electric, physical, or other mechanisms. For example, the solution may be dispensed onto a substrate and subsequently leveled using, e.g., a physical scraper such as a squeegee, to obtain a desired thickness of uniformity across the substrate.

The substrate or a surface thereof may comprise other features that aid in solution or reagent retention on the substrate or thickness uniformity of the solution or reagent on the substrate. In some cases, the surface may comprise a raised edge (e.g., a rim) which may be used to retain solution on the surface. The surface may comprise a rim near the outer edge of the surface, thereby reducing the amount of the solution that flows over the outer edge.

The solution may be a reaction mixture comprising a variety of components. For example, the solution may comprise a plurality of probes configured to interact with the analyte. For example, the probes may have binding specificity to the analyte. In another example, the probes may not have binding specificity to the analyte. A probe may be configured to permanently couple to the analyte. A probe may be configured to transiently couple to the analyte. For example, a nucleotide probe may be permanently incorporated into a growing strand hybridized to a nucleic acid molecule analyte. Alternatively, a nucleotide probe may transiently bind to the nucleic acid molecule analyte. Transiently coupled probes may be subsequently removed from the analyte. Subsequent removal of the transiently coupled probes from an analyte may or may not leave a residue (e.g., chemical residue) on the analyte. A type of probe in the solution may depend on the type of analyte. A probe may comprise a functional group or moiety configured to perform specific functions. For example, a probe may comprise a label (e.g., dye). A probe may be configured to generate a detectable signal (e.g., optical signal), such as via the label, upon coupling or otherwise interacting with the analyte. In some instances, a probe may be configured to generate a detectable signal upon activation (e.g., application of a stimulus). In another example, a nucleotide probe may comprise reversible terminators (e.g., blocking groups) configured to terminate polymerase reactions (until unblocked). The solution may comprise other components to aid, accelerate, or decelerate a reaction between the probe and the analyte (e.g., enzymes, catalysts, buffers, saline solutions, chelating agents, reducing agents, other agents, etc.). In some instances, the solution may be a washing solution. In some instances, a washing solution may be directed to the substrate to bring the washing solution in contact with the array after a reaction or interaction between reagents (e.g., a probe) in a reaction mixture solution with an analyte immobilized on the array. The washing solution may wash away any free reagents from the previous reaction mixture solution.

A detectable signal, such as an optical signal (e.g., fluorescent signal), may be generated upon reaction between a probe in the solution and the analyte. For example, the signal may originate from the probe and/or the analyte. The detectable signal may be indicative of a reaction or interaction between the probe and the analyte. The detectable signal may be a non-optical signal. For example, the detectable signal may be an electronic signal. The detectable signal may be detected by one or more sensors. For example, an optical signal may be detected via one or more optical detectors in an optical detection scheme described elsewhere herein. The signal may be detected during rotation of the substrate. The signal may be detected following termination of the rotation. The signal may be detected while the analyte is in fluid contact with the solution. The signal may be detected following washing of the solution. In some instances, after the detection, the signal may be muted, such as by cleaving a label from the probe and/or the analyte, and/or modifying the probe and/or the analyte. Such cleaving and/or modification may be effected by one or more stimuli, such as exposure to a chemical, an enzyme, light (e.g., ultraviolet light), or temperature change (e.g., heat). In some instances, the signal may otherwise become undetectable by deactivating or changing the mode (e.g., detection wavelength) of the one or more sensors, or terminating or reversing an excitation of the signal. In some instances, detection of a signal may comprise capturing an image or generating a digital output (e.g., between different images).

The operations of directing a solution to the substrate and detection of one or more signals indicative of a reaction between a probe in the solution and an analyte in the array may be repeated one or more times. Such operations may be repeated in an iterative manner. For example, the same analyte immobilized to a given location in the array may interact with multiple solutions in the multiple repetition cycles. For each iteration, the additional signals detected may provide incremental, or final, data about the analyte during the processing. For example, where the analyte is a nucleic acid molecule and the processing is sequencing, additional signals detected for each iteration may be indicative of a base in the nucleic acid sequence of the nucleic acid molecule. The operations may be repeated at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 cycles to process the analyte. In some instances, a different solution may be directed to the substrate for each cycle. For example, at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 solutions may be directed to the substrate.

In some instances, a washing solution may be directed to the substrate between each cycle (or at least once during each cycle). For instance, a washing solution may be directed to the substrate after each type of reaction mixture solution is directed to the substrate. The washing solutions may be distinct. The washing solutions may be identical. The washing solution may be dispensed in pulses during rotation, creating annular waves as described herein. For example, at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 washing solutions may be directed to the substrate.

In some instances, a subset or an entirety of the solution(s) may be recycled after the solution(s) have contacted the substrate. Recycling may comprise collecting, filtering, and reusing the subset or entirety of the solution. The filtering may be molecule filtering.

Nucleic Acid Sequencing Using a Rotating Array

In some instances, a method for sequencing may employ sequencing by synthesis schemes wherein a nucleic acid molecule is sequenced base-by-base with primer extension reactions. For example, a method for sequencing a nucleic acid molecule may comprise providing a substrate comprising an array having immobilized thereto the nucleic acid molecule. The array may be a planar array. The substrate may be configured to rotate with respect to an axis. The method may comprise directing a solution comprising a plurality of nucleotides across the array prior to or during rotation of the substrate. Rotation of the substrate may facilitate coating of the substrate surface with the solution. The nucleic acid molecule may be subjected to a primer extension reaction under conditions sufficient to incorporate or specifically bind at least one nucleotide from the plurality of nucleotides into a growing strand that is complementary to the nucleic acid molecule. A signal indicative of incorporation or binding of at least one nucleotide may be detected, thereby sequencing the nucleic acid molecule.

In some instances, the method may comprise, prior to providing the substrate having immobilized thereto the nucleic acid molecule, immobilizing the nucleic acid molecule to the substrate. For example, a solution comprising a plurality of nucleic acid molecules comprising the nucleic acid molecule may be directed to the substrate prior to, during, or subsequent to rotation of the substrate, and the substrate may be subject to conditions sufficient to immobilize at least a subset of the plurality of nucleic acid molecules as an array on the substrate.

FIG. 2 shows a flowchart for an example of a method 200 for sequencing a nucleic acid molecule. In a first operation 210, the method may comprise providing a substrate, as described elsewhere herein. The substrate may comprise an array of a plurality of individually addressable locations. The array may be a planar array. The array may be a textured array. The array may be a patterned array. For example, the array may define individually addressable locations with wells and/or pillars. A plurality of nucleic acid molecules, which may or may not be copies of the same nucleic acid molecule, may be immobilized to the array. Each nucleic acid molecule from the plurality of nucleic acid molecules may be immobilized to the array at a given individually addressable location of the plurality of individually address-able locations.

The substrate may be configured to rotate with respect to an axis. The axis may be an axis through the center or substantially center of the substrate. The axis may be an off-center axis. For instance, the substrate may be affixed to a chuck (such as a vacuum chuck) of a spin coating apparatus. The substrate may be configured to rotate with a rotational velocity of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, or at least 10,000 rpm. The substrate may be configured to rotate with a rotational velocity that is within a range defined by any two of the preceding values. The substrate may be configured to rotate with different rotational veloci-ties during different operations described herein. The sub-strate may be configured to rotate with a rotational velocity that varies according to a time-dependent function, such as a ramp, sinusoid, pulse, or other function or combination of functions. The time-varying function may be periodic or aperiodic.

In a second operation 220, the method may comprise directing a solution across the array prior to or during rotation of the substrate. The solution may be centrifugally directed across the array. In some instances, the solution may be directed to the array during rotation of the substrate in pulses, thereby creating an annular wave of the solution moving radially outward. The solution may have a tempera-ture different than that of the substrate, thereby providing a source or sink of thermal energy to the substrate or to a nucleic acid molecules located on the substrate. The thermal energy may provide a temperature change to the substrate or to the nucleic acid molecule. The temperature change may be transient. The temperature change may enable, disable, enhance, or inhibit a chemical reaction, such as a chemical reaction to be carried out upon the nucleic acid molecule. The chemical reaction may comprise denaturation, hybrid-ization, or annealing of the plurality of nucleic acid mol-ecules. The chemical reaction may comprise a step in a polymerase chain reaction (PCR), bridge amplification, or other nucleic acid amplification reaction. The temperature change may modulate, increase, or decrease a signal detected from the nucleic acid molecules (or from probes in the solution).

In some instances, the solution may comprise probes configured to interact with nucleic acid molecules. For example, in some instances, such as for performing sequenc-ing by synthesis, the solution may comprise a plurality of nucleotides (in single bases). The plurality of nucleotides may include nucleotide analogs, naturally occurring nucleo-tides, and/or non-naturally occurring nucleotides, collec-tively referred to herein as "nucleotides." The plurality of nucleotides may or may not be bases of the same type (e.g., A, T, G, C, etc.). For example, the solution may or may not comprise bases of only one type. The solution may comprise at least 1 type of base or bases of at least 2, at least 3, at least 4, at least 5, at least 6, at least 7, at least 8, at least 9, or at least 10 types. For instance, the solution may comprise any possible mixture of A, T, C, and G. In some instances, the solution may comprise a plurality of natural nucleotides and non-natural nucleotides. The plurality of natural nucleotides and non-natural nucleotides may or may not be bases of the same type (e.g., A, T, G, C). In some cases, the solution may comprise probes that are oligomeric (e.g., oligonucleotide primers). For example, in some instances, such as for performing sequencing by synthesis, the solution may com-prise a plurality of nucleic acid molecules, e.g., primers, that comprise 1, 2, 3, 4, 5, 6, 7, 8, 9, 10, 20, 30, 40, 50, 60, 70, 80, 90, 100 or more nucleotide bases. The plurality of nucleic acid molecules may comprise nucleotide analogs, naturally occurring nucleotides, and/or non-naturally occur-ring nucleotides, collectively referred to herein as "nucleo-tides." The plurality of nucleotides may or may not be bases of the same type (e.g., A, T, G, C, etc.). For example, the solution may or may not comprise bases of only one type. The solution may comprise at least 1 type of base or bases of at least 2, at least 3, at least 4, at least 5, at least 6, at least 7, at least 8, at least 9, or at least 10 types. For instance, the solution may comprise any possible mixture of A, T, C, and G. In some instances, the solution may comprise a plurality of natural nucleotides and non-natural nucleotides. The plurality of natural nucleotides and non-natural nucleotides may or may not be bases of the same type (e.g., A, T, G, C).

One or more nucleotides of the plurality of nucleotides may be terminated (e.g., reversibly terminated). For example, a nucleotide may comprise a reversible terminator, or a moiety that is capable of terminating primer extension reversibly. Nucleotides comprising reversible terminators may be accepted by polymerases and incorporated into growing nucleic acid sequences analogously to non-revers-ibly terminated nucleotides. A polymerase may be any naturally occurring (i.e., native or wild-type) or engineered variant of a polymerase (e.g., DNA polymerase, Taq poly-merase, etc.). Following incorporation of a nucleotide ana-log comprising a reversible terminator into a nucleic acid strand, the reversible terminator may be removed to permit further extension of the nucleic acid strand. A reversible terminator may comprise a blocking or capping group that is attached to 3'-oxygen atom of a sugar moiety (e.g., a pentose) of a nucleotide or nucleotide analog. Such moieties are referred to as 3'-O-blocked reversible terminators. Examples of 3'-O-blocked reversible terminators include, for example, 3'-ONH$_2$ reversible terminators, 3'-O-allyl reversible terminators, and 3'-O-aziomethyl reversible ter-minators. Alternatively, a reversible terminator may com-prise a blocking group in a linker (e.g., a cleavable linker) and/or dye moiety of a nucleotide analog. 3'-unblocked reversible terminators may be attached to both the base of the nucleotide analog as well as a fluorescing group (e.g., label, as described herein). Examples of 3'-unblocked reversible terminators include, for example, the "virtual terminator" developed by Helicos BioSciences Corp. and the "lightning terminator" developed by Michael L. Metzker et al. Cleavage of a reversible terminator may be achieved by, for example, irradiating a nucleic acid molecule includ-ing the reversible terminator.

One or more nucleotides of the plurality of nucleotides may be labeled with a dye, fluorophore, or quantum dot. For example, the solution may comprise labeled nucleotides. In another example, the solution may comprise unlabeled nucleotides. In another example, the solution may comprise a mixture of labeled and unlabeled nucleotides. Non-limit-ing examples of dyes include SYBR green, SYBR blue, DAPI, propidium iodine, Hoechst, SYBR gold, ethidium bromide, acridine, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5-(or 6-) iodo-acetamidofluorescein, 5-{[2 (and 3)-5-(Acetylmercapto)-succinyl] amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, Atto 390, 425, 465, 488, 495, 532, 565, 594, 633, 647, 647N, 665, 680 and 700 dyes, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores, Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare); Dy-Quenchers (Dyomics), such as DYQ-660 and DYQ-661; and ATTO fluorescent quenchers (ATTO-TEC GmbH), such as ATTO 540Q, 580Q, 612Q. In some cases, the label may be one with linkers. For instance, a label may have a disulfide linker attached to the label. Non-limiting examples of such labels include Cy5-azide, Cy-2-azide, Cy-3-azide, Cy-3.5-azide, Cy5.5-azide and Cy-7-azide. In some cases, a linker may be a cleavable linker. In some cases, the label may be a type that does not self-quench or exhibit proximity quenching. Non-limiting examples of a label type that does not self-quench or exhibit proximity quenching include Bimane derivatives such as Monobromobimane. Alternatively, the label may be a type that self-quenches or exhibits proximity quenching. Non-limiting examples of such labels include Cy5-azide, Cy-2-azide, Cy-3-azide, Cy-3.5-azide, Cy5.5-azide and Cy-7-azide. In some instances, a blocking group of a reversible terminator may comprise the dye.

The solution may be directed to the array using one or more nozzles. In some cases, different reagents (e.g., nucleotide solutions of different types, washing solutions, etc.) may be dispensed via different nozzles, such as to prevent contamination. Each nozzle may be connected to a dedicated fluidic line or fluidic valve, which may further prevent contamination. A type of reagent may be dispensed via one or more nozzles. The one or more nozzles may be directed at or in proximity to a center of the substrate. Alternatively, the one or more nozzles may be directed at or in proximity to a location on the substrate other than the center of the substrate. Two or more nozzles may be operated in combination to deliver fluids to the substrate more efficiently.

The solution may be dispensed on the substrate while the substrate is stationary; the substrate may then be subjected to rotation following the dispensing of the solution. Alternatively, the substrate may be subjected to rotation prior to the dispensing of the solution; the solution may then be dispensed on the substrate while the substrate is rotating. Rotation of the substrate may yield a centrifugal force (or inertial force directed away from the axis) on the solution, causing the solution to flow radially outward over the array.

In a third operation 230, the method may comprise subjecting the nucleic acid molecule to a primer extension reaction. The primer extension reaction may be conducted under conditions sufficient to incorporate at least one nucleotide from the plurality of nucleotides into a growing strand that is complementary to the nucleic acid molecule. The nucleotide incorporated may or may not be labeled.

In some cases, the operation 230 may further comprise modifying at least one nucleotide. Modifying the nucleotide may comprise labeling the nucleotide. For instance, the nucleotide may be labeled, such as with a dye, fluorophore, or quantum dot. The nucleotide may be cleavably labeled. In some instances, modifying the nucleotide may comprise activating (e.g., stimulating) a label of the nucleotide.

In a fourth operation 240, the method may comprise detecting a signal indicative of incorporation of the at least one nucleotide. The signal may be an optical signal. The signal may be a fluorescence signal. The signal may be detected during rotation of the substrate. The signal may be detected following termination of the rotation. The signal may be detected while the nucleic acid molecule to be sequenced is in fluid contact with the solution. The signal may be detected following fluid contact of the nucleic acid molecule with the solution. The operation 240 may further comprise modifying a label of the at least one nucleotide. For instance, the operation 240 may further comprise cleaving the label of the nucleotide (e.g., after detection). The nucleotide may be cleaved by one or more stimuli, such as exposure to a chemical, an enzyme, light (e.g., ultraviolet light), or heat. Once the label is cleaved, a signal indicative of the incorporated nucleotide may not be detectable with one or more detectors.

The method 200 may further comprise repeating operations 220, 230, and/or 240 one or more times to identify one or more additional signals indicative of incorporation of one or more additional nucleotides, thereby sequencing the nucleic acid molecule. The method 200 may comprise repeating operations 220, 230, and/or 240 in an iterative manner. For each iteration, an additional signal may indicate incorporation of an additional nucleotide. The additional nucleotide may be the same nucleotide as detected in the previous iteration. The additional nucleotide may be a different nucleotide from the nucleotide detected in the previous iteration. In some instances, at least one nucleotide may be modified (e.g., labeled and/or cleaved) between each iteration of the operations 220, 230, or 240. For instance, the method may comprise repeating the operations 220, 230, and/or 240 at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 times. The method may comprise repeating the operations 220, 230, and/or 240 a number of times that is within a range defined by any two of the preceding values. The method 200 may thus result in the sequencing of a nucleic acid molecule of any size.

The method may comprise directing different solutions to the array during rotation of the substrate in a cyclical manner. For instance, the method may comprise directing a first solution containing a first type of nucleotide (e.g., in a plurality of nucleotides of the first type) to the array, followed by a second solution containing a second type of nucleotide, followed by a third type of nucleotide, followed by a fourth type of nucleotide, etc. In another example, different solutions may comprise different combinations of types of nucleotides. For example, a first solution may comprise a first canonical type of nucleotide (e.g., A) and a second canonical type of nucleotide (e.g., C), and a second solution may comprise the first canonical type of nucleotide (e.g., A) and a third canonical type of nucleotide (e.g., T), and a third solution may comprise the first canonical type, second canonical type, third canonical type, and a fourth canonical type (e.g., G) of nucleotide. In another example, a first solution may comprise labeled nucleotides, and a second solution may comprise unlabeled nucleotides, and a third solution may comprise a mixture of labeled and unlabeled nucleotides. The method may comprise directing at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, or at least 1,000,000,000 solutions to the array. The method may comprise directing a number of solutions that is within a range defined by any two of the preceding values to the array. The solutions may be distinct. The solutions may be identical.

The method may comprise directing at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000, 000, at least 2,000,000, at least 5,000,000, at least 10,000, 000, at least 20,000,000, at least 50,000,000, at least 100, 000,000, at least 200,000,000, at least 500,000,000, or at least 1,000,000,000 washing solutions to the substrate. For instance, a washing solution may be directed to the substrate after each type of nucleotide is directed to the substrate. The washing solutions may be distinct. The washing solutions may be identical. The washing solution may be dispensed in pulses during rotation, creating annular waves as described herein.

The method may further comprise recycling a subset or an entirety of the solution(s) after the solution(s) have contacted the substrate. Recycling may comprise collecting, filtering, and reusing the subset or entirety of the solution. The filtering may be molecule filtering.

The operations 220 and 230 may occur at a first location and the operation 240 may occur at a second location. The first and second locations may comprise first and second processing bays, respectively, as described herein (for instance, with respect to FIG. 12G). The first and second locations may comprise first and second rotating spindles, respectively, as described herein (for instance, with respect to FIG. 13). The first rotating spindle may be exterior or interior to the second rotating spindle. The first and second rotating spindles may be configured to rotate with different angular velocities. Alternatively, the operation 220 may occur at a first location and the operations 230 and 240 may occur at the second location.

The method may further comprise transferring the substrate between the first and second locations. Operations 220 and 230 may occur while the substrate is rotated at a first angular velocity and operation 240 may occur while the substrate is rotated at a second angular velocity. The first angular velocity may be less than the second angular velocity. The first angular velocity may be between about 0 rpm and about 100 rpm. The second angular velocity may be between about 100 rpm and about 1,000 rpm. Alternatively, the operation 220 may occur while the substrate is rotated at the first angular velocity and the operations 230 and 240 may occur while the substrate is rotated at the second angular velocity.

Many variations, alterations, and adaptations based on the method 200 provided herein are possible. For example, the order of the operations of the method 200 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated. Some of the operations may be manual. Some of the operations may be performed separately, e.g., in different locations or during different steps and/or processes. For example, directing a solution comprising a plurality of probes to the substrate may occur separately from the reaction and detection processes.

For example, in some cases, in the third operation 230, instead of facilitating a primer extension reaction, the nucleic acid molecule may be subject to conditions to allow transient binding of a nucleotide from the plurality of nucleotides to the nucleic acid molecule. The transiently bound nucleotide may be labeled. The transiently bound nucleotide may be removed, such as after detection (e.g., see operation 240). Then, a second solution may be directed to the substrate, this time under conditions to facilitate the primer extension reaction, such that a nucleotide of the second solution is incorporated (e.g., into a growing strand hybridized to the nucleic acid molecule). The incorporated nucleotide may be unlabeled. After washing, and without detecting, another solution of labeled nucleotides may be directed to the substrate, such as for another cycle of transient binding.

In some instances, such as for performing sequencing by ligation, the solution may comprise different probes. For example, the solution may comprise a plurality of oligonucleotide molecules. For example, the oligonucleotide molecules may have a length of about 2 bases, 3 bases, 4 bases, 5 bases, 6 bases, 7 bases, 8 bases, 9 bases, 10 bases or more. The oligonucleotide molecules may be labeled with a dye (e.g., fluorescent dye), as described elsewhere herein. In some instances, such as for detecting repeated sequences in nucleic acid molecules, such as homopolymer repeated sequences, dinucleotide repeated sequences, and trinucleotide repeated sequences, the solution may comprise targeted probes (e.g., homopolymer probe) configured to bind to the repeated sequences. The solution may comprise one type of probe (e.g., nucleotides). The solution may comprise different types of probes (e.g., nucleotides, oligonucleotide molecules, etc.). The solution may comprise different types of probes (e.g., oligonucleotide molecules, antibodies, etc.) for interacting with different types of analytes (e.g., nucleic acid molecules, proteins, etc.). Different solutions comprising different types of probes may be directed to the substrate any number of times, with or without detection between consecutive cycles (e.g., detection may be performed between some consecutive cycles, but not between some others), to sequence or otherwise process the nucleic acid molecule, depending on the type of processing.

Figure 3:
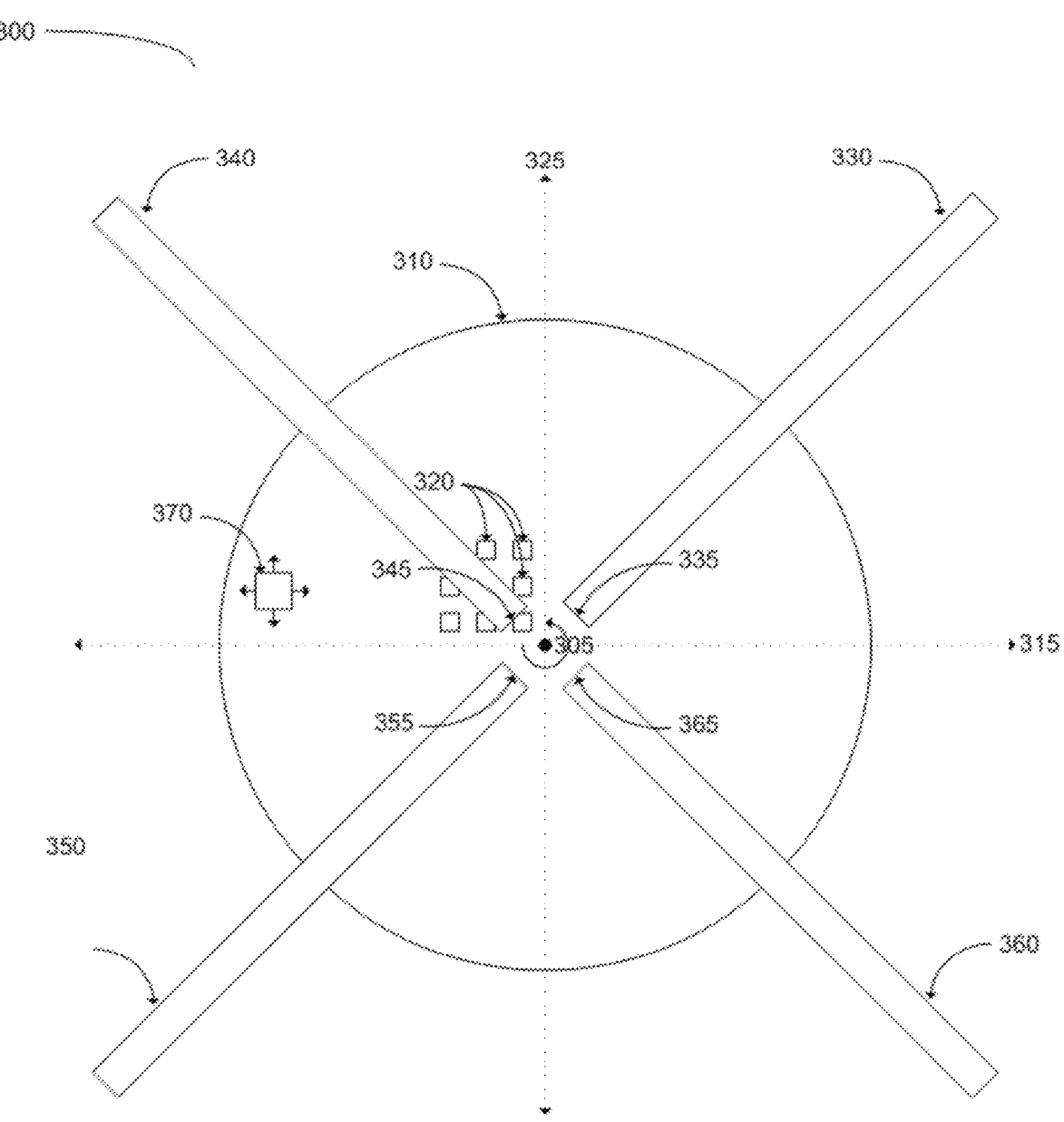
FIG. 3 shows a system for sequencing a nucleic acid molecule.

FIG. 3 shows a system 300 for sequencing a nucleic acid molecule or processing an analyte. The system may be configured to implement the method 200 or 1400. Although the systems (e.g., 300, 400, 500a, 500b, etc.) are described with respect to processing nucleic acid molecules, the systems may be used to process any other type of biological analyte, as described herein.

The system may comprise a substrate 310. The substrate may comprise any substrate described herein, such as any substrate described herein with respect to FIG. 2. The substrate may comprise an array. The substrate may be open. The array may comprise one or more locations 320 configured to immobilize one or more nucleic acid molecules or analytes. The array may comprise any array described herein, such as any array described herein with respect to method 200. For instance, the array may comprise a plurality of individually addressable locations. The array may comprise a linker (e.g., any binder described herein) that is coupled to the nucleic acid molecule to be sequenced. Alternatively or in combination, the nucleic acid molecule to be sequenced may be coupled to a bead; the bead may be immobilized to the array. The array may be textured. The array may be a patterned array. The array may be planar.

The substrate may be configured to rotate with respect to an axis 305. The axis may be an axis through the center of the substrate. The axis may be an off-center axis. The substrate may be configured to rotate at any rotational velocity described herein, such as any rotational velocity described herein with respect to method 200 or 1400.

The substrate may be configured to undergo a change in relative position with respect to first or second longitudinal axes 315 and 325. For instance, the substrate may be translatable along the first and/or second longitudinal axes (as shown in FIG. 3). Alternatively, the substrate may be stationary along the first and/or second longitudinal axes. Alternatively or in combination, the substrate may be translatable along the axis (as shown in FIG. 4). Alternatively or in combination, the substrate may be stationary along the axis. The relative position of the substrate may be configured to alternate between positions. The relative position of the substrate may be configured to alternate between positions with respect to one or more of the longitudinal axes or the axis. The relative position of the substrate may be configured to alternate between positions with respect to any of the fluid channels described herein. For instance, the relative position of the substrate may be configured to alternate between a first position and a second position. The relative position of the substrate may be configured to alternate between at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 positions. The relative position of the substrate may be configured to alternate between a number of positions that is within a range defined by any two of the preceding values. The first or second longitudinal axes may be substantially perpendicular with the axis. The first or second longitudinal axes may be substantially parallel with the axis. The first or second longitudinal axes may be coincident with the axis.

The system may comprise a first fluid channel 330. The first fluid channel may comprise a first fluid outlet port 335. The first fluid outlet port may be configured to dispense a first fluid to the array. The first fluid outlet port may be configured to dispense any fluid described herein, such as any solution described herein. The first fluid outlet port may be external to the substrate. The first fluid outlet port may not contact the substrate. The first fluid outlet port may be a nozzle. The first fluid outlet port may have an axis that is substantially coincident with the axis. The first fluid outlet port may have an axis that is substantially parallel to the axis.

The system may comprise a second fluid channel 340. The second fluid channel may comprise a second fluid outlet port 345. The second fluid outlet port may be configured to dispense a second fluid to the array. The second fluid outlet port may be configured to dispense any fluid described herein, such as any solution described herein. The second fluid outlet port may be external to the substrate. The second fluid outlet port may not contact the substrate. The second fluid outlet port may be a nozzle. The second fluid outlet port may have an axis that is substantially coincident with the axis. The second fluid outlet port may have an axis that is substantially parallel to the axis.

The first and second fluids may comprise different types of reagents. For instance, the first fluid may comprise a first type of nucleotide, such as any nucleotide described herein, or a nucleotide mixture. The second fluid may comprise a second type of nucleotide, such as any nucleotide described herein, or a nucleotide mixture. Alternatively, the first and second fluids may comprise the same type of reagents (e.g., same type of fluid is dispensed through multiple fluid outlet ports (e.g., nozzles) to increase coating speed). Alternatively or in combination, the first or second fluid may comprise a washing reagent. The first fluid channel 330 and the second fluid channel 340 may be fluidically isolated. Beneficially, where the first and second fluids comprise different types of reagents, each of the different reagents may remain free of contamination from the other reagents during dispensing.

The first fluid outlet port may be configured to dispense the first fluid during rotation of the substrate. The second fluid outlet port may be configured to dispense the second fluid during rotation of the substrate. The first and second fluid outlet ports may be configured to dispense at non-overlapping times. Alternatively, the first and second fluid outlet ports may be configured to dispense at overlapping times, such as when the first fluid and the second fluid comprise the same type of reagents. The substrate may be configured to rotate with a different speed or a different number of rotations when the first and second outlet ports dispense. Alternatively, the substrate may be configured to rotate with the same speed and number of rotations when the first and second outlet ports dispense. During rotation, the array may be configured to direct the first fluid in a substantially radial direction away from the axis. The first fluid outlet port may be configured to direct the first fluid to the array during at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, or at least 1,000,000 full rotations of the substrate. The first fluid outlet port may be configured to direct the first fluid to the array during a number of full rotations that is within a range defined by any two of the preceding values.

The system may comprise a third fluid channel 350 comprising a third fluid outlet port 355 configured to dispense a third fluid. The system may comprise a fourth fluid channel 360 comprising a fourth fluid outlet port 365 configured to dispense a fourth fluid. The third and fourth fluid channels may be similar to the first and second fluid channels described herein. The third and fourth fluids may be the same or different fluids as the first and/or second fluids. In some cases, at least 1, 2, 3, 4, 5, 6, 7, 8, 9, 10, 15, 20 or more fluids (or reagents) may be employed. For example, 5-10 fluids (or reagents) may be employed.

Although FIG. 3 shows a change in position of the substrate, as an alternative or in addition to, one or more of the first, second, third, and fourth fluid channels may be configured to undergo a change in position. For instance, any of the first, second, third, or fourth fluid channel may be translatable along the first and/or second longitudinal axes. Alternatively, any of the first, second, third, or fourth fluid channel may be stationary along the first and/or second longitudinal axes. Alternatively or in addition, any of the first, second, third, or fourth fluid channel may be translatable along the axis. Alternatively or in addition, any of the first, second, third, or fourth fluid channel may be stationary along the axis.

The relative position of one or more of the first, second, third, and fourth fluid channels may be configured to alternate between positions with respect to one or more of the longitudinal axes or the axis. For instance, the relative position of any of the first, second, third, or fourth fluid channel may be configured to alternate between a first position and a second position (e.g., by moving such channel, by moving the substrate, or by moving the channel and the substrate). The relative position of any of the first, second, third, or fourth fluid channel may be configured to alternate between at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more positions. The relative position of any of the first, second, third, or fourth fluid channel may be configured to alternate between a number of positions that is within a range defined by any two of the preceding values. The first or second longitudinal axes may be substantially perpendicular to the axis. The first or second longitudinal axes may be substantially parallel to the axis. The first or second longitudinal axes may be coincident with the axis.

Figure 4A:
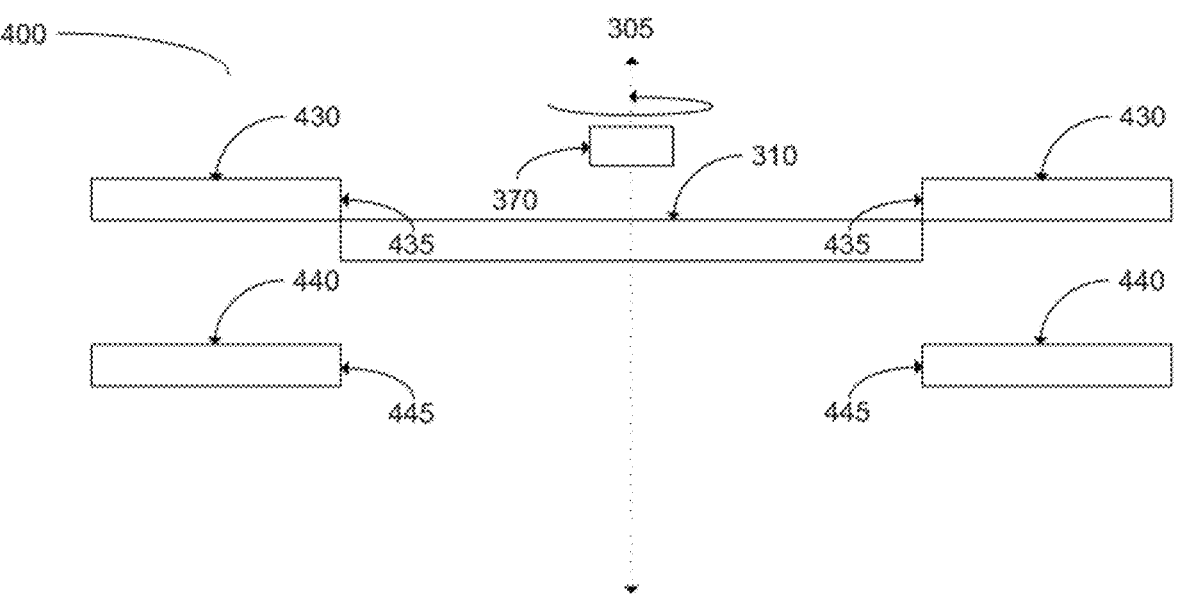
FIG. 4A shows a system for sequencing a nucleic acid molecule in a first vertical level.
Figure 4B:
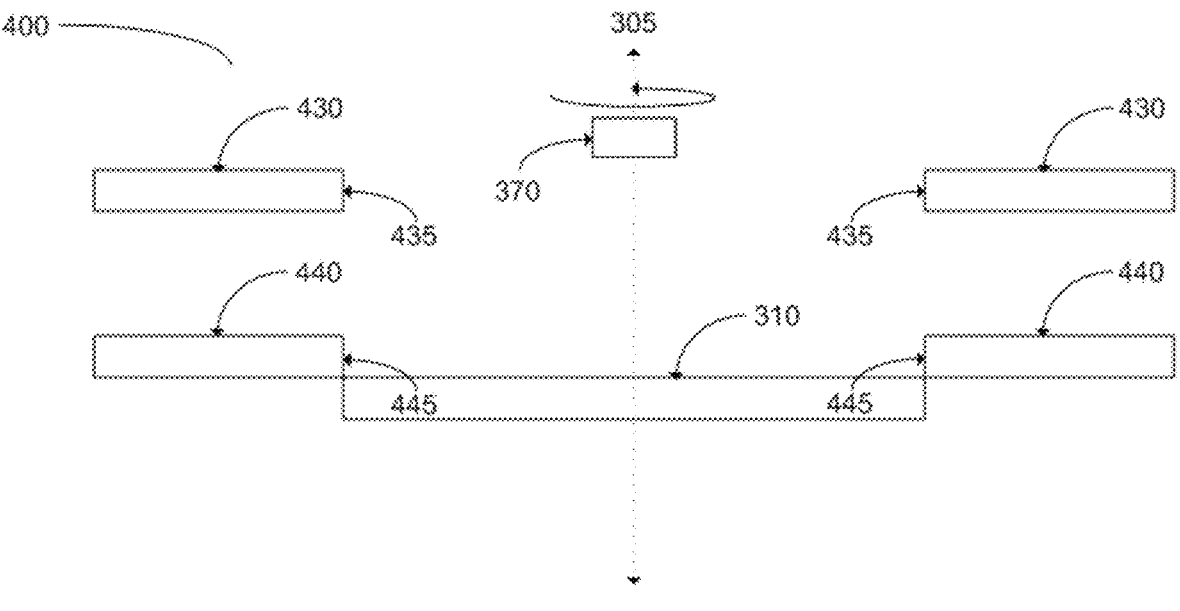
FIG. 4B shows a system for sequencing a nucleic acid molecule in a second vertical level.

In some instances, the system may comprise one or more fluid channels for receiving fluid from the substrate (not shown in FIG. 3). Referring to FIG. 4A-4B, a fifth fluid channel 430 may comprise a first fluid inlet port 435. The first fluid inlet port may be located at a first level of the axis (as shown in FIG. 4). In some instances, the first fluid inlet port may surround the periphery of the substrate 310 (e.g., circularly). The first fluid inlet port may be downstream of and in fluid communication with the substrate 310 when the substrate is in a first position, such as with respect to the axis. The fifth fluid channel may be in fluid communication with the first fluid channel 330. For example, the first fluid inlet port may be configured to receive a solution passing from the first fluid outlet port to the substrate and thereafter off the substrate (e.g., due to inertial forces during rotation of the substrate). For instance, the first fluid inlet port may be configured to receive the solution in a recycling process such as the recycling process described herein with respect to method 200 or 1400. In some instances, the solution received by the fifth fluid channel via the first fluid inlet port may be fed back (e.g., after filtering) to the first fluid channel to be dispensed via the first fluid outlet port to the substrate. The fifth fluid channel and the first fluid channel may define at least part of a first cyclic fluid flow path. The first cyclic fluid flow path may comprise a filter, such as a filter described herein with respect to method 200 or 1400. The filter may be a molecular filter. In other instances, the solution received by the fifth fluid channel may be fed back (e.g., after filtering) to different fluid channels (other than the first fluid channel) to be dispensed via different fluid outlet ports.

The system may comprise a sixth fluid channel 440. The sixth fluid channel may comprise a second fluid inlet port 445. The second fluid inlet port may be located at a second level of the axis (as shown in FIG. 4). In some instances, the second fluid inlet port may surround the periphery of the substrate 310. The second fluid inlet port may be downstream of and in fluid communication with the substrate 310 when the substrate is in a second position, such as with respect to the axis. The sixth fluid channel may be in fluid communication with the second fluid channel 340. For example, the second fluid inlet port may be configured to receive a solution passing from the second fluid outlet port to the substrate and thereafter off the substrate. For instance, the second fluid inlet port may be configured to receive the solution in a recycling process such as the recycling process described herein with respect to method 200 or 1400. In some instances, the solution received by the sixth fluid channel via the second fluid inlet port may be fed back (e.g., after filtering) to the second fluid channel to be dispensed via the second fluid outlet port to the substrate. The sixth fluid channel and the second fluid channel may define at least part of a second cyclic fluid flow path. The second cyclic fluid flow path may comprise a filter, such as a filter described herein with respect to method 200 or 1400. The filter may be a molecular filter.

The system may comprise a shield (not shown) that prevents fluid communication between the substrate and the second fluid inlet port when the substrate is in the first position and between the substrate and the first fluid inlet port when the substrate is in the second position.

The system may further comprise one or more detectors 370. The detectors may be optical detectors, such as one or more photodetectors, one or more photodiodes, one or more avalanche photodiodes, one or more photomultipliers, one or more photodiode arrays, one or more avalanche photodiode arrays, one or more cameras, one or more charged coupled device (CCD) cameras, or one or more complementary metal oxide semiconductor (CMOS) cameras. The cameras may be TDI or other continuous area scanning detectors described herein, including, for example, TDI line-scan cameras. The detectors may be fluorescence detectors. The detectors may be in sensing communication with the array. For instance, the detectors may be configured to detect a signal from the array. The signal may be an optical signal. The signal may be a fluorescence signal. The detectors may be configured to detect the signal from the substrate during rotation of the substrate. The detectors may be configured to detect the signal from the substrate when the substrate is not rotating. The detectors may be configured to detect the signal from the substrate following termination of the rotation of the substrate. FIG. 3 shows an example region 375 on the substrate that is optically mapped to the detector.

Figure 41:
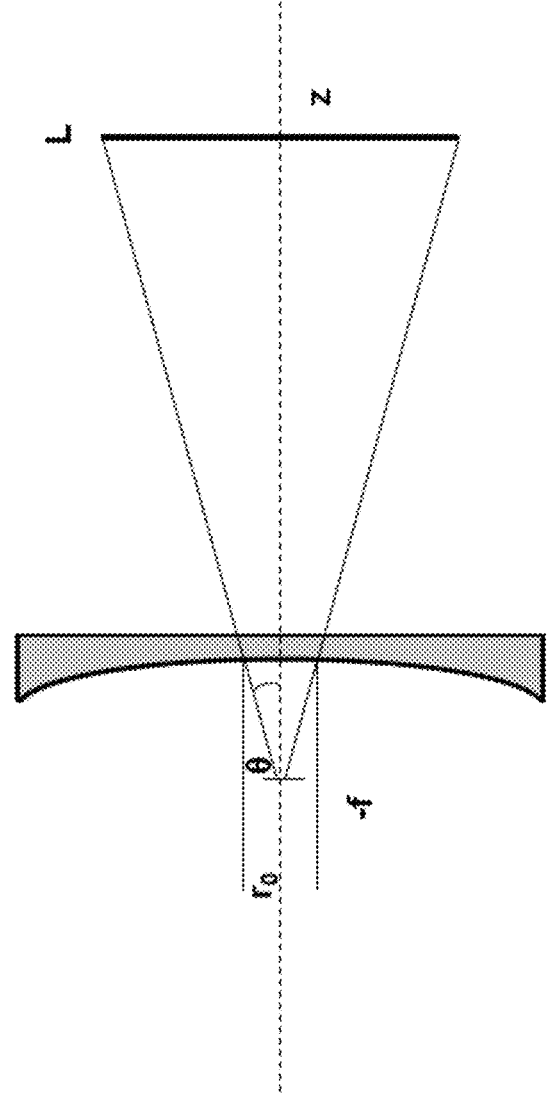
FIG. 41 illustrates schematically a scheme for expanding a laser beam to provide a laser line.

The system may comprise one or more sources (not shown in FIG. 3) configured to deliver electromagnetic radiation to the substrate. The sources may comprise one or more optical sources (e.g., illumination sources). The sources may comprise one or more incoherent or coherent optical sources. The sources may comprise one or more narrow bandwidth or broadband optical sources. The sources may be configured to emit optical radiation having a bandwidth of at most 1 hertz (Hz), at most 2 Hz, at most 5 Hz, at most 10 Hz, at most 20 Hz, at most 50 Hz, at most 100 Hz, at most 200 Hz, at most 500 Hz, at most 1 kilohertz (kHz), at most 2 kHz, at most 5 kHz, at most 10 kHz, at most 20 kHz, at most 50 kHz, at most 100 kHz, at most 200 kHz, at most 500 kHz, at most 1 megahertz (MHz), at most 2 MHz, at most 5 MHz, at most 10 MHz, at most 20 MHz, at most 50 MHz, at most 100 MHz, at most 200 MHz, at most 500 MHz, at most 1 gigahertz (GHz), at most 2 GHz, at most 5 GHz, at most 10 GHz, at most 20 GHz, at most 50 GHz, at most 100 GHz, or a bandwidth that is within a range defined by any two of the preceding values. The source may comprise one or more light emitting diodes (LEDs). The sources may comprise one or more lasers. The sources may comprise one or more single-mode laser sources. The sources may comprise one or more multi-mode laser sources. The sources may comprise one or more laser diodes. A laser may be a continuous wave laser or a pulsed laser. A beam of light emitted by a laser may be a Gaussian or approximately Gaussian beam, which beam may be manipulated using one or more optical elements (e.g., mirrors, lenses, prisms, waveplates, etc.). For example, a beam may be collimated. In some cases, a beam may be manipulated to provide a laser line (e.g., using one or more Powell lenses or cylindrical lenses). FIG. 41 shows an example of beam shaping using a cylindrical lens to provide a laser line. A collimated beam having a radius $r_0$ is incident upon a cylindrical plano-concave lens having a focal length $-f$. The beam will expand with a half-angle $\theta$ equivalent to $r_0/f$. The laser line will have a thickness of approximately $2r_0$ and a length L of approximately $2(r_0/f)(z+f)$ at a distance z from the lens. A laser line may impinge directly on a substrate or may be projected onto the substrate such that is approximately perpendicular to a central axis about which the open substrate may rotate.

The sources (e.g., optical or illumination sources) of a system may be configured to emit light comprising one or more wavelengths in the ultraviolet (about 100 nm to about 400 nm), visible (about 400 nm to about 700 nm), or infrared (about 700 nm to about 10,000 nm) regions of the electromagnetic spectrum, or any combination therefore. For instances, the sources may emit radiation comprising one or more wavelengths in the range from 600 nm to 700 nm. The sources may emit radiation, either individually or in combination, having an optical power of at least 0.05 watts (W), at least 0.1 W, at least 0.2 W, at least 0.5 W, at least 1 W, at least 2 W, at least 5 W, at least 10 W, or an optical power that is within a range defined by any two of the preceding values. The sources may be configured to interact with molecules on the substrate to generate detectable optical signals that may be detected by the optical detectors. For instance, the sources may be configured to generate optical absorption, optical reflectance, scattering, phosphorescence, fluorescence, or any other optical signal described herein.

The system may comprise a seventh, eighth, ninth, tenth, eleventh, twelfth, thirteenth, fourteenth, fifteenth, sixteenth, seventeenth, eighteenth, nineteenth, or twentieth fluid channel. Each fluid channel may comprise a fluid outlet port or a fluid inlet port in fluid communication with the substrate. For instance, the ninth, tenth, thirteenth, fourteenth, seventeenth, or eighteenth fluid channel may comprise a fluid outlet port. The seventh, eighth, eleventh, twelfth, fifteenth, sixteenth, nineteenth, or twentieth fluid channel may comprise a fluid inlet port. Alternatively, the system may comprise more than twenty fluid channels comprising a fluid outlet port or a fluid inlet port.

Thus, the system may comprise fifth, sixth, seventh, eighth, ninth, or tenth fluid outlet ports. The fifth, sixth, seventh, eighth, ninth, or tenth fluid outlet ports may be configured to dispense fifth, sixth, seventh, eighth, ninth, or tenth fluids to the array. The fifth, sixth, seventh, eighth, ninth, or tenth fluid outlet ports may be configured to dispense any fluid described herein, such as any solution described herein. The fifth, sixth, seventh, eighth, ninth, or tenth fluid outlet ports may be similar to the first, second, third, or fourth fluid outlet ports described herein. Alternatively, the system may comprise more than ten fluid outlet ports.

The fluid channels may be fluidically isolated from one another. For instance, the fluid channels may be fluidically isolated upstream of the first, second, third, fourth, fifth, sixth, seventh, eighth, ninth, or tenth fluid outlet ports. The fifth, sixth, seventh, eighth, ninth, or tenth fluid outlet ports may be external to the substrate. The fifth, sixth, seventh, eighth, ninth, or tenth fluid outlet ports may not contact the substrate. The fifth, sixth, seventh, eighth, ninth, or tenth fluid outlet ports may be a nozzle.

The system may comprise third, fourth, fifth, sixth, seventh, eighth, ninth, or tenth fluid inlet ports. The third, fourth, fifth, sixth, seventh, eighth, ninth, or tenth fluid inlet ports may be in fluid communication with the substrate when the substrate is in a third, fourth, fifth, sixth, seventh, eighth, ninth, or tenth position (e.g., with respect to the axis), respectively. Alternatively, the system may comprise more than ten fluid inlet ports.

The ninth, tenth, thirteenth, fourteenth, seventeenth, or eighteenth fluid channel may be in fluid communication with the seventh, eighth, eleventh, twelfth, fifteenth, or sixteenth fluid channel, respectively; each pair of fluid channels may define at least part of a third, fourth, fifth, sixth, seventh, eighth, ninth, or tenth cyclic fluid flow path, respectively. Each cyclic fluid flow path may be configured similarly to the first or second cyclic fluid flow paths described herein, with the fluid inlet port of the cyclic fluid flow path configured to receive a solution passing from the fluid outlet port of the cyclic fluid flow path to the substrate. Each cyclic fluid flow path may be configured to receive the solution in a recycling process as described herein. Each cyclic fluid flow path may comprise a filter as described herein.

The fifth, sixth, seventh, eighth, ninth, or tenth fluids may comprise different types of reagents. For instance, the fifth, sixth, seventh, eighth, ninth, or tenth fluid may comprise a fifth, sixth, seventh, eighth, ninth, or tenth type of nucleotide, respectively, such as any nucleotide described herein. Alternatively or in combination, the fifth, sixth, seventh, eighth, ninth, or tenth fluid may comprise a washing reagent.

The fifth, sixth, seventh, eighth, ninth, or tenth fluid outlet port may be configured to dispense the fifth, sixth, seventh, eighth, ninth, or tenth fluid, respectively, during rotation of the substrate. The fifth, sixth, seventh, eighth, ninth, or tenth fluid outlet ports may be configured to dispense at overlapping or non-overlapping times.

FIG. 4A shows a system 400 for sequencing a nucleic acid molecule in a first vertical level. The system may be substantially similar to system 300 described herein or may differ from system 300 in the arrangement of one or more of its elements. The system 400 may comprise substrate 310 described herein. The system 400 may utilize vertical motion parallel to the axis 305 to expose (e.g., make available fluid communication) the substrate 310 to different fluid channels. The system may comprise first fluid channel 330 and first fluid outlet port 335 described herein. The system may comprise second fluid channel 340 and second fluid outlet port 345 described herein. The system may comprise third fluid channel 350 and third fluid outlet port 355 described herein. The system may comprise fourth fluid channel 360 and fourth fluid outlet port 365 described herein. The system may comprise detector 370 described herein. The detector may be in optical communication with the region shown. The system may comprise any optical source described herein (not shown in FIG. 4A).

The fifth fluid channel 430 and first fluid inlet port 435 may be arranged at a first level along the vertical axis, as shown in FIGS. 4A and 4B. The sixth fluid channel 440 and second fluid inlet port 445 may be arranged at a second level along the vertical axis. In this manner, the system may be viewed as comprising first and second fluid flow paths, with each fluid flow path located at a different vertical level. The substrate 310 may be vertically movable between the first level and the second level, from the first level to the second level, and from the second level to the first level. As an alternative, the substrate may be vertically fixed but the levels may be vertically movable with respect to the substrate 310. As another alternative, the substrate and the levels may be vertically movable.

The system 400 may comprise multiple levels. The levels may be vertically orientated relative to one another. The system may include at least 2, 3, 4, 5, 6, 7, 8, 9, 10, 20, 30, 40, 50, 100 or more levels. Each level may include one or more sub-levels (e.g., an incremental level between any two levels). Each level may be for dispensing and/or recovering a different fluid (or reagent). Some levels may be for dispensing the same fluid (or reagent).

While in the first vertical level, the substrate may be in fluid communication with the fifth fluid channel and the first fluid inlet port, but not the sixth fluid channel and the second fluid inlet port. The substrate may be isolated from the sixth fluid channel and the second fluid inlet port by a shield (not shown), as described herein. A first fluid or first solution described herein may be dispensed to the substrate while the substrate is in this first vertical level. For example, any excess of the first solution spinning off the substrate may be received by the first fluid inlet port while the substrate is at the first vertical level. In another example, a washing solution (e.g., dispensed from a different fluid outlet port than the first fluid) spinning off the substrate with some of the first fluid may be received by the first fluid inlet port while the substrate is at the first vertical level. The substrate may then be moved to a second vertical level by vertically moving the substrate. Alternatively, the fifth or sixth fluid channels may be moved vertically. Alternatively or in addition, the substrate and one or more of the fluid channels may be moved relative to the other (e.g., along the axis).

FIG. 4B shows the system 400 for sequencing a nucleic acid molecule in a second vertical level. While in the second vertical level, the substrate may be in fluid communication with the sixth fluid channel and the second fluid inlet port, but not the fifth fluid channel and the first fluid inlet port. The substrate may be isolated from the fifth fluid channel and the first fluid inlet port by a shield (not shown), as described herein. A second fluid or second solution described herein may be dispensed to the substrate while the substrate is in this second vertical position. Alternatively, the first solution may be removed while the substrate is in the second vertical position. In some cases, the first solution may be recycled while the substrate is in the second vertical position. The substrate may then be moved back to the first vertical level, or to another vertical level described herein, by vertically moving the substrate. Alternatively, the fifth or sixth fluid channels may be moved vertically. Alternatively or in addition, the substrate and one or more of the fluid channels may be moved relative to the other (e.g., along the axis).

The third, fourth, fifth, sixth, seventh, eighth, ninth, or tenth fluid inlet ports may be located at third, fourth, fifth, sixth, seventh, eighth, ninth, or tenth vertical levels, respectively. The substrate may be moved to the third, fourth, fifth, sixth, seventh, eighth, ninth, or tenth vertical levels by vertically moving the substrate or by vertically moving the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth fluid flow channels. At any of the first, second, third, fourth, fifth, sixth, seventh, eighth, ninth, tenth or more vertical levels, any fluid solution described herein may be dispensed to the substrate. At any of the first, second, third, fourth, fifth, sixth, seventh, eighth, ninth, tenth or more vertical levels, any fluid solution described herein may be removed from the substrate. At any of the first, second, third, fourth, fifth, sixth, seventh, eighth, ninth, tenth or more vertical levels, any fluid solution described herein may be recycled from the substrate.

Figure 5A:
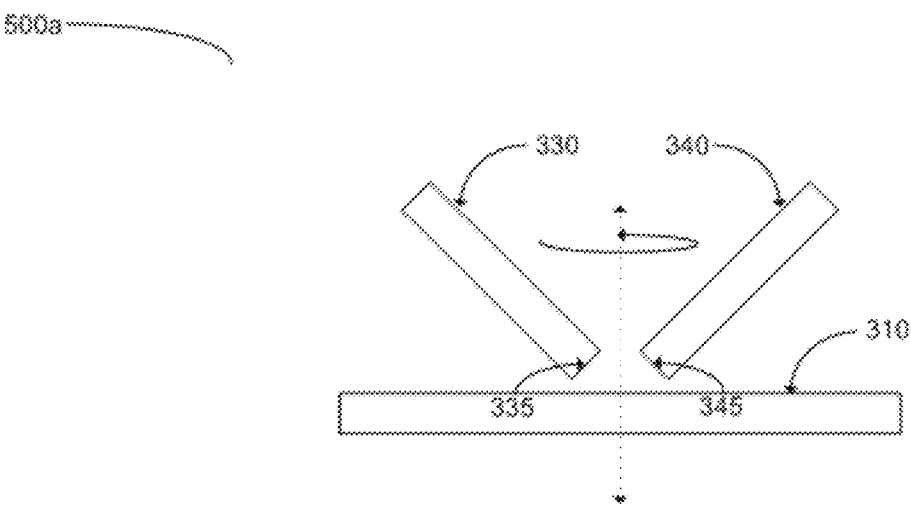
FIG. 5A shows a first example of a system for sequencing a nucleic acid molecule using an array of fluid flow channels.

FIG. 5A shows a first example of a system 500a for sequencing a nucleic acid molecule using an array of fluid flow channels. The system may be substantially similar to system 300 or 400 described herein and may differ from system 300 or 400 in the arrangement of one or more of its elements. The system 500a may utilize a geometrical arrangement of a plurality of fluid flow channels to expose the substrate to different fluids. The system 500a may comprise substrate 310 described herein. The system may comprise first fluid channel 330 and first fluid outlet port 335 described herein. The system may comprise second fluid channel 340 and second fluid outlet port 345 described herein. The system may comprise fifth fluid channel 430 and first fluid inlet port 435 described herein (not shown in FIG. 5A). The system may comprise sixth fluid channel 440 and second fluid inlet port 445 described herein (not shown in FIG. 5A). The system may comprise detector 370 described herein (not shown in FIG. 5A). The system may comprise any optical source described herein (not shown in FIG. 5A).

The first fluid channel and first fluid outlet port may be arranged at a first position, as shown in FIG. 5A. The second fluid channel and second fluid outlet port may be arranged at a second position. The system may be configured to dispense a first fluid from the first fluid outlet port and a second fluid from the second fluid outlet port.

The system may comprise any of third, fourth, seventh, eighth, ninth, tenth, eleventh, twelfth, thirteenth, fourteenth, fifteenth, sixteenth, seventeenth, eighteenth, nineteenth, or twentieth fluid channels described herein. The system may comprise any of third, fourth, fifth, sixth, seventh, eighth, ninth, or tenth fluid outlet ports described herein. The system may comprise any of third, fourth, fifth, sixth, seventh, eighth, ninth, or tenth fluid inlet ports described herein.

The third, fourth, fifth, sixth, seventh, eighth, ninth, or tenth fluid outlet ports may be located at third, fourth, fifth, sixth, seventh, eighth, ninth, or tenth positions, respectively. The system may be configured to dispense a third, fourth, fifth, sixth, seventh, eighth, ninth, or tenth fluid from the third, fourth, fifth, sixth, seventh, eighth, ninth, or tenth fluid outlet port, respectively.

Any two or more of the first, second, third, fourth, seventh, eighth, ninth, tenth, eleventh, twelfth, thirteenth, fourteenth, fifteenth, sixteenth, seventeenth, eighteenth, nineteenth, twentieth, or more fluid channels may form an array of fluid flow channels. The array of fluid flow channels may be moveable. Alternatively, the array of fluid flow channels may be at a fixed location with respect to the substrate. Each fluid flow channel of the array of fluid flow channels may be positioned such that a longitudinal axis of the fluid flow channel forms an angle with the rotational axis of the substrate. The angle may have a value of at least 0 degrees, at least 5 degrees, at least 10 degrees, at least 15 degrees, at least 20 degrees, at least 25 degrees, at least 30 degrees, at least 35 degrees, at least 40 degrees, at least 45 degrees, at least 50 degrees, at least 55 degrees, at least 60 degrees, at least 65 degrees, at least 70 degrees, at least 75 degrees, at least 80 degrees, at least 85 degrees, or at least 90 degrees. The angle may have a value that is within a range defined by any two of the preceding values. Each fluid channel of the array of fluid channels may make a similar angle with the substrate. Alternatively, one or more fluid channels may make different angles with the substrate.

Figure 5B:
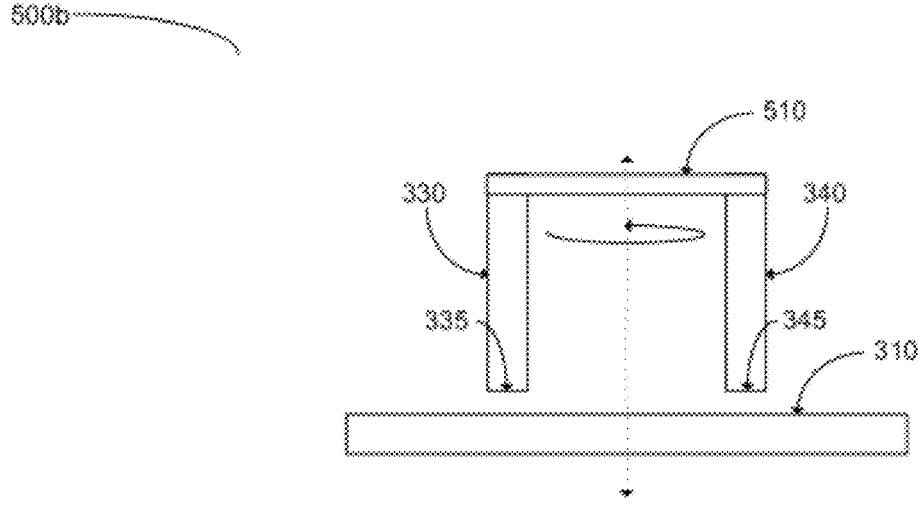
FIG. 5B shows a second example of a system for sequencing a nucleic acid molecule using an array of fluid flow channels.

FIG. 5B shows a second example of a system 500*b* for sequencing a nucleic acid molecule using an array of fluid flow channels.

The system may be substantially similar to system 300 or 400 described herein and may differ from system 300 or 400 in the arrangement of one or more of its elements. The system 500*b* may utilize a plurality of fluid flow channels configured to move relative to the substrate to expose the substrate to different fluids. The system 500*b* may comprise substrate 310 described herein. The system may comprise first fluid channel 330 and first fluid outlet port 335 described herein. The system may comprise second fluid channel 340 and second fluid outlet port 345 described herein. The system may comprise fifth fluid channel 430 and first fluid inlet port 435 described herein (not shown in FIG. 5B). The system may comprise sixth fluid channel 440 and second fluid inlet port 445 described herein (not shown in FIG. 5B). The system may comprise detector 370 described herein (not shown in FIG. 5B). The system may comprise any optical source described herein (not shown in FIG. 5B).

The first fluid channel and first fluid outlet port may be attached to a fluid dispenser 510. The fluid dispenser may be a moveable fluid dispenser, such as comprising a moveable gantry arm, as shown in FIG. 5B. As an alternative, the fluid dispenser may be fixed or stationary. The fluid dispenser may be configured to move to a first position to dispense a first fluid from the first fluid outlet port. The second fluid channel and second fluid outlet port may also be attached to the fluid dispenser. The fluid dispenser may be configured to move to a second position to dispense a second fluid from the second fluid outlet port.

The system may comprise any of third, fourth, seventh, eighth, ninth, tenth, eleventh, twelfth, thirteenth, fourteenth, fifteenth, sixteenth, seventeenth, eighteenth, nineteenth, or twentieth fluid channels described herein. The system may comprise any of third, fourth, fifth, sixth, seventh, eighth, ninth, or tenth fluid outlet ports described herein. The system may comprise any of third, fourth, fifth, sixth, seventh, eighth, ninth, or tenth fluid inlet ports described herein.

The third, fourth, fifth, sixth, seventh, eighth, ninth, or tenth fluid outlet ports may be attached to the fluid dispenser. The fluid dispenser may be configured to move to a third, fourth, fifth, sixth, seventh, eighth, ninth, or tenth position to dispense a third, fourth, fifth, sixth, seventh, eighth, ninth, or tenth fluid from the third, fourth, fifth, sixth, seventh, eighth, ninth, or tenth fluid outlet port, respectively. Alternatively, the fluid dispenser may be kept stationary and the substrate 310 may be moved to different positions to receive different fluids.

Figure 6:
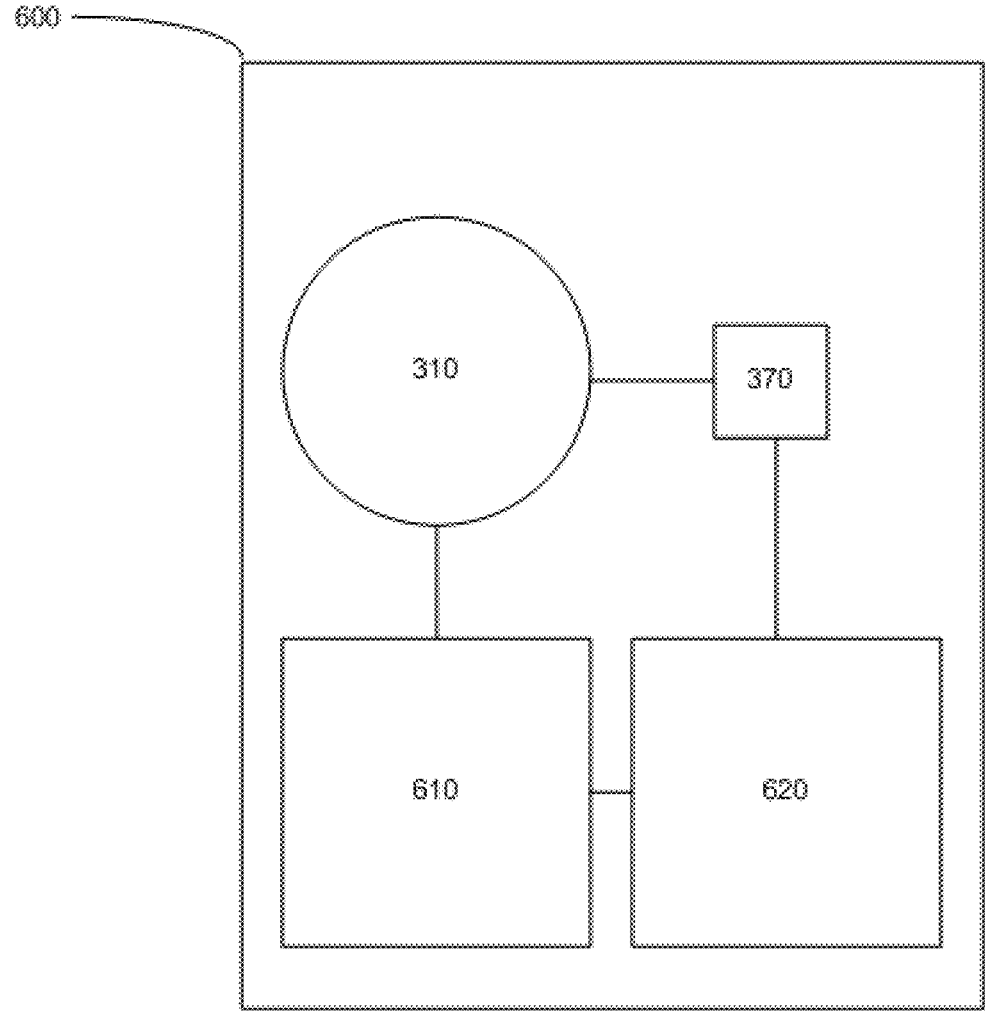
FIG. 6 shows a computerized system for sequencing a nucleic acid molecule.

FIG. 6 shows a computerized system 600 for sequencing a nucleic acid molecule. The system may comprise a substrate 310, such as a substrate described herein with respect to method 200 or 1400, or system 300. The system may further comprise a fluid flow unit 610. The fluid flow unit may comprise any element associated with fluid flow described herein, such as any or all of elements 330, 335, 340, 345, 350, 355, 360, 365, 430, 435, 440, 445, and 370 described herein with respect to system 300, 400, 500*a*, or 500*b*. The fluid flow unit may be configured to direct a solution comprising a plurality of nucleotides described herein to an array of the substrate prior to or during rotation of the substrate. The fluid flow unit may be configured to direct a washing solution described herein to an array of the substrate prior to or during rotation of the substrate. In some instances, the fluid flow unit may comprise pumps, compressors, and/or actuators to direct fluid flow from a first location to a second location. With respect to method 1400, the fluid flow system may be configured to direct any solution to the substrate 310. With respect to method 1400, the fluid flow system may be configured to collect any solution from the substrate 310. The system may further comprise a detector 370, such as any detector described herein with respect to system 300 or 400. The detector may be in sensing communication with the array of the substrate.

The system may further comprise one or more computer processors 620. The one or more processors may be individually or collectively programmed to implement any of the methods described herein. For instance, the one or more processors may be individually or collectively programmed to implement any or all operations of the methods of the present disclosure, such as method 200 or 1400. In particular, the one or more processors may be individually or collectively programmed to: (i) direct the fluid flow unit to direct the solution comprising the plurality of nucleotides across the array during or prior to rotation of the substrate; (ii) subject the nucleic acid molecule to a primer extension reaction under conditions sufficient to incorporate at least one nucleotide from the plurality of nucleotides into a growing strand that is complementary to the nucleic acid molecule; and (iii) use the detector to detect a signal indicative of incorporation of the at least one nucleotide, thereby sequencing the nucleic acid molecule.

While the rotational system has been described with respect to sequencing applications, such rotational schemes may be used for other applications (e.g., pre-sequencing applications, sample preparation, etc.), such as template seeding and surface amplification processes. For example, the reagents dispensed during or prior to rotation of the substrate may be tailored to the other applications. While the reagents dispensed to the substrate in the rotational system have been described with respect to nucleotides, any reagent that may react with a nucleic acid molecule (or any other molecule or cell) immobilized to the substrate, such as probes, adaptors, enzymes, and labelling reagents, may be dispensed to the substrate prior to, during, or subsequent to rotation to achieve high speed coating of the substrate with the dispensed reagents.

The systems described herein (such as any of systems 300, 400, 500a, or 500b, or any other system described herein), or any element thereof, may be environmentally controlled. For instance, the systems may be maintained at a specified temperature or humidity. The systems (or any element thereof) may be maintained at a temperature of at least 20 degrees Celsius (° C.), at least 25° C., at least 30° C., at least 35° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., at most 100° C., at most 95° C., at most 90° C., at most 85° C., at most 80° C., at most 75° C., at most 70° C., at most 65° C., at most 60° C., at most 55° C., at most 50° C., at most 45° C., at most 40° C., at most 35° C., at most 30° C., at most 25° C., at most 20° C., or at a temperature that is within a range defined by any two of the preceding values.

Different elements of the system may be maintained at different temperatures or within different temperature ranges, such as the temperatures or temperature ranges described herein. Elements of the system may be set at temperatures above the dew point to prevent condensation. Elements of the system may be set at temperatures below the dew point to collect condensation.

Figure 35:
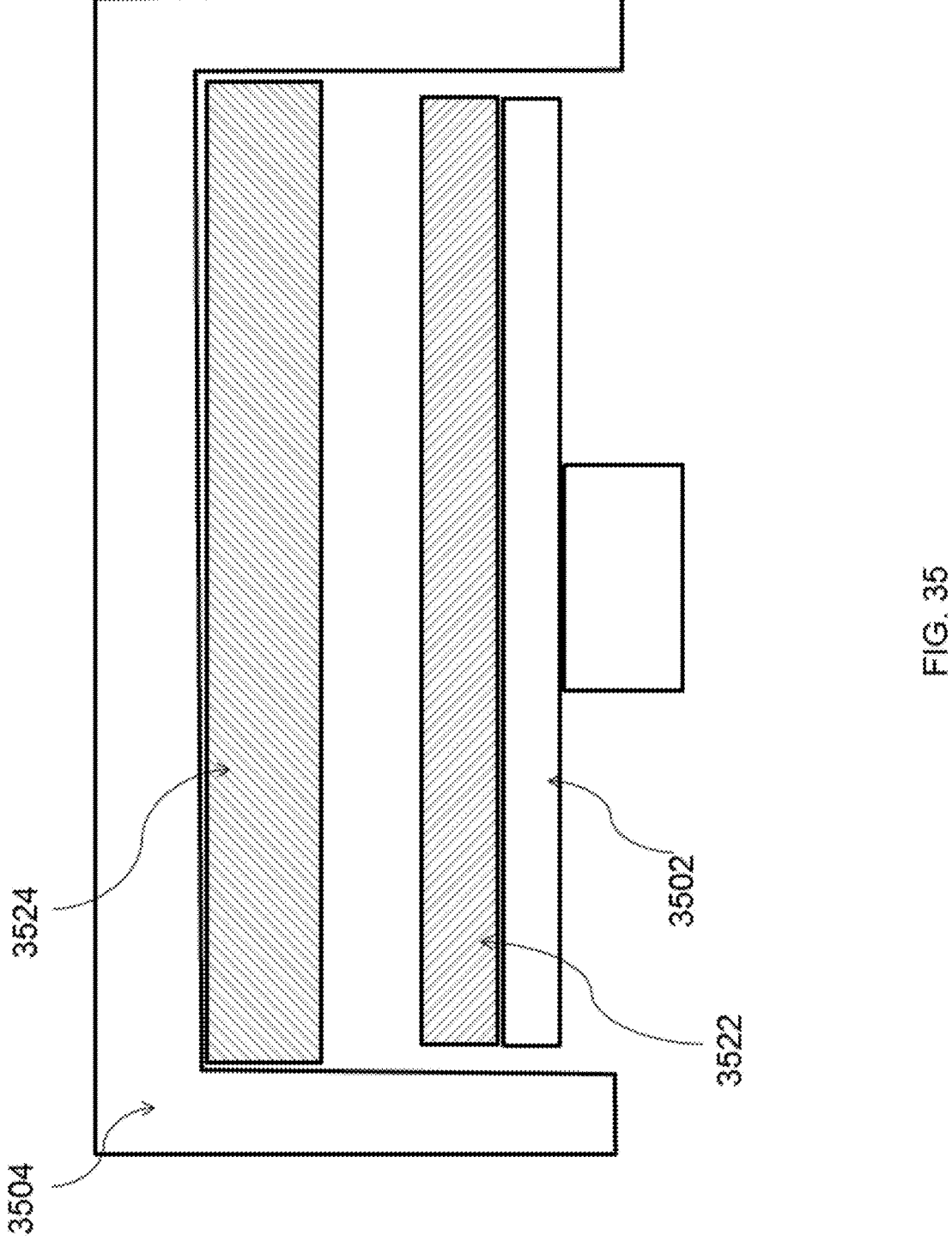
FIG. 35 illustrates a system with different environmental conditions in an open substrate system.

FIG. 35 illustrates a system with different environmental conditions in an open substrate system. An open substrate system may comprise a substrate 3502 and a container 3504 enclosing the substrate. The substrate 3502 may be any substrate described herein. The container 3504 may define a surrounding environment of the substrate 3502. In some instances, the surrounding environment may be confined and/or closed. In some instances, the surrounding environment may be sealed (e.g., hermetically sealed, frictionally sealed, pneumatically, etc.). In some instances, the surrounding environment may be sealed using a pressure differential (e.g., pneumatic pressure, mechanical pressure, etc.). The open substrate system may comprise at least two non-overlapping regions, a first region 3522 and a second region 3524, having different environmental conditions. In some instances, the first region 3522, contacting or in proximity to a surface of the substrate 3502, such as the surface that comprises one or more analytes as described herein, may be maintained at a first set of temperatures and first set of humidities. In some instances, the second region 3524, contacting or in proximity to a top portion of the container 3504 (or otherwise referred to herein as a lid or cover), may be maintained at a second set of temperatures and second set of humidities. The first set of temperatures and first set of humidities may be controlled such as to prevent or minimize evaporation of one or more reagents on the surface of the substrate. For example, the first set of temperatures and first set of humidities may be configured to prevent less than 80%, less than 70%, less than 60%, less than 50%, less than 40%, less than 30%, less than 20%, less than 10%, less than 5%, less than 4%, less than 3%, less than 2%, or less than 1% evaporation of the volume of the solution layer dispensed on the uncovered surface. The second set of temperatures and second set of humidities may also be controlled such as to enhance or restrict condensation. For example, the first set of temperatures may be the lowest temperatures within the surrounding environment of the open substrate system. For example, the second set of temperatures may be the highest temperatures within the surrounding environment of the open substrate system. In some instances, the environmental conditions of the different regions may be achieved by controlling the temperature of the enclosure. In some instances, the environmental conditions of the different regions may be achieved by controlling the temperature of selected parts or whole of the container. In some instances, the environmental conditions of the different regions may be achieved by controlling the temperature of selected parts or whole of the substrate. In some instances, the environmental conditions of the different regions may be achieved by controlling the temperature of reagents dispensed to the substrate. Any combination thereof may be used to control the environmental conditions of the different regions. Heat transfer may be achieved by any method, including for example, conductive, convective, and radiative methods. For example, the first region 3522 may be maintained at cooler temperatures by controlling the temperature of the substrate 3502, and the second region 3524 may be maintained at warmer temperatures by controlling the temperature of a top portion of the container 3504, via conduction.

The systems (or any element thereof) may be maintained at a relative humidity of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at most 100%, at most 95%, at most 90%, at most 85%, at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5%, or a relative humidity that is within a range defined by any two of the preceding values. The systems (or any element thereof) may be configured such that less than 80%, less than 70%, less than 60%, less than 50%, less than 40%, less than 30%, less than 20%, less than 10%, less than 5%, less than 4%, less than 3%, less than 2%, or less than 1% of the volume of the solution layer dispensed on the uncovered surface evaporates.

The systems (or any element thereof) may be contained within a sealed container, housing, or chamber that insulates the system (or any element thereof) from the external environment or atmosphere, allowing for the control of the temperature or humidity. An environmental unit (e.g., humidifiers, heaters, heat exchangers, compressors, etc.) may be configured to regulate one or more operating conditions in each environment. In some instances, each environment may be regulated by independent environmental units. In some instances, a single environmental unit may regulate a plurality of environments. In some instances, a plurality of environmental units may, individually or collectively, regulate the different environments. An environmental unit may use active methods or passive methods to regulate the operating conditions. For example, the temperature may be controlled using heating or cooling elements. The humidity may be controlled using humidifiers or dehumidifiers. In some instances, a part of the internal environment within the container or chamber may be further controlled from other parts of the internal environment. Different parts may have different local temperatures, pressures, and/or humidity. For example, the internal environment may comprise a first internal environment and a second internal environment separated by a seal.

Alternatively or in conjunction, the systems or methods described herein may comprise a solution comprising an agent that may reduce evaporation. For example, the solution may comprise glycerol, which can prevent evaporation of the solution.

In some instances, the seal may comprise an immersion objective lens, which is described in further detail elsewhere herein. For example, an immersion objective lens may be part of a seal that separates the internal environment in the container into a first internal environment having 100% (or substantially 100%) humidity and a second environment having one or more of an ambient temperature, pressure or humidity. The immersion objective lens may be in contact with one or more of a detector and imaging lens.

Substrate Preparation and Contaminant-Resistant Substrates

As described above, a substrate may comprise a surface comprising a plurality of binders coupled thereto. In some cases, the plurality of binders may comprise a plurality of nucleic acid molecules (e.g., a plurality of nucleic acid molecules that are directly coupled to the surface or that are indirectly coupled to the surface via a plurality of linkers, as described herein). Oligonucleotide (e.g., nucleic acid molecule)-coated surfaces (e.g., substantially planar substrates and/or particles, including substrates having a plurality of particles immobilized thereto) may be employed for various applications, including for capturing specific sequences of nucleic acid molecules for, e.g., gene expression analysis by hybridization capture (gene arrays), single nucleotide polymorphism (SNP) genotyping, capturing a subset of sequencing libraries (e.g., targeted capture or exome sequencing), synthesis of cDNA from mRNA via oligo-dT capture, and on-surface amplification of nucleic acid molecules for downstream analysis such as next generation sequencing. An oligonucleotide-coated surface may be prepared in advance of its use in any such application, and may be stored between its generation and its eventual use (e.g., during transport from a manufacturing site to an operating site, sample processing and preparation, etc.). An oligonucleotide-coated surface may be stored for at least 1 hour, and in some cases may be stored for months or even years. During storage, an oligonucleotide-coated surface may come into contact with one or more solutions or other materials that may contain nucleic acid molecules, which may be considered contaminants. Contaminant nucleic acid molecules may hybridize to oligonucleotides coupled to a surface, leading to decreased efficiency in downstream analysis (e.g., during use in an application such as those described herein) and/or erroneous results in downstream analysis. For example, an oligonucleotide-coated surface prepared for use in a sequencing analysis may become contaminated with non-relevant sequencing libraries during handling of the surface prior to its use in the sequencing analysis (e.g., prior to placement of the substrate comprising the surface in a sequencing instrument or to commencement of an amplification process, such as a clonal amplification process).

Non-relevant interactions of oligonucleotides (e.g., binders) coupled to a surface of a substrate may be reduced by blocking the oligonucleotides that are attached to the surface (e.g., bound oligonucleotides) with oligonucleotides comprising sequences that are fully or partially complementary to the sequences of the oligonucleotides that are attached to the surface. Blocking oligonucleotides may be provided in solution and may be considered "free" oligonucleotides. For example, blocking oligonucleotides may fully or partially hybridize to all or a subset of the oligonucleotides coupled to a surface of a substrate, thereby providing a partially double-stranded nucleic acid molecule comprising a bound oligonucleotide and a blocking oligonucleotide. Such a partially double-stranded nucleic acid molecule may be resistant to hybridization to nucleic acid molecules with which the surface may come into contact, including potential contaminant nucleic acid molecules that may not be relevant to any eventual analysis such as eventual nucleic acid sequencing. Blocking oligonucleotides may be removed from the oligonucleotide-coated surface (e.g., via application of an appropriate stimulus, such as a chemical or thermal stimulus, or via enzymatic degradation) to provide an oligonucleotide-coated surface that may be ready to use in an analysis process (e.g., as described herein). The surface may undergo one or more washing processes (e.g., one or more wash flows) to remove blocking oligonucleotides. Removing the blocking oligonucleotides may provide the oligonucleotides coupled to the surface as free oligonucleotides that may participate in various reactions, including capture of complementary or partially complementary nucleic acid molecules of interest.

An oligonucleotide-coated surface may be stored for any useful amount of time. For example, an oligonucleotide-coated surface may be stored for at least 1 hour, such as at least 2 hours, 6 hours, 12 hours, 24 hours, 36 hours, 2 days, 3 days, 4 days, 5 days, 6 days, 1 week, 1 month, 2 months, 3 months, 4 months, 5 months, 6 months, 1 year, or longer. An oligonucleotide-coated surface may be stored under any useful conditions. For example, an oligonucleotide-coated surface may be stored under standard temperature and pressure conditions (e.g., room temperature), such as between about 18° C. to about 30° C., such as between about 20° C. to about 25° C., and about 1 atmosphere. An oligonucleotide-coated surface may be stored in a dry environment (e.g., in air or a nitrogen- or argon-enriched environment) or in a solution (e.g., a buffered solution such as saline sodium citrate).

An oligonucleotide-coated surface may be stored in a package or container, which package or container may contain one or more such oligonucleotide-coated surfaces. For example, multiple oligonucleotide-coated surfaces may be provided in a given package or container. A package or container comprising one or more oligonucleotide-coated surfaces may be a rigid package or container or a flexible package or container. For example, one or more oligonucleotide-coated surfaces, such as one or more substantially planar substrates comprising the one or more oligonucleotide-coated surfaces, may be provided in a flexible package. A package or container may comprise or be formed of, for example, a glass, plastic polymer, metal (e.g., metal foil), or any other material. A package or container comprising one or more oligonucleotide-coated surfaces may be sealed (e.g., hermetically sealed). A package or container comprising one or more oligonucleotide-coated surfaces may be resealable upon opening. For example, a first oligonucleotide-coated surface may be removed from the package or container and a second oligonucleotide-coated surface may be retained within the package or container. An oligonucleotide-coated surface may also be configured for storage outside of a package or container for a period of time, such as for at least about 1 hour, 2 hours, 6 hours, or longer (e.g., as described herein).

An oligonucleotide-coated surface may be prepared at a manufacturing and/or shipping site. Alternatively, an oligonucleotide-coated surface may be prepared by a user, such as a user of a sequencing instrument. In some cases, an oligonucleotide-coated surface comprising a plurality of blocking oligonucleotides coupled (e.g., hybridized) to a plurality of oligonucleotides coupled to the oligonucleotide-coated surface may be prepared at a manufacturing and/or shipping site. Alternatively, an oligonucleotide-coated surface comprising a plurality of blocking oligonucleotides coupled (e.g., hybridized) to a plurality of oligonucleotides coupled to the oligonucleotide-coated surface may be prepared by a user, such as a user of a sequencing instrument. A plurality of blocking oligonucleotides coupled to a plurality of oligonucleotides coupled to the oligonucleotide-coated surface may be removed by a user, such as a user of a sequencing instrument. For example, a plurality of blocking oligonucleotides coupled to a plurality of oligonucleotides coupled to the oligonucleotide-coated surface may be removed by a user shortly before a user makes use of the oligonucleotide-coated surface (e.g., as described herein, such as for a sequencing application).

An oligonucleotide-coated surface may be used one or more times for one or more applications. For example, an oligonucleotide-coated surface may be configured for one-time use. Alternatively, an oligonucleotide-coated surface may be configured to be used multiple times, for the same and/or different applications. For example, oligonucleotides coupled to a surface may be "recharged" for use in a subsequent application, or a surface may be washed clean and new oligonucleotides may be coupled to the surface for use in a subsequent application. In another example, an oligonucleotide-coated surface may comprise one or more different regions comprising one or more different oligonucleotides (e.g., binders) coupled thereto (e.g., as described herein). The one or more different oligonucleotides may be configured for use in one or more different applications. In an example, an oligonucleotide-coated surface comprises a first plurality of oligonucleotides coupled to a first region and a second plurality of oligonucleotides coupled to a second region, where the first plurality of oligonucleotides and the second plurality of oligonucleotides have different nucleic acid sequences. The first plurality of oligonucleotides may be configured to at least partially hybridize to a first plurality of blocking oligonucleotides, while the second plurality of oligonucleotides may be configured to at least partially hybridize to a second plurality of blocking oligonucleotides, where the first plurality of blocking oligonucleotides and the second plurality of blocking oligonucleotides have different nucleic acid sequences. The first plurality of blocking oligonucleotides hybridized to the first plurality of oligonucleotides coupled to the surface may be removable upon application of a first stimulus (e.g., as described herein) and the second plurality of blocking oligonucleotides hybridized to the second plurality of oligonucleotides coupled to the surface may be removable upon application of a second stimulus, which second stimulus differs from the first stimulus. Accordingly, the first and second pluralities of blocking oligonucleotides may be provided to the oligonucleotide-coated surface (e.g., at the same or different times) to provide a doubly-treated surface. The first plurality of blocking oligonucleotides hybridized to oligonucleotides of the first plurality of oligonucleotides coupled to the surface may be removed (e.g., after a first period of storage) by application of the first stimulus to provide the first plurality of oligonucleotides coupled to the first region free to participate in a first application such as a first sequencing assay. Application of the first stimulus may not affect the second plurality of blocking oligonucleotides coupled to the second plurality of oligonucleotides coupled to the second region. Accordingly, the second plurality of blocking oligonucleotides hybridized to oligonucleotides of the second plurality of oligonucleotides coupled to the surface may be retained during the duration of the first application. The second plurality of blocking oligonucleotides hybridized to oligonucleotides of the second plurality of oligonucleotides coupled to the surface may be removed (e.g., after a second period of storage) by application of the second stimulus to provide the second plurality of oligonucleotides coupled to the second region free to participate in a second application such as a second sequencing assay.

Oligonucleotides may be coupled to an oligonucleotide-coated surface via any useful mechanism, including, for example, non-specific interactions (e.g., one or more of hydrophilic interactions, hydrophobic interactions, electrostatic interactions, physical interactions (for instance, adhesion to pillars or settling within wells), and the like) or specific interactions (e.g., as described herein).

Oligonucleotides may be coupled to an oligonucleotide-coated surface randomly or semi-randomly. Alternatively, oligonucleotides may be coupled to an oligonucleotide-coated surface in a predetermined pattern (e.g., as described herein). In some cases, a substrate comprising an oligonucleotide-coated surface may comprise one or more different binders (e.g., dispersed with a plurality of oligonucleotides or disposed on a different region of the substrate). For example, a substrate comprising an oligonucleotide-coated surface may comprise a first set of oligonucleotides coupled to the surface and a second set of oligonucleotides coupled to the surface, where the oligonucleotides of the first set of oligonucleotides have a nucleic acid sequence that differs from a nucleic acid sequence of oligonucleotides of the second set of oligonucleotides. In an example, oligonucleotides of the first set of oligonucleotides may comprise a first nucleic acid sequence and oligonucleotides of the second set of oligonucleotides may comprise a second nucleic acid sequence that differs from the first nucleic acid sequence. In some cases, oligonucleotides of the first set of oligonucleotides and oligonucleotides of the second set of oligonucleotides may comprise a common third nucleic acid sequence, such as a poly(T) sequence.

Oligonucleotides may be coupled to one or more particles immobilized to a surface of a substrate. For example, a surface of a substrate may comprise a plurality of particles (e.g., beads) immobilized thereto (e.g., as described herein), which plurality of particles comprise a plurality of oligonucleotides coupled thereto. In some cases, each particle comprises a different plurality of oligonucleotides coupled thereto (e.g., a plurality of oligonucleotides comprising a nucleic acid sequence that differs from a nucleic acid sequence of another plurality of oligonucleotides coupled to a different particle). For example, each particle of a plurality of particles to a surface of a substrate may comprise a plurality of oligonucleotides coupled thereto, where all of the oligonucleotides coupled to a given particle comprise a common barcode sequence and where each plurality of oligonucleotides coupled to each different particle of the plurality of particles comprises a different barcode sequence (e.g., as described herein).

An oligonucleotide-coated surface may comprise any useful number of oligonucleotides coupled thereto (e.g., as described herein). For example, an oligonucleotide-coated surface may comprise at least 10, 100, 1,000, 10,000, 100,000, 1,000,000, 10,000,000, 100,000,000 or more oligonucleotides. In some cases, an oligonucleotide-coated surface comprises multiple regions comprising multiple different pluralities of oligonucleotides, which different pluralities of oligonucleotides may have the same or different nucleic acid sequences and may comprise the same or different numbers of oligonucleotides. For example, an oligonucleotide-coated surface may comprise a first region comprising a first plurality of oligonucleotides and a second region comprising a second plurality of oligonucleotides, where the first plurality of oligonucleotides and/or the second plurality of oligonucleotides comprises at least 10, 100, 1000, 10,000, 100,000, 1,000,000, 10,000,000, 100, 000,000 or more oligonucleotides. The density of oligonucleotides coupled to a region of a surface may be, for example, at least about 1,000 molecules per mm$^2$, such as at least about 10,000 molecules per mm$^2$, 100,000 molecules per mm$^2$, 1,000,000 molecules per mm$^2$, 10,000,000 molecules per mm$^2$, or more. The density of oligonucleotides coupled to a surface may vary by region. For example, a surface may comprise a first region comprising a first density of oligonucleotides coupled thereto and a second region comprising a second density of oligonucleotides coupled thereto, where the first density is higher than the second density.

Oligonucleotides coupled to a surface of a substrate may comprise one or more different nucleic acid sequences. For example, an oligonucleotide coupled to a surface of a substrate may comprise a barcode sequence, an adapter sequence, a primer sequence (e.g., a universal primer sequence), a poly(T) sequence, a random N-mer sequence, a flow cell adapter sequence, a sequencing primer, a unique molecular identifier, a key sequence, an index sequence, or any other useful sequence. One or more sequences of an oligonucleotide coupled to a surface may be configured to capture a particular sample molecule or population thereof. In some cases, an oligonucleotide-coated surface may comprise a plurality of oligonucleotides coupled thereto, wherein each oligonucleotide of the plurality of oligonucleotides comprises at least one common or shared sequence. For example, each oligonucleotide of a plurality of oligonucleotides coupled to an oligonucleotide-coated surface or a given region thereof may comprise a common barcode sequence. Alternatively or in addition, each oligonucleotide of the plurality of oligonucleotides coupled to an oligonucleotide-coated surface or a given region thereof may comprise a poly(T) sequence (e.g., for capture of sample nucleic acid molecules comprising a poly(A) sequence, such as mRNA molecules) or another specific capture sequence. In some cases, each oligonucleotide of a plurality of oligonucleotides coupled to an oligonucleotide-coated surface or a region thereof may comprise one or more common sequences (e.g., as described herein) and a different unique molecular identifier or key sequence.

Oligonucleotides coupled to a surface of a substrate may have any useful length. For example, an oligonucleotide coupled to a surface of a substrate may comprise at least 6 bases, such as 7, 8, 9, 10, 12, 14, 16, 18, 20, 25, 30, 35, or more bases. In some cases, only a portion of the bases of an oligonucleotide coupled to a surface of a substrate may be accessible to a blocking or other oligonucleotide. For example, one or more nucleotides of an oligonucleotide coupled to a surface of a substrate may comprise a blocking moiety and/or may be coupled to other moieties, such as a moiety immobilizing the oligonucleotide to the surface. In some cases, an oligonucleotide coupled to a surface of a substrate may comprise one or more reversible terminators.

Similarly, a blocking oligonucleotide may have any useful length. For example, a blocking oligonucleotide may comprise at least 6 bases, such as 7, 8, 9, 10, 12, 14, 16, 18, 20, 25, 30, 35, or more bases. In some cases, only a portion of the bases of a blocking oligonucleotide may be available to hybridize to an oligonucleotide coupled to an oligonucleotide-coated surface. For example, one or more nucleotides of a blocking oligonucleotide may comprise a blocking moiety and/or may be coupled to other moieties. In some cases, a blocking oligonucleotide may comprise one or more groups that may be substantially inert or unreactive (e.g., in a buffered solution). In some cases, a blocking oligonucleotide may comprise one or more reversible terminators.

Oligonucleotides coupled to a surface of a substrate may have any useful composition. Oligonucleotides coupled to a surface may comprise nucleotides, nucleotide analogs, non-standard nucleotides, and/or modified analogs (e.g., as described herein). For example, oligonucleotides coupled to a surface may comprise DNA nucleotides, RNA nucleotides, and/or a mixture thereof. Similarly, blocking oligonucleotides coupled to a surface may have any useful composition, provided that the blocking oligonucleotides comprise a nucleic acid sequence that is fully or partially complementary to oligonucleotides coupled to a surface of a substrate. Blocking oligonucleotides may comprise DNA nucleotides, RNA nucleotides, and/or a mixture thereof. In an example, an oligonucleotide coupled to a surface comprises DNA nucleotides and a blocking oligonucleotide configured to hybridize partially or completely to the oligonucleotide coupled to the surface comprises DNA nucleotides. In another example, an oligonucleotide coupled to a surface comprises RNA nucleotides and a blocking oligonucleotide configured to hybridize partially or completely to the oligonucleotide coupled to the surface comprises RNA nucleotides.

An oligonucleotide coupled to a surface may comprise an adapter or complement thereof. For example, an oligonucleotide may comprise a sequence complementary to a sequence of an adapter coupled to a sample nucleic acid molecule (e.g., a single-stranded sample nucleic acid molecule, such as a single-stranded sample RNA molecule). An adapter may be a single-stranded adapter and may have any useful composition. For example, an adapter may comprise DNA nucleotides, RNA nucleotides, or a combination thereof. An adapter may have any useful length and other properties. An adapter may be disposed at an end of an oligonucleotide that is distal from the surface to which the oligonucleotide is coupled. The adapter may comprise a barcode sequence (e.g., as described herein).

An oligonucleotide coupled to a surface and/or a blocking oligonucleotide may comprise a functional feature such as a terminator (e.g., reversible terminator), blocking moiety, or a label or reporter moiety. For example, a blocking oligonucleotide may comprise a label moiety such as a fluorescent label (e.g., a dye, as described herein). A label moiety or other functional feature may be linked to a nucleotide of an oligonucleotide via a linker moiety. For example, a nucleotide of a blocking oligonucleotide may comprise a label moiety (e.g., dye) linked to the base of the nucleotide via a linker moiety. The nucleotide may be disposed at an end of the blocking oligonucleotide. Alternatively or in addition, a nucleotide of a blocking oligonucleotide may comprise a terminator (e.g., reversible terminator). The terminator may be linked to the sugar of the nucleotide via a linker moiety. The nucleotide may be disposed at the end of the blocking oligonucleotide. Such functional features may facilitate control of the interaction between blocking oligonucleotides and oligonucleotides coupled to a surface of a substrate and/or provide a mechanism for identifying where blocking oligonucleotides have hybridized to oligonucleotides coupled to a surface. Alternatively or in addition, an oligonucleotide coupled to a surface may comprise a label or reporter moiety, which label or reporter moiety may emit a first signal when the oligonucleotide is uncoupled and a second signal when the oligonucleotide is coupled to a blocking oligonucleotide. For example, the second signal may be attenuated, decreased, quenched, or amplified relative to the first signal. In some cases, no detectable signal may be emitted by the label or reporter moiety when the oligonucleotide coupled to the surface is hybridized to a blocking oligonucleotide. In this manner, coupling between oligonucleotides coupled to a surface and blocking oligonucleotides may be monitored (e.g., to gauge the blocking efficiency of the blocking oligonucleotides). For example, oligonucleotides coupled a surface may each comprise a dye that emits a signal when the oligonucleotides are "free," which signal is severely attenuated when the oligonucleotides are "blocked" (e.g., hybridized to blocking oligonucleotides). By optically interrogating the surface before and after provision of the blocking oligonucleotides, the blocking efficiency of the blocking oligonucleotides (and thus the contamination resistance of the treated surface) can be gauged. In some cases, different fluorescent dyes may be used for different areas of a surface (e.g., for oligonucleotides having different nucleic acid sequences that may be coupled to different areas of the surface).

A treated surface comprising a plurality of oligonucleotides immobilized thereto and a plurality of blocking oligonucleotides coupled to oligonucleotides of the plurality of oligonucleotides may have any degree of "contamination resistance." The percentage of oligonucleotides of the plurality of oligonucleotides that are coupled to blocking oligonucleotides of the plurality of blocking oligonucleotides may be indicative of the resistance of the treated surface to contamination. In some cases, at least 50% of the oligonucleotides of the plurality of oligonucleotides may be coupled to blocking oligonucleotides. For example, at least 55%, 60%, 65%, 70%, 75%, 80%, 85%, 90%, 95%, 96%, 97%, 98%, 99%, or more of the oligonucleotides of the plurality of oligonucleotides may be coupled to blocking oligonucleotides. Coupling between oligonucleotides coupled to the surface and blocking oligonucleotides may be monitored via optical detection (e.g., as described herein) or any other useful method.

FIG. 38 illustrates a blocking oligonucleotide scheme. In Panel A, a substrate comprising bound oligonucleotides is provided. In Panel B, the bound oligonucleotides are blocked using blocking oligonucleotides (e.g., as described herein). As shown in Panel C, contaminant nucleic acid molecules cannot bind to the bound oligonucleotides while the blocking oligonucleotides are coupled to the bound oligonucleotides. Panel D shows removal of the blocking oligonucleotides using various mechanisms, including heat denaturation, chemical denaturation, chemical degradation, and enzymatic degradation. After the blocking oligonucleotides have been removed, relevant target nucleic acid molecules (e.g., from a sample for various applications such as sequencing) may be able to bind to substrate-bound oligonucleotides (e.g., substrate-bound oligonucleotides comprising sequences that are at least partially complementary to the target nucleic acid molecules, as described herein).

In an aspect, the present disclosure provides a method for storing a substrate comprising a nucleic acid molecule-coated surface. A substrate having a surface comprising a first set of nucleic acid molecules immobilized thereto may be provided. Nucleic acid molecules of the first set of nucleic acid molecules may be configured to capture sample nucleic acid molecules derived from one or more nucleic acid samples (e.g., nucleic acid samples for sequencing). The substrate comprising the surface comprising the first set of nucleic acid molecules may be brought into contact with a second set of nucleic acid molecules under conditions sufficient to yield a treated surface in which at least 70%

(e.g., at least 75%, 80%, 85%, 90%, or more) of nucleic acid molecules of the first set of nucleic acid molecules may be hybridized to nucleic acid molecules of the second set of nucleic acid molecules, wherein the second set of nucleic acid molecules are not the sample nucleic acid molecules. Excess nucleic acid molecules of the second set of nucleic acid molecules may be washed away. The substrate having the treated surface may be stored for a period of time, such as at least 1 hour, 6 hours, 12 hours, 24 hours, 2 days, or longer. The treated surface may be stored under any useful conditions (e.g., as described herein). During storage of the treated surface, each nucleic acid molecule of the first set of nucleic acid molecules that is hybridized to a nucleic acid molecule of the second set of nucleic acid molecules may not hybridize to another nucleic acid molecule.

The second set of nucleic acid molecules may be provided to the surface of the substrate in a solution. Each nucleic acid molecule of the second set of nucleic acid molecules may comprise a sequence that is substantially complementary to a sequence of the first set of nucleic acid molecules. The sequence of the first set of nucleic acid molecules may comprise at least 6 bases, such as at least 10 bases, 20 bases, or more. Each nucleic acid molecule of the first set of nucleic acid molecules may comprise at least 6 bases, such as at least 10 bases, 20 bases, or more. The first set of nucleic acid molecules and/or the second set of nucleic acid molecules may comprise DNA nucleotides, RNA nucleotides, or a combination thereof. Each nucleic acid molecule of the first set of nucleic acid molecules may comprise the same nucleic acid sequence. In some cases, the first set of nucleic acid molecules may comprise one or more different nucleic acid sequences. The first set of nucleic acid molecules may comprise a first subset of nucleic acid molecules comprising a first nucleic acid sequence and a second subset of nucleic acid molecules comprising a second nucleic acid sequence, which first and second nucleic acid sequences are different. The first subset of nucleic acid molecules and the second subset of nucleic acid molecules may both comprise a third nucleic acid sequence. The third nucleic acid sequence may comprise a poly(T) sequence.

The nucleic acid molecules of the first set of nucleic acid molecules may be immobilized to the surface at independently addressable locations. The independently addressable locations may be substantially planar, and may comprise one or more wells. Nucleic acid molecules of the first set of nucleic acid molecules may be immobilized to the surface of the substrate according to a predetermined pattern. A density of the first set of nucleic acid molecules on the surface may be at least 10,000 molecules per $mm^2$, such as at least 100,000, 1,000,000, 10,000,000, or more molecules per $mm^2$. The surface of the substrate may be substantially planar. The substrate may comprise one or more particles immobilized thereto.

The method may further comprise, subsequent to a period of storage of the treated surface, removing nucleic acid molecules of the second set of nucleic acid molecules from the treated surface. The nucleic acid molecules may be removed via, for example, enzymatic degradation or via denaturing via chemical or thermal stimulation (e.g., application of a chemical stimulus such as sodium hydroxide). After removing these nucleic acid molecules, the first set of nucleic acid molecules immobilized to the surface may be used for, e.g., hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof.

In another aspect, the present disclosure provides a method for preparing a substrate having a treated surface for use in nucleic acid processing. A substrate having a treated surface may be provided, which substrate comprises a first set of nucleic acid molecules immobilized thereto. At least 70% (e.g., at least 80%, 85%, 90%, 95%, or more) of nucleic acid molecules of the first set of nucleic acid molecules may be hybridized to nucleic acid molecules of a second set of nucleic acid molecules. Nucleic acid molecules of the first set of nucleic acid molecules may be configured to capture sample nucleic acid molecules derived from one or more nucleic acid samples. The second set of nucleic acid molecules is distinct from the sample nucleic acid molecules. The substrate having the treated substrate may have been stored for a time period of at least 1 hour, such as at least 6 hours, 12 hours, 24 hours, 2 days, or longer. The treated surface may have been stored under any useful conditions (e.g., as described herein). During storage of the treated surface, each nucleic acid molecule of the first set of nucleic acid molecules that is hybridized to a nucleic acid molecule of the second set of nucleic acid molecules may not hybridize to another nucleic acid molecule.

Nucleic acid molecules of the second set of nucleic acid molecules from the treated surface may be removed (e.g., as described herein). For example, the nucleic acid molecules may be removed from the treated surface via enzymatic degradation or via denaturing via chemical or thermal stimulation (e.g., application of a chemical stimulus such as sodium hydroxide). After removing these nucleic acid molecules, the first set of nucleic acid molecules immobilized to the surface may be used for, e.g., hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof.

Each nucleic acid molecule of the second set of nucleic acid molecules may comprise a sequence that is substantially complementary to a sequence of the first set of nucleic acid molecules. The sequence of the first set of nucleic acid molecules may comprise at least 6 bases, such as at least 10 bases, 20 bases, or more. Each nucleic acid molecule of the first set of nucleic acid molecules may comprise at least 6 bases, such as at least 10 bases, 20 bases, or more. The first set of nucleic acid molecules and/or the second set of nucleic acid molecules may comprise DNA nucleotides, RNA nucleotides, or a combination thereof. Each nucleic acid molecule of the first set of nucleic acid molecules may comprise the same nucleic acid sequence. In some cases, the first set of nucleic acid molecules may comprise one or more different nucleic acid sequences. The first set of nucleic acid molecules may comprise a first subset of nucleic acid molecules comprising a first nucleic acid sequence and a second subset of nucleic acid molecules comprising a second nucleic acid sequence, which first and second nucleic acid sequences are different. The first subset of nucleic acid molecules and the second subset of nucleic acid molecules may both comprise a third nucleic acid sequence. The third nucleic acid sequence may comprise a poly(T) sequence.

The nucleic acid molecules of the first set of nucleic acid molecules may be immobilized to the surface at independently addressable locations. The independently addressable locations may be substantially planar, and may comprise one or more wells. Nucleic acid molecules of the first set of nucleic acid molecules may be immobilized to the surface of the substrate according to a predetermined pattern. A density of the first set of nucleic acid molecules on the surface may be at least 10,000 molecules per $mm^2$, such as at least 100,000, 1,000,000, 10,000,000, or more molecules per $mm^2$. The surface of the substrate may be substantially planar. The substrate may comprise one or more particles immobilized thereto.

In another aspect, the present disclosure provides a method for storing a substrate comprising a nucleic acid molecule-coated surface, comprising providing a substrate having a surface comprising a first set of nucleic acid molecules immobilized thereto. Nucleic acid molecules of the first set of nucleic acid molecules may be configured to capture sample nucleic acid molecules derived from one or more nucleic acid samples. Each nucleic acid molecule of the nucleic acid molecules of the first set of nucleic acid molecules may comprise a first nucleic acid sequence. A second set of nucleic acid molecules may also be provided, wherein each nucleic acid molecule of the second set of nucleic acid molecules comprises a second nucleic acid sequence that may be substantially complementary to the first nucleic acid sequence. The second set of nucleic acid molecules may be distinct from the sample nucleic acid molecules. The surface comprising the first set of nucleic acid molecules may be brought into contact with the second set of nucleic acid molecules to generate a treated surface in which at least 70% (e.g., at least 75%, 80%, 85%, 90%, 95%, or more) of nucleic acid molecules of the first set of nucleic acid molecules may be hybridized to nucleic acid molecules of the second set of nucleic acid molecules. For each nucleic acid molecule of the first set of nucleic acid molecules hybridized to a nucleic acid molecule of the second set of nucleic acid molecules, the first nucleic acid sequence may be hybridized to the second nucleic acid sequence. The first nucleic acid sequence hybridized to the second nucleic acid sequence may at least partially denature between about 40° C. and 60° C., such as between about 50° C. and 60° C. The treated surface may then be stored for a period of time, such as for at least one hour, 2 hours, 6 hours, 12 hours, 24 hours, 2 days, or longer. The treated surface may be stored under any useful conditions (e.g., as described herein). During storage of the treated surface, each nucleic acid molecule of the first set of nucleic acid molecules that is hybridized to a nucleic acid molecule of the second set of nucleic acid molecules may not hybridize to another nucleic acid molecule.

The second set of nucleic acid molecules may be provided to the surface of the substrate in a solution. The first nucleic acid sequence and the second nucleic acid sequence may each comprise at least 6 bases, such as at least 10 bases, 20 bases, or more. Each nucleic acid molecule of the second set of nucleic acid molecules may comprise at least 6 bases, such as at least 10 bases, 20 bases, or more. Similarly, each nucleic acid molecule of the first set of nucleic acid molecules may comprise at least 6 bases, such as at least 10 bases, 20 bases, or more. A given nucleic acid molecule of the first set of nucleic acid molecules and a given nucleic acid molecule of the second set of nucleic acid molecules may comprise the same number of nucleotides. Alternatively, a given nucleic acid molecule of the first set of nucleic acid molecules and a given nucleic acid molecule of the second set of nucleic acid molecules may comprise a different number of nucleotides. The first set of nucleic acid molecules and/or the second set of nucleic acid molecules may comprise DNA nucleotides, RNA nucleotides, or a combination thereof. In some cases, the first set of nucleic acid molecules may comprise one or more different nucleic acid sequences. The first set of nucleic acid molecules may comprise a first subset of nucleic acid molecules comprising the first nucleic acid sequence and a second subset of nucleic acid molecules comprising a third nucleic acid sequence, which first and third nucleic acid sequences are different. The first subset of nucleic acid molecules and the second subset of nucleic acid molecules may both comprise a fourth nucleic acid sequence. The fourth nucleic acid sequence may comprise a poly(T) sequence.

The nucleic acid molecules of the first set of nucleic acid molecules may be immobilized to the surface at independently addressable locations. The independently addressable locations may be substantially planar, and may comprise one or more wells. Nucleic acid molecules of the first set of nucleic acid molecules may be immobilized to the surface of the substrate according to a predetermined pattern. A density of the first set of nucleic acid molecules on the surface may be at least 10,000 molecules per $mm^2$, such as at least 100,000, 1,000,000, 10,000,000, or more molecules per $mm^2$. The surface of the substrate may be substantially planar, and may comprise a plurality of wells. The substrate may comprise one or more particles immobilized thereto.

The method may further comprise, subsequent to a period of storage of the treated surface, removing nucleic acid molecules of the second set of nucleic acid molecules from the treated surface. The nucleic acid molecules may be removed via, for example, enzymatic degradation or via denaturing via chemical or thermal stimulation (e.g., application of a chemical stimulus such as sodium hydroxide). The nucleic acid molecules of the second set of nucleic acid molecules may be removed from said treated surface by denaturing said first nucleic acid sequence hybridized to the second nucleic acid sequence, e.g., by heating the treated surface or a solution in contact with the treated surface to between about 40° C. and 60° C. After removing these nucleic acid molecules, the first set of nucleic acid molecules immobilized to the surface may be used for, e.g., hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof.

In some cases, a single nucleic acid molecule may play the role of both a nucleic acid molecule coupled to a surface and a blocking nucleic acid molecule. For example, a nucleic acid molecule coupled to a surface may comprise a first sequence and a second sequence, which second sequence may be complementary to the first sequence. The second sequence may hybridize to the first sequence to provide a hairpin molecule that is immobilized to the surface. Such a scheme may provide a higher blocking efficiency and thus a higher contamination resistance. The portion of the nucleic acid molecule including the second sequence may be separated from the immobilized portion of the nucleic acid molecule including the first sequence (e.g., by cleaving the molecule at a cleavage site disposed between the first and second sequences) and the portion of the nucleic acid molecule including the second sequence may be removed (e.g., via denaturation or enzymatic degradation) and washed away.

Accordingly, in another aspect, the present disclosure may provide a method for storing a substrate comprising a nucleic acid molecule-coated surface, comprising providing a substrate having a surface comprising a first set of nucleic acid molecules immobilized thereto, wherein nucleic acid molecules of the first set of nucleic acid molecules may be configured to capture sample nucleic acid molecules derived from one or more nucleic acid samples. Each nucleic acid molecule of the first set of nucleic acid molecules may comprise a first nucleic acid sequence and a second nucleic acid sequence, which second nucleic acid sequence is substantially complementary to the first nucleic acid sequence. The first sequence and the second sequence may each comprise at least 6 bases, such as at least 10 bases, 12 bases, 15 bases, 20 bases, or more. A treated surface may be generated by subjecting the surface to conditions sufficient to bind the first nucleic acid sequence of a nucleic acid molecule of the first set of nucleic acid molecules to the second nucleic acid sequence of the nucleic acid molecule to provide an immobilized hairpin molecule. The substrate having the treated surface may then be stored for a time period of at least 1 hour, such as at least 2 hours, 6 hours, 12 hours, 24 hours, 2 days, or longer. The treated surface may be stored under any useful conditions (e.g., as described herein). During storage of the treated surface, each nucleic acid molecule of the first set of nucleic acid molecules may not hybridize to another nucleic acid molecule. At least 70% (e.g., at least 75%, 80%, 85%, 90%, 95%, or more) of nucleic acid molecules of the first set of nucleic acid molecules may be present as immobilized hairpin molecules during storage of the treated surface.

The nucleic acid molecules of the first set of nucleic acid molecules may be immobilized to the surface at independently addressable locations. The independently addressable locations may be substantially planar, and may comprise one or more wells. Nucleic acid molecules of the first set of nucleic acid molecules may be immobilized to the surface of the substrate according to a predetermined pattern. A density of the first set of nucleic acid molecules on the surface may be at least 10,000 molecules per $mm^2$, such as at least 100,000, 1,000,000, 10,000,000, or more molecules per $mm^2$. The surface of the substrate may be substantially planar, and/or may comprise a plurality of wells. The substrate may comprise one or more particles immobilized thereto.

The first set of nucleic acid molecules may comprise one or more different nucleic acid sequences. For example, the first set of nucleic acid molecules may comprise a first subset of nucleic acid molecules comprising the first nucleic acid sequence and the second nucleic acid sequence, and a second subset of nucleic acid molecules comprising a third nucleic acid sequence and a fourth nucleic acid sequence. The third nucleic acid sequence may be substantially complementary to the fourth nucleic acid sequences. The first nucleic acid sequence may be different from the third and fourth nucleic acid sequences. The first subset of nucleic acid molecules and the second subset of nucleic acid molecules may both comprise a fifth nucleic acid sequence, which fifth nucleic acid sequence may comprise a poly(T) sequence.

The method may further comprise, subsequent to storage of the treated surface for a period of time, separating the second sequence from the first sequence of the immobilized hairpin molecule. Separating the first and second sequences may be achieved via enzymatic degradation or denaturation using a chemical or thermal stimulus (e.g., a chemical stimulus such as sodium hydroxide). After separating these sequences, the first set of nucleic acid molecules immobilized to the surface may be used for, e.g., hybridization capture, single nucleotide polymorphism (SNP) genotyping, sequencing library capture, synthesis of nucleic acid molecules, on-surface amplification, downstream processing or analysis of nucleic acid molecules or derivatives thereof, or combinations thereof. Each nucleic acid molecule of the first set of nucleic acid molecules may comprise a cleavable base. The cleavable base may be disposed between the first and second sequences of the nucleic acid molecule. Subsequent to separating the first and second sequences of the immobilized hairpin molecule, the nucleic acid molecule may be cleaved at the cleavable base, thereby removing the second sequence of the nucleic acid molecule from the surface.

The present disclosure also provides kits including treated surfaces and kits for preparing treated surfaces. A kit may include a substrate comprising a treated surface and one or more reagents for processing the treated surface (e.g., for removing blocking oligonucleotides from the treated surface and preparing the surface for use in a subsequent application). A kit may include a substrate comprising a surface and a plurality of oligonucleotides for coupling to the substrate. The kit may also include a plurality of blocking oligonucleotides configured to hybridize to the plurality of oligonucleotides, as well as reagents for removing the blocking oligonucleotides and/or preparing the surface for use in a subsequent application. A kit provided herein may also comprise reagents for use in a subsequent application, and/or instructions for storing, preparing, unblocking, or otherwise utilizing a surface of a substrate.

In an aspect, the present disclosure provides a kit comprising a substrate comprising a treated surface, wherein the treated surface comprises a plurality of pairs of bound nucleic acid molecules, wherein each pair of the plurality of pairs comprises a first nucleic acid molecule of a first set of nucleic acid molecules at least partially hybridized to a second nucleic acid molecule of a second set of nucleic acid molecules. The first set of nucleic acid molecules may be immobilized to the surface. At least 70% (e.g., 75%, 80%, 85%, 90%, 95%, or more) of nucleic acid molecules of the first set of nucleic acid molecules may be paired with a nucleic acid molecule of the second set of nucleic acid molecules. Nucleic acid molecules of the first set of nucleic acid molecules may be configured to capture sample nucleic acid molecules derived from one or more nucleic acid samples when the nucleic acid molecules of the first set of nucleic acid molecules are not paired with nucleic acid molecules of the second set of nucleic acid molecules.

The treated surface may be stored for a period of time, such as for at least 6 hours, 12 hours, 24 hours, 2 days, or longer. The treated surface may be stored under any useful conditions (e.g., as described herein). During storage of the treated surface, each nucleic acid molecule of the first set of nucleic acid molecules in each pair of the plurality of pairs may not hybridize to another nucleic acid molecule (e.g., a sample nucleic acid molecule).

The kit may comprise one or more reagents for processing nucleic acid molecules. For example, the kit may comprise a kit further comprising a chemical stimulus (e.g., sodium hydroxide) configured to remove second nucleic acid molecules from the treated surface.

The surface of the substrate may be substantially planar, and/or may comprise a plurality of wells. In some cases, the substrate may comprise one or more particles (e.g., beads) immobilized thereto. Nucleic acid molecules of the first set of nucleic acid molecules may be immobilized to the surface at independently addressable locations. The independently addressable locations may be substantially planar, and/or may comprise one or more wells. In some cases, a density of the first set of nucleic acid molecules on the surface may be at least 10,000 molecules per $mm^2$, such as at least 100,000, 1,000,000, 10,000,000, or more molecules per $mm^2$. Nucleic acid molecules of the first set of nucleic acid molecules may be immobilized to the surface according to a predetermined pattern, or may be randomly distributed on the surface.

The second nucleic acid molecule may comprise a sequence that is substantially complementary to a sequence of the first nucleic acid molecule. The sequence of the first nucleic acid molecule and/or the second nucleic acid molecule may comprise at least 6 bases, such as at least 10, 12, 16, 20, or more bases. In some cases, the first nucleic acid molecule and the second nucleic acid molecule may comprise the same number of nucleotides. Alternatively, the first nucleic acid molecule and the second nucleic acid molecule may comprise different numbers of nucleotides. Each nucleic acid molecule of the second set of nucleic acid molecules may comprise at least 6 bases. The first and/or second set of nucleic acid molecules may comprise DNA nucleotides, RNA nucleotides, or a mixture thereof.

Each nucleic acid molecule of the first set of nucleic acid molecules may comprise the same nucleic acid sequence. Alternatively, the first set of nucleic acid molecules may comprise one or more different nucleic acid sequences. For example, the first set of nucleic acid molecules may comprise a first subset of nucleic acid molecules comprising a first nucleic acid sequence and a second subset of nucleic acid molecules comprising a second nucleic acid sequence. The first and second nucleic acid sequences may be different. The first and second subsets of nucleic acid molecules may both comprise a third nucleic acid sequence, which third nucleic acid sequence may comprise a poly(T) sequence.

In another aspect, the present disclosure provides a kit comprising a substrate comprising a surface comprising a first set of nucleic acid molecules immobilized thereto, wherein the first set of nucleic acid molecules comprises one or more first nucleic acid molecules. One or more first nucleic acid molecules may be configured to capture sample nucleic acid molecules derived from one or more nucleic acid samples. The kit may also comprise a solution comprising a second set of nucleic acid molecules, wherein the second set of nucleic acid molecules comprises one or more second nucleic acid molecules, which one or more second nucleic acid molecules are not said sample nucleic acid molecules. The second set of nucleic acid molecules may be selected such that, upon bringing the solution in contact with the surface, at least 70% of the one or more first nucleic acid molecules (e.g., at least 75%, 80%, 85%, 90%, 90%, or more) bind to a second nucleic acid molecule of the second set of nucleic acid molecules to generate one or more pairs of bound nucleic acid molecules. Each pair of the one or more pairs may comprise (i) a first nucleic acid molecule of the first set of nucleic acid molecules and a second nucleic acid molecule of the second set of nucleic acid molecules, and (ii) a section of substantially complementary sequences. Each nucleic acid molecule of the first set of nucleic acid molecules in each pair of the one or more pairs may not hybridize to another nucleic acid molecule (e.g., during storage of the treated surface). For example, paired nucleic acid molecules may not hybridize to a sample nucleic acid molecule.

The treated surface may be stored for a period of time, such as for at least 6 hours, 12 hours, 24 hours, 2 days, or longer. The treated surface may be stored under any useful conditions (e.g., as described herein).

The kit may comprise one or more reagents for processing nucleic acid molecules. For example, the kit may comprise a kit further comprising a chemical stimulus (e.g., sodium hydroxide) configured to remove second nucleic acid molecules from the treated surface.

The surface of the substrate may be substantially planar, and/or may comprise a plurality of wells. In some cases, the substrate may comprise one or more particles (e.g., beads) immobilized thereto. Nucleic acid molecules of the first set of nucleic acid molecules may be immobilized to the surface at independently addressable locations. The independently addressable locations may be substantially planar, and/or may comprise one or more wells. In some cases, a density of the first set of nucleic acid molecules on the surface may be at least 10,000 molecules per $mm^2$, such as at least 100,000, 1,000,000, 10,000,000, or more molecules per $mm^2$. Nucleic acid molecules of the first set of nucleic acid molecules may be immobilized to the surface according to a predetermined pattern, or may be randomly distributed on the surface.

The section of substantially complementary sequences of each pair of the one or more pairs may comprise a first sequence of a first nucleic acid molecule of the one or more first nucleic acid molecules and a second sequence of a second nucleic acid molecule of the one or more second nucleic acid molecules. The first sequence may be substantially complementary to the second sequence. The first and second sequences may each comprise the same number of bases. In some cases, the first and second sequences may each comprise between about 6-20 bases. A first nucleic acid molecule of the one or more first nucleic acid molecules and a second nucleic acid molecule of the one or more second nucleic acid molecules may comprise the same number of nucleotides. Alternatively, a first nucleic acid molecule of the one or more first nucleic acid molecules and a second nucleic acid molecule of the one or more second nucleic acid molecules may comprise different numbers of nucleotides. Each nucleic acid molecule of the second set of nucleic acid molecules may comprise at least 6 bases. The first and/or second set of nucleic acid molecules may comprise DNA nucleotides, RNA nucleotides, or a mixture thereof. The sequence of a nucleic acid molecule of the first nucleic acid molecules and/or a nucleic acid molecule of the second nucleic acid molecules may comprise at least 6 bases, such as at least 10, 12, 16, 20, or more bases.

Each nucleic acid molecule of the first set of nucleic acid molecules may comprise the same nucleic acid sequence. Alternatively, the first set of nucleic acid molecules may comprise one or more different nucleic acid sequences. For example, the first set of nucleic acid molecules may comprise a first subset of nucleic acid molecules comprising a first nucleic acid sequence and a second subset of nucleic acid molecules comprising a second nucleic acid sequence. The first and second nucleic acid sequences may be different. The first and second subsets of nucleic acid molecules may both comprise a third nucleic acid sequence, which third nucleic acid sequence may comprise a poly(T) sequence.

Optical Systems for Imaging a Rotating Substrate

For a substrate exhibiting a smooth, stable rotational motion, it may be simpler or more cost-effective to image the substrate using a rotational motion system instead of a rectilinear motion system. Rotational motion, as used herein, may generally refer to motion in a polar coordinate system that is predominantly in an angular direction. Prior optical imaging systems have utilized time delay and integration (TDI) cameras to achieve high duty cycles and maximum integration times per field point. A TDI camera (e.g., a TDI line-scan camera) may use a detection principle similar to a charge coupled device (CCD) camera. Compared to a CCD camera, the TDI camera may shift electric charge, row by row, across a sensor at the same rate as an image traverses the focal plane of the camera. In this manner, the TDI camera may allow longer image integration times while reducing artifacts such as blurring that may be otherwise associated with long image exposure times. A TDI camera may perform integration while simultaneously reading out and may therefore have a higher duty cycle than a camera that performs these functions in a serial manner. Use of a TDI camera to extend integration times may be important for high throughput fluorescent samples, which may be limited in signal production by fluorescent lifetimes. For instance, alternative imaging techniques, such as point scanning, may be precluded from use in high throughput systems as it may not be possible to acquire an adequate number of photons from a point in the limited amount of integration time required for high speeds due to limits imposed by fluorescence lifetimes of dye molecules.

Figures 40A, 40B, 40C, 40D:
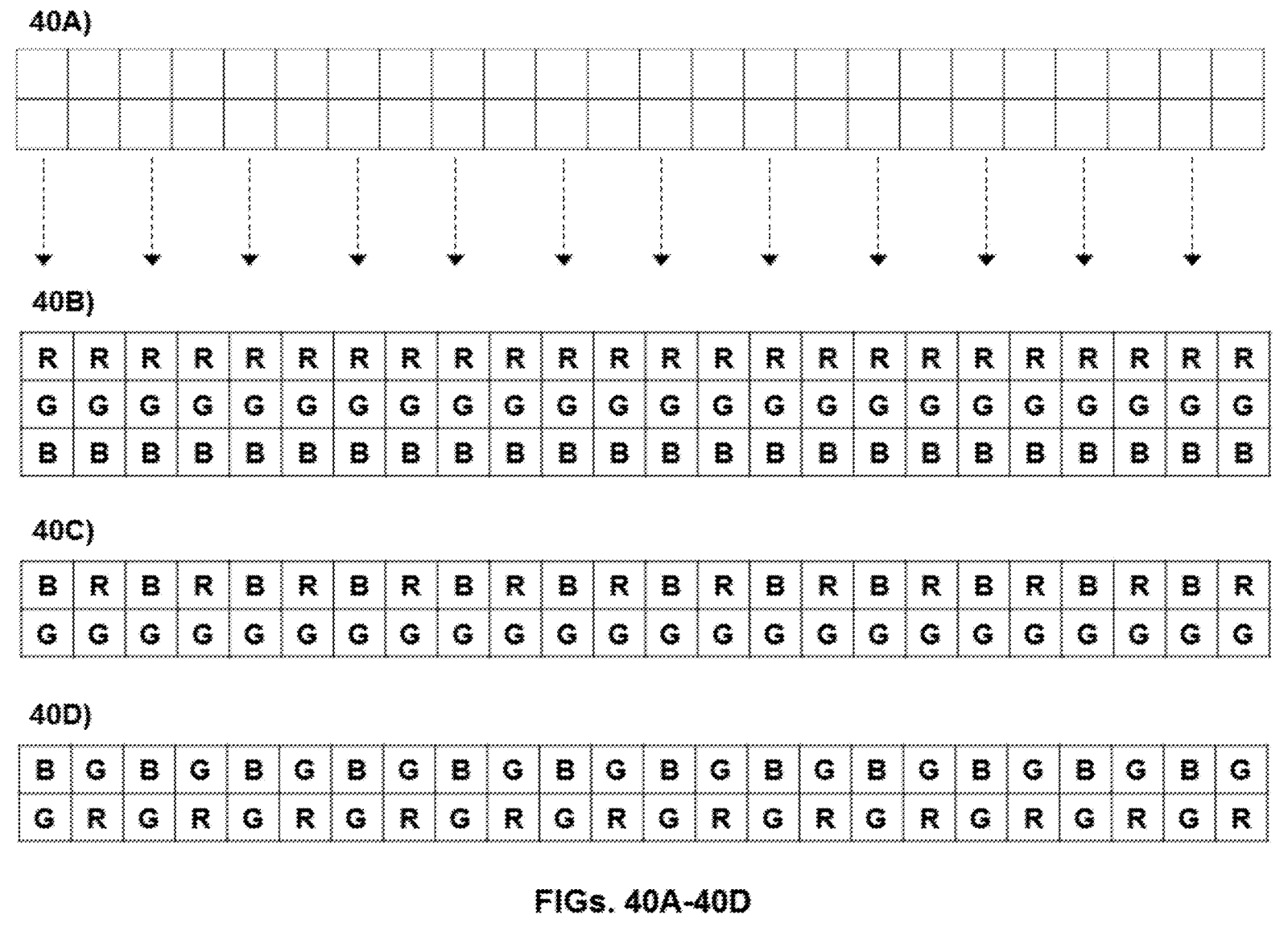

FIGS. 40A-40D illustrate example schemes for a line-scan camera. As shown in FIG. 40A, a TDI line-scan camera may comprise two or more vertically arranged rows of pixels (such as 3, 4, 5, 6, 7, 8, 9, 10, 24, 36, 48, 50, 60, 72, 84, 96, 100, 108, 120, 128, 132, 150, 200, 256, or more pixels). During operation of the camera (e.g., movement of the camera relative to an open substrate), photoelectrons from each pixel in a given row may be summed into the row below the given row (e.g., in the direction of relative object motion) by shifting accumulated charges between pixel rows. FIGS. 40B and 40C show pixel schemes for use in color line-scan cameras. Such cameras may include rows of pixels having different color filters to detect and/or block light of different wavelengths. For example, FIG. 40B shows a trilinear pixel scheme including rows of red, green, and blue filters. This trilinear pixel scheme may be replicated one or more times to facilitate TDI applications. FIG. 40C shows a bilinear pixel scheme including a row of alternating red and blue filters and a row of green filters. FIG. 40D shows an alternative bilinear pixel scheme including multiple Bayer patterns (e.g., 2×2 pixel arrays including a first row alternating blue and green pixels and a second row alternating green and red pixels). Like the trilinear scheme, the bilinear patterns may be replicated one or more times to facilitate TDI applications. The color line-scan schemes depicted in FIGS. 40B-40D may be substituted by alternative color combinations, including cyan, yellow, green, and magenta; red, green, blue, and emerald; cyan, magenta, yellow, and white; or any other color combination, in any arrangements (e.g., alternating, non-alternating).

Prior TDI detection schemes may be limited in their applicability to the imaging of rotating systems, such as the rotating nucleic acid sequencing systems described herein. When scanning a curved path, such as the curved path generated by the rotating systems described herein, a TDI sensor may only be able to shift charge (commonly referred to as clocking or line triggering) at the correct rate for a single velocity. For instance, the TDI sensor may only be able to clock at the correct rate along an arc located at a particular distance from the center of rotation. Locations at smaller distances from the center of rotation may clock too quickly, while locations at smaller distances from the center of rotation may clock too slowly. In either case, the mismatch between the rotational speed of the rotating system and the clock rate of the TDI sensor may cause blurring that varies with the distance of a location from the center of the rotating system. This effect may be referred to as tangential velocity blur. The tangential velocity blur may produce an image distortion of a magnitude $\sigma$ defined by equation (2):

$$\sigma = \frac{hw}{2R} = \frac{A}{2R} \tag{2}$$

Here, h, w, and A are the effective height, width, and area, respectively, of the TDI sensor projected to the object plan. These values may be adjusted using one of more optical elements (e.g., lenses, prisms, mirrors, etc.). R is the distance of the center of the field from the center of the rotating system. The effective height, width, and area of the sensor are the height, width, and area, respectively, that produce signal. In the case of fluorescence imaging, the effective height, width, and area of the sensor may be the height, width, and area, respectively, that correspond to illuminated areas on the sample. In addition to the tangential velocity blur effect, Equation (2) implies that increasing sensor area, which may be a goal of many imaging systems, may introduce imaging complications for TDI imaging of rotating systems. Consequently, prior TDI systems may require small image sensors to image rotating systems and may thus be unfit for simultaneous high-sensitivity and high-throughput imaging of such systems.

Described herein are systems and methods for imaging rotating systems that can address at least the abovementioned problems. The systems and methods described herein may benefit from higher efficiency, such as from faster imaging time.

FIG. 7 shows an optical system 700 for continuous area scanning of a substrate during rotational motion of the substrate. The term "continuous area scanning (CAS)," as used herein, generally refers to a method in which an object in relative motion is imaged by repeatedly, electronically or computationally, advancing (clocking or triggering) an array sensor at a velocity that compensates for object motion in the detection plane (focal plane). CAS can produce images having a scan dimension larger than the field of the optical system. TDI scanning may be an example of CAS in which the clocking entails shifting photoelectric charge on an area sensor during signal integration. For a TDI sensor, at each clocking step, charge may be shifted by one row, with the last row being read out and digitized. Other modalities may accomplish similar function by high speed area imaging and co-addition of digital data to synthesize a continuous or stepwise continuous scan.

The optical system may comprise one or more sensors 710. As shown, in FIG. 7, the sensors may be optically projected to the sample. The optical system may comprise one or more optical elements, such as the optical element 810 described in the context of FIG. 8. An optical element may be, for example, a lens, prism, mirror, wave plate, filter, attenuator, grating, diaphragm, beam splitter, diffuser, polarizer, depolarizer, retroreflector, spatial light modulator, or any other optical element. The system may comprise a plurality of sensors, such as at least 2, at least 5, at least 10, at least 20, at least 50, at least 100, at least 200, at least 500, or at least 1,000 sensors. The system may comprise a at least 2, at least 4, at least 8, at least 16, at least 32, at least 64, at least 128, at least 256, at least 512, or at least 1,024 sensors. The plurality of sensors may be the same type of sensor or different types of sensors. Alternatively, the system may comprise at most about 1000, 500, 200, 100, 50, 20, 10, 5, 2, or fewer sensors. Alternatively, the system may comprise at most about 1024, 512, 256, 128, 64, 32, 16, 8, 4, 2, or fewer sensors. The system may comprise a number of sensors that is within a range defined by any two of the preceding values. The sensors may comprise image sensors. The sensors may comprise CCD cameras. The sensors may comprise CMOS cameras. The sensors may comprise TDI cameras (e.g., TDI line-scan cameras). The sensors may comprise pseudo-TDI rapid frame rate sensors. The sensors may comprise CMOS TDI or hybrid cameras. The sensors may be integrated together in a single package. The sensors may be integrated together in a single semiconductor substrate. The system may further comprise any optical source described herein (not show in FIG. 7).

The sensors may be configured to detect an image from a substrate, such as the substrate 310 described herein, during rotational motion of the substrate. The rotational motion may be with respect to an axis of the substrate. The axis may be an axis through the center of the substrate. The axis may be an off-center axis. The substrate may be configured to rotate at any rotational speed described herein. The rotational motion may comprise compound motion. The compound motion may comprise rotation and an additional component of radial motion. The compound motion may be a spiral (or substantially spiral). The compound motion may be a ring (or substantially ring-like).

Each sensor may be located at a focal plane in optical communication with the substrate. The focal plane may be the approximate plane in an imaging system (e.g., CAS sensor) at which an image of a region of the substrate forms. The focal plane may be segmented into a plurality of regions, such as at least 2, at least 5, at least 10, at least 20, at least 50, at least 100, at least 200, at least 500, or at least 1000 regions. The focal plane may be segmented into at least 2, at least 4, at least 8, at least 16, at least 32, at least 64, at least 128, at least 256, at least 512, or at least 1,024 regions. The focal plane may be segmented into a number of regions that is within a range defined by any two of the preceding values. The focal plane may be segmented into a plurality of regions along an axis substantially normal to a projected direction of the rotational motion. An angle between the axis and the projected direction of the rotational motion may be no more than 1 degree, no more than 2 degrees, no more than 3 degrees, no more than 4 degrees, no more than 5 degrees, no more than 6 degrees, no more than 7 degrees, no more than 8 degrees, no more than 9 degrees, no more than 10 degrees, no more than 11 degrees, no more than 12 degrees, no more than 13 degrees, no more than 14 degrees, or no more than 15 degrees from normal, or an angle that is within a range defined by any two of the preceding values. The focal plane may be segmented into a plurality of regions along an axis parallel to a projected direction of the rotational motion. The focal plane may be spatially segmented. For instance, the focal plane may be segmented by abutting or otherwise arranging a plurality of sensors in a single focal plane and clocking each of the sensors independently.

Alternatively or in combination, the focal plane may be segmented by optically splitting the focal plane into a plurality of separate paths, each of which may form a sub-image on an independent sensor of the plurality of sensors and which may be clocked independently. The focal path may be optically split using one or more optical elements, such as a lens array, mirror, or prism. Each sensor of the plurality of sensors may be in optical communication with a different region of the rotating substrate. For instance, each sensor may image a different region of the rotating substrate. Each sensor of the plurality of sensors may be clocked at a rate appropriate for the region of the rotating substrate imaged by the sensor, which may be based on the distance of the region from the center of the rotating substrate or the tangential velocity of the region.

One or more of the sensors may be configured to be in optical communication with at least 2 of the plurality of regions in the focal plane. One or more of the sensors may comprise a plurality of segments. Each segment of the plurality of segments may be in optical communication with a region of the plurality of regions. Each segment of the plurality of segments may be independently clocked. The independent clocking of a segment may be linked to a velocity of an image in an associated region of the focal plane. The independent clocking may comprise TDI line rate or pseudo-TDI frame rate.

The system may further comprise a controller (not shown). The controller may be operatively coupled to the one or more sensors. The controller may be programmed to process optical signals from each region of the rotating substrate. For instance, the controller may be programmed to process optical signals from each region with independent clocking during the rotational motion. The independent clocking may be based at least in part on a distance of each region from a projection of the axis and/or a tangential velocity of the rotational motion. The independent clocking may be based at least in part on the angular velocity of the rotational motion. While a single controller has been described, a plurality of controllers may be configured to, individually or collectively, perform the operations described herein.

FIG. 8A shows an optical system 800 for imaging a substrate during rotational motion of the substrate using tailored optical distortions. The optical system may comprise one or more sensors 710. The one or more sensors may comprise any sensors described herein. The optical system may comprise any optical sources described herein (not shown in FIG. 8A).

The sensors may be configured to detect an image from a substrate, such as the substrate 310 described herein, during rotational motion of the substrate. The rotational motion may be with respect to an axis of the substrate. The axis may be an axis through the center of the substrate. The axis may be an off-center axis. The substrate may be configured to rotate at any rotational speed described herein.

The system 800 may further comprise an optical element 810. The optical element may be in optical communication with the sensor. The optical element may be configured to direct optical signals from the substrate to the sensor. The optical element may produce an optical magnification gradient across the sensor. At least one of the optical element and the sensor may be adjustable. For instance, at least one of the optical element and the sensor may be adjustable to generate an optical magnification gradient across the sensor. The optical magnification gradient may be along a direction substantially perpendicular to a projected direction of the rotational motion of the substrate. The optical element may be configured to rotate, tilt, or otherwise be positioned to engineer the optical magnification gradient. The optical element may produce a magnification that scales approximately as the inverse of the distance to the axis of the substrate. The magnification gradient may be produced by selecting a relative orientation of the substrate, optical element, and sensor. For instance, the magnification gradient may be produced by tilting the object and image planes as shown in FIG. 8A. The magnification gradient may display geometric properties. For instance, a ratio of a first optical magnification of a first region at a minimum distance from the center of the substrate to a second optical magnification of a second region at a maximum distance from the center of the substrate may be substantially equal to a ratio of the maximum distance to the minimum distance. In this manner, the first and second optical magnifications may be in the same ratio as the radii of their respective sample regions. Although the system 800 as shown includes a single optical element 810, the system 800 may include a plurality of optical elements, such as at least 2, 3, 4, 5, 6, 7, 8, 9, 10, 20, 30, 40, 50, 100, or more optical elements. Various arrangements or configurations of optical elements may be employed. For example, the system 800 may include a lens and a mirror for directing light.

Figure 8B:
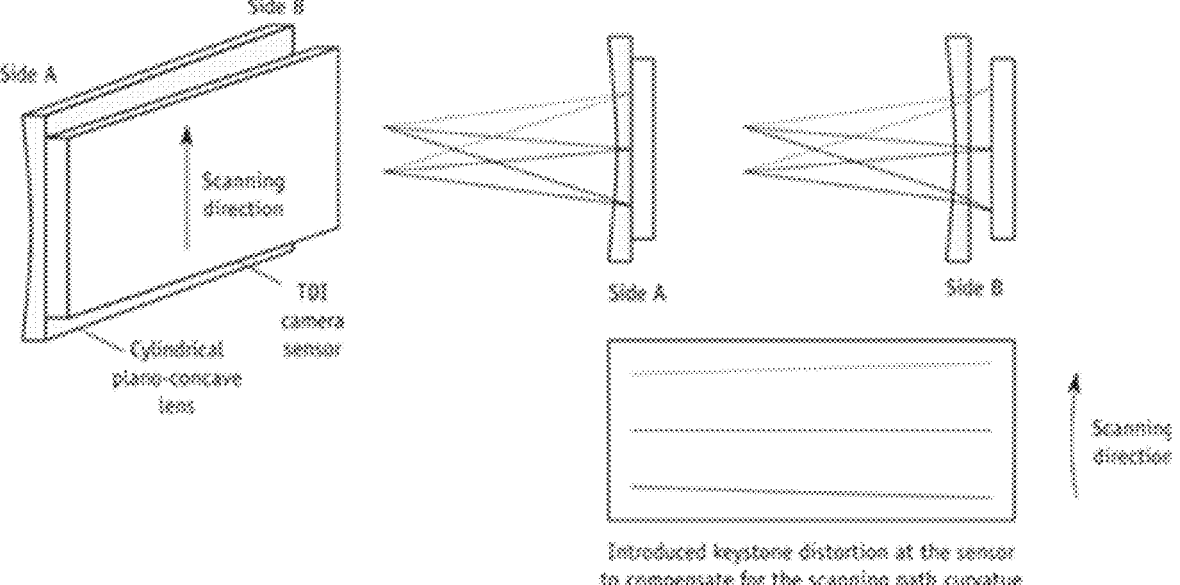
FIG. 8B shows an example of induced tailored optical distortions using a cylindrical lens.

The optical element may be a lens. The lens may be a field lens. The lens may be a cylindrical lens (for instance, as shown in FIG. 8B). The cylindrical lens may be plano-cylindrical. The lens may be plano-concave or plano-convex. The cylindrical lens may have a positive or negative curvature. The curvature of the cylindrical lens may vary. The curvature of the cylindrical lens may vary in a direction perpendicular to a projected direction of rotational motion. The shape of a surface of the lens may be conical. The lens may be tilted with respect to the sensor, thereby producing an anamorphic magnification gradient. The tilt of the lens may be adjustable, thereby producing an adjustable anamorphic magnification gradient.

FIG. 8B shows an example of induced tailored optical distortions using a cylindrical lens. As shown in FIG. 8B, a cylindrical lens may have a first side A and a second side B. The first side A may be located closer to an image sensor (such as a TDI camera sensor described herein) than the second side B. Such a configuration may be achieved by tilting the cylindrical lens in relation to the image sensor. In this manner, the cylindrical lens may direct light to different locations on the image sensor, with light passing through side B being directed more divergently than light passing through side A. In this manner, the cylindrical lens may provide an anamorphic magnification gradient across the image sensor, as depicted in FIG. 8B.

Tilting of the lens may provide an anamorphic magnification gradient across the sensor. The tilt and hence anamorphic gradient may be in a direction substantially perpendicular to the image motion on the sensor. The tilt of the lens may be adjustable. The adjustment may be automatic by using a controller. The adjustment may be coupled to the radius of the scanned substrate region relative to the substrate axis of rotation. The ratio of the minimum to maximum anamorphic magnification may be exactly or approximately in the ratio of the minimum to maximum projected radii relative to the substrate axis of rotation.

Alternatively or in combination, a gradient in the radius of curvature of the lens may provide an anamorphic magnification gradient across the sensor. The curvature gradient may be in a direction substantially direction perpendicular to the image motion on the sensor.

The system may further comprise a controller (not shown). The controller may be operatively coupled to the sensor and the optical element. The controller may be programmed to direct the adjustment of at least one of the sensor and the optical element to generate an optical magnification gradient across the sensor. The magnification gradient may be generated along a direction substantially perpendicular to a projected direction of the rotational motion. The controller may be programmed to direct adjustment of the sensor and/or the optical element to produce an anamorphic optical magnification gradient. The optical magnification gradient may be across the sensor in a direction substantially perpendicular to a projected direction of the rotational motion. The controller may be programmed to direct rotation or tilt of the optical element. The controller may be programmed to direct adjustment of the magnification gradient. For instance, the controller may be programmed to direct adjustment of the magnification gradient at least in part on a radial range of a field dimension relative to a projection about the axis of the substrate. The controller may be programmed to subject the rotational motion to the substrate. While a single controller has been described, a plurality of controllers may be configured to, individually or collectively, perform the operations described herein.

The optical systems described herein may utilize multiple scan heads. The multiple scan heads may be operated in parallel along different imaging paths. For instance, the scan heads may be operated to produce interleaved spiral scans, nested spiral scans, interleaved ring scans, nested ring scans, or a combination thereof. A scan head may comprise one or more of a detector element such as a camera (e.g., a TDI line-scan camera), an illumination source (e.g., as described herein), and one or more optical elements (e.g., as described herein).

Figure 9A:
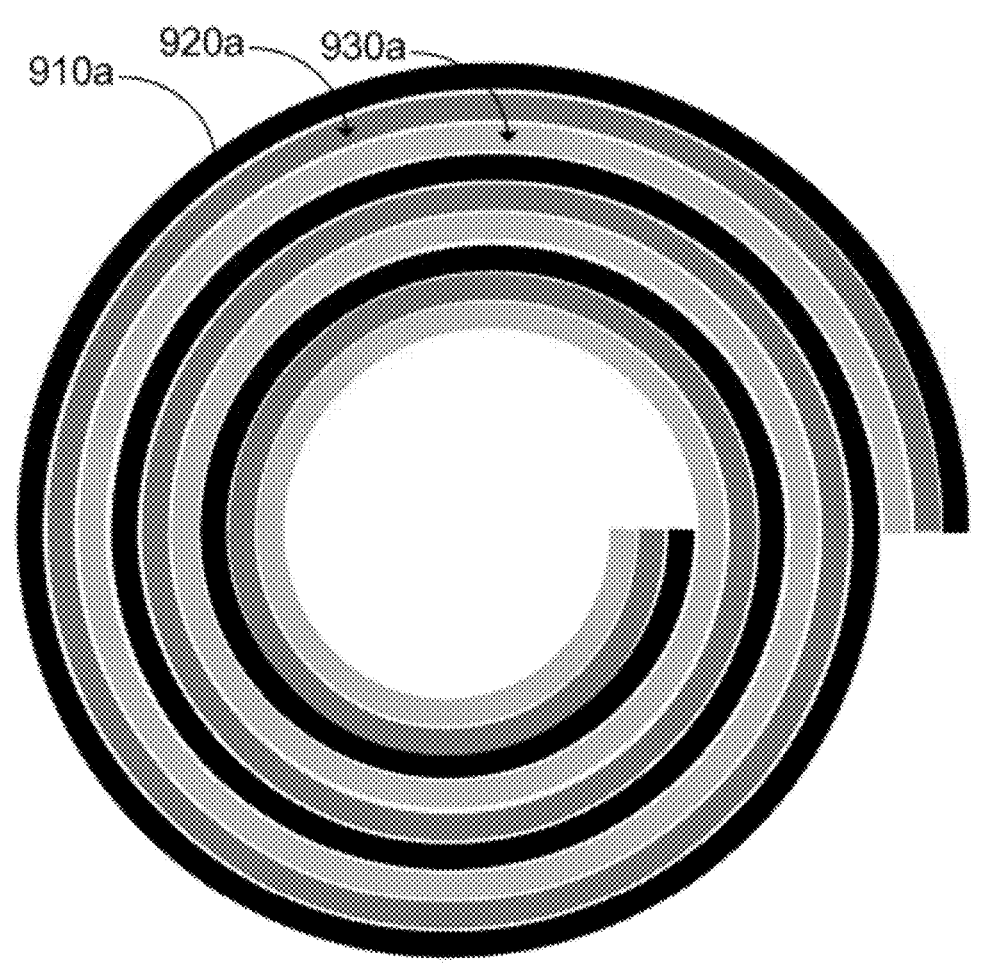
FIG. 9A shows a first example of an interleaved spiral imaging scan.

FIG. 9A shows a first example of an interleaved spiral imaging scan. A first region of a scan head may be operated along a first spiral path 910a. A second region of a scan head may be operated along a second spiral path 920a. A third region of a scan head may be operated along a third spiral path 930a. Each of the first, second, and third regions may be independently clocked. The scan head may comprise any optical systems described herein. The use of multiple imaging scan paths may increase imaging throughput by increasing imaging rate.

Figure 9B:
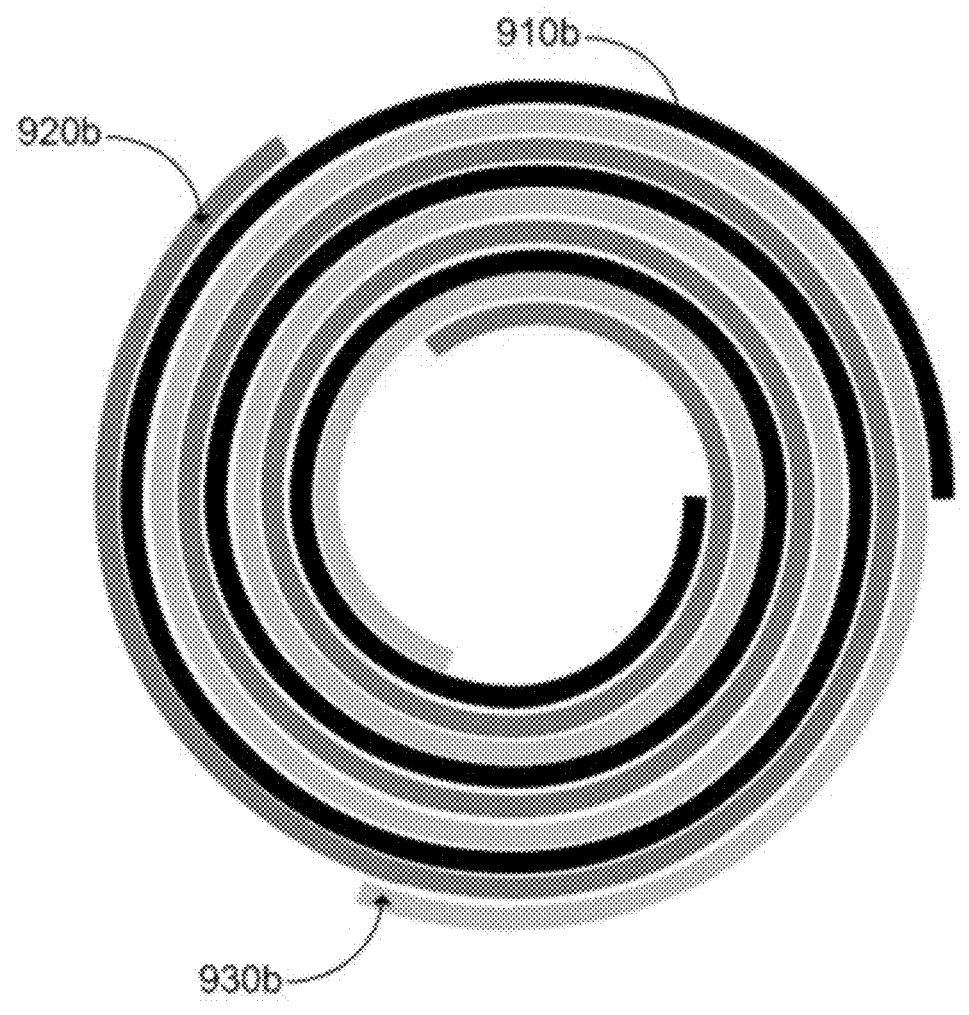
FIG. 9B shows a second example of an interleaved imaging scan.

FIG. 9B shows a second example of an interleaved spiral imaging scan. A first scan head may be operated along a first spiral path 910b. A second scan head may be operated along a second spiral path 920b. A third scan head may be operated along a third spiral path 930b. Each of the first, second, and third scan heads may be independently clocked or clocked in unison. Each of the first, second, and third scan heads may comprise any optical systems described herein. The use of multiple imaging scan paths may increase imaging throughput by increasing net imaging rate. Throughput of the optical system can be multiplied by operating many scan heads of a field width in parallel. For example, each scan head may be fixed at a different angle relative to the center of substrate rotation.

Figure 9C:
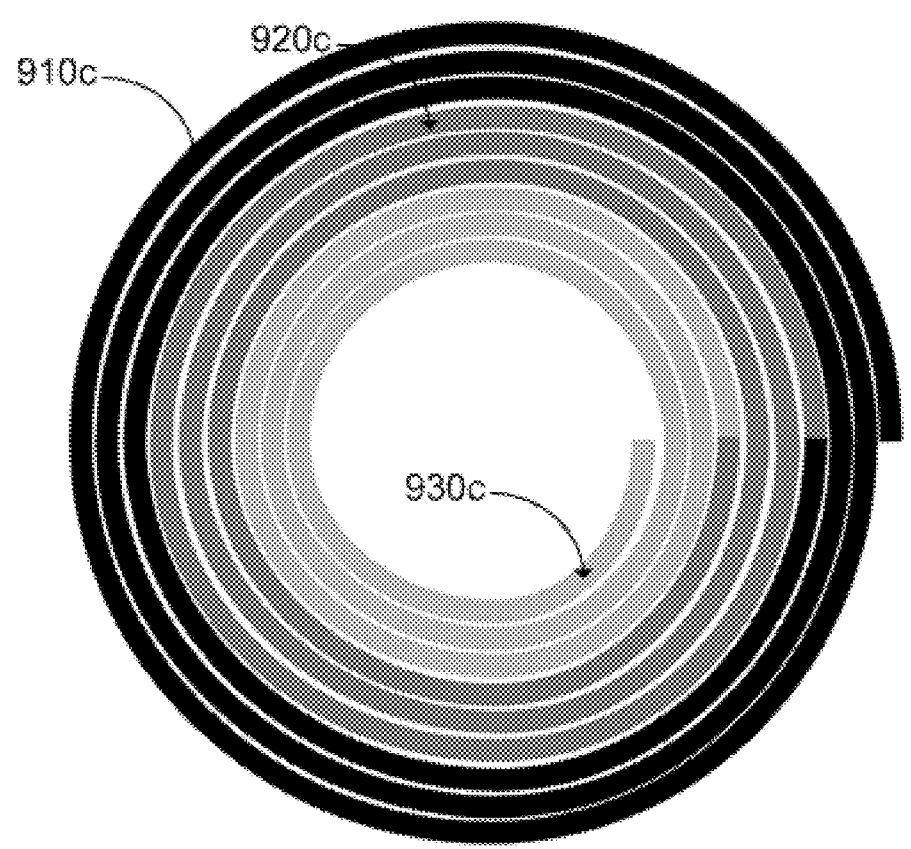
FIG. 9C shows an example of a nested imaging scan.

FIG. 9C shows an example of a nested spiral imaging scan. A first scan head may be operated along a first spiral path 910c. A second scan head may be operated along a second spiral path 920c. A third scan head may be operated along a third spiral path 930c. Each of the first, second, and third scan heads may be independently clocked. Each of the first, second, and third scan heads may comprise any optical systems described herein. The use of multiple imaging scan paths may increase imaging throughput by increasing imaging rate. The scan heads may move together in the radial direction. Throughput of the optical system can be multiplied by operating many scan heads of a field width in parallel. For example, each scan head may be fixed at a different angle. The scans may be in discrete rings rather or spirals.

While FIGS. 9A-9C illustrate three imaging paths, there may be any number of imaging paths and any number of scan heads. For example, there may be at least about 2, 3, 4, 5, 6, 7, 8, 9, 10, or more imaging paths or scan heads. Alternatively, there may be at most about 10, 9, 8, 7, 6, 5, 4, 3, 2, or less imaging paths or scan heads. Each scan head may be configured to receive light having a wavelength within a given wavelength range. For instance, the first scan head may be configured to receive first light having a wavelength within a first wavelength range. The second scan head may be configured to receive second light having a wavelength within a second wavelength range. The third scan head may be configured to receive third light having a wavelength within a third wavelength range. Similarly, fourth, fifth, sixth, seventh, eighth, ninth, or tenth scan heads may be configured to receive fourth, fifth, sixth, seventh, eighth, ninth, or tenth light, respectively, each of the fourth, fifth, sixth, seventh, eighth, ninth, or tenth light having a wavelength within a fourth, fifth, sixth, seventh, eighth, ninth, or tenth wavelength range, respectively. The first, second, third, fourth, fifth, sixth, seventh, eighth, ninth, or tenth wavelength ranges may be identical. The first, second, third, fourth, fifth, sixth, seventh, eighth, ninth, or tenth wavelength ranges may partially overlap. Any 2, 3, 4, 5, 6, 7, 8, 9, or 10 of the first, second, third, fourth, fifth, sixth, seventh, eighth, ninth, or tenth wavelength ranges may be distinct. The first, second, third, fourth, fifth, sixth, seventh, eighth, ninth, or tenth wavelength ranges may be in the ultraviolet, visible, or near infrared regions of the electromagnetic spectrum. Each of the first, second, third, fourth, fifth, sixth, seventh, eighth, ninth, or tenth wavelength ranges may comprise a wavelength emitted by a fluorophore, dye, or quantum dot described herein. In this manner, the system may be configured to detect optical signals from a plurality of fluorophores, dyes, or quantum dots.

Figure 10:
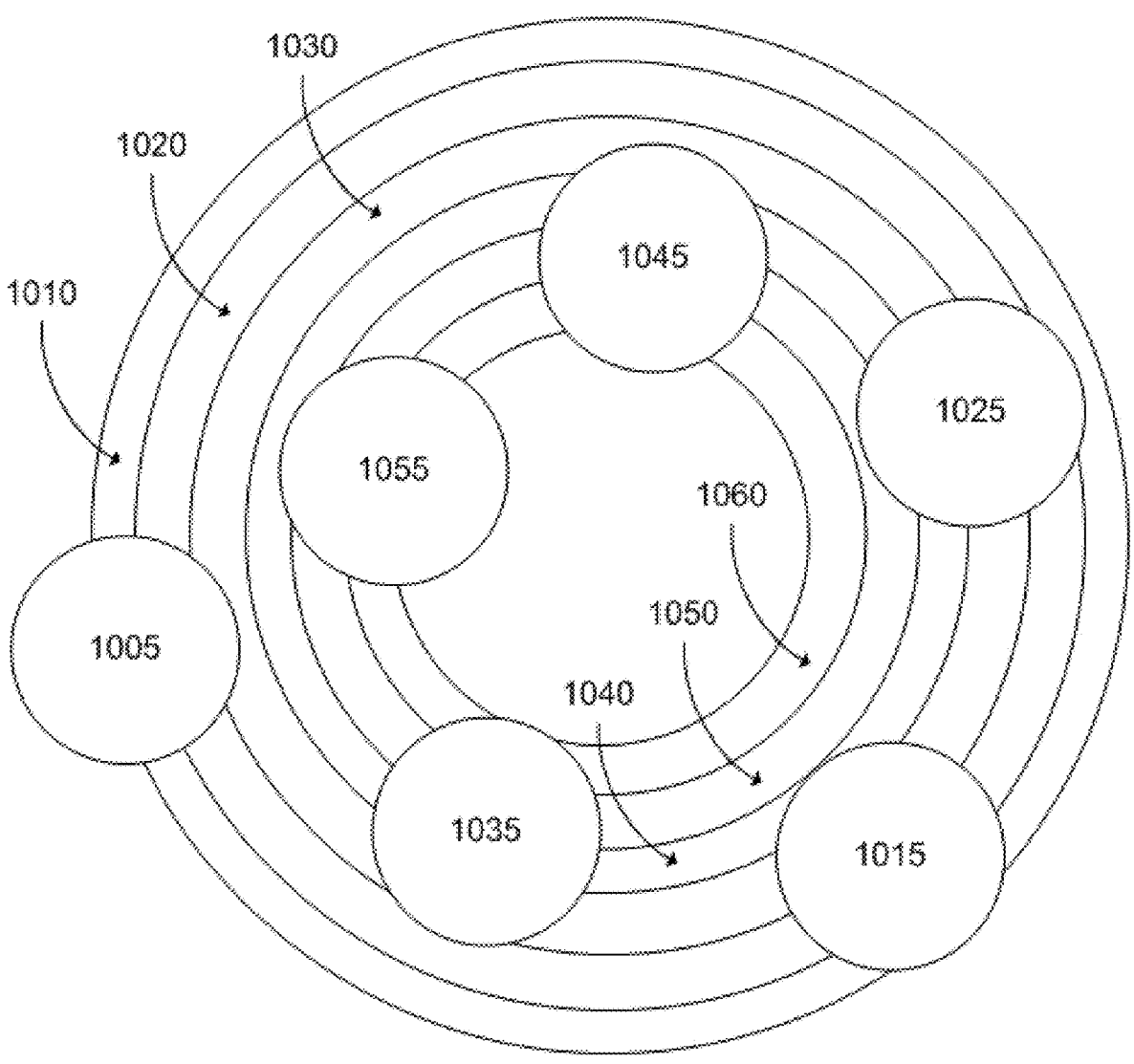
FIG. 10 shows a configuration for a nested circular imaging scan.

FIG. 10 shows a nested circular imaging scan. A first scan head 1005 may be operated along a first approximately circular path 1010. A second scan head 1015 may be operated along a second approximately circular path 1020. A third scan head 1025 may be operated along a third approximately circular path 1030. A fourth scan head 1035 may be operated along a fourth approximately circular path 1040. A fifth scan head 1045 may be operated along a fifth approximately circular path 1050. A sixth scan head 1055 may be operated along a sixth approximately circular path 1060. Each of the first, second, third, fourth, fifth, and sixth scan heads may be independently clocked. Each of the first, second, third, fourth, fifth, and sixth scan heads may comprise any optical systems described herein. Each of the first, second, third, fourth, fifth, and sixth scan heads may be configured to remain in a fixed location during scanning of a substrate. Alternatively, one or more of the first, second, third, fourth, fifth, and sixth scan heads may be configured to move during scanning of a substrate. The use of a plurality of scan heads imaging along approximately circular imaging paths may greatly increase imaging throughput. For instance, the configuration of scan heads depicted in FIG. 10 may allow all addressable locations on a substrate to be imaged during a single rotation of the substrate. Such a configuration may have the additional advantage of simplifying the mechanical complexity of an imaging system by requiring only one scanning motion (e.g., the rotation of the substrate).

While FIG. 10 illustrates six imaging paths and six scan heads, there may be any number of imaging paths and any number of scan heads. For example, there may be at least about 2, 3, 4, 5, 6, 7, 8, 9, 10, or more imaging paths or scan heads. Alternatively, there may be at most about 10, 9, 8, 7, 6, 5, 4, 3, 2, or less imaging paths or scan heads. Each scan head may be configured to receive light having a wavelength within a given wavelength range. For instance, the first scan head may be configured to receive first light having a wavelength within a first wavelength range. The second scan head may be configured to receive second light having a wavelength within a second wavelength range. The third scan head may be configured to receive third light having a wavelength within a third wavelength range. The fourth scan head may be configured to receive fourth light having a wavelength within a fourth wavelength range. The fifth scan head may be configured to receive fifth light having a wavelength within a fifth wavelength range. The sixth scan head may be configured to receive sixth light having a wavelength within a sixth wavelength range. Similarly, seventh, eighth, ninth, or tenth scan heads may be configured to receive seventh, eighth, ninth, or tenth light, respectively, each of the seventh, eighth, ninth, or tenth light having a wavelength within a seventh, eighth, ninth, or tenth wavelength range, respectively. The first, second, third, fourth, fifth, sixth, seventh, eighth, ninth, or tenth wavelength ranges may be identical. The first, second, third, fourth, fifth, sixth, seventh, eighth, ninth, or tenth wavelength ranges may partially overlap. Any 2, 3, 4, 5, 6, 7, 8, 9, or 10 of the first, second, third, fourth, fifth, sixth, seventh, eighth, ninth, or tenth wavelength ranges may be distinct. The first, second, third, fourth, fifth, sixth, seventh, eighth, ninth, or tenth wavelength ranges may be in the ultraviolet, visible, or near infrared regions of the electromagnetic spectrum. Each of the first, second, third, fourth, fifth, sixth, seventh, eighth, ninth, or tenth wavelength ranges may comprise a wavelength emitted by a fluorophore, dye, or quantum dot described herein. In this manner, the system may be configured to detect optical signals from a plurality of fluorophores, dyes, or quantum dots.

Figure 18A:
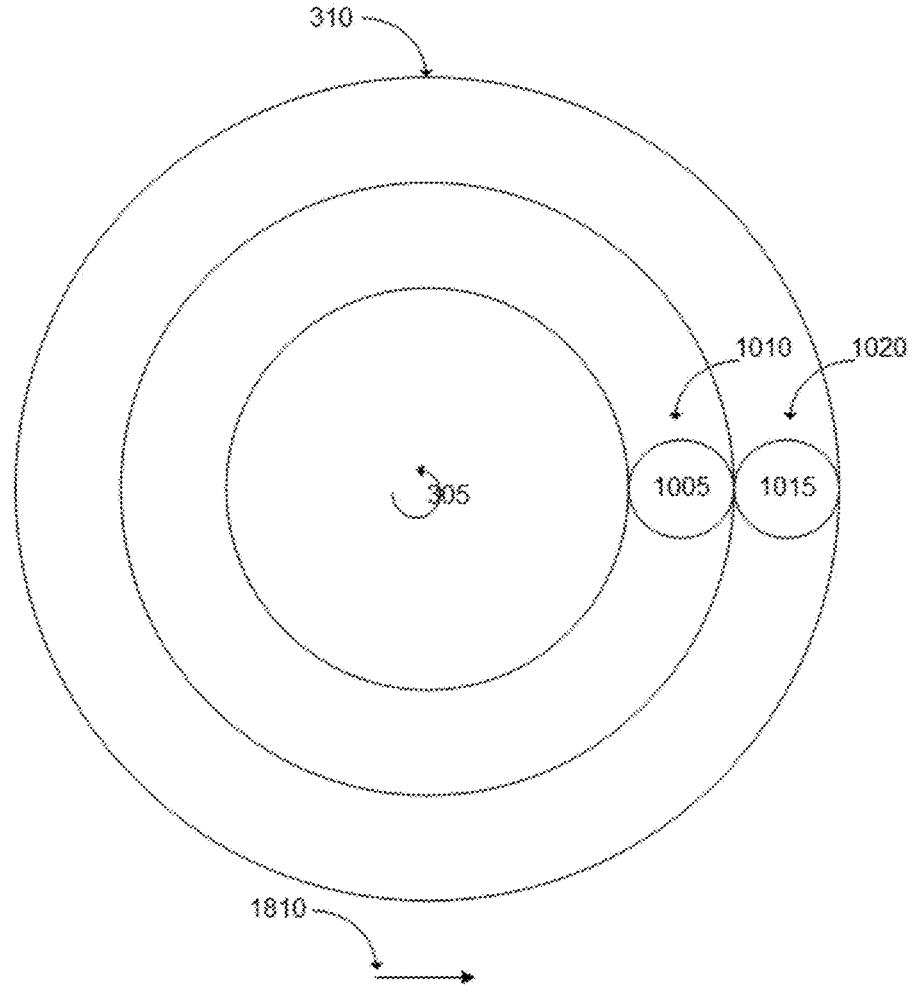
FIG. 18A shows motion of a substrate relative to two imaging heads located on the same side of an axis of rotation of the substrate.
Figure 18B:
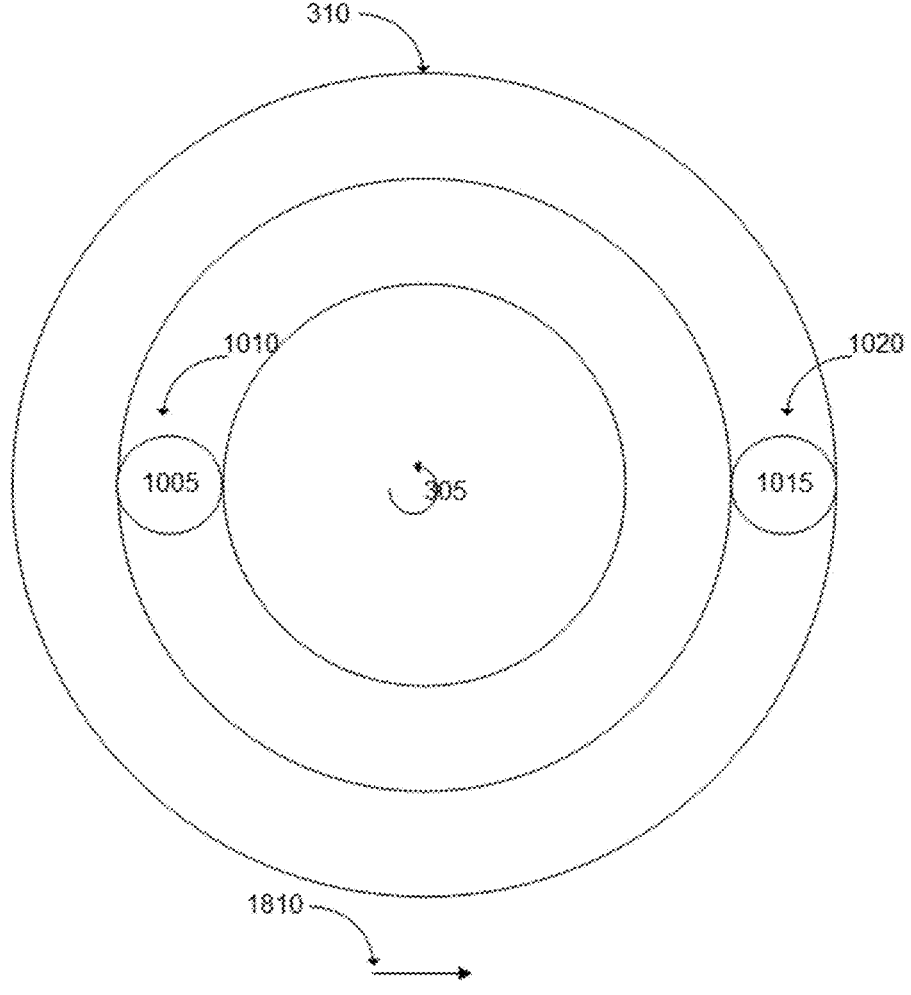
FIG. 18B shows motion of a substrate relative to two imaging heads located on opposite sides of an axis of rotation of the substrate.
Figure 18C:
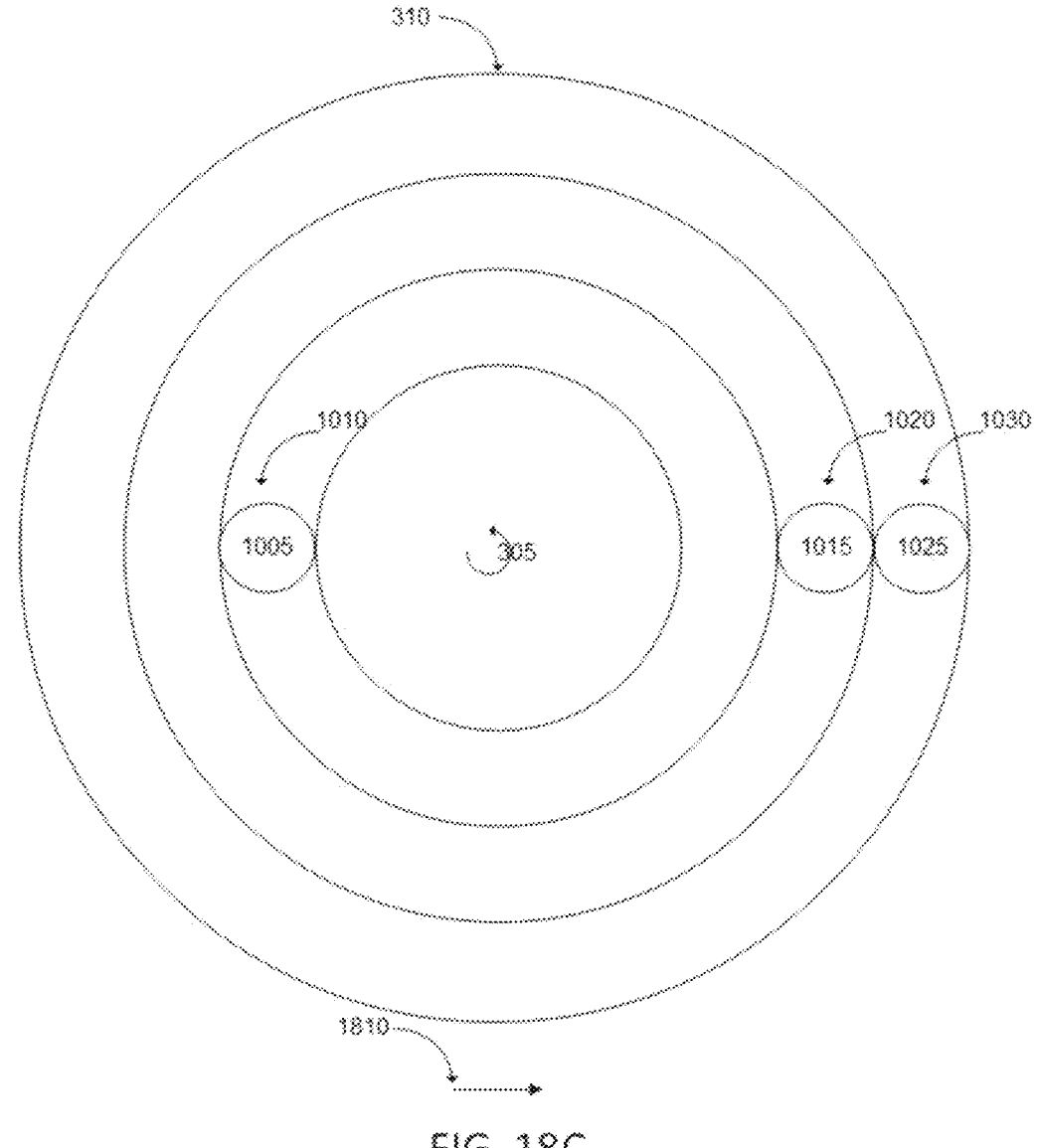
FIG. 18C shows motion of a substrate relative to three imaging heads.
Figure 18D:
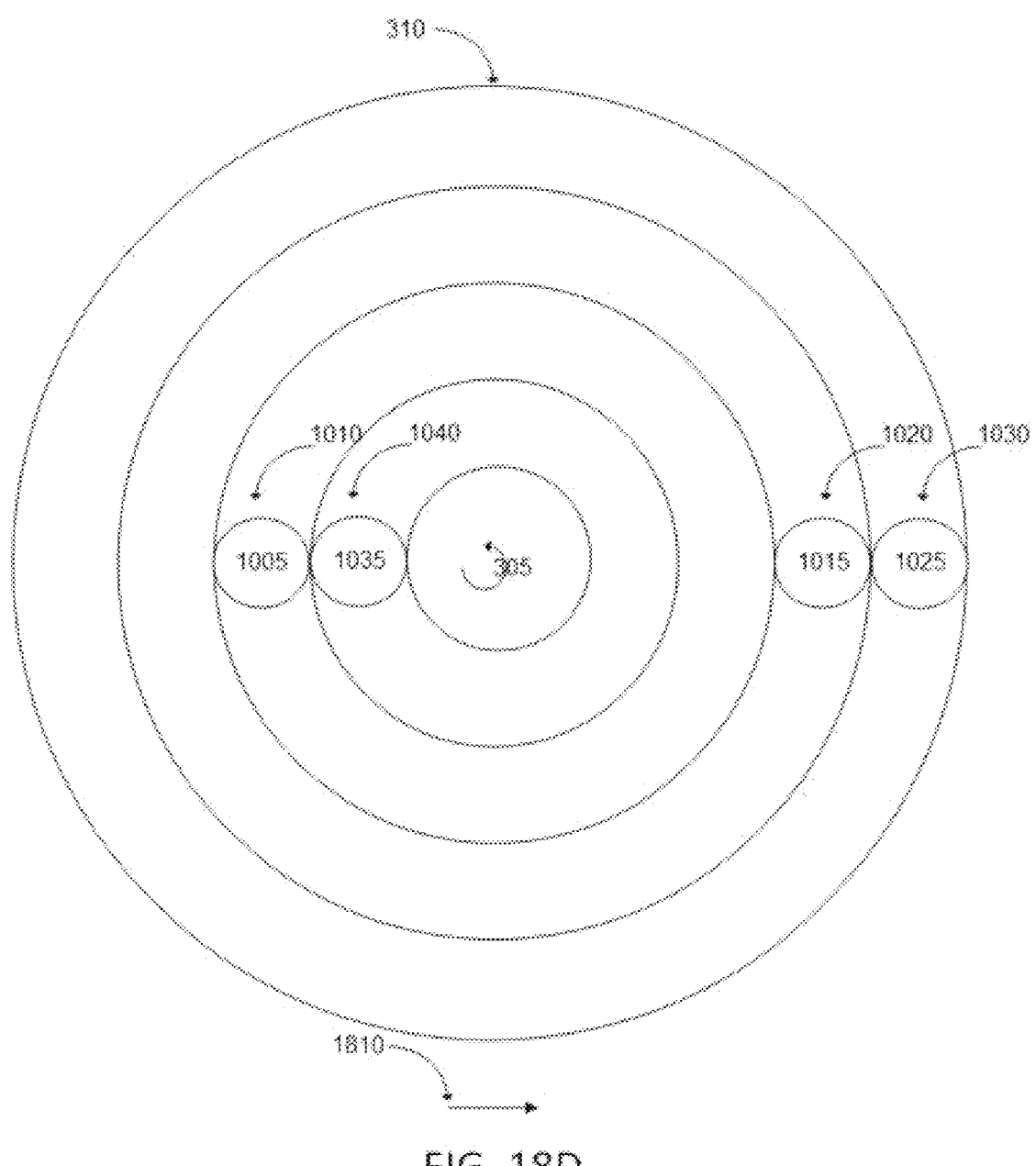
FIG. 18D shows motion of a substrate relative to four imaging heads.
Figure 19A:
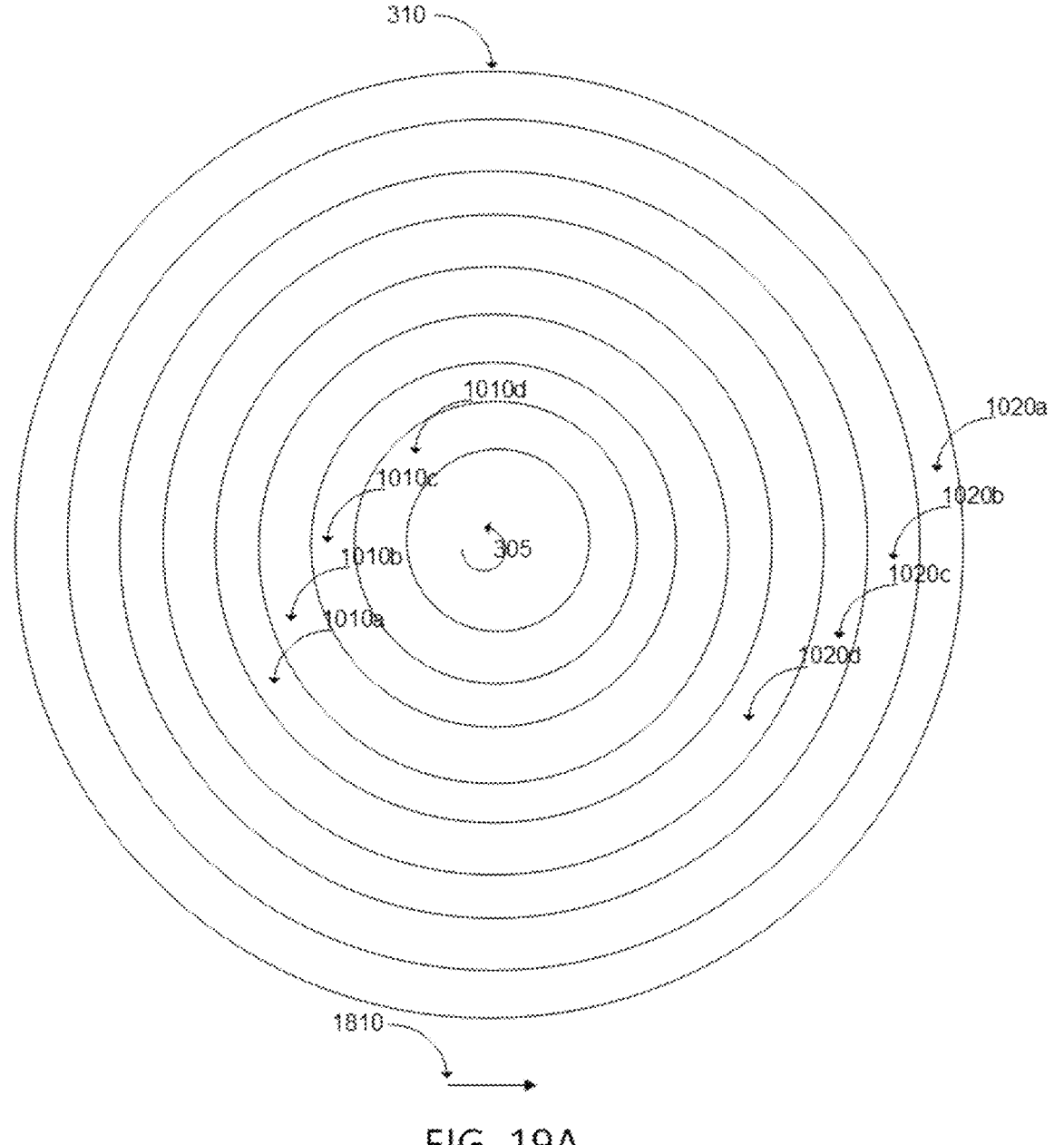
FIG. 19A shows successive ring paths of two imaging heads located on the same side of an axis of rotation of a substrate.
Figure 19B:
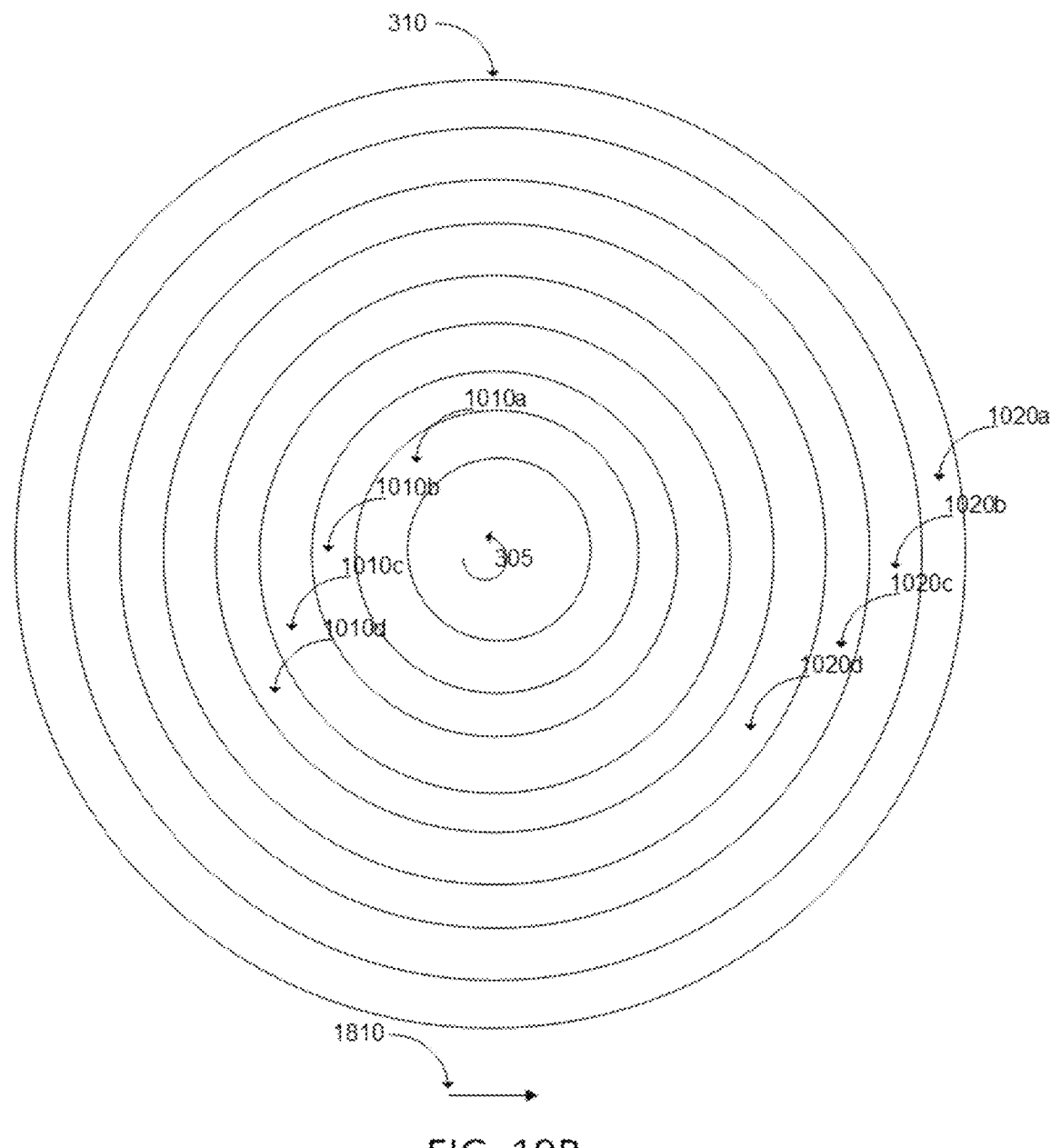
FIG. 19B shows successive ring paths of two imaging heads located on opposite sides of an axis of rotation of a substrate.
Figure 19C:
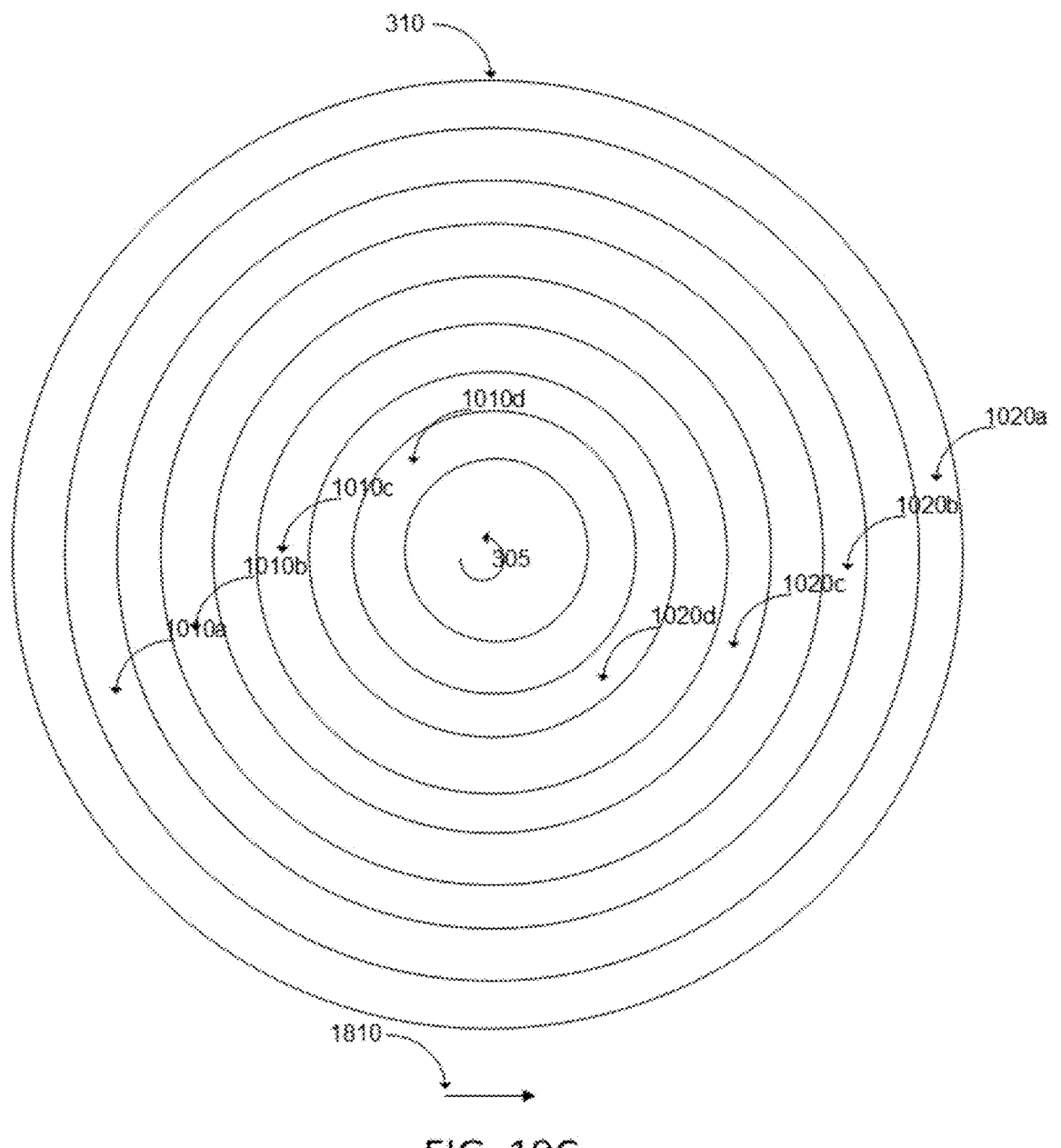
FIG. 19C shows staggered ring paths of two imaging heads located on the same side of an axis of rotation of a substrate.
Figure 19D:
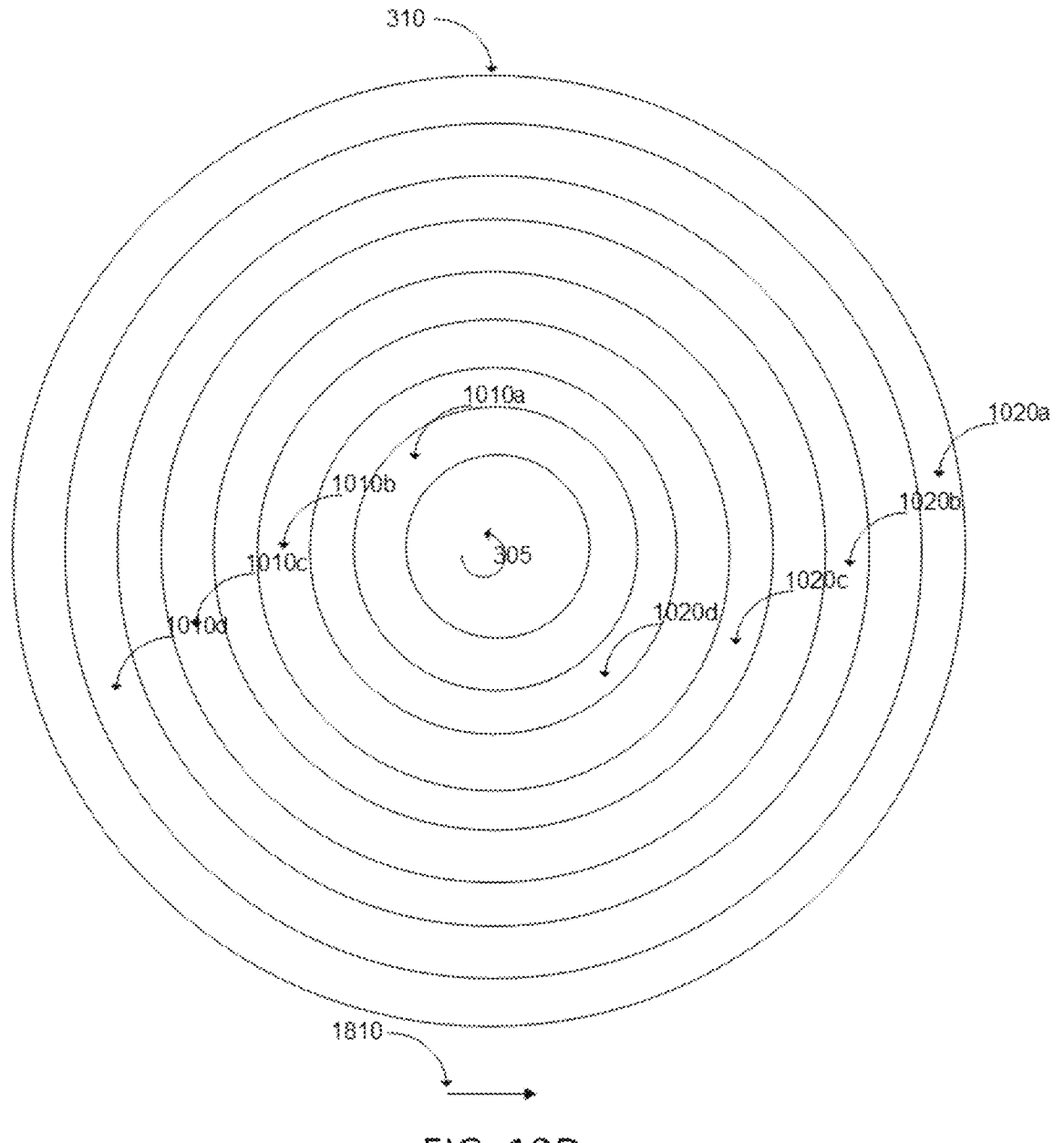
FIG. 19D shows staggered ring paths of two imaging heads located on opposite sides of an axis of rotation of a substrate.
Figure 20:
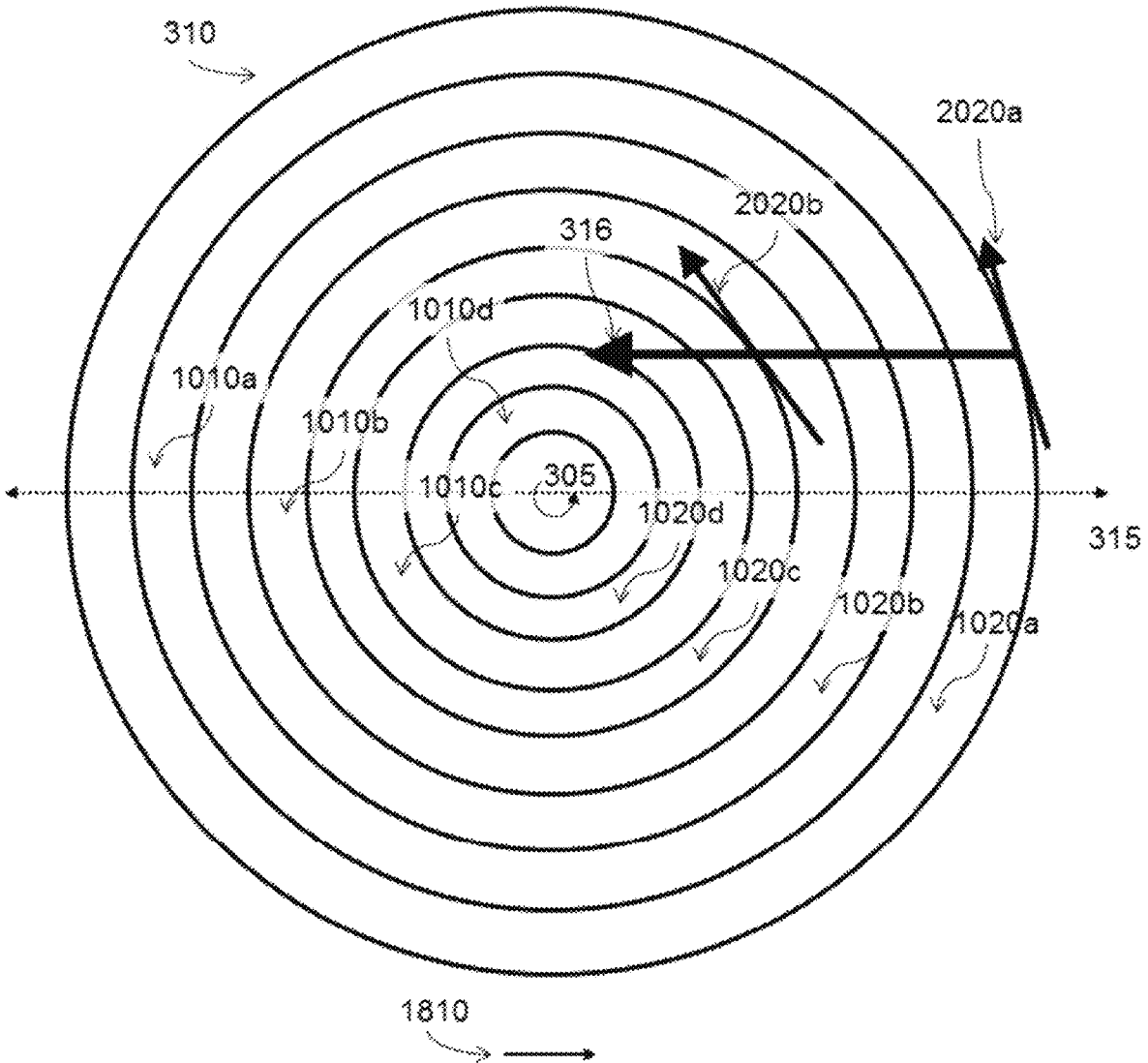
FIG. 20 shows rotating scan directions of imaging heads due to non-radial motion of a substrate.

FIGS. 18A-18D, 19A-19D, and 20 show additional examples of imaging schemes involving multiple imaging heads. For example, FIG. 20 shows rotating scan directions of multiple imaging heads due to non-radial motion of a substrate.

FIG. 11 shows a cross-sectional view of an immersion optical system 1100. The system 1100 may be used to optically image the substrates described herein. The system 1100 may be integrated with any other optical system or system for nucleic acid sequencing described herein (such as any of systems 300, 400, 500a, 500b, 700, or 800), or any element thereof. The system may comprise an optical imaging objective 1110. The optical imaging objective may be an immersion optical imaging objective. The optical imaging objective may be configured to be in optical communication with a substrate, such as substrate 310 described herein. The optical imaging objective may be configured to be in optical communication with any other optical elements described herein. The optical imaging objective may be partially or completely surrounded by an enclosure 1120. The enclosure may partially or completely surround a sample-facing end of the optical imaging objective. The enclosure and fluid may comprise an interface between the atmosphere in contact with the substrate and the ambient atmosphere. The atmosphere in contact with the substrate and the ambient atmosphere may differ in relative humidity, temperature, and/or pressure. The enclosure may have a generally cup-like shape or form. The enclosure may be any container. The enclosure may be configured to contain a fluid or immersion fluid 1140 (such as water or an aqueous or organic solution) in which the optical imaging objective is to be immersed. The enclosure may be configured to maintain a minimal distance 1150 between the substrate and the enclosure in order to avoid contact between the enclosure and the substrate during rotation of the substrate. In some instances, air or a pressure differential may be used to maintain the minimal distance. The minimal distance may be at least 100 nm, at least 200 nm, at least 500 nm, at least 1 µm, at least 2 µm, at least 5 µm, at least 10 µm, at least 20 µm, at least 50 µm, at least 100 µm, at least 200 µm, at least 500 µm, at least 1 mm, or a distance that is within a range defined by any two of the preceding values. Even with a minimal distance, the enclosure may contain the fluid due to surface tension effects. The system may comprise a fluid flow tube 1130 configured to deliver fluid to the inside of the enclosure. The fluid flow tube may be connected to the enclosure through an adaptor 1135. The adaptor may comprise a threaded adaptor, a compression adaptor, or any other adaptor. An electrical field application unit (not shown) can be configured to regulate a hydrophobicity of one or more surfaces of a container to retain at least a portion of the fluid contacting the immersion objective lens and the open substrate, such as by applying an electrical field.

As used herein, the fluid contacting the immersion objective lens may be referred to as "immersion fluid" or "fluid". The immersion fluid may comprise any suitable immersion medium for imaging. For example, the immersion medium may comprise an aqueous solution. Non-limiting examples of aqueous immersion fluids include water. In some cases, the aqueous solution may comprise salts, surfactants, oils and/or any other chemicals or reagents useful in imaging. In some cases, the immersion medium comprises an organic solution. Non-limiting examples of organic immersion fluids include oils, perfluorinated polyethers, perfluorocarbons, and hydrofluorocarbons. In some cases, the immersion fluid may be substantially the same as the wash buffer, as described elsewhere herein, or any buffer used in the processes described herein. The immersion fluid may be tuned based on the optical requirements of the systems and methods described herein. For example, where a high numerical aperture (NA) is required, the appropriate immersion fluid (e.g., oil) may be used for imaging.

The fluid may be in contact with the substrate. The optical imaging objective and enclosure may be configured to provide a physical barrier between a first location in which chemical processing operations are performed and a second location in which detection operations are performed. In this manner, the chemical processing operations and the detection operations may be performed with independent operation conditions and contamination of the detector may be avoided. The first and second locations may have different humidities, temperatures, pressures, or atmospheric admixtures.

A system of the present disclosure may be contained in a container or other closed environment. For example, a container may isolate an internal environment 1160 from an external environment 1170. The internal environment 1160 may be controlled such as to localize temperature, pressure, and/or humidity, as described elsewhere herein. In some instances, the external environment 1170 may be controlled. In some instances, the internal environment 1160 may be further partitioned, such as via, or with aid of, the enclosure 1120 to separately control parts of the internal environment (e.g., first internal environment for chemical processing operations, second internal environment for detection operations, etc.). The different parts of the internal environment may be isolated via a seal. For example, the seal may comprise the immersion objective described herein.

A system of the present disclosure may be configured to analyze a dynamic (e.g., rotating or otherwise moving) open substrate (e.g., as described herein) using a stationary detector system. Alternatively or additionally, one or more components of a detector system may be in motion. For example, a detector system may comprise a sensor (e.g., camera) and an illumination source. The sensor may be in motion while an optical element (e.g., prism) remains stationary. The illumination source may move in tandem with the sensor. For example, the sensor may be a line-scan camera (e.g., a TDI line-scan camera) and the illumination source may be an LED line light or a laser (e.g., a laser having a beam expanded to a line), and the illumination source may illuminate the area being detected by the sensor. The sensor (and, optionally, the illumination source) may rotate at a same or different rate as the open substrate. In some cases, the sensor (and, optionally, the illumination source) may translate across the open substrate in a predefined pattern, such as a spiral pattern. Alternatively, the sensor (and, optionally, the illumination source) may translate radially across the open substrate. In some cases, the sensor (and, optionally, the illumination source) may remain in a same physical location but may rotate about a central axis of the detector system or component(s) thereof. In other cases, the illumination source may illuminate an area of the open substrate that may be larger than an area that is detectable by the sensor in a given scan or collection of scans. However, illumination over a broad swath of the open substrate may promote bleaching of beads and/or fluorophores that may be disposed on the open substrate. Accordingly, the illumination source may be configured to illuminate only a limited area of the open substrate at a given time (e.g., an area that may be, at least partially overlaps with, or is within an area detectable by the sensor).

In another example, a detector system may comprise a sensor (e.g., camera), an illumination source, and one or more optical elements (e.g., lenses, mirrors, prisms, etc.), and the sensor and illumination source may remain stationary while an optical element (e.g., prism) is in motion. For instance, the optical element may rotate at a same rate as the open substrate, or the optical element may translate across the open substrate (e.g., radially or in a predefined pattern, such as a spiral pattern). In some cases, the optical element may remain in a same physical location but may rotate about a central axis (e.g., of the optical element or the detector system). Motion of an optical element of a detector system relative to an open substrate in motion may have the effect of enabling detection at one or more different areas of the open substrate. For example, the movement of one or more optical elements of the detector system may result in illumination of different areas of the open substrate to permit detection of signal associated with the different areas of the open substrate. Distortions of the illumination (e.g., laser light) and variation in detection sensitivities over different areas of the open substrate may be compensated for via subsequent processing (e.g., using a processor, as described herein).

Alternatively, a system of the present disclosure may be configured to analyze a stationary open substrate using a detector system comprising one or more dynamic components. For example, a detector system may comprise a sensor (e.g., camera) and an illumination source. The sensor may be in motion while an optical element (e.g., prism) remains stationary. The illumination source may move in tandem with the sensor. For example, the sensor may be a line-scan camera (e.g., a TDI line-scan camera) and the illumination source may be an LED line light or a laser (e.g., a laser having a beam expanded to a line), and the illumination source may illuminate the area being detected by the sensor. The sensor (and, optionally, the illumination source) may rotate (e.g., about a central axis of the open substrate). In some cases, the sensor (and, optionally, the illumination source) may translate across the open substrate in a predefined pattern, such as a spiral pattern. Alternatively, the sensor (and, optionally, the illumination source) may translate radially across the open substrate. In some cases, the sensor (and, optionally, the illumination source) may remain in a same physical location but may rotate about a central axis of the detector system or component(s) thereof.

In another example, a detector system may comprise a sensor (e.g., camera), an illumination source, and one or more optical elements (e.g., lenses, mirrors, prisms, etc.), and the sensor and illumination source may remain stationary while an optical element (e.g., prism) is in motion. For instance, the optical element may rotate (e.g., about a central axis of the open substrate or about a central axis of the optical element or the detector system) or translate across the open substrate (e.g., radially or in a predefined pattern, such as a spiral pattern). Motion of an optical element of a detector system relative to a stationary open substrate may have the effect of enabling detection at one or more different areas of the open substrate. For example, the movement of one or more optical elements of the detector system may result in illumination of different areas of the open substrate to permit detection of signal associated with the different areas of the open substrate. Distortions of the illumination (e.g., laser light) and variation in detection sensitivities over different areas of the open substrate may be compensated for via subsequent processing (e.g., using a processor, as described herein).

A system may be calibrated (e.g., using an open substrate that does not comprise an analyte, or comprises a known analyte or collection thereof) to facilitate any detection schemes provided herein.

In any of the preceding examples, multiple sensors and/or illumination sources may be used (e.g., to detect different areas of the open substrate, as described herein). The multiple sensors and/or illumination sources may all remain stationary or may all be in motion during a detection process. In other cases, certain sensors and/or illumination sources may be in motion and other sensors and/or illumination sources may be stationary during a detection process. Some or all sensors may analyze the substrate. For example, only sensors in motion, or only sensors that are stationary, may detect signals from the open substrate.

The scan direction of one or more detector systems (e.g., imaging head) may rotate due to non-radial motion of the detector system relative to a substrate. For example, a detector system may have different tangential velocity vectors relative to the substrate while tracing different imaging paths at different radial positions along the substrate, which tangential velocity vectors may point in substantially different directions. Such an effect may be manifested as a rotation of the imaging field as a first detector system traces a first set of imaging paths or as a second detector system traces a second set of imaging paths (see, e.g., FIG. 20).

The present disclosure provides an apparatus in which processing of an analyte on an open substrate and detection of a signal associated with the analyte are performed in the same environment. For example, the open substrate may be retained in the same or approximately the same physical location during processing of an analyte and subsequent detection of a signal associated with a processed analyte. For a system in which the detector system or a component thereof is in motion during detection, the apparatus may comprise a mechanical component configured to affect motion of the detector system of component thereof.

The present disclosure also provides an apparatus in which processing of an analyte on an open substrate and detection of a signal associated with the analyte are performed in different environments. For example, the open substrate may be retained in a first physical location during processing of an analyte and the in a second physical location during detection of a signal associated with a processed analyte. The open substrate may be transferred between various physical locations via, for example, a mechanical component. In some cases, the open substrate may be transferred between various physical locations using a robotic arm, elevator mechanism, or another mechanism. The first physical location may be disposed, for example, above, below, adjacent to, or across from the second physical location. For example, the first physical location may be disposed above the second physical location, and the open substrate may be transferred between these locations between analyte processing and detection. In another example, the first physical location may be disposed adjacent to the second physical location, and the open substrate may be transferred between these locations between analyte processing and detection. The first and second physical locations may be separated by a barrier, such as a retractable barrier.

Figure 39A:
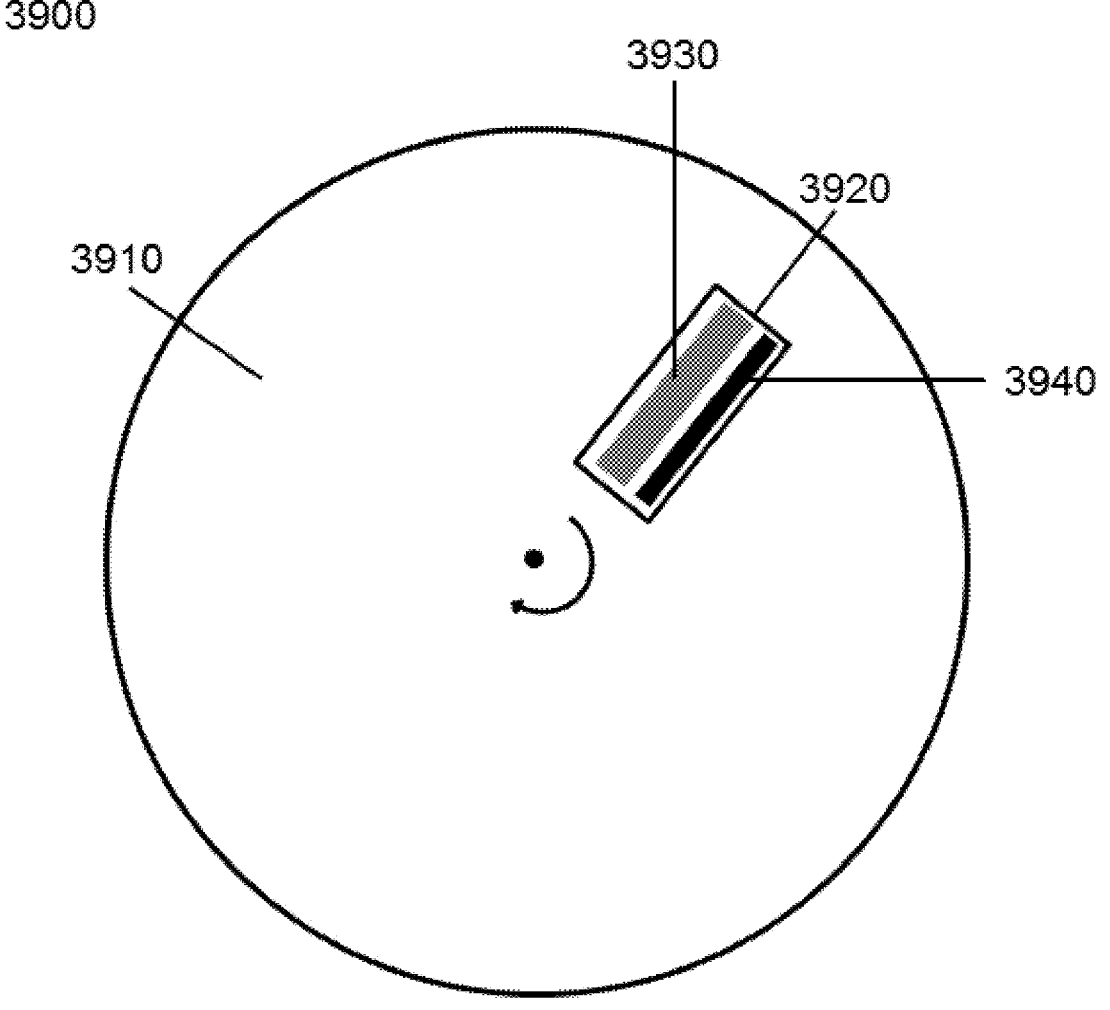
FIGS. 39A-39C illustrate schemes for detection of signals emitted by a material coupled to an open substrate.
Figure 39B:
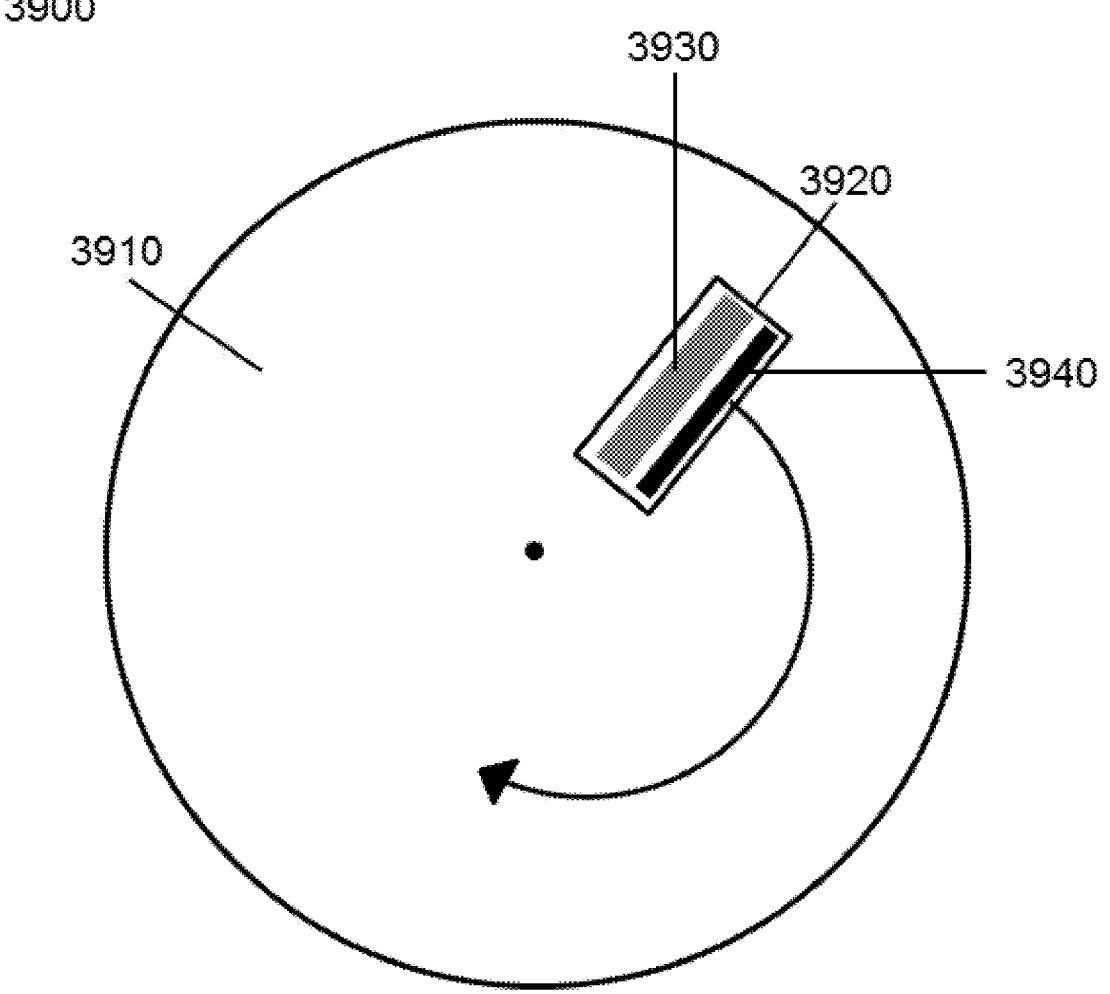
Figure 39C:
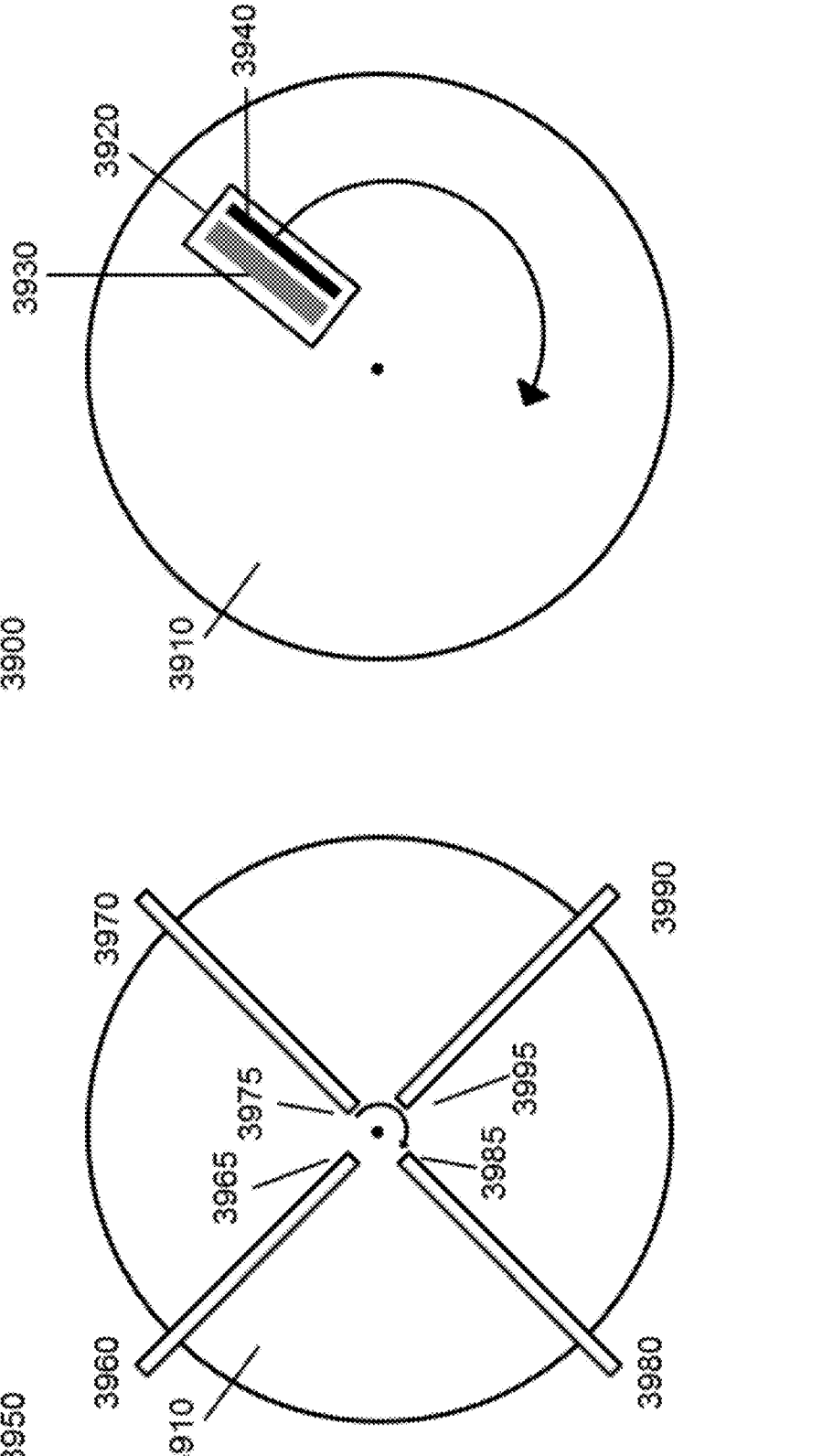

FIGS. 39A-39C illustrate various detection schemes. FIG. 39A illustrates a scheme involving a system 3900 in which open substrate 3910 rotates and detector system 3920 remains stationary during detection. Detector system 3920 may comprise line-scan camera (e.g., TDI line-scan camera) 3930 and illumination source 3940. FIG. 39B illustrates an alternative scheme involving a system 3900 in which open substrate 3910 remains stationary and detector system 3920 rotates during detection. FIG. 39C illustrates a scheme involving an apparatus comprising a first system 3950 in which open substrate 3910 is subjected to analyte processing. As shown in FIG. 3, first system 3950 may comprise a plurality of fluid channels 3960, 3970, 3980, and 3990, which plurality of fluid channels may comprise a plurality of fluid outlet ports 3965, 3975, 3985, and 3995. The apparatus may be configured to transfer open substrate 3910 to second system 3900, in which open substrate 3910 is configured to remain stationary and detector system 3920 is configured to rotate during detection. While examples described herein provide relative rotational motion of the substrates and/or detector systems, the substrates and/or detector systems may alternatively or additionally undergo relative non-rotational motion, such as relative linear motion, relative non-linear motion (e.g., curved, arcuate, angled, etc.), and any other types of relative motion.

In an aspect, the present disclosure provides a method for analyte detection or analysis comprising providing an open substrate comprising a central axis (e.g., as described herein). The open substrate may be, for example, a wafer or disc, such as a wafer or disc having one or more substances patterning its surface. The open substrate may be substantially planar. The open substrate may have an array of immobilized analytes thereon (e.g., as described herein). The immobilized analytes may be immobilized to the array via one or more binders. The array may comprise at least 100,000 such binders. In some cases, an immobilized analyte of the immobilized analytes may be coupled to a bead, and the bead may be immobilized to the array. An immobilized analyte may comprise a nucleic acid molecule.

A solution having a plurality of probes may be delivered (e.g., as described herein) to a region proximal to the central axis to introduce the solution to the open substrate. The solution may be dispersed across the open substrate such that at least one probe of the plurality of probes may bind to at least one immobilized analyte of the immobilized analytes to form a bound probe. The plurality of probes may comprise a plurality of oligonucleotide molecules. Alternatively, the plurality of probes may comprise a plurality of nucleotides or nucleotide analogs. All or a subset of the plurality of nucleotides or nucleotide analogs may be fluorescently labeled. In an example, the immobilized analytes may comprise nucleic acid molecules and the plurality of probes may comprise fluorescently labeled nucleotides, such that at least one fluorescently labeled nucleotide of the fluorescently labeled nucleotides binds to at least one nucleic acid molecule of the nucleic acid molecules via nucleotide complementarity binding. All or a subset of the plurality of nucleotides or nucleotide analogs may comprise the same base (e.g., the same canonical nucleobase, such as A, T, C, or G). Similarly, all or a subset of the plurality of nucleotides or nucleotide analogs may be reversibly terminated. Reversible terminators and, in some cases, fluorescent moieties such as dyes, may be cleaved from nucleotides (e.g., subsequent to their incorporation into a growing nucleic acid strand) using a cleaving agent, which cleaving agent may be included in another solution provided to the open substrate (e.g., as described herein). The open substrate may also be provided with a wash solution to remove excess probes and other reagents, which wash solution may be dispersed across the open substrate (e.g., during rotation of the open substrate using at least centrifugal force, as described herein).

After generation of the bound probe, a detector system may be used to detect at least one signal from the bound probe. The detector system may comprise a line-scan camera (e.g., a TDI line-scan camera) and an illumination source (e.g., an LED line light or a laser, such as a continuous wave laser). In some cases, the illumination source may comprise a laser and the detector system may comprise an optical element (e.g., a cylindrical lens) configured to change a shape of a beam (e.g., Gaussian beam) emitted by the laser (e.g., as described herein). The open substrate may comprise a first area and a second area, where the first area and the second area comprise subsets of the array of immobilized analytes, are at different radial positions of the open substrate with respect to the central axis, and are spatially resolvable by the detector system. The bound probe may be disposed in the first area of the open substrate. The detector system may perform a non-linear scan of the open substrate.

During the dispersal and delivery processes, the open substrate may be rotating (e.g., in a first physical location). The detector system (e.g., sensor and illumination source) may be stationary during these processes.

During the detection process, the open substrate may be stationary. The sensor and/or the illumination source of the detector system may be in motion during detection. For example, the sensor and the illumination source may be rotating during detection, optionally at the same rate. The sensor and/or the illumination source may rotate about a central axis of the open substrate. Alternatively, the sensor and/or the illumination source may rotate about a central axis of the detector system or a component thereof and remain in a same physical location. The sensor and/or illumination source may translate relative to the open substrate in a predetermined pattern, such as a spiral pattern. Alternatively, the line-scan camera and/or illumination source may translate (e.g., radially translate) across the open substrate. The detector system may further comprise a prism (e.g., a Dove prism), which prism may rotate during the detection process (e.g., about a central axis of the open substrate or about a central axis of the detector system or a component thereof while remaining in a same physical location). In an example, the prism may rotate or otherwise translate relative to the open substrate while the sensor and illumination source remain stationary. Such a prism may be used to disperse light to and from the open substrate, e.g., to disperse light from the illumination source to the open substrate and to detect optical signal from the open substrate, such as fluorescence.

The detector system may be configured to illuminate an area of the open substrate using the illumination source and subsequently detect a signal from the area using a sensor (e.g., line-scan camera). For example, the illumination source may illuminate an area of the open substrate (e.g., a stationary open substrate) prior to its detection by the sensor. In such a situation, the sensor and illumination source may move in tandem relative to the open substrate. One or more optical elements, such as one or more lenses, mirrors, filters, or other optical elements, may move in tandem with these other components of the detector system (e.g., to manipulate light provided to or detected from the open substrate).

During the dispersal and/or delivery processes, an additional probe may be formed, which additional bound probe may be disposed in the second area of the open substrate. During detection, at least one signal may be detected from the additional bound probe at the same time as the at least one signal from the bound probe. These signals may be detected with different sensitivities.

The detector system may compensate for velocity differences at different radial positions of the array with respect to the central axis within a scanned area. The detector system may comprise an optical imaging system having an anamorphic magnification gradient substantially transverse to a scanning direction along the open substrate, where the anamorphic magnification gradient may at least partially compensate for tangential velocity differences that are substantially perpendicular to the scanning direction. Detection may comprise reading two or more regions on the open substrate at two or more different scan rates, respectively, to at least partially compensate for tangential velocity differences in the two or more regions. Detection may further comprise using an immersion objective lens in optical communication with the detector system and the open substrate to detect the at least one signal (e.g., as described herein). The immersion objective lens may be in contact with a fluid that is in contact with the open substrate. The fluid may be in a container, and an electric field may be used to regulate a hydrophobicity of one or more surfaces of the container to retain at least a portion of the fluid contacting the immersion objective lens and the open substrate.

The delivery and/or dispersal processes may be performed in a first environment having a first operating condition, the detection process may be performed in a second environment having a second operating condition different from the first operating condition. The first and second environments may be disposed in the same physical location. For example, the delivery and/or dispersal processes may be performed under a first set of conditions while the open substrate is retained in a first physical location, and the detection process may be performed under a second set of conditions while the open substrate is retained in the same physical location. Alternatively, the first environment may comprise a first physical location in which the open substrate is accessible to a rotational unit configured to rotate the open substrate during the delivery and/or dispersal processes. The second environment may comprise a second physical location in which the open substrate is accessible to the detector system. As noted above, one or more components of the detector system and/or the open substrate may be in motion during the detection process. The second physical location may comprise a mechanism for supporting the open substrate while retaining it in a stationary state as well as a mechanism (e.g., a rotational unit) for moving the detector system or a component thereof relative to the open substrate (e.g., as described herein). The first and second environments may in physical proximity to one another. In an example, the first environment may be disposed in a first physical location of an apparatus that is located above a second physical location of the apparatus that is part of the second environment. In another example, the first environment may be disposed in a first physical location of an apparatus that is located adjacent or somewhat adjacent to a second physical location of the apparatus that is part of the second environment. The first and second environments may be separable by one or more barriers. In an example, a retractable barrier such as a sliding door separates the first and second environments. The retractable barrier may remain in a closed state during delivery and/or dispersal processes and may then be retracted to permit translation of the open substrate from the first environment to the second environment for subsequent detection. The retractable barrier may be retained in a closed state during the detection process. The open substrate may be retained in a container, which container is transferred with the open substrate between the first and second environments.

The first and second environments may comprise one or more different operating conditions. For example, the first environment may comprise a first temperature, humidity, and pressure and the second environment may comprise a second temperature, humidity, and pressure, where at least one of temperature, humidity, and pressure differ between the first and second environments. A given environment may comprise multiple temperature, humidity, and/or pressure zones, and one or more such zones may differ in the first and second environments.

The present disclosure also provides apparatus and computer readable media for implementing the methods provided herein. For example, the present disclosure provides a computer-readable medium comprising non-transitory instructions stored thereon, which when executed cause one or more computer processors to implement the methods provided herein. The present disclosure also provides an apparatus for analyte detection or analysis comprising a housing configured to receive an open substrate having an array of immobilized analytes thereon (e.g., as described herein). The apparatus may comprise one or more dispensers configured to deliver a solution having a plurality of probes to a region proximal to a central axis of the open substrate. The apparatus may also comprise a rotational unit configured to rotate the open substrate about the central axis to disperse the solution across the open substrate at least by centrifugal force, such that at least one probe of the plurality of probes binds to at least one immobilized analyte of the immobilized analytes to form a bound probe. The rotational unit may be disposed in a first area of the apparatus, which first area is distinct from a second area of the apparatus. The apparatus may also comprise a detector system, which detector system may comprise a sensor (e.g., line-scan camera) and an illumination source (e.g., as described herein). The detector system may be disposed in the second area of the apparatus. Alternatively, the detector system may be disposed in the first area of the apparatus. The open substrate may comprise a first area and a second area, where the first area and the second area comprise subsets of the array of immobilized analytes, are at different radial positions of the open substrate with respect to the central axis, and are spatially resolved by the detector system. The bound probe may be disposed in the first area of the open substrate, and the detector system may be programmed to perform a non-linear scan of the open substrate and detect at least one signal from the bound probe at the first area of the open substrate. The apparatus may comprise one or more processors configured to, for example, direct dispersal and delivery of one or more solutions to the open substrate or direct the detector system to detect one or more signals from the open substrate. The processor may be programmed to direct the detector system to compensate for velocity differences at different radial positions of the array with respect to the central axis of the open substrate within a scanned area. For example, the processor may be programmed to direct the detector system to scan two or more regions of the open substrate at two or more different scan rates, respectively, to at least partially compensate for tangential velocity differences in the two or more regions. The apparatus may further comprise one or more optics, such as one or more optics that are configured to generate an anamorphic magnification gradient that is, e.g., substantially transverse to a scanning direction along the open substrate (e.g., as described herein). A processor may be programmed to adjust the gradient to compensate for different imaged radial positions with respect to the central axis of the open substrate.

System Architectures for High-Throughput Processing

The nucleic acid sequencing systems and optical systems described herein (or any elements thereof) may be combined in a variety of architectures.

Figure 12A:
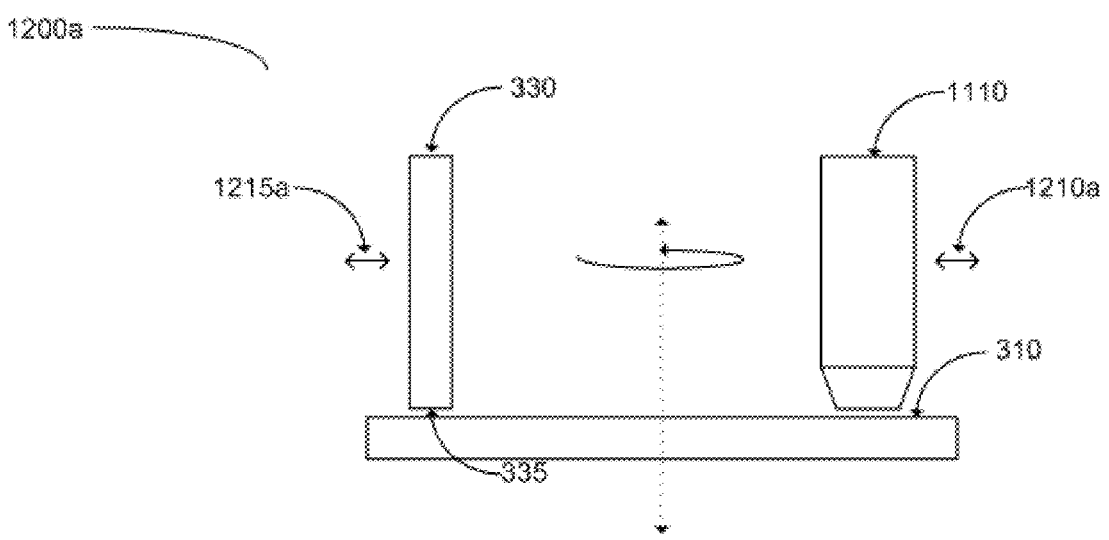
FIG. 12A shows an architecture for a system comprising a stationary axis substrate and moving fluidics and optics.

FIG. 12A shows an architecture for a system 1200a comprising a stationary substrate and moving fluidics and optics. The system 1200a may comprise substrate 310 described herein. The substrate may be configured to rotate, as described herein. The substrate may be adhered or otherwise affixed to a chuck (not shown in FIG. 12A), as described herein. The system may further comprise fluid channel 330 and fluid outlet port 335 described herein, and/or any other fluid channel and fluid outlet port described herein. The fluid channel and fluid outlet port may be configured to dispense any solution described herein. The fluid channel and fluid outlet port may be configured to move 1215a relative to the substrate. For instance, the fluid channel and fluid outlet port may be configured to move to a position above (such as near the center of) the substrate during periods of time in which the fluid channel and fluid outlet port are dispensing a solution. The fluid channel and fluid outlet port may be configured to move to a position away from the substrate during the period in which the fluid channel and fluid outlet port are not dispensing a solution. Alternatively, the reverse may apply. The system may further comprise optical imaging objective 1110 described herein. The optical imaging objective may be configured to move 1210a relative for the substrate. For instance, the optical imaging objective may be configured to move to a position above (such as near the center of) the substrate during periods of time in which the substrate is being imaged. The optical imaging objective may be configured to move to a position away from the substrate during the period in which the substrate is not being imaged. The system may alternate between dispensing of solutions and imaging, allowing rapid sequencing of the nucleic acids attached to the substrate using the systems and methods described herein.

Figure 12B:
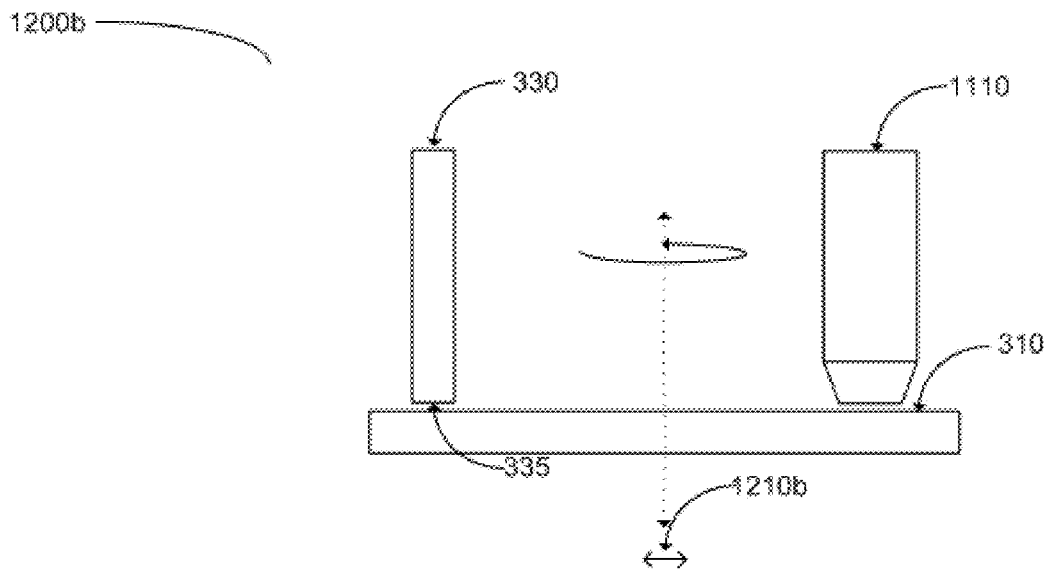
FIG. 12B shows an architecture for a system comprising a translating axis substrate and stationary fluidics and optics.

FIG. 12B shows an architecture for a system 1200b comprising a moving substrate and stationary fluidics and optics. The system 1200b may comprise substrate 310 described herein. The substrate may be configured to rotate, as described herein. The substrate may be adhered or otherwise affixed to a chuck (not shown in FIG. 12B), as described herein. The system may further comprise fluid channel 330 and fluid outlet port 335 described herein, or any other fluid channel and fluid outlet port described herein. The fluid channel and fluid outlet port may be configured to dispense any solution described herein. The system may further comprise optical imaging objective 1110 described herein. The fluid channel, fluid outlet port, and optical imaging objective may be stationary. The substrate may be configured to move 1210b relative to the fluid channel, fluid outlet port, and optical imaging objective. For instance, the substrate may be configured to move to a position such that the fluid channel and fluid outlet port are above (such as near the center of) the substrate during periods of time in which the fluid channel and fluid outlet port are dispensing a solution. The substrate may be configured to move to a position away from the fluid channel and fluid outlet port during the period in which the fluid channel and fluid outlet port are not dispensing a solution. The substrate may be configured to radially scan the objective over the substrate during periods of time in which the substrate is being imaged. The substrate may be configured to move to a position away from the optical imaging objective during the period in which the substrate is not being imaged. The system may alternate between dispensing of solutions and imaging, allowing rapid sequencing of the nucleic acids attached to the substrate using the systems and methods described herein.

Figure 12C:
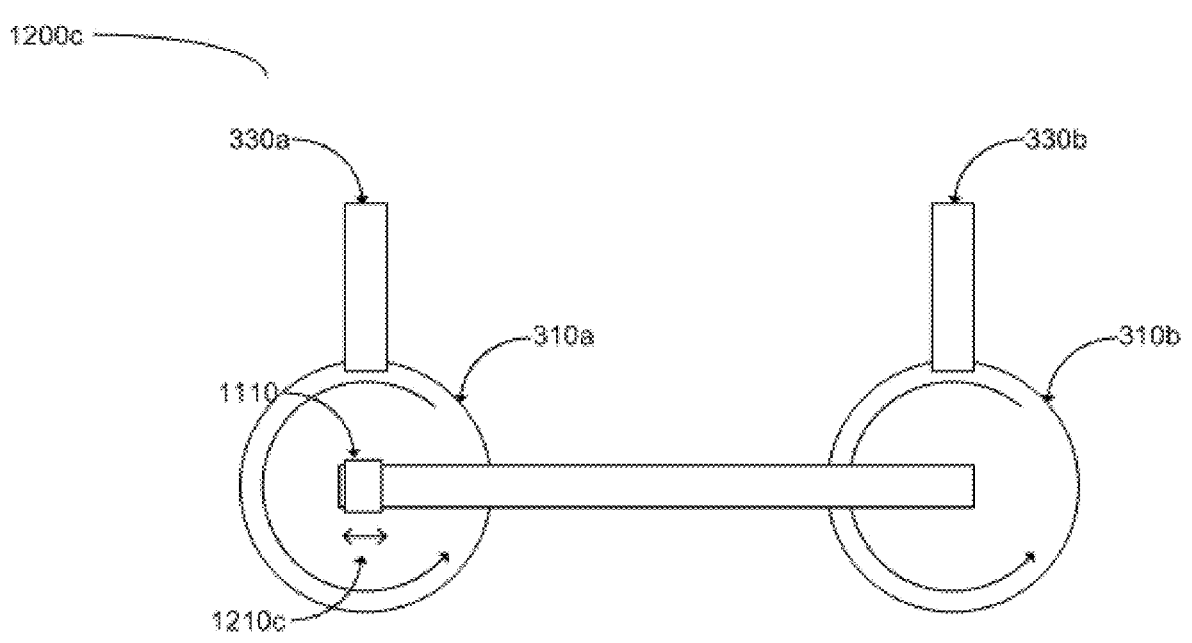
FIG. 12C shows an architecture for a system comprising a plurality of stationary substrates and moving fluidics and optics.

FIG. 12C shows an architecture for a system 1200c comprising a plurality of stationary substrates and moving fluidics and optics. The system 1200c may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 12C), as described herein. The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The system may further comprise second fluid channel 330b and second fluid outlet port 335b. Second fluid channel 330b may be similar to fluid channel 330 described herein or any other fluid channel described herein. Second fluid outlet port 335a may be similar to fluid outlet port 335 described herein or any other fluid outlet port described herein. The first fluid channel and first fluid outlet port may be configured to dispense any solution described herein. The second fluid channel and second fluid outlet port may be configured to dispense any solution described herein.

The system may further comprise optical imaging objective 1110. Optical imaging objective 1110 may be configured to move 1210c relative to the first and second substrates. For instance, the optical imaging objective may be configured to move to a position above (such as near the center of, or radially scanning) the first substrate during periods of time in which the first fluid channel and first fluid outlet port are not dispensing a solution to the second substrate (and during which the first substrate is to be imaged). The optical imaging objective may be configured to move to a position away from the first substrate during the period in which the first fluid channel and first fluid outlet port are dispensing a solution. The optical imaging objective may be configured to move to a position above (such as near the center of, or radially scanning) the second substrate during periods of time in which the second fluid channel and second fluid outlet port are not dispensing a solution to the second substrate (and during which the second substrate is to be imaged). The optical imaging objective may be configured to move to a position away from the second substrate during the period in which the second fluid channel and second fluid outlet port are dispensing a solution.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the optical imaging objective may be moved from the second substrate to the first substrate. A solution may then be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 12C, system 1200c may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and/or at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. Each optical imaging objective may be moved between substrates as described herein.

Figure 12D:
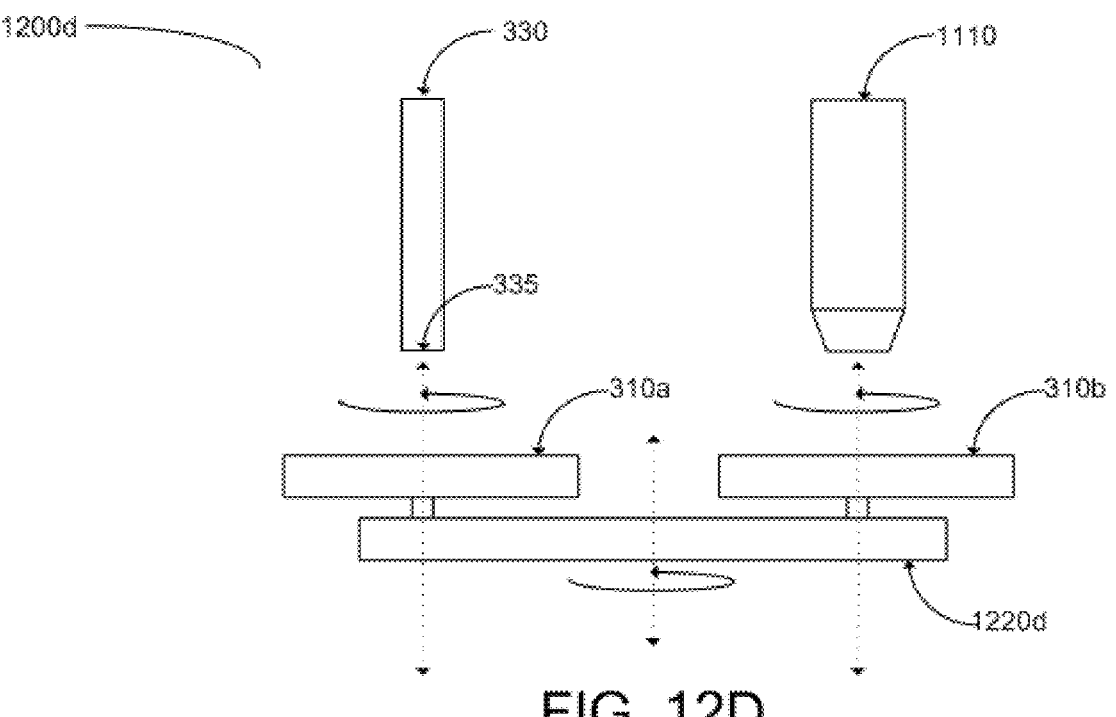
FIG. 12D shows an architecture for a system comprising a plurality of moving substrates on a rotary stage and stationary fluidics and optics.

FIG. 12D shows an architecture for a system 1200d comprising a plurality of moving substrates on a rotary stage and stationary fluidics and optics. The system 1200d may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 12D), as described herein. The first and second substrates may be affixed to a rotating stage 1220d (such as approximately at opposing ends of the rotating stage). The rotating stage may be configured to rotate about an axis. The axis may be an axis through the center of the substrate. The axis may be an off-center axis. The rotating stage may approximately scan the radius of the substrate 310b. The system may further comprise fluid channel 330 and fluid outlet port 335. The fluid channel and fluid outlet port may be configured to dispense any solution described herein. The system may further comprise optical imaging objective 1110. A longitudinal axis of the imaging objective 1110 may not be coincident with a central axis of the second substrate 310b (although this is difficult to distinguish in FIG. 12D). The imaging objective 1110 may be positioned at some distance from a center of the second substrate 310b.

The rotating stage may be configured to alter the relative positions of the first and second substrates to carry out different sequencing operations. For instance, the rotating stage may be configured to rotate such that the optical imaging objective is in a position above (such as near the center of, or radially scanning) the first substrate during periods of time in which the fluid channel and fluid outlet port are not dispensing a solution to the first substrate (and during which the first substrate is to be imaged). The rotating stage may be configured to rotate such that the optical imaging objective is away from the first substrate during the period in which the fluid channel and fluid outlet port are dispensing a solution to the first substrate. The rotating stage may be configured to rotate such that the optical imaging objective is in a position above (such as near the center of, or radially scanning) the second substrate during periods of time in which the fluid channel and fluid outlet port are not dispensing a solution to the second substrate (and during which the second substrate is to be imaged). The rotating stage may be configured to rotate such that the optical imaging objective is away from the second substrate during the period in which the fluid channel and fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the rotating stage may be rotated such that a solution may be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, one fluid channel, one fluid outlet port, and one optical imaging objective in FIG. 12D, system 1200d may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The rotating stage may be rotated to place any substrate under any fluid channel, fluid outlet port, or optical imaging objective at any time.

Figure 12E:
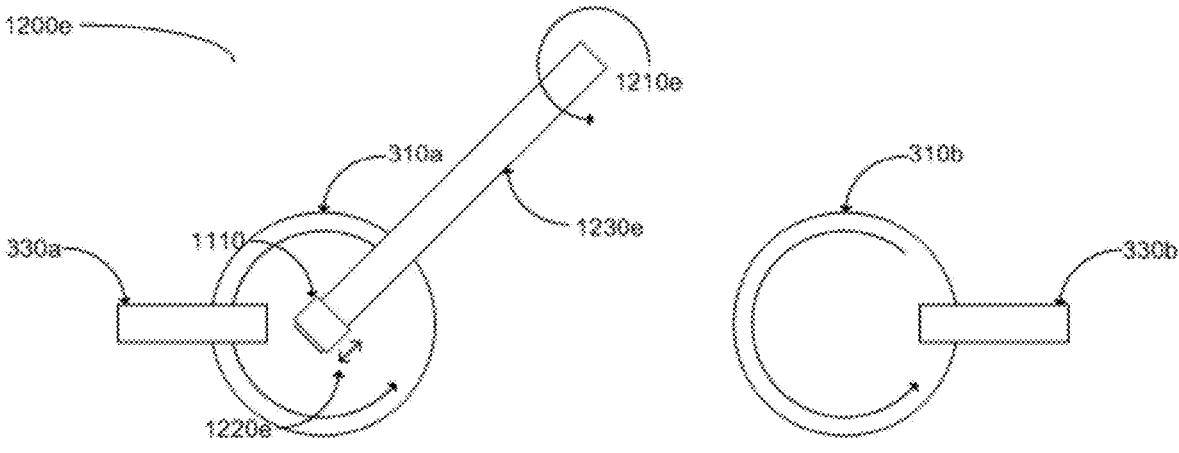
FIG. 12E shows an architecture for a system comprising a plurality of stationary substrates and moving optics.

FIG. 12E shows an architecture for a system 1200e comprising a plurality of stationary substrates and moving optics. The system 1200d may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 12E), as described herein. The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The first fluid channel and first fluid outlet port may be configured to dispense any solution described herein. The system may further comprise second fluid channel 330b and second fluid outlet port 335b. Second fluid channel 330b may be similar to fluid channel 330 described herein or any other fluid channel described herein. Second fluid outlet port 335b may be similar to fluid outlet port 335 described herein or any other fluid outlet port described herein. The second fluid channel and second fluid outlet port may be configured to dispense any solution described herein.

The system may further comprise optical imaging objective 1110. The optical imaging objective may be attached to an imaging arm 1230e. The optical imaging objective may be configured to move 1220e along the optical imaging arm to image an entire area of the first or second substrate. The optical imaging arm may be configured to rotate 1210e. The optical imaging arm may be configured to rotate such that the optical imaging objective is in a position above (such as near the center of, or radially scanning) the first substrate during periods of time in which the first fluid channel and first fluid outlet port are not dispensing a solution to the first substrate (and during which the first substrate is to be imaged). The optical imaging arm may be configured to rotate such that the optical imaging objective is away from the first substrate during the period in which the first fluid channel and first fluid outlet port are dispensing a solution to the first substrate. The optical imaging arm may be config- ured to rotate such that the optical imaging objective is in a position above (such as near the center of, or radially scanning) the second substrate during periods of time in which the second fluid channel and second fluid outlet port are not dispensing a solution to the second substrate (and during which the second substrate is to be imaged). The optical imaging arm may be configured to rotate such that the optical imaging objective is away from the second substrate during the period in which the second fluid channel and second fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the optical imaging arm may be rotated such that a solution may be dispensed to the second substrate during a period of time in which the first substrate is being imaged. This alternating pattern of dis- pensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 12E, system 1200e may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The optical imaging arm may be rotated to place any substrate under any fluid channel, fluid outlet port, or optical imaging objective at any time.

Figure 12F:
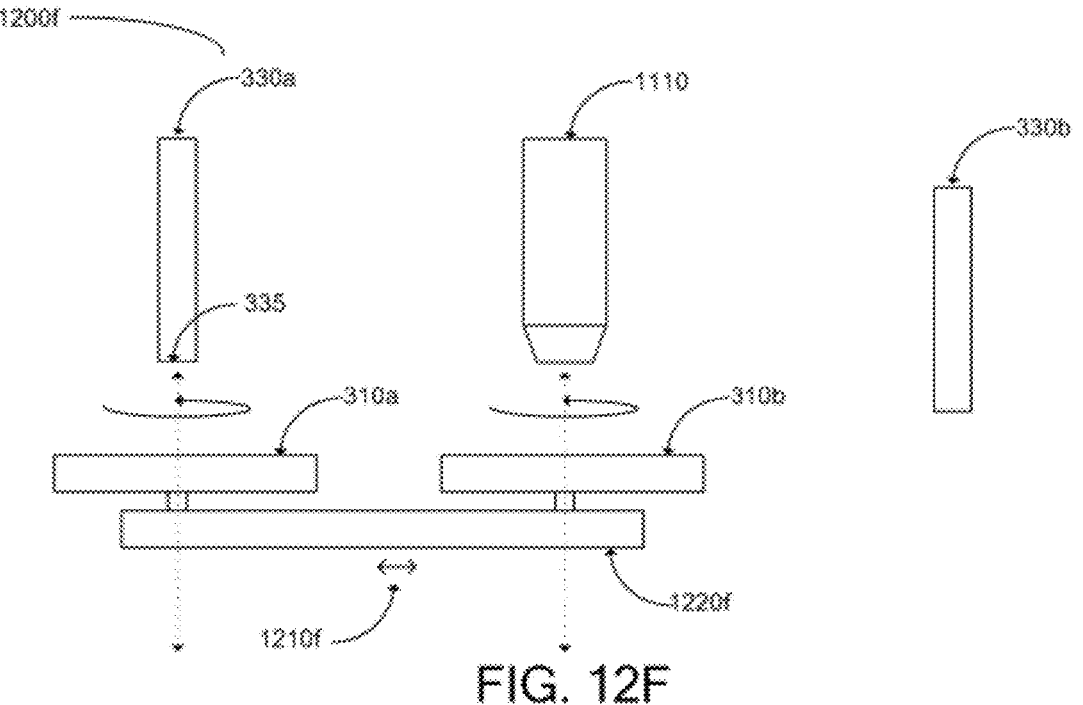
FIG. 12F shows an architecture for a system comprising a plurality of moving substrates and stationary fluidics and optics.

FIG. 12F shows an architecture for a system 1200f comprising a plurality of moving substrates and stationary fluidics and optics. The system 1200f may comprise first and second substrates 310a and 310b. The first and second substrates may be similar to substrate 310 described herein. The first and second substrates may be configured to rotate, as described herein. The first and second substrates may be adhered or otherwise affixed to first and second chucks (not shown in FIG. 12F), as described herein. The first and second substrates may be affixed to opposing ends of a moving stage 1220f. The moving stage may be configured to move 1210f. The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The first fluid channel and first fluid outlet port may be configured to dispense any solution described herein. The system may further comprise second fluid channel 330b and second fluid outlet port 335b. Second fluid channel 330b may be similar to fluid channel 330 described herein or any other fluid channel described herein. Second fluid outlet port 335b may be similar to fluid outlet port 335 described herein or any other fluid outlet port described herein. The second fluid channel and second fluid outlet port may be configured to dispense any solution described herein. The system may further comprise optical imaging objective 1110.

The moving stage may be configured to move such that the optical imaging objective is in a position above (such as near the center of, or radially scanning) the first substrate during periods of time in which the first fluid channel and first fluid outlet port are not dispensing a solution to the first substrate (and during which the first substrate is to be imaged). The moving stage may be configured to move such that the optical imaging objective is away from the first substrate during the period in which the first fluid channel and first fluid outlet port are dispensing a solution to the first substrate. The moving stage may be configured to move such that the optical imaging objective is in a position above (such as near the center of, or radially scanning) the second substrate during periods of time in which the second fluid channel and second fluid outlet port are not dispensing a solution to the second substrate (and during which the second substrate is to be imaged). The moving stage may be configured to move such that the optical imaging objective is away from the second substrate during the period in which the second fluid channel and second fluid outlet port are dispensing a solution to the second substrate.

The timing of dispensing of a solution and imaging of a substrate may be synchronized. For instance, a solution may be dispensed to the first substrate during a period of time in which the second substrate is being imaged. Once the solution has been dispensed to the first substrate and the second substrate has been imaged, the moving stage may move such that a solution may be dispensed to the second substrate during a period of time in which the first substrate is being imaged. This alternating pattern of dispensing and imaging may be repeated, allowing rapid sequencing of the nucleic acids attached to the first and second substrates using the systems and methods described herein. The alternating pattern of dispensing and imaging may speed up the sequencing by increasing the duty cycle of the imaging process or the solution dispensing process.

Though depicted as comprising two substrates, two fluid channels, two fluid outlet ports, and one optical imaging objective in FIG. 12F, system 1200f may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The moving stage may move so as to place any substrate under any fluid channel, fluid outlet port, or optical imaging objective at any time.

Figure 12G:
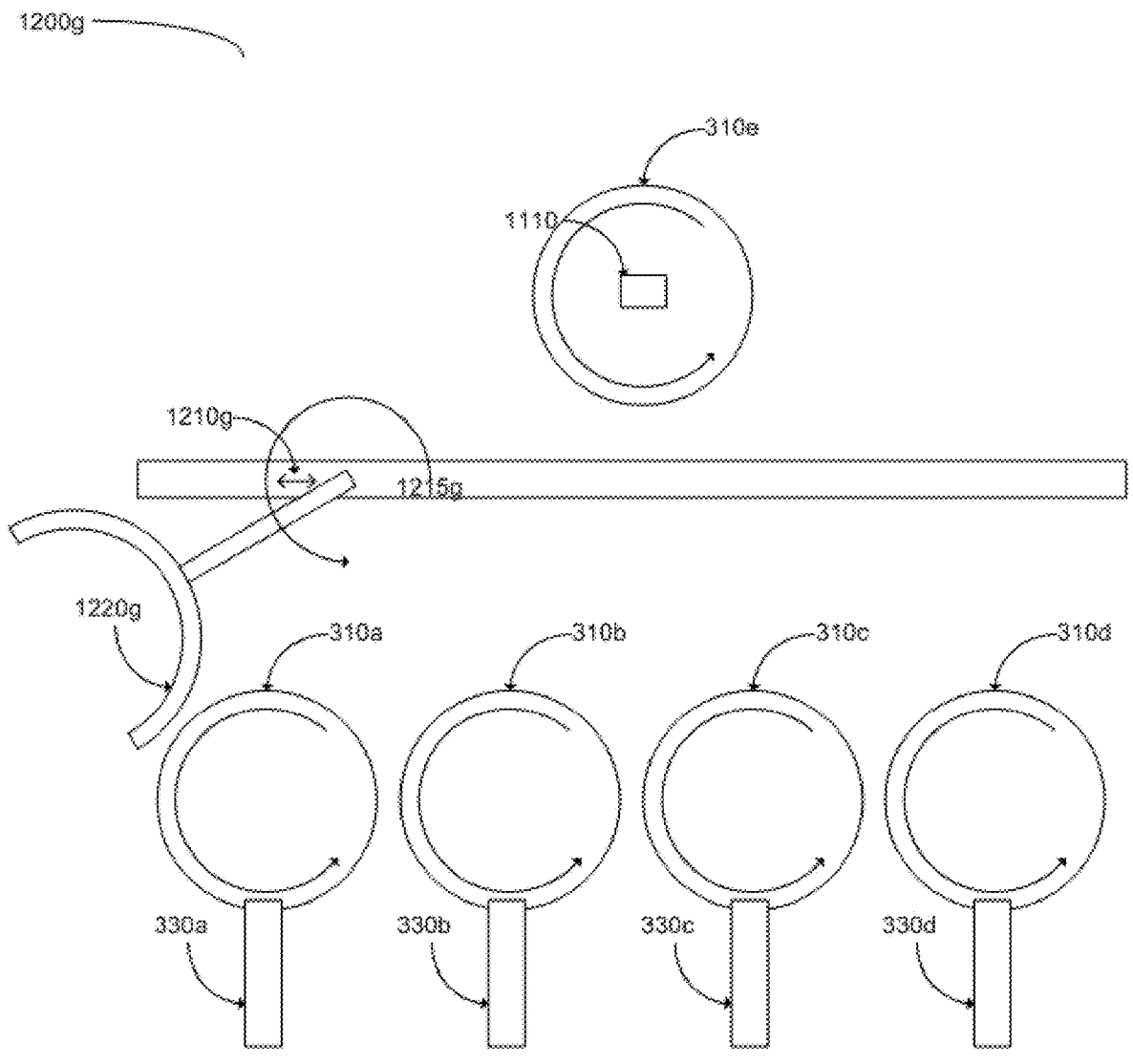
FIG. 12G shows an architecture for a system comprising a plurality of substrates moved between a plurality of processing bays.

FIG. 12G shows an architecture for a system 1200g comprising a plurality of substrates moved between a plurality of processing bays. The system 1200g may comprise first, second, third, and fourth substrates 310a, 310b, 310c, 310d, and 310e, respectively. The first, second, third, fourth, and fifth substrates may be similar to substrate 310 described herein. The first, second, third, fourth, and fifth substrates may be configured to rotate, as described herein. The first, second, third, fourth, and fifth substrates may be adhered or otherwise affixed to first, second, third, fourth, and fifth chucks (not shown in FIG. 12G), respectively, as described herein.

The system may further comprise first fluid channel 330a and first fluid outlet port 335a. First fluid channel 330a may be similar to fluid channel 330 described herein or any other fluid channel described herein. First fluid outlet port 335a may be similar to fluid outlet port 335 described herein or any other fluid outlet port described herein. The first fluid channel and first fluid outlet port may be configured to dispense any solution described herein. The first fluid channel and first fluid outlet port may be regarded as a first processing bay. The first processing bay may be configured to perform a first processing operation, such as dispensing of a first solution to any of the first, second, third, fourth, or fifth substrates.

The system may further comprise second fluid channel 330b and second fluid outlet port 335b. Second fluid channel 330b may be similar to fluid channel 330 described herein or any other fluid channel described herein. Second fluid outlet port 335b may be similar to fluid outlet port 335 described herein or any other fluid outlet port described herein. The second fluid channel and second fluid outlet port may be configured to dispense any solution described herein. The second fluid channel and second fluid outlet port may be regarded as a second processing bay or processing station. The second processing bay may be configured to perform a second processing operation, such as dispensing of a second solution to any of the first, second, third, fourth, or fifth substrates.

The system may further comprise third fluid channel 330c and third fluid outlet port 335c. Third fluid channel 330c may be similar to fluid channel 330 described herein or any other fluid channel described herein. Third fluid outlet port 335c may be similar to fluid outlet port 335 described herein or any other fluid outlet port described herein. The third fluid channel and third fluid outlet port may be configured to dispense any solution described herein. The third fluid channel and third fluid outlet port may be regarded as a third processing bay or processing station. The third processing bay may be configured to perform a third processing operation, such as dispensing of a third solution to any of the first, second, third, fourth, or fifth substrates.

The system may further comprise fourth fluid channel 330d and fourth fluid outlet port 335d. Fourth fluid channel 330d may be similar to fluid channel 330 described herein or any other fluid channel described herein. Fourth fluid outlet port 335d may be similar to fluid outlet port 335 described herein or any other fluid outlet port described herein. The fourth fluid channel and fourth fluid outlet port may be configured to dispense any solution described herein. The fourth fluid channel and fourth fluid outlet port may be regarded as a fourth processing bay or processing station. The fourth processing bay may be configured to perform a fourth processing operation, such as dispensing of a fourth solution to any of the first, second, third, fourth, or fifth substrates.

The system may further comprise a scanning optical imaging objective 1110. The optical imaging objective may be regarded as a fifth processing bay or processing station.

The system may further comprise a moving arm 1220g. The moving arm may be configured to move laterally 1210g or rotate 1215g. The moving arm may be configured to move any of the first, second, third, fourth, or fifth substrates between different processing stations (such as by picking up substrates and moving them to new locations). For instance, at a first point in time, the first substrate may undergo a first operation (such as dispensing of a first solution) at the first processing bay, the second substrate may undergo a second operation (such as dispensing of a second solution) at the second processing bay, the third substrate may undergo a third operation (such as dispensing of a third solution) at the first processing bay, the fourth substrate may undergo a fourth operation (such as dispensing of a fourth solution) at the fourth processing bay, and the fifth substrate may be imaged at the fifth processing bay. Upon completion of one or more of the first, second, third, or fourth operations, or of imaging, the moving arm may move one or more of the first, second, third, fourth, or fifth substrates to one or more of the first, second, third, fourth, or fifth processing bays, where another operation may be completed. The pattern of completing one or more operations and moving one or more substrates to another processing bay to complete another operation may be repeated, allowing rapid sequencing of the nucleic acids attached to the first, second, third, fourth, and fifth substrates using the systems and methods described herein. The alternating pattern of dispensing and imaging may speed up the sequencing by increasing the duty cycle of the imaging process or the solution dispensing process.

Though depicted as comprising five substrates, four fluid channels, four fluid outlet ports, and one optical imaging objective in FIG. 12G, system 1200g may comprise any number of each of the substrates, fluid channels, fluid outlet ports, and optical imaging objectives. For instance, the system may comprise at least 1, at least 2, at least 3, at least 4, at least 5, at least 6, at least 7, at least 8, at least 9, or at least 10 substrates. Each substrate may be adhered or otherwise affixed to a chuck as described herein. The system may comprise at least 1, at least 2, at least 3, at least 4, at least 5, at least 6, at least 7, at least 8, at least 9, or at least 10 fluid channels and at least 1, at least 2, at least 3, at least 4, at least 5, at least 6, at least 7, at least 8, at least 9, or at least 10 fluid outlet ports. Each fluid channel and fluid outlet port may be configured to dispense a solution as described herein. The system may comprise at least 1, at least 2, at least 3, at least 4, at least 5, at least 6, at least 7, at least 8, at least 9, or at least 10 optical imaging objectives. The moving arm may move so as to place any substrate under any fluid channel, fluid outlet port, or optical imaging objective at any time.

Figure 12H:
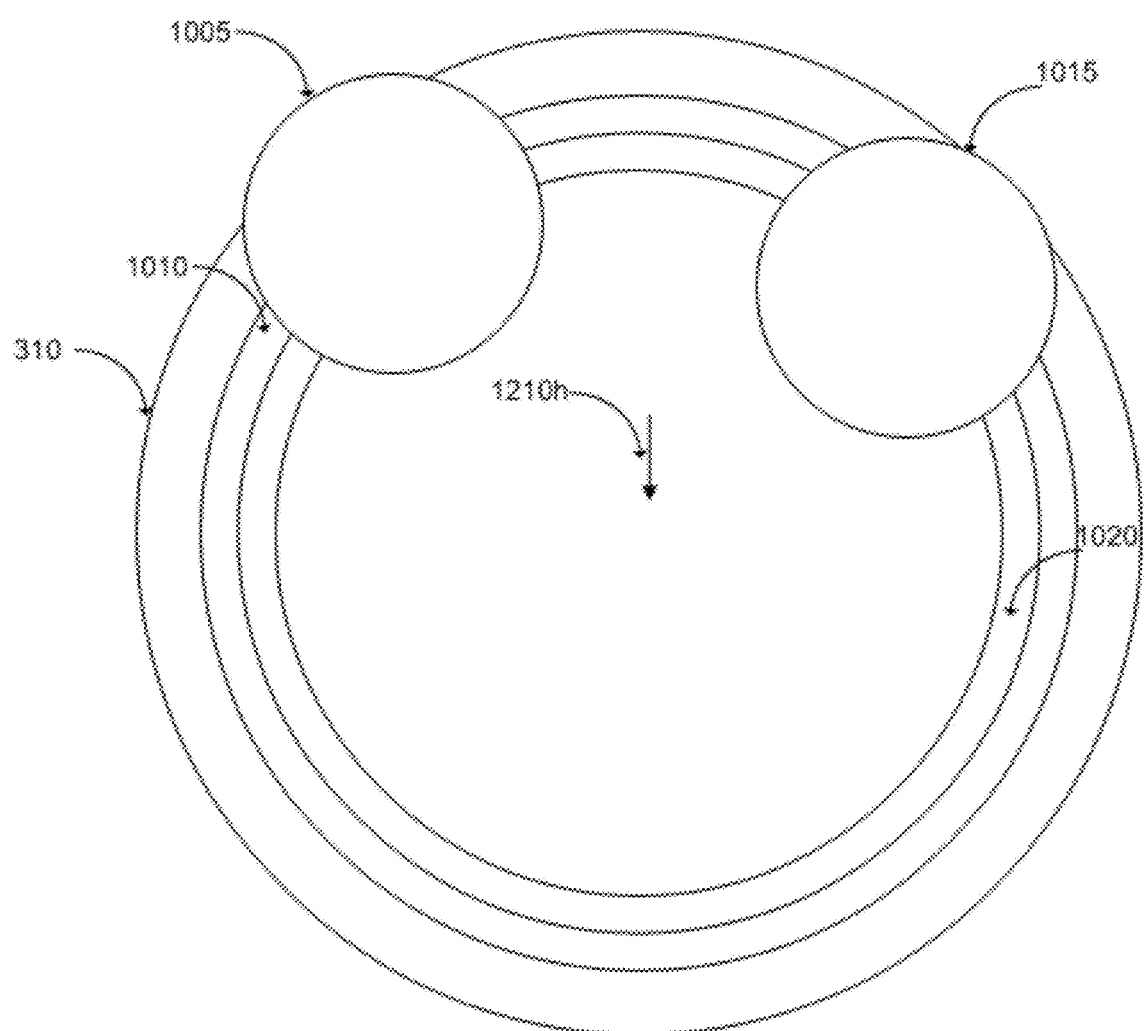
FIG. 12H shows an architecture for a system comprising a plurality of imaging heads scanning with shared translation and rotational axes and independently rotating fields.

FIG. 12H shows an architecture for a system 1200h comprising a plurality of imaging heads scanning with shared translation and rotational axes and independently rotating fields. The system may comprise first and second read heads 1005 and 1015, respectively, configured to image substrate 310. The first and second read heads may be similar to any read head described herein (such as with respect to FIG. 10). At a particular point in time, the first and second read heads may be configured to image first and second paths 1010 and 1020, respectively. The first and second paths may be similar to any paths described herein (such as with respect to FIG. 10). The first and second read heads may be configured to move 1210h in a substantially radial direction over the spinning substrate, thereby scanning the substrate. In the event that either the first or second read head does not move precisely radially, an image field or sensor of the read head may rotate to maintain a substantially tangential scan direction. A field rotation may be accomplished using rotating prisms. Alternatively or in addition, mirrors or other optical elements may be used.

Though depicted as comprising two read heads and two imaging paths in FIG. 12H, system 1200h may comprise any number of read heads or imaging paths. For instance, the system may comprise at least 1, at least 2, at least 3, at least 4, at least 5, at least 6, at least 7, at least 8, at least 9, or at least 10 read heads. The system may comprise at least 1, at least 2, at least 3, at least 4, at least 5, at least 6, at least 7, at least 8, at least 9, or at least 10 imaging paths.

FIG. 12I shows an architecture for a system 1200i comprising multiple spindles scanning with a shared optical detection system. The system may comprise first and second substrates 310a and 310b, respectively. The first and second substrates may be similar to substrate 310 described herein. The first and second substrates may be affixed to first and second spindles, respectively. The first and second spindles may impart rotational motion to the first and second substrates, respectively. The system may comprise first and second optical imaging objectives 1110a and 1110b, respectively. The first and second optical imaging objectives may be similar to optical imaging objective 1110 described herein. The first and second optical imaging objectives may be configured to collect light from the first and second substrates, respectively. The first and second optical imaging objectives may pass light collected from the first and second substrates, respectively, to first and second mirrors 1280a and 1280b, respectively. In some cases, only one of the first and second optical imaging objective will collect light at a particular instance in time.

The first and second mirrors may pass the light to a shared movable mirror. When in a first configuration 1285a, the shared movable mirror may direct light from the first substrate to a beamsplitter 1295. The beamsplitter may comprise a dichroic mirror. The beamsplitter may pass light to a detector 370, allowing the first substrate to be imaged. The first substrate may be configured to be translated 1210i, allowing different locations on the first substrate to be imaged.

When in a second configuration 1285b, the shared movable mirror may direct light from the second substrate to the beamsplitter 1295. The beamsplitter may pass light to a detector 370, allowing the second substrate to be imaged. The second substrate may be configured to be translated 1210i, allowing different locations on the second substrate to be imaged. Thus, by moving the movable mirror, the first and second substrates may be imaged by a shared optical system.

The system may further comprise an excitation light source 1290. The light source may be configured to provide excitation light (such as for fluorescence imaging) to the first or second substrate. The excitation light may be selectively delivered to the first or second substrate using the movable mirror in a similar manner as for detection described herein.

Though depicted as comprising two substrates, two imaging optical objectives, and two mirrors in FIG. 12I, system 1200i may comprise any number of substrates, imaging optical objectives, or mirrors. For instance, the system may comprise at least 1, at least 2, at least 3, at least 4, at least 5, at least 6, at least 7, at least 8, at least 9, or at least 10 substrates. The system may comprise at least 1, at least 2, at least 3, at least 4, at least 5, at least 6, at least 7, at least 8, at least 9, or at least 10 imaging optical objectives. The system may comprise at least 1, at least 2, at least 3, at least 4, at least 5, at least 6, at least 7, at least 8, at least 9, or at least 10 mirrors.

FIG. 12H shows an architecture for a system comprising a plurality of imaging heads scanning with shared translation and rotational axes and independently rotating fields.

FIG. 12I shows an architecture for a system comprising multiple spindles scanning with a shared optical detection system.

FIG. 13 shows an architecture for a system 1300 comprising a plurality of rotating spindles. The system 1300 may comprise substrate 310 described herein. The substrate may be configured to rotate, as described herein. The system may further comprise fluid channel 330 and fluid outlet port 335 described herein, or any other fluid channel and fluid outlet port described herein. The fluid channel and fluid outlet port may be configured to dispense any solution described herein. The fluid channel and fluid outlet port may be configured to move 1315a relative to the substrate. For instance, the fluid channel and fluid outlet port may be configured to move to a position above (such as near the center of) the substrate during periods of time in which the fluid channel and fluid outlet port are dispensing a solution. The fluid channel and fluid outlet port may be configured to move to a position away from the substrate during the period in which the fluid channel and fluid outlet port are not dispensing a solution. The system may further comprise optical imaging objective 1110 described herein. The optical imaging objective may be configured to move 1310a relative for the substrate. For instance, the optical imaging objective may be configured to move to a position above (such as near the center of, or radially scanning) the substrate during periods of time in which the substrate is being imaged. The optical imaging objective may be configured to move to a position away from the substrate during the period in which the substrate is not being imaged.

The system may further comprise a first spindle 1305a and a second spindle 1305b. The first spindle may be interior to the second spindle. The first spindle may be exterior to the second spindle. The second spindle may be interior to the first spindle. The second spindle may be exterior to the first spindle. The first and second spindles may each be configured to rotate independently of each other. The first and second spindles may be configured to rotate with different angular velocities. For instance, the first spindle may be configured to rotate with a first angular velocity and the second spindle may be configured to rotate with a second angular velocity. The first angular velocity may be less than the second angular velocity. The first spindle may be configured to rotate at a relatively low angular velocity (such as an angular velocity between about 0 rpm and about 100 rpm) during periods in which a solution is being dispensed to the substrate. The second spindle may be configured to rotate at a relatively high angular velocity (such as an angular velocity between about 100 rpm and about 1,000 rpm) during periods in which the substrate is being imaged. Alternatively, the reverse may apply. The substrate may be transferred between the first and second spindles to complete each of the dispensing and imaging operations.

The system may comprise any number of spindles. For example, the system may comprise at least about 2, 3, 4, 5, 6, 7, 8, 9, 10, 20, or more spindles. Alternatively or in addition, the system may comprise at most about 20, 10, 9, 8, 7, 6, 5, 4, 3, 2, or 1 spindle. A given spindle may be interior or exterior relative to one or more other spindles in the system. In some instances, each of the spindles may rotate independently of each other. In some instances, at least a subset of the spindles may rotate independently of each other. In some instances, at least a subset of the spindles may rotate dependently of each other (e.g., simultaneously at the same angular velocity). The spindles may rotate with respect to the same axis or different axes. In some instances, each spindle may rotate with different angular velocities. In some instances, at least a subset of the spindles may rotate with different angular velocities.

Though depicted as utilizing a moving fluid channel and optical imaging objective in FIG. 13, the system 1300 may be configured in other manners as described herein. For instance, the system may be configured such that the fluid channel and optical imaging objective are stationary and the substrate is configured to move. The system may be configured in any other manner described herein.

Application to Other Analytes

Though described herein as useful for sequencing nucleic acids, the systems and method described herein may be applied to other analytes and/or other applications processing such analytes. FIG. 14 shows a flowchart for an example of a method 1400 for processing an analyte.

In a first operation 1410, the method may comprise providing a substrate comprising a planar array having immobilized thereto an analyte, wherein the substrate is configured to rotate with respect to an axis. The axis may be an axis through the center of the substrate. The axis may be an off-center axis. The substrate may be any substrate described herein. In some instances, the planar array may comprise a single type of analyte. In other instances, the planar array may comprise two or more types of analytes. The two or more types of analytes may be arranged randomly. The two or more types of analytes may be arranged in a regular pattern. For example, two types of analytes may be arranged in a radially alternating pattern. The analyte may be any biological sample described herein or derivative thereof. For example, the analyte may be a single cell analyte. The analyte may be a nucleic acid molecule. The analyte may be a protein molecule. The analyte may be a single cell. The analyte may be a particle. The analyte may be an organism. The analyte may be part of a colony. In some cases, the analyte may be or be derived from a non-biological sample. The analyte may be immobilized in an individually addressable location on the planar array. The analyte may be immobilized to the substrate via a linker configured to bind to the analyte. For example, the linker may comprise a carbohydrate molecule. The link may comprise an affinity binding protein. The linker may be hydrophilic. The linker may be hydrophobic. The linker may be electrostatic. The linker may be labeled. The linker may be integral to the substrate. The linker may be an independent layer on the substrate.

In a second operation 1420, the method may comprise directing a solution comprising a plurality of adaptors across the planar array during rotation of the substrate. The solution may comprise any solution or reagent described herein. The plurality of adaptors may be configured to interact with the analyte immobilized to the planar array. For example, where the analyte is a nucleic acid molecule, the plurality of adaptors may comprise a plurality of probes. A given probe of the plurality of probes may comprise a random sequence or a targeted sequence, such as a homopolymer sequence or a dibase or tribase repeating sequence. In some instances, the probe may be a dibase probe. In some instances, the probe may be about 1 to 10 bases in length. In some instances, the probe may be about 10 to 20 bases in length. In some instances, the probe may be at least about 1, 2, 3, 4, 5, 6, 7, 8, 9, 10, 11, 12, 13, 14, 15, 16, 17, 18, 19, 20, 30, 40, 50, or more bases. Alternatively or in combination the probe may be at most about 50, 40, 30, 20, 19, 18, 17, 16, 15, 14, 13, 12, 11, 10, 9, 8, 7, 6, 5, 4, 3, 2, 1 base. In another example, where the analyte is a protein molecule, the plurality of adaptors may comprise a plurality of antibodies. A given antibody of the plurality of antibodies may have binding specificity to one or more types of proteins. In other instances, the plurality of adaptors may comprise any combination of a plurality of oligonucleotide molecules, carbohydrate molecules, lipid molecules, affinity binding proteins, aptamers, antibodies, enzymes, or other reagents. The plurality of adaptors may be hydrophilic. The plurality of adaptors may be hydrophobic. The plurality of adaptors may be electrostatic. The plurality of adaptors may be labeled. The plurality of adaptors may comprise a mixture of labeled and unlabeled components. In some instances, the plurality of adaptors may not be labeled.

In an operation 1430, the method may comprise subjecting the analyte to conditions sufficient to cause a reaction between the analyte and the plurality of adaptors. In an operation 1440, the method may comprise detecting a signal indicative of the reaction between the analyte and the plurality of adaptors, thereby analyzing the analyte.

The method may further comprise, prior to operation 1410, directing the analyte across the substrate comprising the linker. For example, prior to or during dispensing of the analyte, the substrate may be rotated to coat the substrate surface and/or the planar array with the analyte. In some instances, the analyte may be coupled to a bead, which bead is immobilized to the planar array.

The method may further comprise recycling, as described elsewhere herein, a subset of the solution that has contacted the substrate. The recycling may comprise collecting, filtering, and reusing the subset of the solution. The filtering may comprise molecular filtering. The molecular filtering may comprise specific nucleic acid filtering (i.e. filtering for a specific nucleic acid). The nucleic acid filtering may comprise exposure of the solution to an array of oligonucleotide extension compounds which may specifically bind to contaminant nucleotides or nucleic acids.

The signal may be an optical signal. The signal may be a fluorescence signal. The signal may be a light absorption signal. The signal may be a light scattering signal. The signal may be a luminescent signal. The signal may be a phosphorescence signal. The signal may be an electrical signal. The signal may be an acoustic signal. The signal may be a magnetic signal. The signal may be any detectable signal. Alternatively or in addition to the optical sensors described herein, the system may comprise one or more other detectors (e.g., acoustic detector, etc.) configured to detect the detectable signal.

In some instances, the method may further comprise, prior to operation 1420, subjecting the substrate to rotation with respect to the central axis.

In some instances, the method may further comprise terminating rotation of the substrate prior to detecting the signal in operation 1440. In other instances, the signal may be detected in operation 1440 while the substrate is rotating.

The signal may be generated by binding of a label to the analyte. The label may be bound to a molecule, particle, cell, or organism. The label may be bound to the molecule, particle, cell, or organism prior to operation 1410. The label may be bound to the molecule, particle, cell, or organism subsequent to operation 1410. The signal may be generated by formation of a detectable product by a chemical reaction. The reaction may comprise an enzymatic reaction. The signal may be generated by formation of a detectable product by physical association. The signal may be generated by formation of a detectable product by proximity association. The proximity association may comprise Förster resonance energy transfer (FRET). The proximity association may comprise association with a complementation enzyme. The signal may be generated by a single reaction. The signal may be generated by a plurality of reactions. The plurality of reactions may occur in series. The plurality of reactions may occur in parallel. The plurality of reactions may comprise one or more repetitions of a reaction. For example, the reaction may comprise a hybridization reaction or ligation reaction. The reaction may comprise a hybridization reaction and a ligation reaction.

The method may further comprise repeating operations 1420, 1430, and 1440 one or more times. Different solutions may be directed to the planar array during rotation of the substrate for consecutive cycles.

Many variations, alterations, and adaptations based on the method 1400 provided herein are possible. For example, the order of the operations of the method 1400 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated. Some of the operations may be manual.

FIG. 15 shows a first example of a system 1500 for isolating an analyte. The system may comprise a plurality of linkers 1510a, 1510b, 1510c, and 1510d. The plurality of linkers may be adhered or otherwise affixed to substrate 310 described herein. For instance, each linker may be bound to a particular individually addressable location of the plurality of individually addressable locations described herein. Linkers 1510a, 1510b, 1510c, and 1510d may comprise any linker described herein. Some or all of linkers 1510a, 1510b, 1510c, and 1510d may be the same. Some or all of linkers 1510a, 1510b, 1510c, and 1510d may be different. The linkers may be configured to interact with analytes 1520a and 1520b. For instance, the linkers may be configured to bind to analytes 1520a and 1520b through any interaction described herein. Analytes 1520a and 1520b may comprise any analyte described herein. Analytes 1520a and 1520b may be the same. Analytes 1520a and 1520b may be different. The linkers may be configured to interact specifically with particular analytes and/or types thereof. For instance, linker 1510b may be configured to interact specifically with analyte 1520a. Linker 1510d may be configured to interact specifically with analyte 1520b. Any linker may be configured to interact with any analyte. In this manner, specific analytes may be bound to specific locations on the substrate. Though shown as comprising four linkers and two analytes in FIG. 15, system 1500 may comprise any number of linkers and analytes. For instance, system 1500 may comprise at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000, 000, at least 5,000,000, at least 10,000,000, at least 20,000, 000, at least 50,000,000, at least 100,000,000, at least 200,000,000, at least 500,000,000, at least 1,000,000,000 linkers, or a number of linkers that is within a range defined by any two of the preceding values. System 1500 may comprise at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, at least 1,000,000,000 analytes, or a number of analytes that is within a range defined by any two of the preceding values.

FIG. 16 shows a second example of a system 1600 for isolating an analyte. The system may comprise a well configured to physically trap a particle. The well may comprise an individually addressable location of the plurality of individually addressable locations described herein. The well may be configured to trap an analyte. For instance, the well may be configured to trap a droplet of blood 1630. For example, the droplet of blood may comprise white blood cells 1640, red blood cells 1650, and circulating tumor cells 1660. The well may be configured to trap any other analyte described herein. The well may be constructed in layers using microfabrication materials and techniques. For instance, the well may comprise a base layer 1605. The base layer may comprise silicon. The well may comprise an oxide layer 1610. The oxide layer may comprise silicon oxide. The well may comprise a metal layer 1615. The metal may comprise nickel or aluminum. The well may comprise a nanotube layer 1620. The nanotube layer may comprise one or more carbon nanotubes. The well may comprise a confinement layer 1625. The confinement layer may comprise a photoresist. The photoresist may comprise SU-8. The nanotube layer and confinement layer may be configured to together trap the cell.

Figure 17:
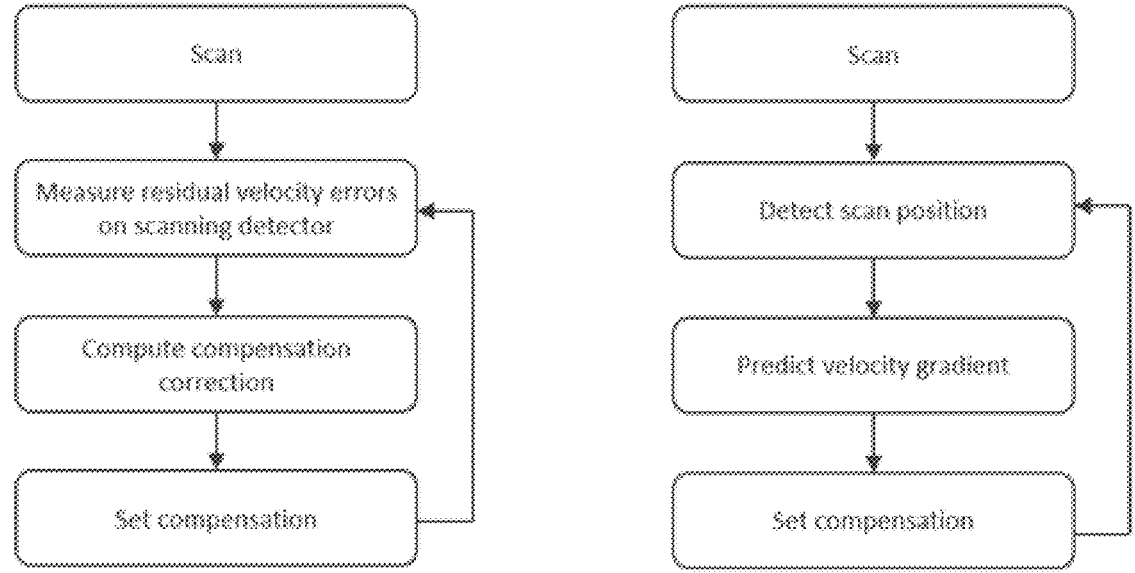
FIG. 17 shows examples of control systems to compensate for velocity gradients during scanning.

FIG. 17 shows examples of control systems to compensate for velocity gradients during scanning. Such control system may algorithmically compensate for velocity gradients. The control system may predictive or adaptively compensate for tangential velocity gradients. In a first control system, illustrated on the left of FIG. 17, the control system may, based on scanning of a rotating substrate, measure residual (uncorrected) velocity errors during scanning, compute a compensation correction factor, and use the compensation correction factor to set (or adjust) a compensation factor to reduce the velocity errors for subsequent scanning results. The first control system may be a closed loop control system that removes (or otherwise reduces) velocity errors.

In a second control system, illustrated on the right of FIG. 17, the control system may, based on knowledge of the geometry and relative position of the scanning relative to the substrate, directly compute (or predict) the expected velocity gradient, and set (or adjust) the system to remove the expected gradient.

Multi-Head Imaging Using a Common Linear Motion

Systems and methods described herein may utilize multiple imaging heads (e.g., detector systems, such detector systems comprising a sensor and an illumination source), with each imaging head responsible for imaging different locations on a substrate described herein. For instance, as described herein, a first imaging head may image the substrate along a first imaging path. The first imaging path may comprise a first series of (one or more) rings, a first series of (one or more) spirals, or a different first imaging path. Second, third, fourth, fifth, sixth, seventh, eighth, ninth, or tenth imaging heads may image the substrate along second, third, fourth, fifth, sixth, seventh, eighth, ninth, or tenth imaging paths. The second, third, fourth, fifth, sixth, seventh, eighth, ninth, or tenth imaging paths may comprise second, third, fourth, fifth, sixth, seventh, eighth, ninth, or tenth series of rings, second, third, fourth, fifth, sixth, seventh, eighth, ninth, or tenth spirals, or different second, third, fourth, fifth, sixth, seventh, eighth, ninth, or tenth imaging paths. An imaging path or scan path may be an imaging path or scan path on the substrate or on the sample.

Such multi-head imaging systems and methods may increase a rate of imaging of the substrate and/or decrease an amount of time that may be required to image the substrate. In some cases, multiple imaging heads may move independently relative to the substrate, such as by independently controlling motions of each of the imaging heads.

As described herein, during detection (e.g., imaging) of a substrate or region thereof, the substrate may be stationary and one or more detector systems or components thereof may be in motion (e.g., rotating). For example, the substrate may be stationary and both a sensor (e.g., line-scan camera) and an illumination source of a detector system may be in motion (e.g., rotating) during detection. Alternatively, the substrate may be in motion (e.g., rotating) and one or more detector systems or components thereof may be stationary. In some cases, the substrate and a detector system or component thereof may be in motion. For example, the substrate may be rotating and a sensor and an illumination source of a detector system may be in motion. For instance, the sensor and illumination source may translate (e.g., radially translate) across the substrate or the sensor and illumination source may remain disposed in a same physical location but may rotate about a central axis of the detector system.

The required motions of the imaging heads may be reduced by moving the substrate relative to each of the imaging heads such that each of the imaging heads shares a single linear motion with respect to the substrate. Such an improvement may be achieved by positioning each scan head at a different initial distance (e.g., radial distance) from a center of the substrate and operating each scan head at a different scan rate which depend on the scan head's initial distance from the center of the substrate. The single shared linear motion may be along a linear vector. For example, the single shared linear motion may result in radial motion (e.g., directed through an axis of rotation) or non-radial motion (e.g., not directed through an axis of rotation) of one or more scan heads. The imaging heads may operate on the same side of the axis of rotation of the substrate or on opposite sides of the axis of rotation of the substrate. In the case of non-radial linear motion of the one or more heads, the scan direction of each imaging head may rotate due to a change in angle relative to the axis of rotation. Such rotations may be compensated by counter-rotating (for instance, using a prism) to allow for a fixed scan direction for each imaging head.

FIG. 18A shows motion of a substrate relative to two imaging heads located on the same side of an axis of rotation of the substrate. The substrate 310 may be any substrate described herein. A first imaging head 1005 may be similar to any first imaging head described herein. A second imaging head 1015 may be similar to any second imaging head described herein. At a first moment in time, the first imaging head 1005 and second imaging head 1015 may be located on the same side of an axis of rotation 305 of the substrate, such that the first imaging head 1005 traces a first imaging path 1010 during rotation of the substrate and the second imaging head 1015 traces a second imaging path 1020 during rotation of the substrate. The substrate may be configured to move in a linear, radial direction 1810 relative to the first and second imaging heads. Thus, the first and second imaging paths may vary in location with respect to the substrate over the course of time.

FIG. 18B shows motion of a substrate relative to two imaging heads located on opposite sides of an axis of rotation of the substrate. In comparison with FIG. 18A, at a first moment in time, the first imaging head 1005 and second imaging head 1015 may be located on opposite sides of an axis of rotation 305 of the substrate, such that the first imaging head 1005 traces a first imaging path 1010 during rotation of the substrate and the second imaging head 1015 traces a second imaging path 1020 during rotation of the substrate. The substrate may be configured to move in a linear, radial direction 1810 relative to the first and second imaging heads. Thus, the first and second imaging paths may vary in location with respect to the substrate over the course of time.

FIG. 18C shows motion of a substrate relative to three imaging heads. A third imaging head 1025 may be similar to any third imaging head described herein. At a first moment in time, the first imaging head 1005 may be located on one side of an axis of rotation 305 of the substrate, and the second imaging head 1015 and third imaging head 1025 may be located on the opposite side of the axis of rotation of the substrate, such that the first imaging head 1005 traces a first imaging path 1010 during rotation of the substrate, the second imaging head 1015 traces a second imaging path 1020 during rotation of the substrate, and the third imaging head 1025 traces a third imaging path 1030 during rotation of the substrate. The substrate may be configured to move in a linear, radial direction 1810 relative to the first, second, and third imaging heads. Thus, the first, second, and third imaging paths may vary in location with respect to the substrate over the course of time.

FIG. 18D shows motion of a substrate relative to four imaging heads. A fourth imaging head 1035 may be similar to any fourth imaging head described herein. At a first moment in time, the first imaging head 1005 and the fourth imaging head 1035 may be located on one side of an axis of rotation 305 of the substrate, and the second imaging head 1015 and third imaging head 1025 may be located on the opposite side of the axis of rotation of the substrate, such that the first imaging head 1005 traces a first imaging path 1010 during rotation of the substrate, the second imaging head 1015 traces a second imaging path 1020 during rotation of the substrate, the third imaging head 1025 traces a third imaging path 1030, and the fourth imaging head 1025 traces a fourth imaging path 1030 during rotation of the substrate. The substrate may be configured to move in a linear, radial direction 1810 relative to the first, second, third, and fourth imaging heads. Thus, the first, second, third, and fourth imaging paths may vary in location with respect to the substrate over the course of time.

FIG. 19A shows successive ring paths of two imaging heads located on the same side of an axis of rotation of a substrate. At a first moment in time, the first imaging head (not depicted in FIG. 19A) and second imaging head (not depicted in FIG. 19A) may be located on the same side of an axis of rotation 305 of the substrate 310, such that the first imaging head traces a first imaging path 1010*a* at a first time point during rotation of the substrate and the second imaging head traces a second imaging path 1020*a* at the first time point during rotation of the substrate. For example, the two imaging heads may be located and configured as in FIG. 18A. As the substrate moves in a linear, radial direction 1810 relative to the first and second imaging heads, the first and second imaging heads may trace a series of imaging paths during rotation of the substrate. For instance, if the first and second imaging heads are located on the same side of the axis of rotation of the substrate, the first imaging head may trace imaging path 1010*b* at a second time point, imaging path 1010*c* at a third time point, and imaging path 1010*d* at a fourth time point while the second imaging path may trace imaging path 1020*b* at the second time point, imaging path 1020*c* at the third time point, and imaging path 1020*d* at the fourth time point. When the first and second imaging heads are located on the same side of the axis of rotation, the succession of imaging paths {1010*a*, 1010*b*, 1010*c*, 1010*d*} and {1020*a*, 1020*b*, 1020*c*, 1020*d*} may proceed in the same direction with respect to the substrate. For instance, as depicted in FIG. 19A, the succession of imaging paths {1010*a*, 1010*b*, 1010*c*, 1010*d*} and {1020*a*, 1020*b*, 1020*c*, 1020*d*} may both proceed in a direction toward the center of the substrate.

FIG. 19B shows successive ring paths of two imaging heads located on opposite sides of an axis of rotation of a substrate. In comparison with FIG. 19A, at a first moment in time, the first imaging head (not depicted in FIG. 19B) and second imaging head (not depicted in FIG. 19B) may be located on opposite sides of an axis of rotation 305 of the substrate, such that the first imaging head traces a first imaging path 1010*a* at a first time point during rotation of the substrate and the second imaging head traces a second imaging path 1020*a* at the first time point during rotation of the substrate. For example, the two imaging heads may be located and configured as in FIG. 18B. As the substrate moves in a linear, radial direction 1810 relative to the first and second imaging heads, one of the heads moves towards the central axis and the other head moves away from the central axis, the first and second imaging heads each tracing a series of imaging paths during rotation of the substrate. For instance, if the first and second imaging heads are located on opposite sides of the axis of rotation of the substrate, the first imaging head may trace imaging path 1010*b* at a second time point, imaging path 1010*c* at a third time point, and imaging path 1010*d* at a fourth time point while the second imaging path may trace imaging path 1020*b* at the second time point, imaging path 1020*c* at the third time point, and imaging path 1020*d* at the fourth time point. When the first and second imaging heads are located on the opposite sides of the axis of rotation, the succession of imaging paths {1010*a*, 1010*b*, 1010*c*, 1010*d*} and {1020*a*, 1020*b*, 1020*c*, 1020*d*} may proceed in opposite directions with respect to the substrate. For instance, as depicted in FIG. 19B, the succession of imaging paths {1010*a*, 1010*b*, 1010*c*, 1010*d*} may proceed in a direction toward the center of the substrate while the succession of imaging paths {1020*a*, 1020*b*, 1020*c*, 1020*d*} may proceed in a direction away from the center of the substrate.

FIG. 19C shows staggered ring paths of two imaging heads located on the same side of an axis of rotation of a substrate. At a first moment in time, the first imaging head (not depicted in FIG. 19C) and second imaging head (not depicted in FIG. 19C) may be located on the same side of an axis of rotation 305 of the substrate 310, such that the first imaging head traces a first imaging path 1010*a* at a first time point during rotation of the substrate and the second imaging head traces a second imaging path 1020*a* at the first time point during rotation of the substrate. As the substrate moves in a linear, radial direction 1810 relative to the first and second imaging heads, the first and second imaging heads may trace a series of imaging paths during rotation of the substrate. For instance, if the first and second imaging heads are located on the same side of the axis of rotation of the substrate, the first imaging head may trace imaging path 1010*b* at a second time point, imaging path 1010*c* at a third time point, and imaging path 1010*d* at a fourth time point while the second imaging path may trace imaging path 1020*b* at the second time point, imaging path 1020*c* at the third time point, and imaging path 1020*d* at the fourth time point. The succession of imaging paths {1010*a*, 1010*b*, 1010*c*, 1010*d*} and {1020*a*, 1020*b*, 1020*c*, 1020*d*} may be staggered, such that successive imaging paths toward or away from the center of the substrate are traced by alternating imaging heads. When the first and second imaging heads are located on the same side of the axis of rotation, the succession of imaging paths {1010*a*, 1010*b*, 1010*c*, 1010*d*} and {1020*a*, 1020*b*, 1020*c*, 1020*d*} may proceed in the same direction with respect to the substrate. For instance, as depicted in FIG. 19C, the succession of imaging paths {1010*a*, 1010*b*, 1010*c*, 1010*d*} and {1020*a*, 1020*b*, 1020*c*, 1020*d*} may both proceed in a direction toward the center of the substrate.

FIG. 19D shows staggered ring paths of two imaging heads located on opposite sides of an axis of rotation of a substrate. At a first moment in time, the first imaging head (not depicted in FIG. 19D) and second imaging head (not depicted in FIG. 19D) may be located on opposite sides of an axis of rotation 305 of the substrate 310, such that the first imaging head traces a first imaging path 1010*a* at a first time point during rotation of the substrate and the second imaging head traces a second imaging path 1020*a* at the first time point during rotation of the substrate. As the substrate moves in a linear, radial direction 1810 relative to the first and second imaging heads, one of the heads moves towards the central axis and the other head moves away from the central axis, the first and second imaging heads each tracing a series of imaging paths during rotation of the substrate. For instance, if the first and second imaging heads are located on opposite sides of the axis of rotation of the substrate, the first imaging head may trace imaging path 1010*b* at a second time point, imaging path 1010*c* at a third time point, and imaging path 1010*d* at a fourth time point while the second imaging path may trace imaging path 1020*b* at the second time point, imaging path 1020*c* at the third time point, and imaging path 1020*d* at the fourth time point. The succession of imaging paths {1010*a*, 1010*b*, 1010*c*, 1010*d*} and {1020*a*, 1020*b*, 1020*c*, 1020*d*} may be staggered, such that successive imaging paths toward or away from the center of the substrate are traced by alternating imaging heads. When the first and second imaging heads are located on the opposite sides of the axis of rotation, the succession of imaging paths {1010a, 1010b, 1010c, 1010d} and {1020a, 1020b, 1020c, 1020d} may proceed in opposite directions with respect to the substrate. For instance, as depicted in FIG. 19D, the succession of imaging paths {1010a, 1010b, 1010c, 1010d} may proceed in a direction toward the center of the substrate while the succession of imaging paths {1020a, 1020b, 1020c, 1020d} may proceed in a direction away from the center of the substrate.

FIG. 20 shows rotating scan directions of an imaging head due to non-radial motion of the head relative to a substrate. For example, the head may be moving along direction 316 relative to the substrate, which is not through the central axis. At a first point in time, the first imaging head (not depicted in FIG. 20) or second imaging head (not depicted in FIG. 20) may be located off-axis from a longitudinal axis 315 of the substrate 310. In such a case, the first or second imaging head may have a tangential velocity relative to the substrate that changes in direction as the substrate moves with respect to the first or second imaging head. For instance, as depicted in FIG. 20, the second imaging head may have a tangential velocity vector 2020a relative to the substrate while tracing the imaging path 1020a and a tangential velocity vector 2020b relative to the substrate while tracing the imaging path 1020c. As shown in FIG. 20, the tangential velocity vectors 2020a and 2020b may point in substantially different directions. Such an effect may be manifested as a rotation of the imaging field as the first imaging head traces the succession of imaging paths {1010a, 1010b, 1010c, 1010d} or as the second imaging head traces the succession of imaging paths {1020a, 1020b, 1020c, 1020d}.

Such a rotation of the imaging field may be compensated by counter-rotating the imaging field. For instance, the imaging field may be counter-rotated using a prism system, such as a delta rotator prism, a Schmidt rotator, or a Dove prism. Alternatively or in addition, the compensation may be achieved by using one or more mirrors or other optical elements (e.g., beamsplitter (e.g., dichroic mirror)), as described herein. Alternatively or in addition, the compensation may be achieved by rotating one or more sensors in the optical head(s).

FIG. 21 shows a flowchart for an example of a method 2100 for analyte detection or analysis. In a first operation 2110, the method 2100 may comprise rotating an open substrate about a central axis, the open substrate having an array of immobilized analytes thereon.

In a second operation 2120, the method 2100 may comprise delivering a solution having a plurality of probes to a region proximal to the central axis to introduce the solution to the open substrate.

In a third operation 2130, the method 2100 may comprise dispersing the solution across the open substrate (for instance, at least by centrifugal force) such that at least one of the plurality of probes binds to at least one of the immobilized analytes to form a bound probe.

In a fourth operation 2140, the method 2100 may comprise, during rotation of the open substrate, simultaneously using a first detector to perform a first scan of the open substrate along a first set of one or more scan paths and a second detector to perform a second scan of the open substrate along a second set of one or more scan paths. The first set of one or more scan paths and the second set of one or more scan paths may be different. The first detector or the second detector may detect at least one signal from the bound probe. The first detector may be disposed at a first radial position relative to the central axis. The second detector is disposed at a second radial position relative to the central axis. The first detector and the second detector may undergo relative motion with respect to the central axis along a same linear vector, to generate the first set of one or more scan paths and the second set of one or more scan paths, respectively.

The first detector and the second detector may operate at different scan rates. For instance, the different scan rates of the first detector and the second detector may be a function of the first radial position and the second radial position, respectively. Alternatively, the detectors may operate at a fixed line rate. For example, algorithmic processing may resolve oversampling of the optical head located in the inner radial positions.

The first set of one or more scan paths may comprise one or more circular scan paths having different radii. For instance, the first set of one or more scan paths may comprise at least about 1, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, or more circular scan paths, at most about 100, at most about 90, at most about 80, at most about 70, at most about 60, at most about 50, at most about 40, at most about 30, at most about 20, at most about 10, at most about 9, at most about 8, at most about 7, at most about 6, at most about 5, at most about 4, at most about 3, at most about 2, or at most about 1 circular scan paths, or a number of circular scan paths that is within a range defined by any two of the preceding values.

The second set of one or more scan paths may comprise one or more circular scan paths having different radii. For instance, the second set of one or more scan paths may comprise at least about 1, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, or more circular scan paths, at most about 100, at most about 90, at most about 80, at most about 70, at most about 60, at most about 50, at most about 40, at most about 30, at most about 20, at most about 10, at most about 9, at most about 8, at most about 7, at most about 6, at most about 5, at most about 4, at most about 3, at most about 2, or at most about 1 circular scan paths, or a number of circular scan paths that is within a range defined by any two of the preceding values.

The first set of one or more scan paths may comprise one or more spiral scan paths. For instance, the first set of one or more scan paths may comprise at least about 1, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, or more spiral scan paths, at most about 100, at most about 90, at most about 80, at most about 70, at most about 60, at most about 50, at most about 40, at most about 30, at most about 20, at most about 10, at most about 9, at most about 8, at most about 7, at most about 6, at most about 5, at most about 4, at most about 3, at most about 2, or at most about 1 spiral scan paths, or a number of spiral scan paths that is within a range defined by any two of the preceding values.

The second set of one or more scan paths may comprise one or more spiral scan paths. For instance, the second set of one or more scan paths may comprise at least about 1, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, or more spiral scan paths, at most about 100, at most about 90, at most about 80, at most about 70, at most about 60, at most about 50, at most about 40, at most about 30, at most about 20, at most about 10, at most about 9, at most about 8, at most about 7, at most about 6, at most about 5, at most about 4, at most about 3, at most about 2, or at most about 1 spiral scan paths, or a number of spiral scan paths that is within a range defined by any two of the preceding values.

The same linear vector may be in a radial direction through the central axis. The same linear vector may not be in a radial direction (e.g., not through the central axis). The method may further comprise compensating for velocity differences (such as tangential velocity differences, as described herein with respect to FIG. 20) of different areas at different radial positions with respect to the central axis. A given scan path of the first set of one or more scan paths may comprise the different areas. A given scan path of the second set of one or more scan paths may comprise the different areas. The compensating may comprise using one or more prisms, such as one or more delta rotator prisms, Schmidt rotators, or Dove prisms.

The first detector and the second detector may be substantially stationary during the relative motion. The open substrate may undergo both rotational and translation motion during the relative motion. The first detector and the second detector may undergo motion during the relative motion. The open substrate may undergo rotational motion relative to the first detector and the second detector and the first detector and second detector may undergo linear motion relative to the central axis. The first detector may undergo the relative motion during rotation of the open substrate. The second detector may undergo the relative motion during rotation of the open substrate. The first detector may undergo the relative motion when the open substrate is substantially stationary. The second detector may undergo the relative motion when the open substrate is substantially stationary.

A given scan path of the first set of one or more scan paths may include an area scanned during the relative motion. A given scan path of the second set of one or more scan paths may include an area scanned during the relative motion. A given scan path of the first set of one or more scan paths may not include an area scanned during the relative motion. A given scan path of the second set of one or more scan paths may not include an area scanned during the relative motion.

The first detector and the second detector may have the same angular position relative to the central axis. The first detector and the second detector may have different angular positions relative to the central axis. The first detector and second detector may have opposite angular positions (e.g., having 180 degrees separation) relative to the central axis.

The first detector may have an angular position of at least about 1 degree, at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 81 degrees, at least about 82 degrees, at least about 83 degrees, at least about 84 degrees, at least about 85 degrees, at least about 86 degrees, at least about 87 degrees, at least about 88 degrees, at least about 89 degrees, or more relative to the central axis, at most about 89 degrees, at most about 88 degrees, at most about 87 degrees, at most about 86 degrees, at most about 85 degrees, at most about 84 degrees, at most about 83 degrees, at most about 82 degrees, at most about 81 degrees, at most about 80 degrees, at most about 75 degrees, at most about 70 degrees, at most about 65 degrees, at most about 60 degrees, at most about 55 degrees, at most about 50 degrees, at most about 45 degrees, at most about 40 degrees, at most about 35 degrees, at most about 30 degrees, at most about 25 degrees, at most about 20 degrees, at most about 15 degrees, at most about 10 degrees, at most about 9 degrees, at most about 8 degrees, at most about 7 degrees, at most about 6 degrees, at most about 5 degrees, at most about 4 degrees, at most about 3 degrees, at most about 2 degrees, at most about 1 degree, or less relative to the central axis, or an angular position relative to the central axis that is within a range defined by any two of the preceding values.

The second detector may have an angular position of at least about 1 degree, at least about 2 degrees, at least about 3 degrees, at least about 4 degrees, at least about 5 degrees, at least about 6 degrees, at least about 7 degrees, at least about 8 degrees, at least about 9 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 81 degrees, at least about 82 degrees, at least about 83 degrees, at least about 84 degrees, at least about 85 degrees, at least about 86 degrees, at least about 87 degrees, at least about 88 degrees, at least about 89 degrees, or more relative to the central axis, at most about 89 degrees, at most about 88 degrees, at most about 87 degrees, at most about 86 degrees, at most about 85 degrees, at most about 84 degrees, at most about 83 degrees, at most about 82 degrees, at most about 81 degrees, at most about 80 degrees, at most about 75 degrees, at most about 70 degrees, at most about 65 degrees, at most about 60 degrees, at most about 55 degrees, at most about 50 degrees, at most about 45 degrees, at most about 40 degrees, at most about 35 degrees, at most about 30 degrees, at most about 25 degrees, at most about 20 degrees, at most about 15 degrees, at most about 10 degrees, at most about 9 degrees, at most about 8 degrees, at most about 7 degrees, at most about 6 degrees, at most about 5 degrees, at most about 4 degrees, at most about 3 degrees, at most about 2 degrees, at most about 1 degree, or less relative to the central axis, or an angular position relative to the central axis that is within a range defined by any two of the preceding values.

A given scan path of the first set of one or more scan paths may include a first area and a second area. The first area and second area may be at different radial positions of the open substrate with respect to the central axis. The first area and second area may be spatially resolved by the first detector. A given scan path of the second set of one or more scan paths may include a first area and a second area. The first area and second area may be at different radial positions of the open substrate with respect to the central axis. The first area and second area may be spatially resolved by the second detector.

Reel-to-Reel Processing of Biological Analytes

In some instances, an open substrate system of the present disclosure may comprise a substantially flexible substrate. For example, the substantially flexible substrate may comprise a film. The substantially flexible substrate may have any degree of deformability. In some instances, an open substrate system of the present disclosure may achieve dispensing via contact with a reagent reservoir or bath. In some instances, a substantially flexible substrate may be used with a reagent reservoir or bath. In some instances, a substantially rigid substrate may be used with a reagent reservoir or bath. In some instances, a substantially flexible substrate may be used with other dispensing mechanisms (e.g., nozzles) described herein. In some instances, a substantially rigid substrate may be used with other dispensing mechanisms (e.g., nozzles) described herein.

In an aspect, provided herein are methods for processing a biological analyte, comprising (a) providing a flexible substrate comprising an array having immobilized thereto the biological analyte, wherein the flexible substrate is able to be moved through a reel; (b) bringing the flexible substrate in contact with a reservoir comprising a solution that comprises a plurality of probes; (c) subjecting the biological analyte to conditions sufficient to conduct a reaction between at least one probe of the plurality of probes and the biological analyte, to couple the at least one probe to the biological analyte; and (d) detecting one or more signals from the at least one probe coupled to the biological analyte, thereby analyzing the biological analyte.

In some embodiments, the method further comprises using a recirculation tank.

In some cases, a dimension of the flexible substrate is the width of a field of view of the imaging method.

In some embodiments, the process of bringing the flexible substrate in contact with a reservoir and/or the process of subjecting the biological analyte to conditions sufficient to conduct a reaction is performed while the flexible substrate is moved through the reel.

In some embodiments, the flexible substrate is moved through a reel to contact the solution with the biological analyte. In some embodiments, the flexible substrate is further moved through a second reel to bring the flexible substrate in contact with a second reservoir comprising a second solution. In some cases the second solution comprises a wash buffer. In some cases, the second solution comprises a plurality of probes, wherein the solution and the second solution are different.

In some embodiments, the processes of bringing the flexible substrate in contact with the reservoir, subjecting the biological analyte to conditions sufficient to conduct the reaction, and detecting may be repeated any number of times, for example, a number of times sufficient to complete an assay (e.g., determining a sequence of a nucleic acid molecule).

In some embodiments, the method further comprises repeating the processes of bringing the flexible substrate in contact with the reservoir, subjecting the biological analyte to conditions sufficient to conduct the reaction, and detecting with an additional plurality of probes that is different than the plurality of probes. In some cases, the plurality of probes can comprise any probe described elsewhere herein. For example, the probe may comprise an oligonucleotide molecule having any length. For example, the probe may comprise oligonucleotides 1 to 10 bases in length. A given probe may be a dibase probe. A given probe may be between 10 to 20 bases in length. In some instances, the plurality of probes may be labeled.

In some embodiments, the biological analyte is a nucleic acid molecule, and analyzing the biological analyte comprises identifying a sequence of the nucleic acid molecule. In some embodiments, the plurality of probes is a plurality of nucleotides. In some embodiments, the plurality of probes is a plurality of oligonucleotide molecules. In some cases, subjecting the biological analyte to the conditions sufficient to conduct the reaction comprises subjecting the nucleic acid molecule to a primer extension reaction under conditions sufficient to incorporate at least one nucleotide from the plurality of nucleotides into a growing strand that is complementary to the nucleic acid molecule. In some embodiments, the one or more signals are indicative of incorporation of at least one nucleotide. In some embodiments, the plurality of nucleotides comprises nucleotide analogs. In some embodiments, the method further comprises repeating the processes of bringing the flexible substrate in contact with a reservoir and subjecting the biological analyte to conditions sufficient to conduct a reaction with an additional plurality of nucleotides that are of a second canonical base type, wherein the second canonical base type is different than the first canonical base type. In some embodiments, the plurality of probes is a plurality of oligonucleotide molecules. In some embodiments, the biological analyte is a nucleic acid molecule, and the subjecting comprises conducting a complementarity binding reaction between the at least one probe and the nucleic acid molecule to identify a presence of homology between the at least one probe and the biological analyte in the detection.

In some embodiments, the detecting is conducted using a sensor that continuously scans the array. In some embodiments, the detecting is conducted using a sensor that scans the array linearly. In some cases, the detecting is conducted using any sensor or sensing mechanism described herein.

In some embodiments, the method further comprises using a pulling mechanism to move the flexible substrate through the reel and into contact with the reservoir, thereby dispensing the solution on the flexible substrate. Any other motion units or mechanisms may be used to actuate the flexible substrate.

In some embodiments, the fluid viscosity of the solution or a velocity of the flexible substrate is selected to yield a predetermined thickness of a layer of the solution adjacent to the array. In some embodiments a squeegee near the substrate may be used to yield a predetermined thickness of a layer. In some embodiments, the flexible substrate is textured or patterned. In some embodiments the flexible substrate is substantially planar.

In some embodiments, the flexible substrate comprises an array which comprises a plurality of individually addressable locations, and wherein the biological analyte is disposed at a given individually addressable location of the plurality of individually addressable locations. In some embodiments, the array has immobilized thereto one or more additional biological analytes.

In some embodiments, bringing the flexible substrate in contact with the reservoir comprises achieving contact at an area of contact between the flexible substrate and the reservoir. In some embodiments, bringing the flexible substrate in contact with the reservoir comprises achieving contact along a line of contact between the substrate and the reservoir.

In some cases, the biological analyte can comprise any analyte described elsewhere herein. The analyte may be a single cell analyte. The analyte may be a nucleic acid molecule or clonal population of nucleic acids. The analyte may be a protein molecule. The analyte may be a single cell.

The analyte may be a particle. The analyte may be an organism. The analyte may be part of a colony. The analyte may be immobilized in an individually addressable location on the planar array. The array on the flexible substrate may comprise two or more types of analytes. The two or more types of analytes may be arranged randomly. The two or more types of analytes may be arranged in a regular pattern.

In some instances, the analyte can be immobilized to the flexible substrate via a linker. The flexible substrate may comprise the linker that is coupled to the analyte. The linker can be any linker described herein. The linker may comprise a carbohydrate molecule. The linker may comprise an affinity binding protein. The linker may be hydrophilic. The linker may be hydrophobic. The linker may be electrostatic. The linker may be labeled. The linker may be integral to the substrate. The linker may be an independent layer on the substrate. In some embodiments, the biological analyte is coupled to a bead, which bead is immobilized to the flexible substrate. The method may further comprise, prior to providing the flexible substrate, directing the biological analyte across the flexible substrate comprising the linker. The biological analyte may be coupled to a bead, which bead is immobilized to the substrate. In some instances, for example, the flexible substrate comprising the linker may be brought into contact with a reservoir comprising a solution comprising the biological analyte. Alternatively or in addition, the biological analyte may be dispensed onto the flexible substrate in accordance with any other dispensing mechanism described herein.

The method may further comprise recycling a subset of the solution that has contacted the substrate. The recycling may comprise collecting, filtering, and reusing the subset of the solution. The filtering may be molecular filtering. For example, the solution in the reservoir (after the substrate has passed through) may be recycled.

The signal may be an optical signal. The signal may be a fluorescence signal. The signal may be a light absorption signal. The signal may be a light scattering signal. The signal may be a luminescent signal. The signal may be a phosphorescence signal. The signal may be an electrical signal. The signal may be an acoustic signal. The signal may be a magnetic signal. The signal may be generated by binding of a label to the analyte. The label may be bound to a molecule, particle, cell, or organism. The label may be bound to the analyte (e.g., molecule, particle, cell, or organism) prior to deposition on the substrate. The label may be bound to the analyte subsequent to deposition on the substrate. The signal may be generated by formation of a detectable product by a chemical reaction. The reaction may comprise an enzymatic reaction. The signal may be generated by formation of a detectable product by physical association. The signal may be generated by formation of a detectable product by proximity association. The proximity association may comprise Förster resonance energy transfer (FRET). The proximity association may comprise association with a complementation enzyme. The signal may be generated by a single reaction. The signal may be generated by a plurality of reactions. The plurality of reactions may occur in series. The plurality of reactions may occur in parallel. The plurality of reactions may comprise one or more repetitions of a reaction. The reaction may comprise a hybridization reaction or ligation reaction. The reaction may comprise a hybridization reaction and a ligation reaction.

One or more processes of the methods described herein may be repeated in a continuous fashion. One or more methods described herein may offer higher efficiency in reagent usage. One or more methods described herein may allow for detection of one or more signals at multiple locations along the array contemporaneously. In some cases, throughput may be altered by changing the dimensions of the flexible substrate. For example, the flexible substrate may be a rectangular film, wherein a wider film allows for increased throughput. In another example, the length of the reel may be changed to match the detection method.

Figure 27:
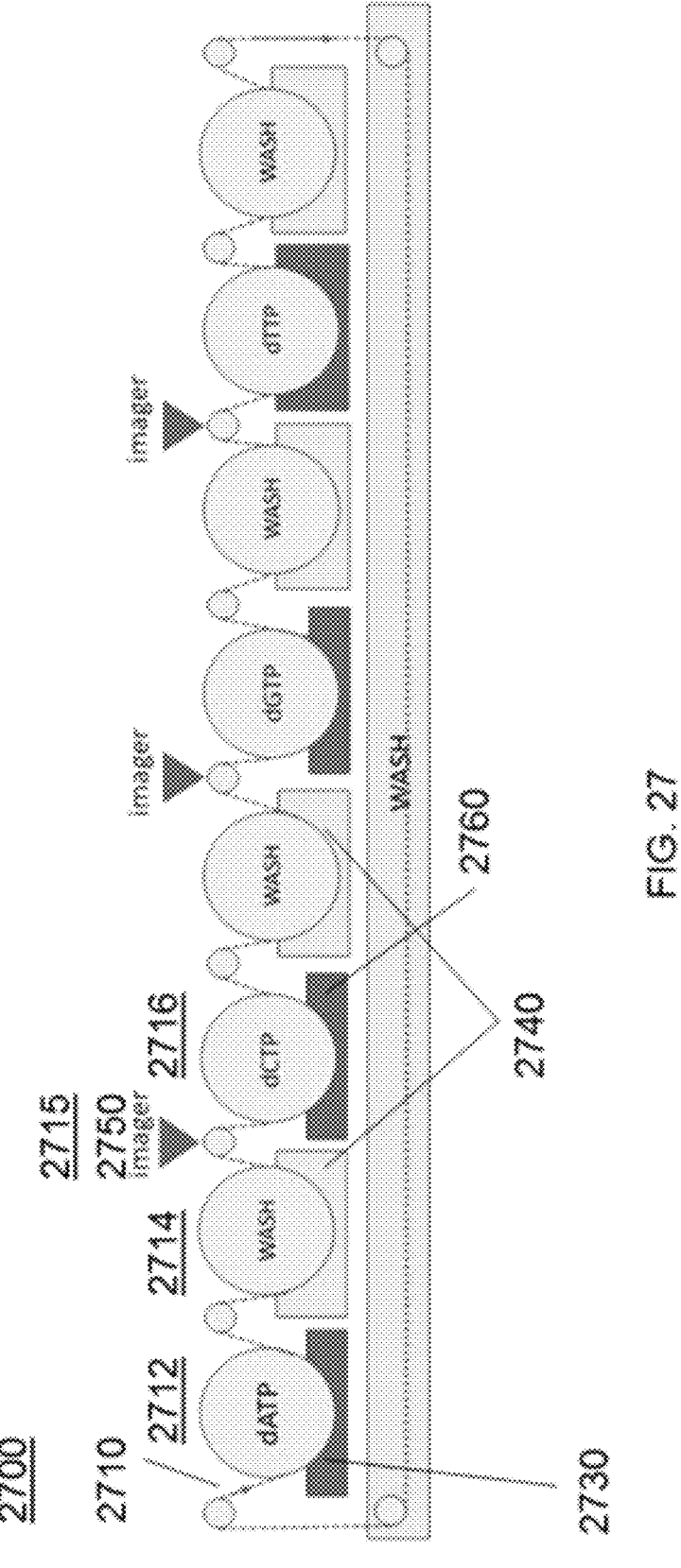
FIG. 27 illustrates schematically a method for processing a biological analyte.

FIG. 27 schematically illustrates a method for processing a biological analyte. A flexible substrate such as a film 2710 has immobilized thereto the biological analyte. In some cases, the biological analyte is immobilized to the film in an arrayed pattern in individually addressable locations. In other embodiments, the biological analyte is immobilized to the film in a random orientation. The film 2710 comprising the biological analyte immobilized thereto is capable of being moved through a reel or a series of reels. In process 2712, the film 2710 comprising the biological analyte immobilized thereto is moved through a reel and brought into contact with a reservoir 2730 comprising a plurality of probes, such as a plurality of labeled probes. In some cases, the labeled probe is a fluorescently labeled nucleotide. The labeled probes may couple to a subset of the individually addressable locations comprising the biological analyte, e.g., based on sequence complementarity. In process 2714, the film is then moved through a second reel and brought into contact with a reservoir 2740 comprising a wash buffer. The wash buffer may allow for removal of uncoupled probes, such as probes that are unbound or unhybridized to the film. Detection of one or more signals from the at least one probe coupled to the biological analyte may be performed. In process 2715, detection can occur using a sensor, such as an imager 2750, in which an image of the film is taken. In some cases, the field of view of the image is one of the dimensions (e.g., the width) of the film. In process 2716, the film 2710 is moved through a third reel and brought into contact with a reservoir 2760 comprising a plurality of probes, such as a plurality of labeled probes. The labeled probes in reservoir 2760 may be different than the labeled probes in reservoir 2730. As in process 2712, the labeled probes in reservoir 2760 may couple to a subset of the individually addressable locations comprising the biological analyte e.g., based on sequence complementarity. Processes 2714, 2715 may then be repeated. In some cases, one or more processes may be performed iteratively.

In some cases, the biological analyte is a nucleic acid molecule or clonal population of nucleic acid molecules, and the film 2710 is moved through a first reel to contact the film with a first reservoir comprising a plurality of adenine (e.g., fluorescently labeled adenine) molecules. The adenine molecules may then hybridize with a thymine molecule within the biological analyte. The film may then be moved through the reel to contact the film with a wash reservoir to remove unhybridized probes. Detection of the hybridized molecules may occur. Since the sequence of the probe molecule is known, detection of one or more signals may yield knowledge of the sequence of the biological analyte. Subsequently, the film may then be brought into contact with a reservoir comprising a labeled cytosine, a labeled guanine, or a labeled thymine, etc. Again, as each sequence of the probe is known, detection of one or more signals may yield knowledge of the sequence of the biological analyte. As will be appreciated, the specific nucleotide added to each reservoir can vary; e.g., the first reservoir may comprise an adenine, cytosine, guanine, thymine, etc, and the next reservoir may comprise an adenine, cytosine, guanine, thymine, etc.

As will be appreciated, any of the processes within the method described herein may occur at any convenient step. For example, the flexible substrate may first be brought into contact with a first reservoir, followed by a wash reservoir, followed by a second reservoir, prior to detection. In other examples, the flexible substrate may be brought into contact with a plurality of reservoirs comprising probes prior to detection. In other examples, the flexible substrate may be brought into contact with a detector prior to or following contacting the flexible substrate with any number of reservoirs. Additionally, any number of reels may be used. For example, it may be desirable to use a single reel for an operation. In some cases, more than one reel may be used. For example, 2, 3, 4, 5, 6, 7, 8, 9, 10, 20, 30, 40, 50, 60, 70, 80, 90, 100, 200, 300, 400, 500, 600, 700, 800, 900, 1000 or more reels may be used.

In some cases, the detection method may comprise multi-channel imaging.

Immersion Optics

Disclosed herein, in certain embodiments, are systems for using optical sensors, such as optical imaging objectives. The present disclosure provides systems for modulation and management of temperature for one or more systems or methods of the disclosure. In some embodiments of one or more systems and methods described herein, an optical imaging objective is used during the detection method. In some cases, the optical imaging objective is immersed in a fluid in contact with the substrate, and the optical imaging objective is in optical communication with the detector. In some embodiments, the substrate performs optimally at a non-ambient temperature (e.g., ~50 degrees Celsius). In some cases, the optical imaging objective may be close to ambient temperature. In such cases, a substrate that is operating at a higher temperature (e.g., ~50 degree Celsius) may be in contact with the objective that operates at ambient temperature (~20 degrees Celsius), thereby generating a temperature gradient between the substrate and the optical imaging objective. In some cases, it may be desirable to control the temperature gradient location and the magnitude of the temperature gradient. Thus, provided herein are methods and systems for temperature modulation.

Figure 28:
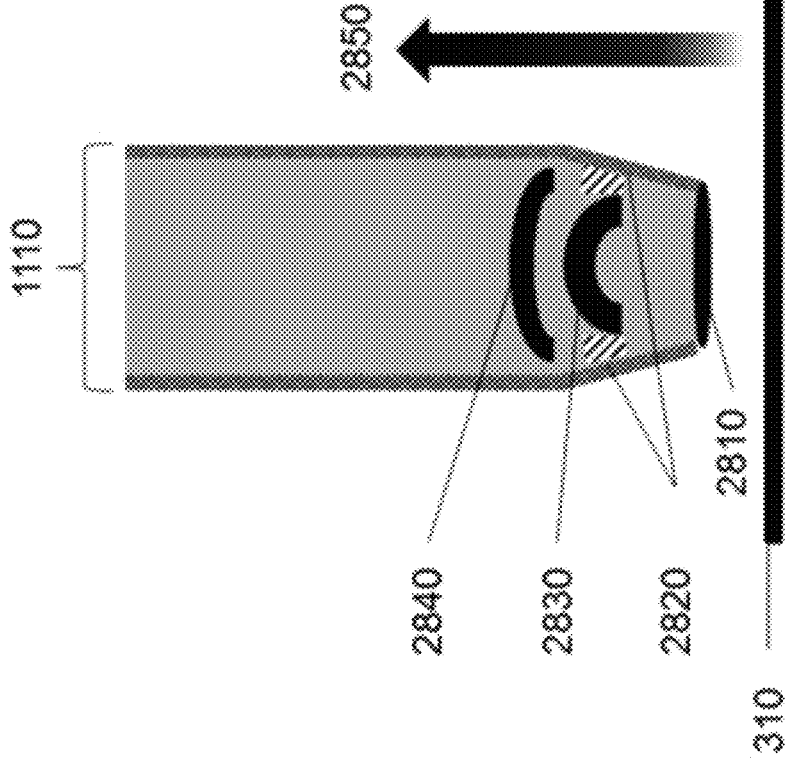
FIG. 28 illustrates schematically an exemplary temperature gradient during optical imaging.

FIG. 28 illustrates schematically an exemplary temperature gradient that may arise between an optical imaging objective and a substrate. The optical imaging objective 1110 (e.g., as described with respect to FIG. 11) may comprise a first element 2810, a second element 2830, a third element 2840, and, in some cases, one or more spacers 2820. The optical imaging objective 1110 may be at ambient temperature. The substrate 310 may be a substrate described herein and may comprise a biological analyte. In some cases, the substrate 310 is heated to a temperature that is greater than ambient temperature. In some cases, the difference in temperature between the substrate 310 and the optical imaging objective 1110 may generate a temperature gradient 2850. The temperature gradient 2850 may result in heat transfer between the substrate and the optical imaging objective 1110 as well as the surrounding environment. In some cases, it may be desirable to modulate or regulate the temperature of the system or the substrate so that the substrate maintains a constant temperature.

Figures 29A, 29B:
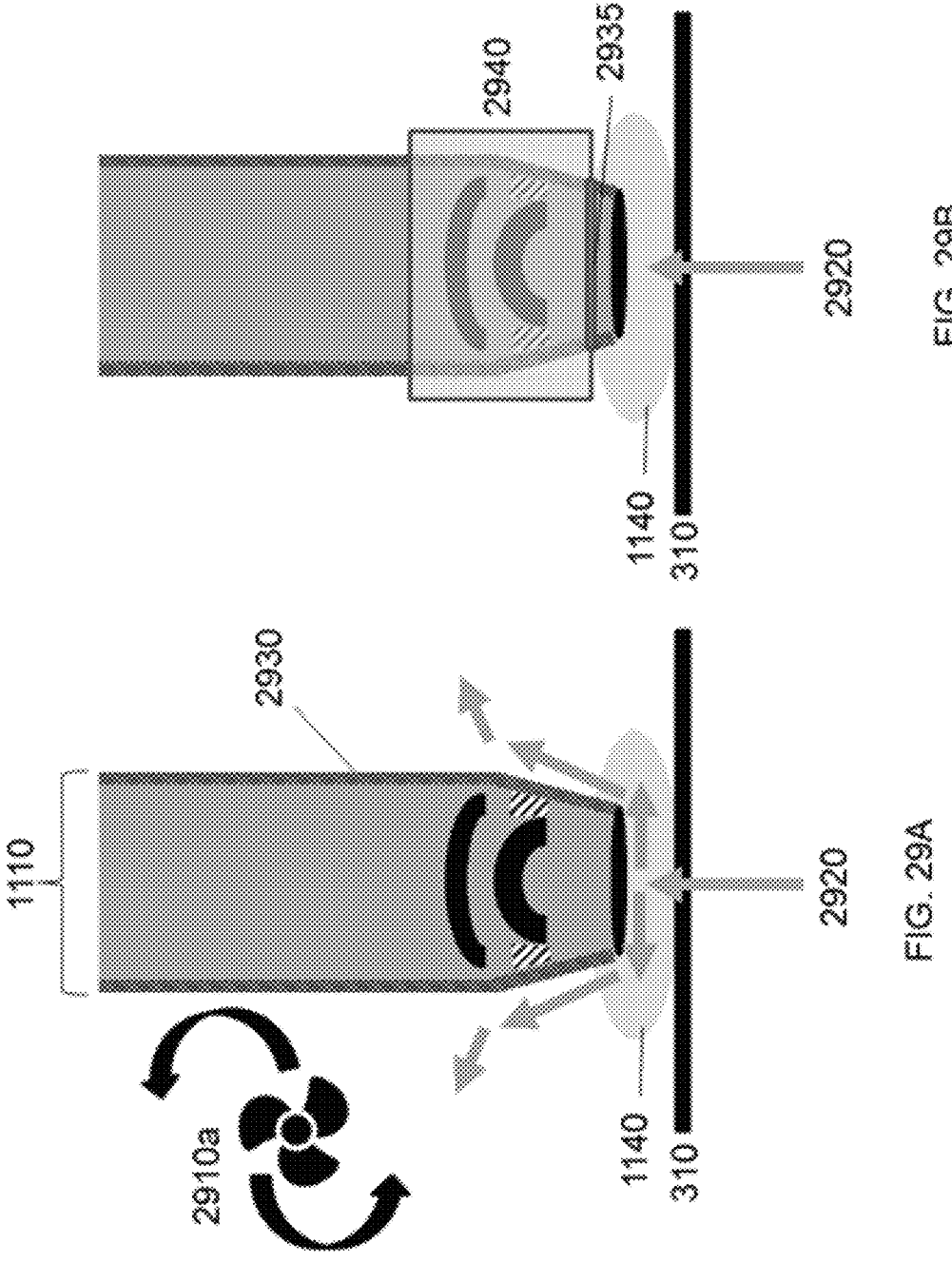
FIGS. 29A-29E illustrates schematically exemplary methods to regulate temperature of the substrate.

FIGS. 29A-29E illustrate schematically example methods to regulate temperature of the substrate. FIG. 29A illustrates an embodiment of such a temperature regulation method of a system. The system may comprise a substrate 310, which may be any substrate described herein, an optical imaging objective 1110 as described herein, and an immersion fluid 1140. In some embodiments, it is desirable to maintain the substrate 310 at an elevated temperature (e.g., 50 degrees Celsius) while keeping other components of the system (e.g., 2830, 2840, 2820) at ambient temperature. In some cases, heat 2920 may be applied to the substrate 310. The heat may transfer to other components of the system, such as the immersion fluid 1140, and part of the optical imaging objective 1110. In some cases, the first element 2810 of the optical imaging objective 1110 may be robust to a large temperature gradient and may not be critical to the optical path or detection method. In one non-limiting example, the first element 2810 may be a substantially flat (e.g., planar) surface. In such cases, the first element 2810 may be robust to a large temperature gradient and may not influence the optical path, detection, or magnification of the substrate or contents disposed thereof. In some cases, the heat 2920 applied to the substrate 310 may be transferred conductively away from the optical imaging objective 1110. For example, the heat 2920 applied to the substrate 310 may transfer to the immersion fluid 1140, to the first element 2810, to the one or more spacers 2820, then toward the outer layer 2930 of the optical imaging objective. The transferred heat may then travel convectively away from the optical imaging objective 1110. In some cases, the heat may be transferred away from the optical imaging objective and may travel from the substrate 310 to the immersion fluid 1140, to the first element 2810. The heat may travel convectively to the second element 2830 and to the one or more spacers 2820 and may travel convectively away from the optical imaging objective 1110. In some embodiments, the thermal resistance of one or more components of the optical imaging objective 1110 may be modulated. For example, the outer layer 2930 of the imaging optical imaging objective 1110 may be configured to optimally disperse heat (e.g., using brass or a low resistivity material, designing thin layers, etc.).

In some embodiments, the method may comprise heating the immersion fluid. In some cases, the immersion fluid 1140 may be pre-heated and applied to the substrate 310, so that the substrate maintains an elevated temperature (e.g., 50 degrees Celsius). The immersion fluid may be continuously replenished. For example, the system may comprise a fluid flow tube (e.g., 1130 in FIG. 11) that is configured to deliver immersion fluid in an enclosed system. In such cases, the heat may be transferred away from the optical imaging objective via convection and conduction. In some cases, additional heat may be transferred away from the optical imaging objective using a cooling element 2910a, such as a fan, which may direct heat (e.g., convectively) away from the optical imaging objective 1110 and reduce the temperature of the components of the optical imaging objective 1110.

FIG. 29B illustrates schematically another embodiment of a temperature regulation method of a system. The system may comprise a substrate 310, as described herein, an optical imaging objective 1110, as described herein, and an immersion fluid 1140. In some embodiments, the immersion fluid 1140 may be heated. In some embodiments, heat 2920 is added to the substrate 310. In some embodiments, the system comprises an insulating spacer 2935, which may be configured to generate an insulated region 2940, comprising the second element 2830 and the third element 2840, which is insulated from the elevated temperature region (e.g., the first element 2810, the immersion fluid 1140, and the substrate 310). In such cases, the greatest temperature gradient may occur in the space between the first element 2810 and the second element 2830. In some cases, the insulating spacer 2935 may have a higher thermal resistance than glass. In some embodiments, a cooling element 2910a may be used to further cool the optical imaging objective 1110. In some embodiments, the first element 2810 may be configured to rapidly disperse heat (e.g., may be thin). In some embodiments, the insulating spacer 2935 may have a higher resistance than the first element 2810, which may reduce heat transfer to the second 2830 and third 2840 elements. Alternatively or in addition to the insulating spacer, there may be a gap (e.g., air gap) disposed between the first element 2810 and the rest of the objective 1110. In some embodiments, the first element 2810 may have optical properties that are insensitive to temperature. In some embodiments, the first element 2810 may have zero or very low optical power, e.g., may be a window or substantially flat (e.g., planar) element, thereby reducing the sensitivity of the first element 2810 to temperature or thermally induced dimension fluctuations.

Figures 29C, 29D:
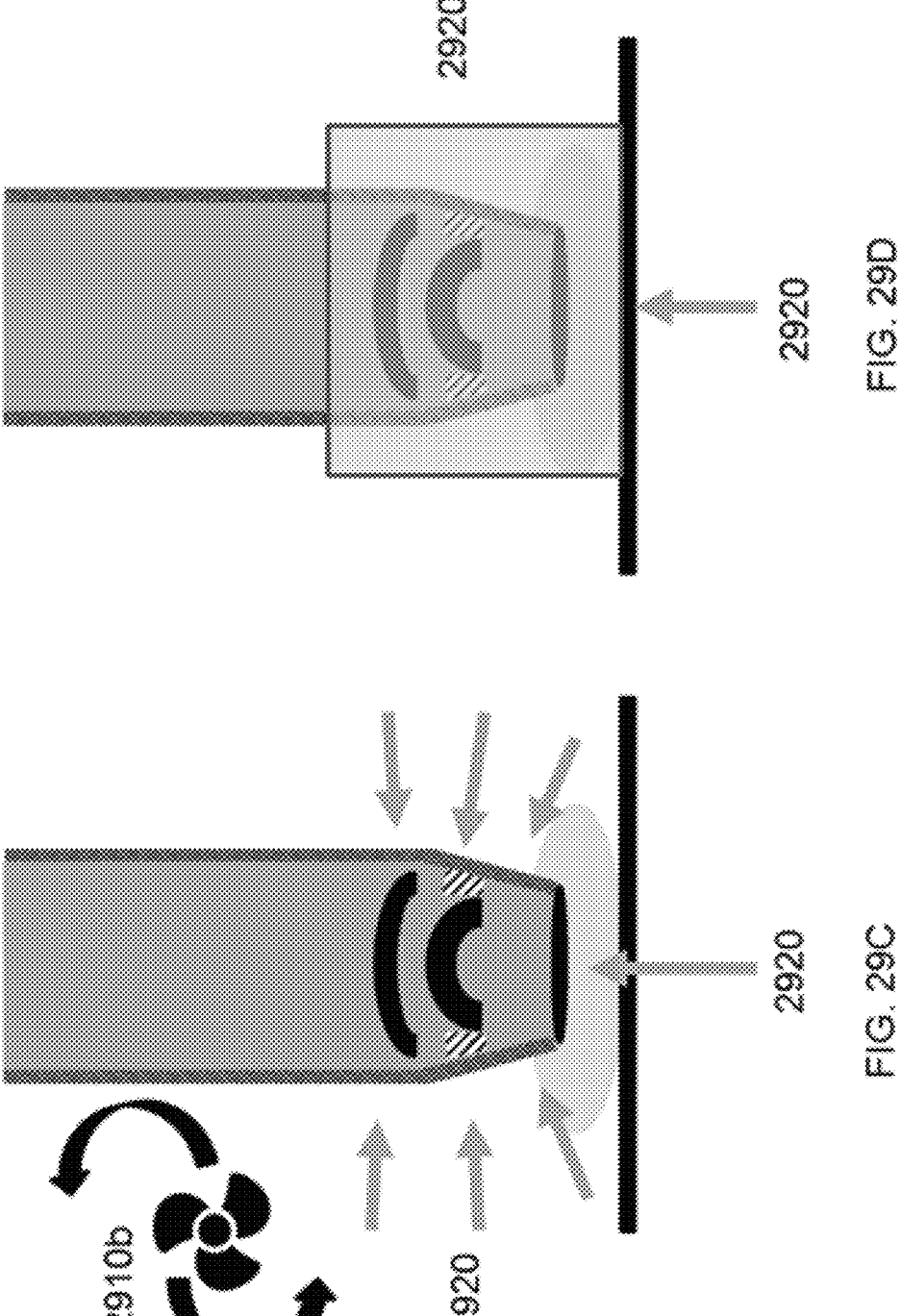

FIG. 29C illustrates schematically another embodiment of a temperature regulation method of a system. The system may comprise a substrate 310, as described herein, an optical imaging objective 1110, as described herein, an immersion fluid 1140, and a heating element 2910*b*. In some embodiments, the optical imaging objective 1110 may be heated to a desired temperature (e.g., 50 degrees Celsius) or to a temperature to match the desired temperature of the substrate 310. In some cases, resistive heaters may be used for the optical imaging objective. Heating of the optical imaging objective may result in heat transfer to the substrate 310. In some cases, heat 2920 may also be applied to the substrate 310. In some embodiments, the heating element 2910*b* may be used to apply heat to the optical imaging objective, e.g., via convection.

FIG. 29D illustrates schematically another embodiment of a temperature regulation method of a system. The system may comprise a substrate 310, as described herein, an optical imaging objective 1110, as described herein, and an immersion fluid 1140. In some embodiments, the optical imaging objective 1110 may be cooled. For example, cooled immersion fluid 1140 may be continuously circulated between the optical imaging objective 1110 and the substrate 310. In some cases, the immersion fluid 1140 may be recycled to minimize reagent use, as described elsewhere herein. In some embodiments, heat 2920 may be applied to the substrate 310.

Figure 29E:
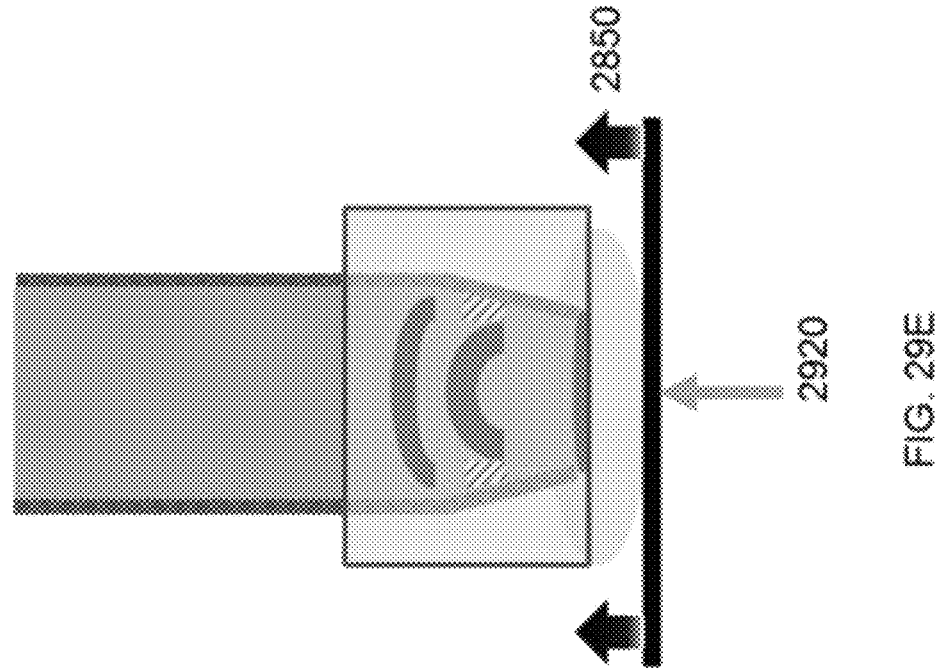

FIG. 29E illustrates schematically another embodiment of a temperature regulation method of a system. The system may comprise a substrate 310, as described herein, an optical imaging objective 1110, as described herein, and an immersion fluid 1140. In some embodiments, the optical imaging objective 1110 may be cooled while the substrate 310 is heated. For example, cooled immersion fluid 1140 may be continuously circulated between the optical imaging objective 1110 and the substrate 310. In some cases, the flow rate of the immersion fluid 1140 may be controlled such that the temperature gradient 2850 exists primarily in the immersion fluid 1140, and the immersion fluid 1140 close to the substrate is at an elevated temperature, but the immersion fluid 1140 close to the optical imaging objective 1110 is cooled. In some cases, the immersion fluid 1140 may be recycled to minimize reagent use, as described elsewhere herein.

As will be appreciated, any combination of mechanisms for temperature regulation and/or modulation may be used. For example, the optical imaging objective may comprise (i) an outer layer that may conduct heat away from the optical imaging objective and (ii) a flat or planar first element with zero or low optical power that is robust to temperature. In some cases, the immersion fluid may be heated in addition or alternatively to using an optical imaging objective with a conductive outer layer and/or flat first element. Similarly, a cooling element may be implemented with any of the described methods and systems. Any suitable combination of temperature modulation methods may be used in conjunction with the systems and methods described herein.

Also disclosed herein, in certain embodiments, are methods for fluid and bubble control in optical detection systems. In some embodiments, an optical imaging objective is used during the detection method. In some cases, the optical imaging objective is immersed in a fluid in contact with the substrate, and the optical imaging objective is in optical communication with the detector. In some cases, the optical imaging objective may comprise a camera or may be connected to a camera. In some cases, the camera or the optical imaging objective comprising the camera may be in fluidic communication with the substrate. In some embodiments, the optical imaging objective or camera is located at a suitable working distance from the substrate. In some cases, the optical imaging objective may be immersed in a fluid. In some embodiments, the optical imaging objective or camera comprises an adapter that is configured to maintain a fluid-filled cavity around the outlet of the optical imaging objective or camera. In some cases, the adapter may allow for imaging of the substrate (or an uncovered surface thereof) at greater working distances. The adapter may be attached to or encase the optical imaging objective or camera. In some cases, the adapter comprises a hydrophobic region, such as the area that interfaces with the immersion fluid. The hydrophobic region may allow for fluid to be directed towards or stay near the imaging region of the optical imaging objective. For example, the hydrophobic region may be configured to retain a volume of fluid between the optical imaging objective or camera and the imaged region of the substrate (or uncovered surface thereof). In some cases, the adapter comprises a hydrophilic region, such as the area that interfaces with the immersion fluid. The hydrophilic region may allow for fluid to be directed towards or stay near the imaging region of the optical imaging objective. For example, the hydrophilic region may be configured to retain a volume of fluid between the optical imaging objective or camera and the imaged region of the substrate (or uncovered surface thereof). In some cases, the adapter comprises both a hydrophilic and a hydrophobic region, which may allow for fluid to be directed towards or stay near the imaging region of the optical imaging objective or camera.

Figure 31:
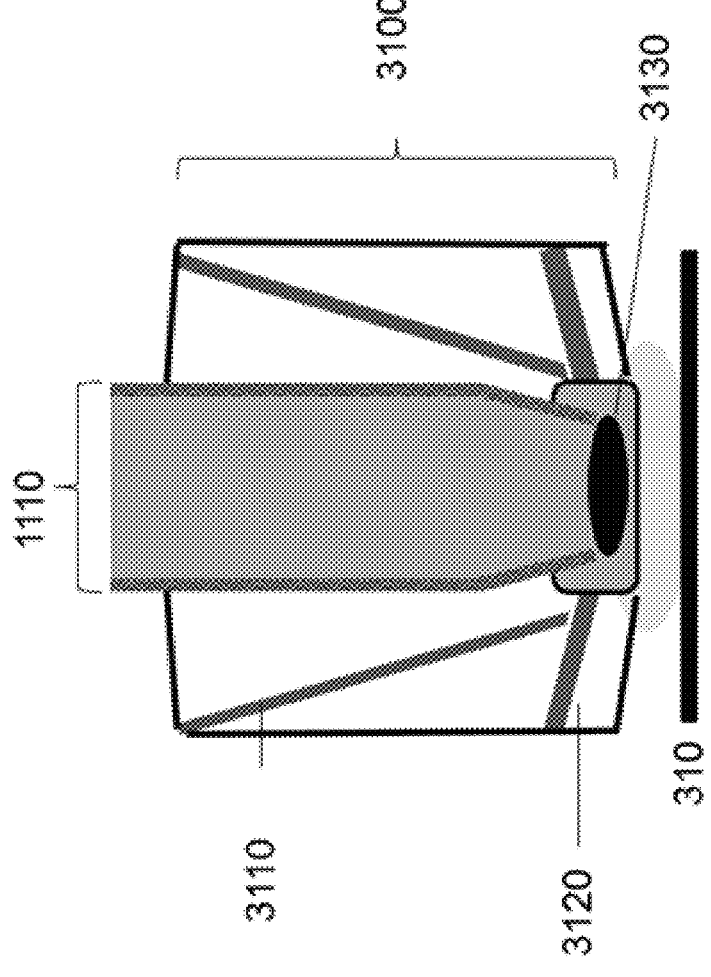
FIG. 31 illustrates schematically an adapter for an optical imaging system.

FIG. 31 illustrates schematically an exemplary adapter that may be attached to or encase the optical imaging objective. The adapter 3100 may allow for imaging of the substrate at greater working distances (e.g., greater than 500 microns). In some cases, the adapter simulates a shorter working distance by forming a fluid-filled cavity around the optical imaging objective 1110. In some embodiments, the adapter 3100 comprises one or more inlet ports 3110, which may dispense the immersion fluid. In some embodiments, the adapter 3100 also comprises one or more other ports 3120 (e.g., outlet ports, additional inlet ports, etc.). Fluid may be directed to a cavity 3130 surrounding the optical imaging objective 1110. In some cases, the fluid may be immersion fluid and may be dispensed on the substrate 310. In some cases, the adapter 3100 retains a volume of immersion fluid between the adapter and the substrate 310, e.g., via surface tension. Use of an adapter may allow for greater working distances while maintaining immersion of the optical imaging objective 1110 in the immersion fluid. In some cases, the adapter may comprise a hydrophobic region that allows for the immersion fluid to remain or be directed toward the imaging path of the optical imaging objective 1110.

Suitable working distances between the optical imaging objective and the substrate may be any suitable distance for imaging the substrate. In some cases, a working distance between 100 and 500 microns is suitable. For example, a suitable working distance may be 100, 150, 200, 250, 300, 350, 400, 450, 500 microns. In some cases, a working distance may be less than 100 microns. For example, a working distance may be 1, 2, 3, 4, 5, 10, 15, 20, 25, 30, 35, 40, 45, 50, 55, 60, 65, 70, 75, 80, 85, 90, or 95 microns. In some cases, a working distance may be greater than 500 microns. For example, a suitable working distance may be 550, 600, 650, 700, 750, 800, 850, 900, 950, or 1000 or more microns. In some cases, a suitable working distance may be more than 1000, 1500, 2000, 2500, 3000, 3500, 4000, 4500 or more microns.

In some cases, a working distance may be sufficiently small such that an immersion fluid may be retained (e.g., via surface tension) between the optical imaging objective and the substrate. In some cases, a working distance may be greater, such that the immersion fluid does not touch the optical imaging objective or the substrate. In some cases, an adapter may be added to the objective that can form a fluid-filled cavity around the objective, such that an immersion fluid may be retained (e.g., via surface tension) between the optical imaging objective and/or adapter and the substrate.

In some embodiments, bubbles may form in the immersion fluid, which may affect the optical and/or detection performance of the system. For example, bubbles may form in the optical path of the optical imaging objective, which may reduce the performance of imaging, focusing, and the path of light (e.g., laser, LED, transmitted light, etc.). In some cases, it is desirable to prevent bubble formation and/or remove bubbles from the optical path. Thus, provided herein are methods and systems for preventing formation of bubbles and for removal of bubbles from the optical path.

Figure 30:
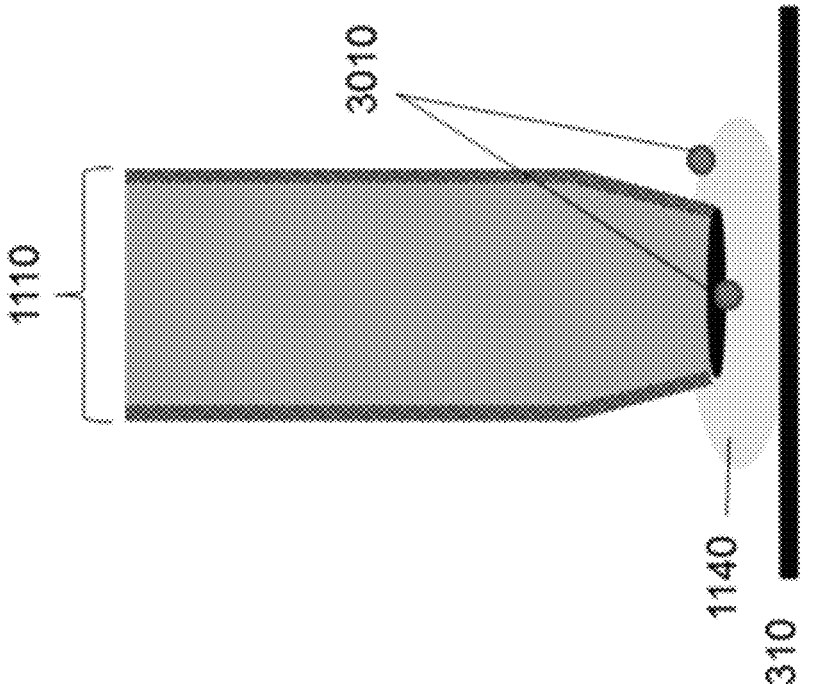
FIG. 30 illustrates schematically bubble formation in a fluid.

FIG. 30 demonstrates schematically the formation of bubbles in an immersion fluid. An optical imaging objective 1110, as described herein, may be positioned over a substrate 310, such as a rotatable substrate, a planar substrate, and/or any substrate described herein. Disposed between the optical imaging objective 1110 and the substrate 310 is an immersion fluid 1140, as described herein. In some cases, the immersion fluid may comprise bubbles 3010. The bubbles 3010 may occur along the optical path of the optical imaging objective 1110, which may reduce the imaging performance of the detection method.

In some embodiments, the method may comprise substrate modification to prevent bubble formation. In some cases, the method comprises degassing the immersion fluid before use in imaging. In some cases, the substrate modification may comprise immersion lithography. In some cases, a hydrophobic material, such as a resist, may be deposited onto the surface of the substrate. Increasing the hydrophobicity of the substrate may increase the contact angle of a fluid on the surface of the substrate and reduce bubble formation.

In some cases, e.g., in immersion lithography, it may be desirable to minimize the exposure of the immersion fluid to the substrate. Thus, the method may comprise methods to minimize the area and duration of immersion fluid contact with the substrate. In some embodiments, the method comprises dispensing and recovery ports that dispense immersion fluid onto the substrate and remove the immersion fluid from the substrate, respectively. Recovery of the fluid may be obtained by a variety of means such as application of pressure or aspiration, gravity forces, centrifugal forces, capillary forces, electric forces, magnetic forces, etc. In some cases, the dispensing and recovery parts may be used to minimize usage of reagents (e.g., immersion fluid). In such cases, the immersion fluid may be recycled, as described elsewhere herein.

Figure 33:
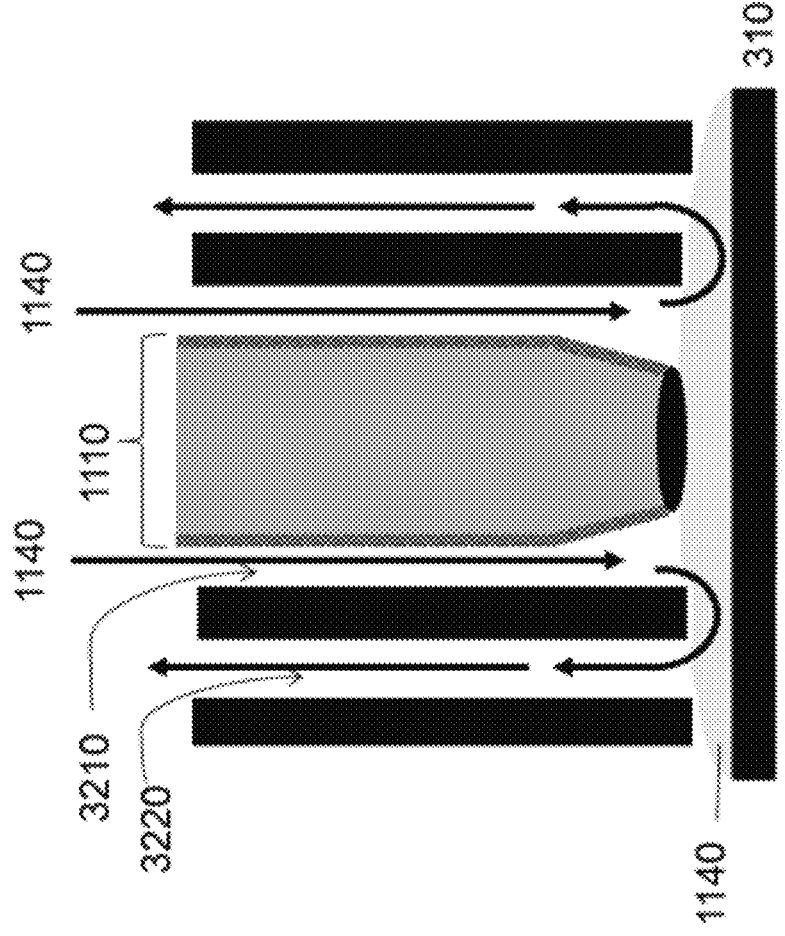
FIG. 33 illustrates schematically a method for dispensing and removing immersion fluid onto a substrate.

FIG. 33 illustrates schematically a method for dispensing and removing immersion fluid onto a substrate. The substrate 310 may be any substrate described herein. The immersion fluid 1140 may comprise an imaging buffer. In some cases, minimization of amount of immersion fluid may be desired, or minimization of exposure of the substrate 310 to the immersion fluid 1140 is desired. In some embodiments, the method comprises dispensing the immersion fluid 1140 through a dispensing port 3210 and recovering the immersion fluid 1140 through a recovery port 3220. In some cases, the dispensing port is located close to the optical imaging objective 1110. In some cases, the recovery port is located outside, i.e., radially outward, of the optical imaging objective 1110 and the dispensing port 3210. In some cases, a plurality of dispensing and recovery parts may be used. As will be appreciated, any number of dispensing and removal ports may be used. For example, 1, 2, 3, 4, 5, 6, 7, 8, 9, 10, 20, 30, 40, 50, 60, 70, 80, 90, 100 or more dispensing ports or removal ports may be used. In some embodiments, the number of dispensing ports used may not be equal to the number of removal ports used. In some cases, more dispensing ports may be used than removal ports. In other cases, more removal ports are used than dispensing ports. In some embodiments, the dispensing and removal ports may be part of an adapter 3100 (see FIG. 31).

In some embodiments, the generation of bubbles may be minimized by controlling the flow rate of the immersion fluid. In some cases, e.g., in immersion lithography, the flow rate of fluid dispensing may be optimized. For example, the flow rate of fluid dispensing may be 1 picoliter/min, 10 picoliters/min, 100 picoliters/min, 1 nanoliter/min, 10 nanoliters/min, 100 nanoliters/min, 1 microliter/min, 10 microliters/min, 100 microliters/min, 1 milliliter/min, 10 milliliters/min, 100 milliliters/min, or up to 1 liter/min. The flow rate of fluid dispensing may be between any of these flow rates. Alternatively, the flow rate of fluid dispensing may be at most any of these flow rates. The flow rate may be sufficiently low such that bubble generation is minimized. In some embodiments, the flow rate may allow air or bubbles to rise above the objective and away from the optical path.

Figure 32:
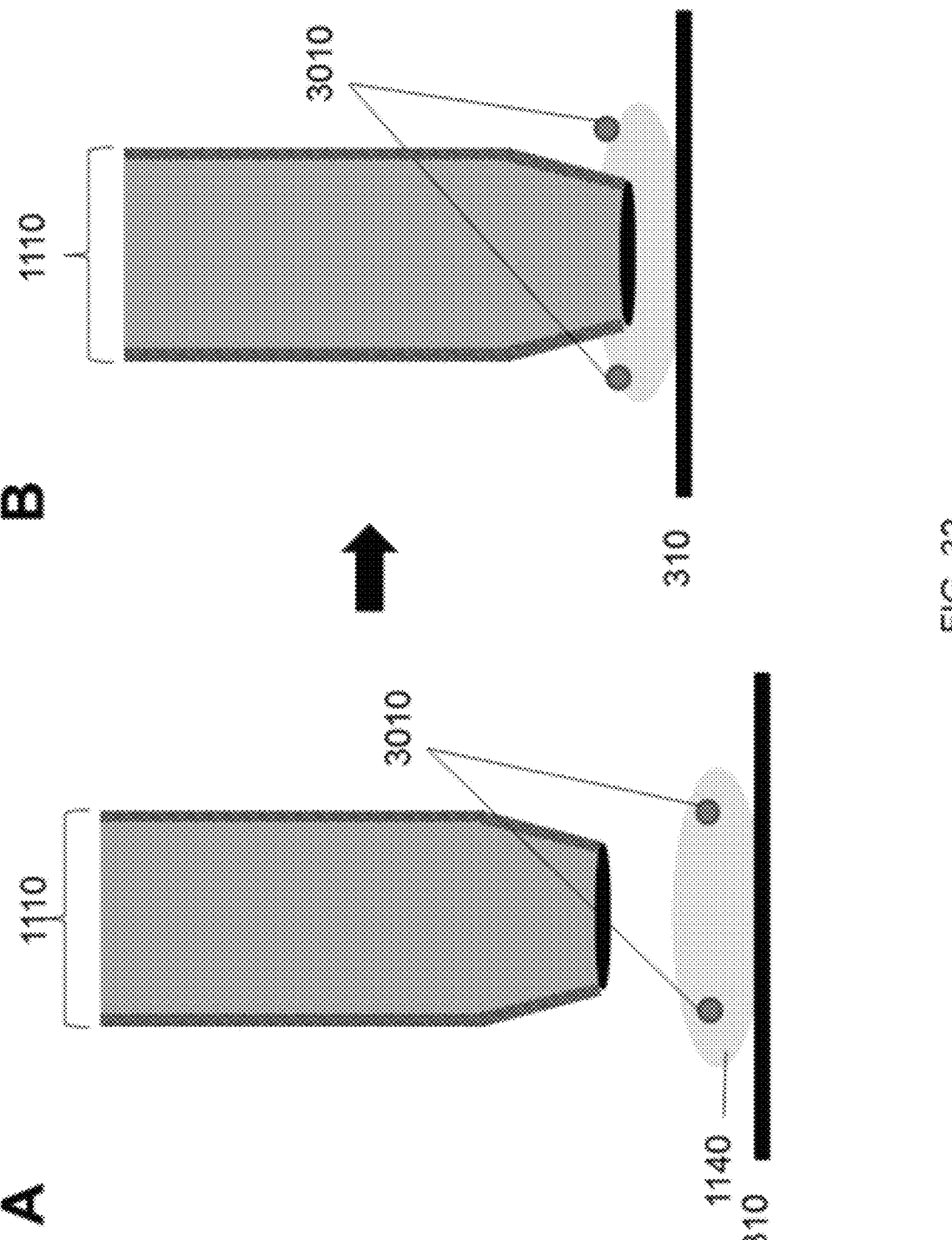
FIG. 32 illustrates schematically an exemplary method to displace bubbles. Panel A shows a substrate with a fluid dispensed thereto and Panel B shows an optical imaging objective in contact with the fluid.

In some embodiments, the method may comprise dispensing a fluid on the substrate and then using the optical imaging objective to displace bubbles. FIG. 32 illustrates schematically a method to displace bubbles. In Panel A, a substrate 310 may have dispensed thereto an immersion fluid 1140, as described herein. The immersion fluid 1140 may comprise bubbles 3010. In Panel B, the optical imaging objective 1110 may be brought into contact with the immersion fluid 1140, thus displacing the bubbles 3010. In some embodiments, the optical imaging objective 1110 may have attached thereto an adapter 3100 (not shown). In some cases, the adapter 3100 may comprise a plurality of dispensing and recovery ports. In such cases, the dispensing port or the recovery port may be used to pull the fluid (e.g., via pressure differences, capillary forces, etc.) into the adapter and thus away from the optical imaging objective.

In some embodiments, the method may comprise using an adapter to prevent bubble formation, or to trap or capture bubbles. As described herein, the adapter may be attached to the optical imaging objective. In some cases, the adapter may interface with the immersion fluid. In some cases, the adapter comprises dispensing ports that may dispense the immersion fluid onto the substrate. In some embodiments, the surface of the adapter that interfaces with the immersion fluid may be flat. In some cases, a thin layer of glass may be placed between the optical imaging objective and the substrate to form a closed cavity to minimize bubble formation. In such an embodiment, the thin layer of glass may be placed between the objective and the wafer to form a closed cavity. The closed cavity may be filled with an immersion liquid without bubbles. On the other end of the thin layer of glass, the fluid may be introduced between the thin layer of glass and the substrate.

In some embodiments, the adapter may be used to remove bubbles from the immersion fluid. In some cases, the adapter comprises one or more dispensing and/or recovery ports. In some embodiments, the dispensing ports may be used to rapidly flush immersion fluid onto the substrate, thereby breaking or disrupting larger bubbles into smaller bubbles, which may be cleared by a separate mechanism, or which may break. A high rapid flush may also push bubbles out of the adapter or away from the optical imaging objective.

In some embodiments, the adapter may comprise ports that may be used to remove bubbles. For example, a suction (i.e., negative pressure) port may be placed in the adapter that may attach to the optical imaging objective. In some embodiments, the suction port may be used to remove bubbles in the vicinity. In other cases, the adapter may comprise a dispensing port that rapidly dispenses fluid onto the substrate to move bubbles toward another area of the substrate. The adapter in some cases may also comprise a suction port to aspirate the bubbles. As will be appreciated, any combination of the features of the adapter (e.g., dispensing port, recovery port, suction ports) may be used.

In some embodiments, the adapter may be flat relative to the plane in which the adapter interfaces with the immersion fluid. In some embodiments, the adapter may be convex along the plane or area that interfaces with the immersion fluid. For example, the bottom surface of the adapter may interface with the immersion fluid and may be partly angled, e.g., in a cone shape. The angled shape may reduce the area of contact between the immersion fluid and the adapter. In some cases, the angled shape may guide or direct fluid to the optical path. In some cases, the optical imaging objective may be the closest part to the substrate and/or immersion fluid. In some embodiments, the adapter may be asymmetrical in shape to reduce the area of the adapter in contact with the immersion fluid.

In some embodiments wherein the adapter is angled, the angle between the adapter and the immersion fluid may be any suitable angle. The angle may be, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 degrees. In some cases, the angle may be at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 degrees. In some cases, the angle may be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 degrees. In some cases, the angle may be a non-integer angle.

In some embodiments, the adapter may comprise a trap that may capture and remove bubbles from the optical path. For example, the adapter may comprise a cavity that may direct bubbles into an internal region of the adapter. Alternatively, the cavity may be connected to an outlet port that allows for disruption of the bubble or removal of the bubble.

Figures 34A, 34B:
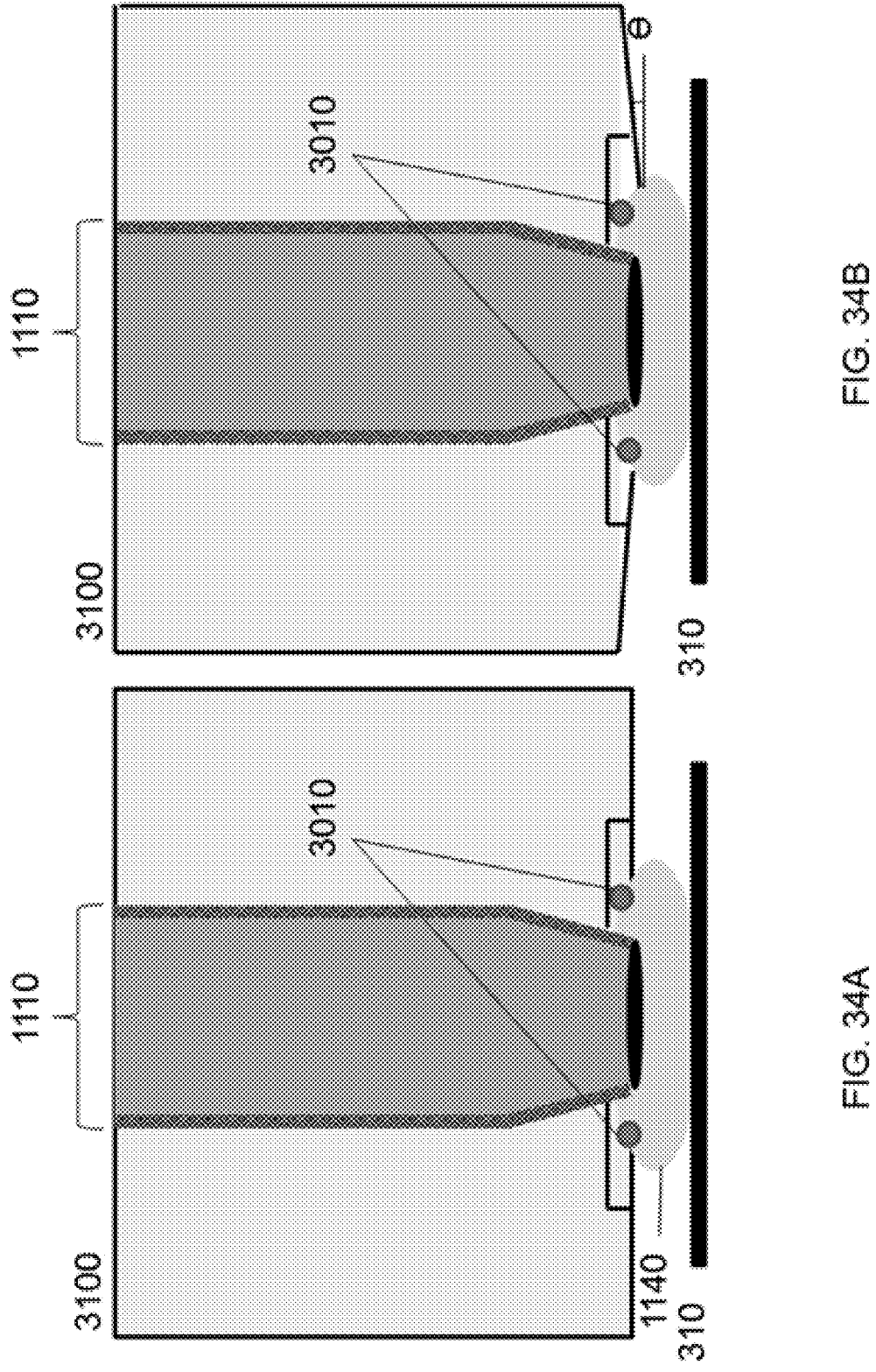
FIGS. 34A-34B illustrate schematically a method for trapping bubbles.

FIGS. 34A-34B illustrate schematically a method for trapping bubbles. FIG. 34A illustrates an exemplary adapter 3100, as described herein, which encases an optical imaging objective 1110, as described herein. The adapter 3100 may be flat or may be angled (see, FIG. 34B). The adapter 3100 may interface with an immersion fluid 1140, which may comprise bubbles 3010. The adapter 3100 may comprise a cavity that can capture entrained bubbles 3010. In some cases, the bubbles may disrupt, break, or pop in the cavity. In other cases, the cavity may be connected to a port (not shown). In FIG. 34B, the adapter may have an angled bottom, which may reduce the area of contact between the immersion fluid 1140 and the adapter 3100. The angle, θ, may be any suitable or useful angle.

In some cases, one or more components of the system may be moved (e.g., translated) to remove bubbles. In one non-limiting example, the optical imaging objective may be moved vertically away from the substrate and then repositioned to an imaging position, thereby allowing entrained bubbles to displace and/or break. In some cases, the substrate may be moved relative to the objective, thereby allowing entrained bubbles to displace and/or break. In another non-limiting example, the substrate may be moved in the plane, e.g., in a circular motion or linear motion (e.g., as shown in FIG. 12). In some cases, motion of the substrate may generate a shear force and velocity field that causes bubbles to displace and/or break. In some cases, a combination of motion planes may be employed. For example, either the optical imaging objective or the substrate, or both, may be moved both in a vertical and planar direction. At any step in the motion, an immersion fluid may be dispensed onto the substrate.

In some embodiments, the immersion fluid may be recollected and recycled (or recirculated). In some cases, the immersion fluid may be treated prior to recycling or recirculation. Treatment may comprise removing debris, removing analytes (e.g., nucleotides, proteins, lipids, carbohydrates, etc.), removing beads, or any other contaminants. Treatment may comprise degassing, de-bubbling, or removing entrained air. As will be appreciated any treatment may comprise any combination of these processes in any convenient order.

Computer Control Systems

The present disclosure provides computer control systems that are programmed to implement methods of the disclosure. FIG. 1 shows a computer system 101 that is programmed or otherwise configured to sequence a nucleic acid sample. The computer system 101 can regulate various aspects of methods and systems of the present disclosure.

The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130, in some cases with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and writeback.

The CPU 105 can be part of a circuit, such as an integrated circuit. One or more other components of the system 101 can be included in the circuit. In some cases, the circuit is an application specific integrated circuit (ASIC).

The storage unit 115 can store files, such as drivers, libraries and saved programs. The storage unit 115 can store user data, e.g., user preferences and user programs. The computer system 101 in some cases can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, nucleic acid sequencing information to a user. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 105.

EXAMPLES

Example 1. Imaging of Sequencing of a Nucleic
Acid Molecule

Figure 22:
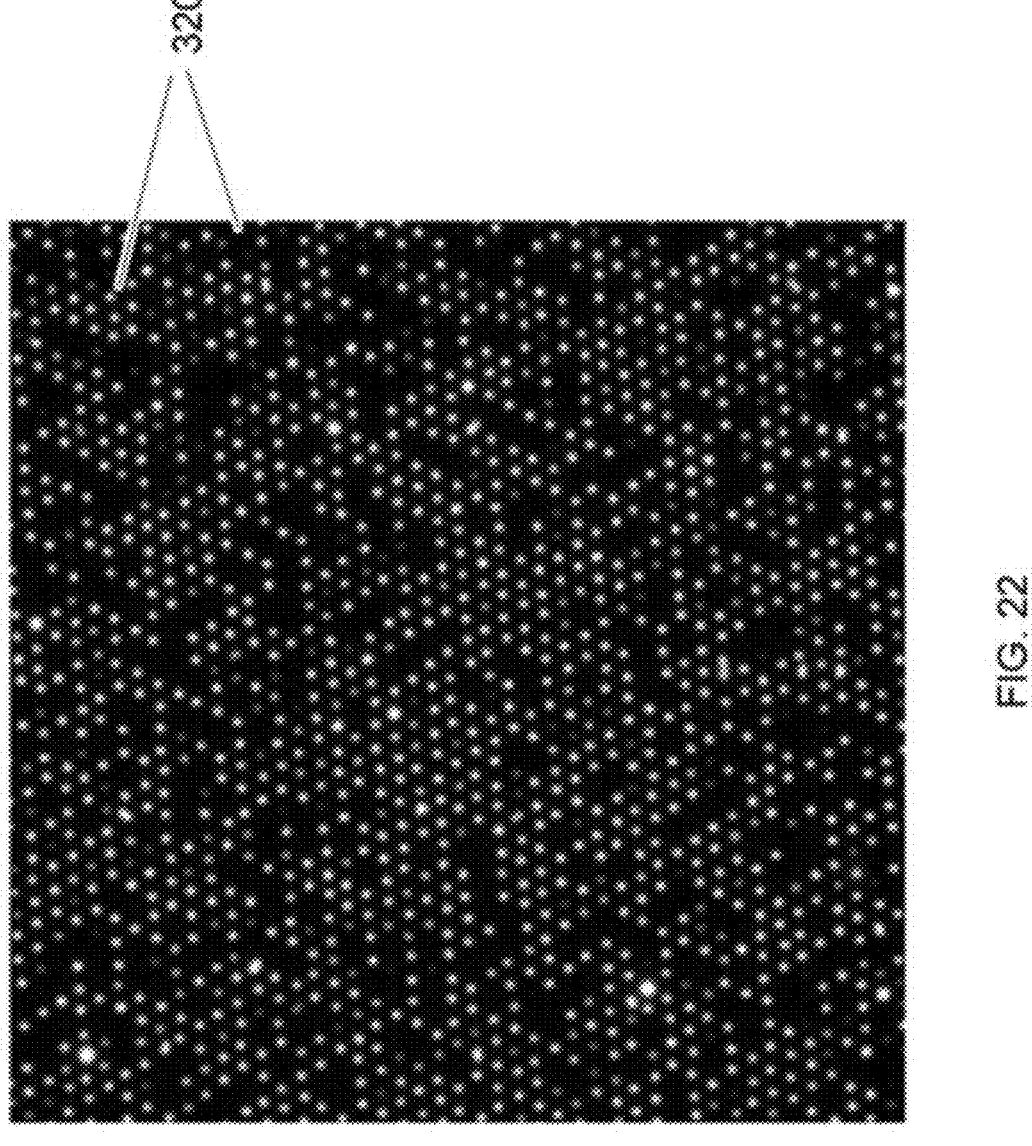
FIG. 22 shows an example of an image generated by imaging a substrate with an analyte immobilized thereto.

FIG. 22 shows an example of an image generated by imaging a substrate with an analyte immobilized thereto. A substrate 310 comprising a substantially planar array has immobilized thereto the biological analyte, e.g., nucleic acid molecules. The substantially planar array comprises a plurality of individually addressable locations 320, and a plurality of the individually addressable locations comprises a biological analyte, e.g., one or more nucleic acid molecules. The individually addressable locations 320 may be randomly arranged or arranged in an ordered pattern. The biological analyte may be attached to a bead, which is immobilized to the array. A single bead may comprise a plurality of analytes, such as at least 10, 20, 30, 40, 50, 100, 150 or more analytes. A bead may be associated with an individually addressable location. A plurality of fluorescent probes (e.g., a plurality of fluorescently-labeled, A, T, C, or G) is dispensed onto the substrate 310. In some embodiments, the substrate is configured to rotate with respect to a central axis; a fluid flow unit comprising a fluid channel configured to dispense a solution comprising a plurality of probes to the array, wherein during rotation of the substrate, the solution is directed centrifugally along a direction away from the central axis and brought in contact with the biological analyte. In other embodiments, the substrate is not rotated. The substrate 310 is then subjected to conditions sufficient to conduct a reaction between at least one probe of the plurality of probes and the biological analyte, to couple the at least one probe to the biological analyte. The uncoupled probes are washed away. The coupling of the at least one probe to the biological analyte is detected using photometry, which comprises imaging at least a part of the substrate 310 (e.g., via scanning or fixed field imaging) and measuring the signal of each individually addressable location 320. Nucleic acid molecules comprising a nucleotide complementary to the fluorescent probes are fluorescent in an individually addressable location 320. The operations may then be iterated, and signals from an image are collated with signals from prior images of the same substrate to generate traces of signals in time for each biological analyte in each individually addressable location 320. The sequence of the plurality of fluorescent probes is known for each iteration of the operations, generating a known sequence for the analyte in each of the individually addressable locations 320.

Example 2. Diagnostic Procedure for Nucleic Acid
Incorporation

Figure 23:
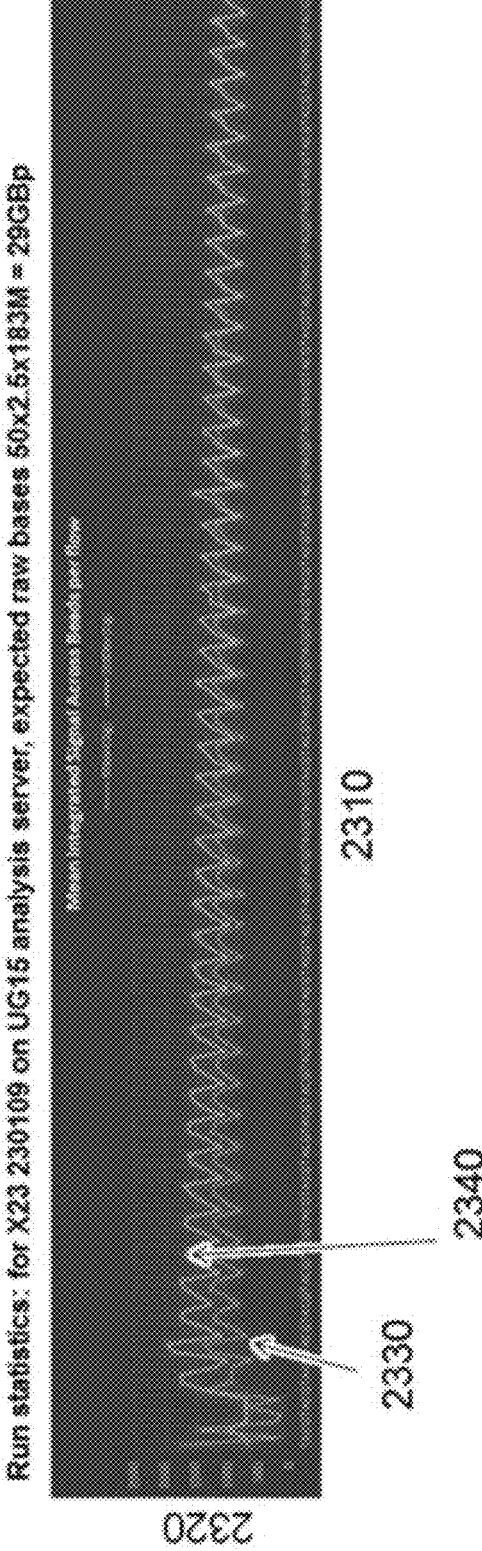
FIG. 23 shows an example of data obtained from a diagnostic procedure.

Diagnostic procedures are run to determine whether a probe has coupled with a biological analyte (e.g., nucleic acid molecule). FIG. 23 shows example data of such a diagnostic procedure, running approximately 29 giga base pairs (Gbp) from about 183 million beads. A substrate, similar to that depicted in 310, comprises an array configured to immobilize the biological analyte. The biological analyte may be attached to a bead, which is immobilized to the array. A single bead may comprise a plurality of analytes, such as at least 10, 20, 30, 40, 50, 100, 150 or more analytes. The biological analyte in some cases is genomic DNA from *E. Coli* bacteria. In some cases, human DNA may be used as the biological analyte. In some cases, the biological analyte is a shotgun library of DNA from a clonal population. In some cases, the substrate is configured to rotate with respect to a central axis. In other embodiments, the substrate is not configured to rotate and may be stationary. In other embodiments, the substrate is not configured to rotate and may be movable laterally or longitudinally, as described elsewhere herein. In some cases, a fluid flow unit comprising a fluid channel is used to dispense a solution comprising a plurality of probes (e.g., fluorescently labeled nucleotides) to the array, wherein during rotation of the substrate, the solution is directed centrifugally along a direction away from the central axis and brought in contact with the biological analyte under conditions sufficient to couple at least one probe (e.g., nucleotide) of the plurality of probes to the biological analyte. In other cases, the probes may be dispensed on the substrate via nebulization, a spray, a pressurized gas (e.g., blown gas) system, etc., as described elsewhere herein. The substrate 310 is then subjected to conditions sufficient to conduct a reaction between at least one probe of the plurality of probes and the biological analyte, to couple the at least one probe to the biological analyte. The uncoupled probes are washed away. The coupling of the at least one probe to the biological analyte is detected using photometry, which comprises imaging at least a part of the substrate. Nucleic acid molecules comprising a nucleotide complementary to the fluorescent probes are fluorescent in an individually addressable location. One or more of the processes may be repeated or iterated in a cycle.

From the images, the signal 2320 of each individually addressable location or a plurality of individually addressable locations is measured. The mean signal 2330 of multiple individually addressable locations can also be obtained for each cycle. Since the probe applied to the substrate is known each cycle, the mean signal 2330 can be plotted as a function of the known nucleotide sequence 2310. Additionally, the standard deviation of the signal 2340 can also be plotted for each cycle. The plot 2300 may then yield information on the nucleic acid sequence of the biological analyte. One or more of these operations may be performed in real time.

Example 3. Scanning Image Pattern of a Biological
Analyte

Figure 24:
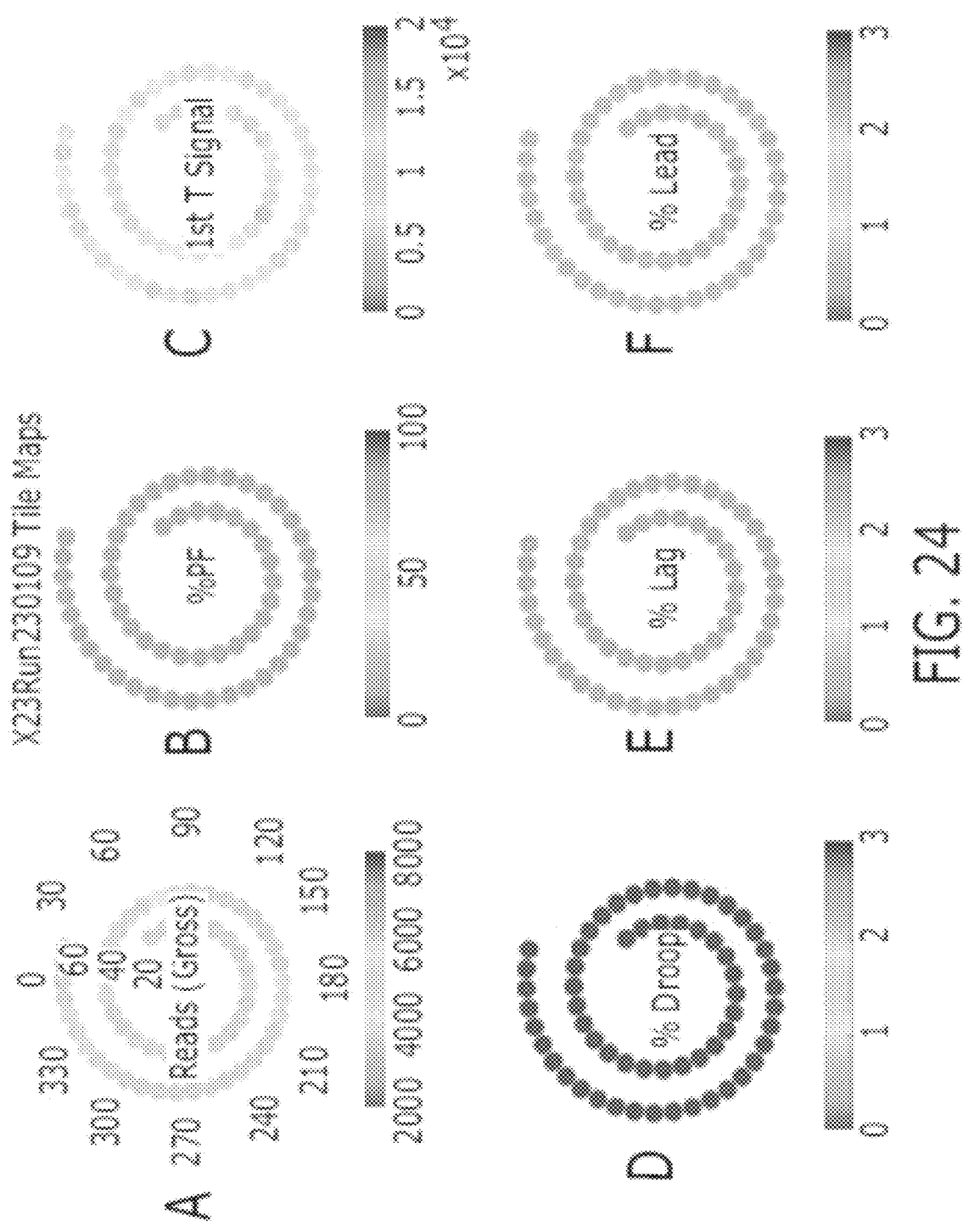
FIG. 24 shows example data of a diagnostic procedure. Panels A-F show spatial plots of diagnostic metrics computed on scanned images at different individually addressable locations.

FIG. 24 shows example data of a diagnostic procedure that informs quality control metrics of scanning imaging. A substrate, similar to that depicted in 310, may be subjected to rotation. The substrate in some cases is rotatable with respect to a central axis. In other embodiments, the substrate may not be rotatable or may not be rotated. The substrate comprises the biological analyte, such as human and *E. Coli* shotgun libraries. In one example, the substrate comprises a shotgun library and ~15% synthetic monotemplates that are spiked into the sample. In such an example, the shotgun library and synthetic monotemplates may be labeled (e.g., fluorescently). In other examples, the shotgun library and synthetic monotemplates are associated with a bead, which may associate with the substrate (e.g., via a linker). In some cases, the beads may associate with the substrate in a pattern. In some cases, a subset of beads on the substrate may be detected in a pattern, such as a spiral pattern (e.g., according to a scan path). The library and synthetic monotemplates may be detected directly using an optical measurement. In other examples, a plurality of probes is added to the substrate and the substrate is subjected to conditions sufficient to conduct a reaction between at least one probe of the plurality of probes and the biological analyte, to couple the at least one probe to the biological analyte. One or more signals are detected from the at least one probe coupled to the biological analyte.

Diagnostic metrics may be computed of imaged segments. FIG. 24 Panels A-F show plots depicting image or process metrics at different individually addressable locations (e.g., varying R and θ on a circular substrate). Each scan field of view is depicted as a small circle on each plot (Panels A-F). The images may then be analyzed for the number of reads per image (Panel A), percentage of reads passing filter (Panel B), mean first incorporation signal of a nucleotide (Panel C), droop (signal loss per cycle, Panel D), lag phasing, which may be indicative of false negatives, e.g., the fraction of the clonal population that fails to advance per cycle (Panel E), and lead phasing, which may be indicative of false positives, e.g., the fraction of the clonal population that incorrectly advances per cycle (Panel F). Uniform signal level and lead/lag phasing across R and θ indicate consistent fluidic and biochemical reactions over the course of many incorporation cycles in this instance and predict high quality sequence reads.

Example 4. Linearity and Accuracy of Homopolymers

Figure 25A:
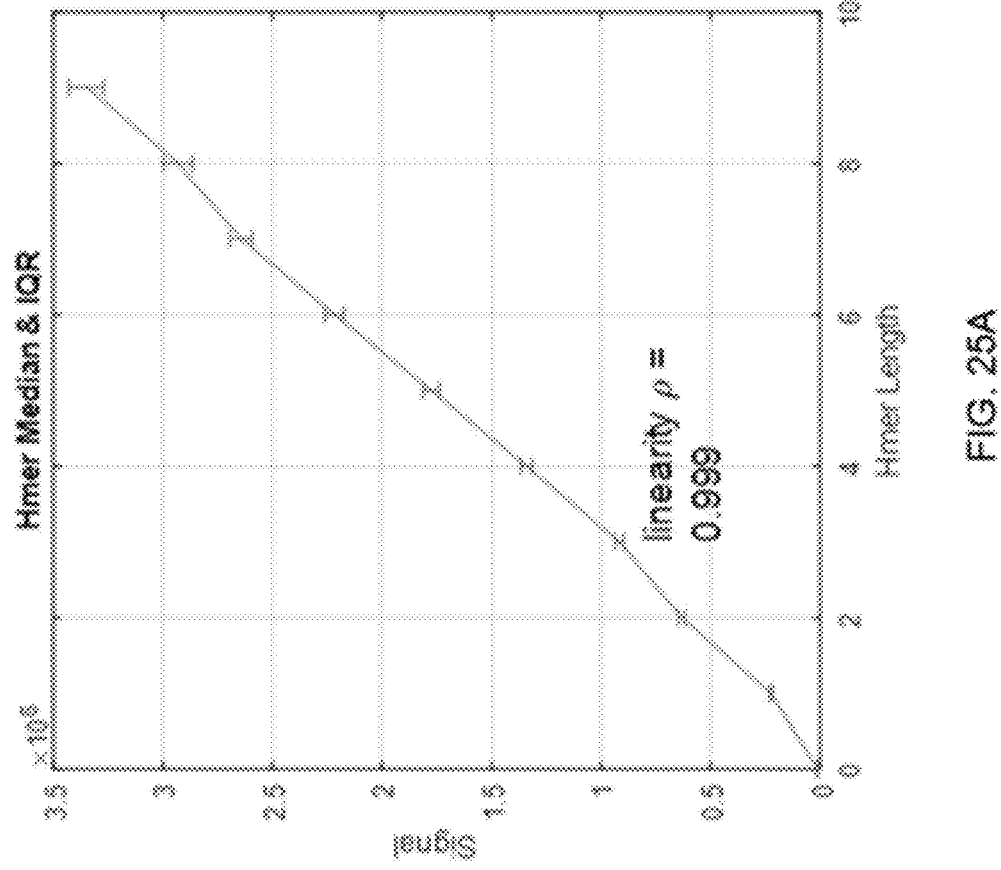
FIG. 25A shows example data of flow-based sequencing.

In sequencing by synthesis chemistries based on single nucleotide flows it is necessary to determine the length of hompolymers as they are synthesized in order to determine the sequence. A homopolymer can be of varying lengths and comprise a sequence of identical nucleotides (e.g., one nucleotide, two nucleotides, three nucleotides, four nucleotides, five nucleotides, six nucleotides, seven nucleotides, eight nucleotides, nine nucleotides, and ten nucleotides, wherein the nucleotides are all the same, i.e., all A, all T, all C, all G, etc.). FIG. 25A shows exemplary data of flow-based sequencing by synthesis. Many homopolymers of different lengths were coupled to the substrate. A complementary probe was added to the substrate, and the substrate was washed and imaged, and the process was repeated. Signal was measured from each bead position. As can be visualized in the plot, the signals from the images are quite linear with the homopolymer length, up to the maximum of 9 nucleotides tested here. Thus, the signal from the obtained images (e.g., of an individually addressable location) can be used to determine the homopolymer length up to 5 bases with sufficiently high accuracy and low noise (>99% accuracy).

Example 5. Sequencing of Nucleic Acid Molecules and Signal Processing

Figures 25B, 25C:
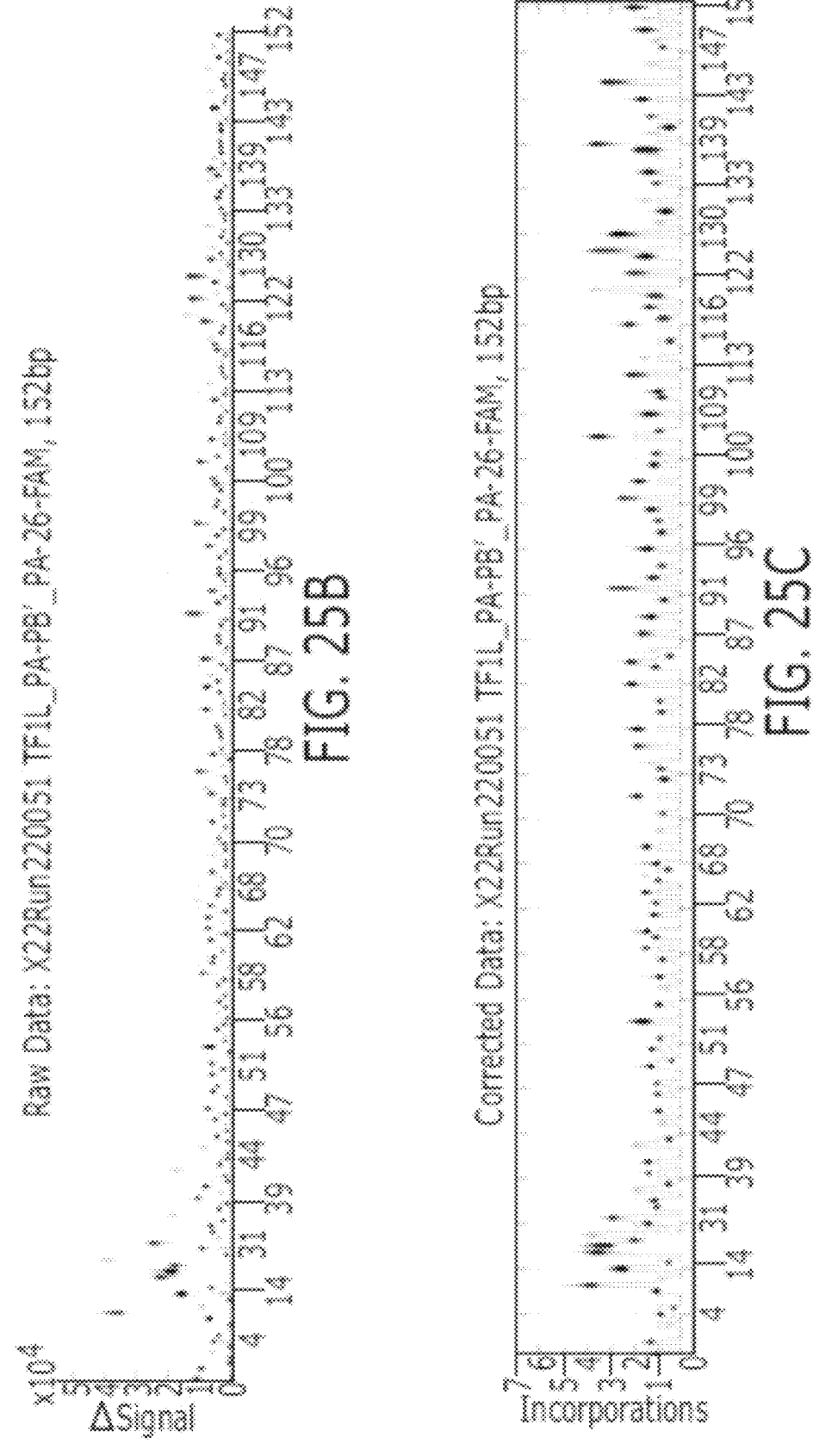
FIGS. 25B-25C illustrate exemplary data from processed images.

A substrate comprising a substantially planar array has immobilized thereto the biological analyte, e.g. nucleic acid molecules from E. coli. Sequencing by synthesis was performed using a flow-based chemistry. Imaging was performed, as described elsewhere herein. FIG. 25B shows the signal distributions for a set of several hundred colonies, each a replicate of a single synthetic monotemplate. The x-axis is labeled with the length of the sequencing after each cycle (e.g., each chemistry flow step). In FIG. 25C, the same data have been processed with a parametric model. The parametric model accounts for different template counts (amplitude) and background level for each colony. The signal is deconvolved with a model of lead and lag phasing and also accounts for global signal loss per cycle. In the example depicted here, the nominal phasing was 0.54% lag, 0.41% lead, and a signal loss of 0.45%. The residual systematic variation may be attributable to signal variation with sequence context can be further corrected using other algorithms (not shown).

Example 6. Sequencing of Shotgun Library from E. coli

Figure 26A:
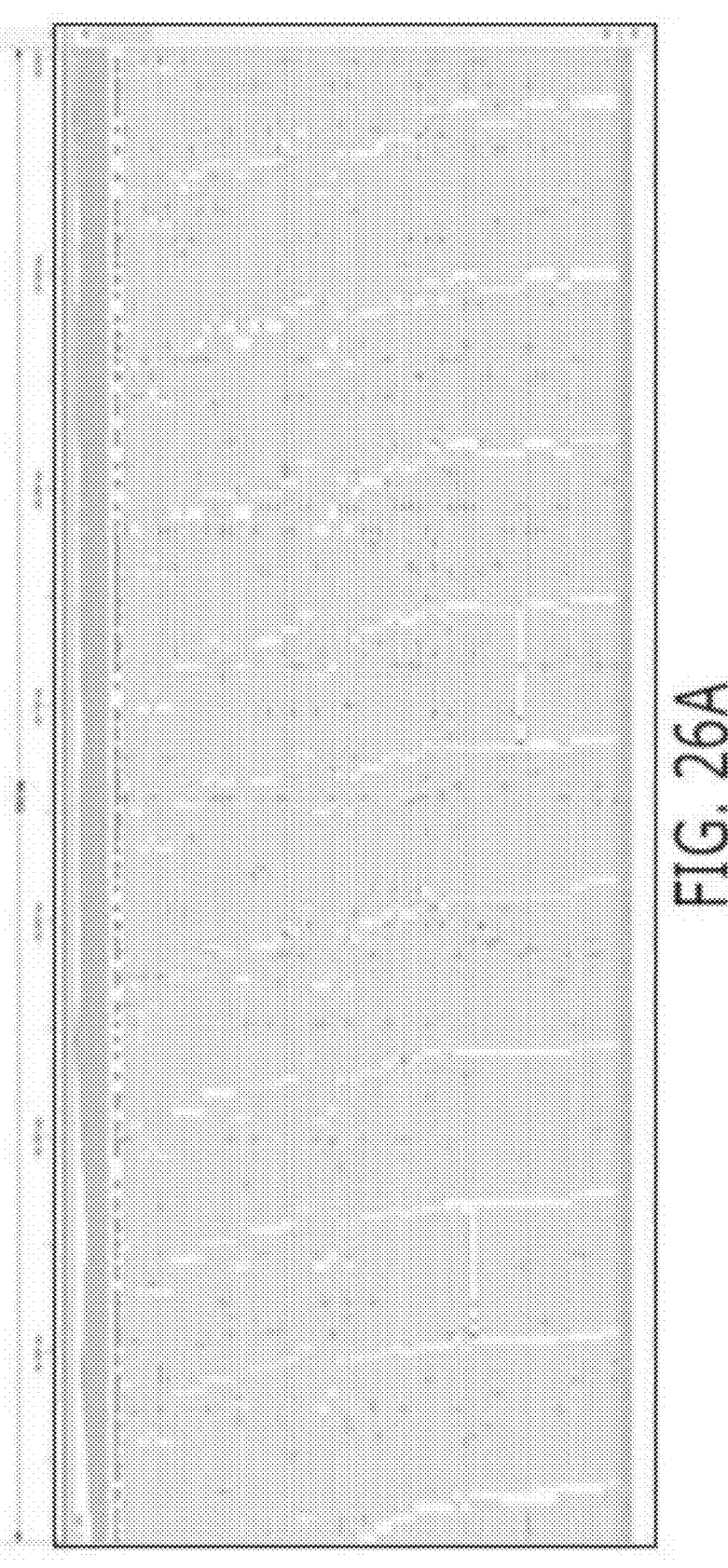
FIG. 26A shows a plot of aligned genomic reads.
Figure 26B:
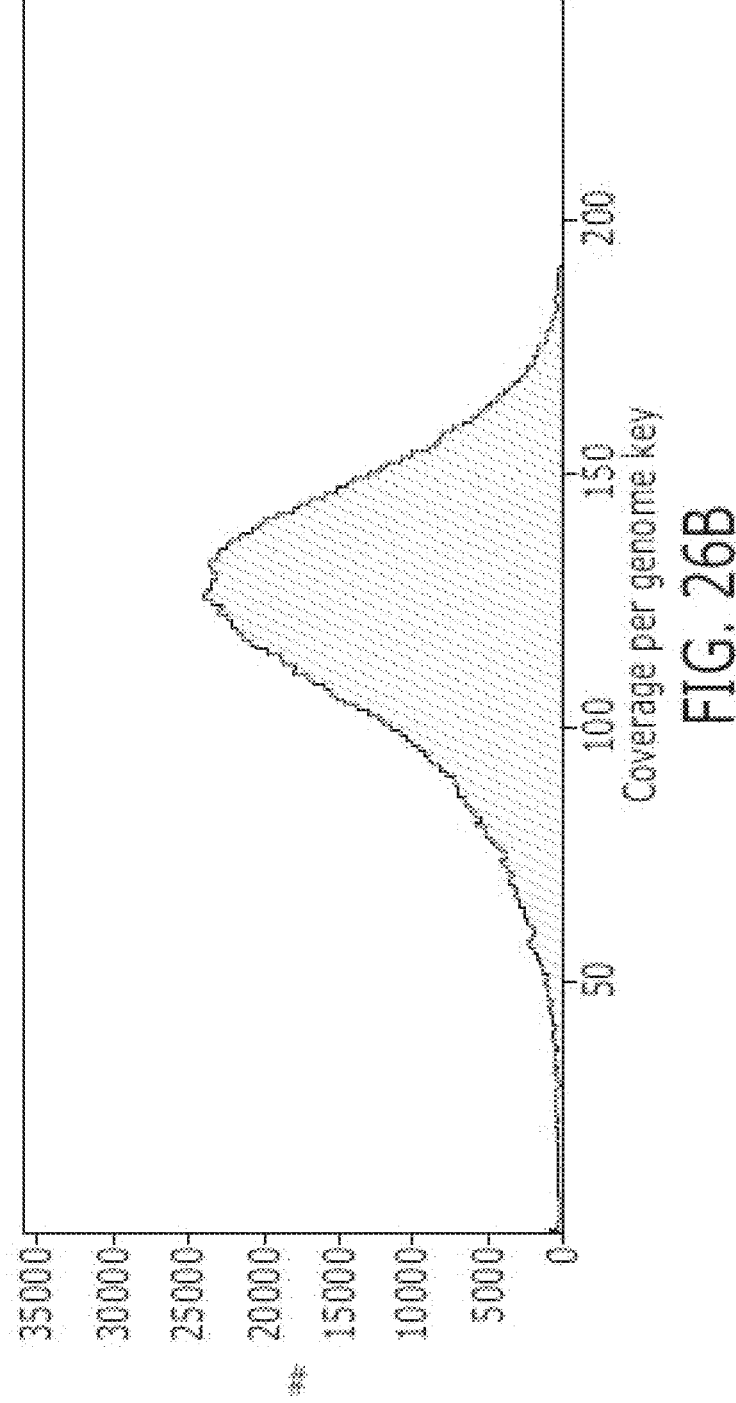
FIG. 26B shows aligned coverage distribution over a reference genome.

A substrate comprising a substantially planar array has immobilized thereto the biological analyte, e.g. nucleic acid molecules from E. coli. Sequencing by synthesis was performed using a flow-based chemistry. Imaging was performed, as described elsewhere herein. Images were then processed. FIG. 26A shows individual aligned reads for a segment of the E. coli reference genome. FIG. 26B shows a plot derived from the image processing of the aligned read depth for each position in the E. coli genome for a set of shotgun reads. The x-axis shows the coverage level at each E. coli reference key position and the y-axis shows the frequency.

Example 7. Calculation of Reel-to-Reel Dimensions

A flexible substrate comprising a biological analyte may be designed in a manner such that the throughput of processing nucleic acid molecules is improved. In one example, biological analytes are nano-imprinted on a flexible substrate, such as a film, that is pulled through a first reel to contact the flexible substrate with a reservoir comprising a solution comprising a plurality of probes. The dimensions of the film may be modulated to be compatible with the detector (e.g., an optical sensor). In some cases, the length of the film may be rolled around a reel. The film may be ~85 meters long and 7 millimeters (mm) wide, yielding an area of ~6000 square centimeters ($cm^2$). Compared to a planar, circular substrate that has a diameter of 5.9 centimeter (cm), the usable area of the film may be over 60 times greater than the usable area of the planar, circular substrate. Given an optical sensor rate of 10 centimeters per second (cm/s), the entire film may be imaged within ~14 minutes. Alternatively, the dimensions (e.g., length and width) of the film may be modulated to improve the detection rate, the imprinting rate, the contact area, etc.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

175

176

What is claimed is:

1. A system for nucleic acid sample processing, comprising:

a substrate comprising a first region and a second region different from said first region, wherein said first region or said second region comprises at least 10,000 indexed locations;

a first source comprising a first set of nucleic acid molecules, wherein said first region of said substrate comprises a first set of indexed locations comprising nucleic acid molecules of said first set of nucleic acid molecules;

a second source comprising a second set of nucleic acid molecules, wherein said second source is different than said first source, wherein said second region of said substrate comprises a second set of indexed locations comprising nucleic acid molecules of said second set of nucleic acid molecules;

a detector configured to detect signals from said first set of indexed locations that are indicative of at least one nucleotide having been incorporated into a growing nucleic acid strand that is complementary to a nucleic acid molecule of said first set of nucleic acid molecules; and one or more processors, individually or in combination, configured to (i) receive said signals from said detector and (ii) associate each nucleic acid molecule of said first set of indexed locations with said first source or (iii) associate each nucleic acid molecule of said second set of indexed locations with said second source.

2. The system of claim 1, wherein said one or more processors are operatively coupled to said first source and said second source.

3. The system of claim 2, wherein said one or more processors are individually or collectively programmed to direct a fluid flow unit to dispense a solution from said first source or said second source to said substrate.

4. The system of claim 1, wherein said detector comprises an optical imaging unit that is operatively coupled to said one or more processors.

5. The system of claim 4, wherein said optical imaging unit is configured to detect (i) signals from said first region to determine a first set of sequences of said nucleic acid molecules of said first set of indexed locations and (ii) signals from said second region to determine a second set of sequences of said nucleic acid molecules of said second set of indexed locations.

6. The system of claim 5, wherein said one or more processors are configured, individually or in combination, (1) to associate said first set of sequences to said first source using said first set of indexed locations and (2) to associate said second set of sequences to said second source using said second set of indexed locations.

7. The system of claim 6, wherein said first set of sequences is associated with said first source and said second set of sequences is associated with said second source in absence of determining a barcode sequence of said first set of nucleic acid molecules and said second set of nucleic acid molecules.

8. The system of claim 1, wherein each nucleic acid molecule of said first set of nucleic acid molecules and said second set of nucleic acid molecules comprises a synthetic sequence of no more than 6 bases in length, and wherein a subset of nucleic acid molecules originating from a same source each comprises a common synthetic sequence, which common synthetic sequence is different from synthetic sequences of another subset of nucleic acid molecules originating from a different source.

9. The system of claim 1, wherein said substrate comprises a plurality of binders, wherein a binder of said plurality of binders is capable of immobilizing both said nucleic acid molecules of said first set of nucleic acid molecules and said nucleic acid molecules of said second set of nucleic acid molecules, wherein said nucleic acid molecules of said first set of nucleic acid molecules are immobilized to said first set of indexed locations via a first set of binders of said plurality of binders, and wherein said nucleic acid molecules of said second set of nucleic acid molecules are immobilized to said second set of indexed locations via a second set of binders of said plurality of binders different from said first set of binders.

10. The system of claim 9, wherein said binder is configured to immobilize said first set of nucleic acid molecules or said second set of nucleic acid molecules using one or more interactions selected from a group consisting of: hydrophilic interactions, hydrophobic interactions, electrostatic interactions, and hybridization interactions.

11. The system of claim 1, wherein said first region and said second region are adjacent and in contact on said substrate.

12. The system of claim 1, wherein said substrate comprises (1) a plurality of first regions, including said first region, configured to receive nucleic acid molecules of said first source and (2) a plurality of second regions, including said second region, configured to receive nucleic acid molecules of said second source, which plurality of first regions and plurality of second regions are arranged on said substrate such that a given first region of said plurality of first regions is not in contact with another first region of said plurality of first regions.

13. The system of claim 12, wherein said plurality of first regions and said plurality of second regions are arranged as alternating regions on said substrate.

14. The system of claim 12, wherein said plurality of first regions and said plurality of second regions are arranged as radially alternating regions on said substrate.

15. The system of claim 12, wherein (i) said plurality of first regions are chemically distinct from said plurality of second regions, or (ii) said plurality of first regions and said plurality of second regions are separated by barriers.

16. The system of claim 1, wherein said first region and said second region are of different sizes or comprise different numbers of individually addressable locations on said substrate.

17. The system of claim 1, further comprising, a first loading fluid comprising said first set of nucleic acid molecules and a second loading fluid comprising said second set of nucleic acid molecules, wherein said first loading fluid and said second loading fluid are immiscible.

18. The system of claim 1, further comprising a magnetic source configured to direct said first set of nucleic acid molecules or said second set of nucleic acid molecules to said substrate.

19. The system of claim 1, wherein said first region and said second region are separated by a barrier on said substrate, and wherein said barrier comprises a viscous solution, polyethylene glycol (PEG), a fluid that is immiscible with a loading solution comprising said first set of nucleic acid molecules and said second set of nucleic acid molecules, an air knife, an injection molded guide, or a hydrophobic region.

20. The system of claim 1, wherein said substrate is substantially planar.

21. The system of claim 1, wherein said substrate is patterned.

22. The system of claim 1, wherein said substrate is rotatable about a rotational axis.

23. The system of claim 22, wherein said first set of indexed locations and said second set of indexed locations have different radial distances from said rotational axis.

24. The system of claim 1, wherein said nucleic acid molecules of said first set of nucleic acid molecules have sequences that are different from sequences of said nucleic acid molecules of said second set of nucleic acid molecules.

25. The system of claim 1, wherein said nucleic acid molecules of said first set of nucleic acid molecules have the same sequences as said nucleic acid molecules of said second set of nucleic acid molecules.

26. The system of claim 1, wherein said first set of nucleic acid molecules is attached to a plurality of beads, which plurality of beads is immobilized adjacent to said substrate at said first set of indexed locations.

27. The system of claim 26, wherein a bead of said plurality of beads comprises a plurality of nucleic acid molecules attached thereto, and wherein said plurality of nucleic acid molecules comprises amplification products derived from a template nucleic acid molecule.

28. The system of claim 27, wherein said first set of indexed locations comprises at least 100 individually addressable locations, and wherein said second set of indexed locations comprises at least 100 individually addressable locations.

29. The system of claim 28, wherein said first set of indexed locations and said second set of indexed locations comprise at least about 5,000,000,000 individually addressable locations.

30. The system of claim 28, wherein said first set of nucleic acid molecules is attached to a first plurality of beads and said second set of nucleic acid molecules is attached to a second plurality of beads, and wherein said first plurality of beads and said second plurality of beads are associated to said at least 100 individually addressable locations of said first set of indexed locations or said at least 100 individually addressable locations of said second set of indexed locations.

* * * * *